(12) United States Patent
Isaacs et al.

(10) Patent No.: US 10,501,734 B2
(45) Date of Patent: Dec. 10, 2019

(54) COMPOSITIONS AND METHODS OF USE THEREOF FOR MAKING POLYPEPTIDES WITH MANY INSTANCES OF NONSTANDARD AMINO ACIDS

(71) Applicant: Yale University, New Haven, CT (US)

(72) Inventors: Farren J. Isaacs, Stamford, CT (US); Miriam Amiram, Stamford, CT (US); Adrian Haimovich, New Haven, CT (US); Dieter Söll, Guilford, CT (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 15/117,406

(22) PCT Filed: Feb. 6, 2015

(86) PCT No.: PCT/US2015/014841
§ 371 (c)(1),
(2) Date: Aug. 8, 2016

(87) PCT Pub. No.: WO2015/120287
PCT Pub. Date: Aug. 13, 2015

(65) Prior Publication Data
US 2016/0355802 A1  Dec. 8, 2016

Related U.S. Application Data

(60) Provisional application No. 61/936,507, filed on Feb. 6, 2014.

(51) Int. Cl.
*C12N 9/00* (2006.01)
*C12N 15/10* (2006.01)
*C12N 1/20* (2006.01)

(52) U.S. Cl.
CPC ............. *C12N 9/93* (2013.01); *C12N 15/102* (2013.01); *C12N 15/1058* (2013.01); *C12Y 601/01* (2013.01)

(58) Field of Classification Search
CPC .... C12N 9/93; C12N 15/102; C12N 15/1058; C12Y 601/01
See application file for complete search history.

(56) References Cited

U.S. PATENT DOCUMENTS

| 6,852,834 | B2 | 2/2005 | Chilkoti |
| 8,153,432 | B2 | 4/2012 | Church |
| 2003/0148422 | A1 | 8/2003 | Volker |

FOREIGN PATENT DOCUMENTS

| WO | 2002086075 | 10/2002 |
| WO | 2008036392 | 5/2008 |
| WO | 2009049223 | 4/2009 |

OTHER PUBLICATIONS

Nowatzki et al. (Macromolecules, 2008, 41:1839-1845).*
(Continued)

*Primary Examiner* — Jeremy C Flinders
(74) *Attorney, Agent, or Firm* — Pabst Patent Group LLP

(57) ABSTRACT

Compositions, systems, and methods for preparation of polypeptides having multiple iterations of non-standard amino acids are provided. The compositions and method can be used to produce recombinant proteins at a greater yield than the same or similar polypeptides made using conventional compositions, systems, and methods. Accordingly, in some embodiments, the polypeptides are ones that could not be made using conventional methods and reagents, or could not be made a sufficient yield or purity to serve a practical purpose using conventional methods and reagents. Polypeptides made using the disclosed compositions, systems, and methods are also provided.

38 Claims, 26 Drawing Sheets
Specification includes a Sequence Listing.

(56) References Cited

OTHER PUBLICATIONS

Johnson et al. (Nat. Chem. Biol., 2011, 7:779-786 supplemental material) (Year: 2011).*
Best (Biochem., 2009, 48:6571-6584) (Year: 2009).*
Lajoie, et al., "Supplemental Materials for Genomically recoded organisms expand biological functions", Science, Supplementary Materials, http://science.sciencemag.org/content/suppl/2013/10/16/342.6156.357.DC1, 78 pages, (2013).
Aerni, et al., "Revealing the amino acid composition of proteins within an expanded genetic code", Nuclric Acids Res., 43(2):e8 (2015).
Alfonta, et al., "Site-specific incorporation of a redox-active amino acid into proteins", J Am Chem Soc., 125(48):14662-3 (2003).
Atkins and Baranov, "The distinction between recoding and codon reassignment", Genetics, 185:1535-6 (2010).
Bae, et al., "Incorporation of beta-selenolo[3,2-b]pyrrolyl-alanine into proteins for phase determination in protein X-ray crystallography", J Mol Biol, 309:925-36 (2001).
Bonde, et al., "Direct mutagenesis of thousands of genomic targets using microarray-derived oligonucleotides", ACS Synth Biol., 4(1):17-22 (2015).
Chin, "Expanding and reprogramming the genetic code of cells and animals", Annu Rev Biochem, 83:379-408 (2014).
Chin, et al., "Addition of p-azido-L-phenylalanine to the genetic code of *Escherichia coli*", J Am Chem Soc, 124:9026-7 (2002).
Cooley, et al., "Structural basis of improved second-generation 3-nitro-tyrosine tRNA synthetases", Biochemistry, 53(12):1916-24 (2014).
Davis and Chin, "Designer proteins: applications of genetic code expansion in cell biology", Nat Rev Mol Cell Biol., 13:168-82 (2012).
Devito, et al., "Recombineering with tolC as a selectable/counter-selectable marker: remodeling the rRNA operons of *Escherichia coli*", Nucleic Acids Res., 36(1):e4 (2008).
Dieterich, et al., "Selective identification of newly synthesized proteins in mammalian cells using bioorthogonal noncanonical amino acid tagging (BONCAT).", PNAS, 103:9482-7 (2006).
Dougherty, et al., "Synthesis of a genetically engineered repetitive polypeptide containing periodic selenomethionine residues", Macromolecules, 26:1779-81 (1993).
Dumas, et al., Designing logical codon reassignment—Expanding the chemistry in biology Chem. Sci., 6:50-69 (2015).
Furman, et al., "A genetically encoded aza-Michael acceptor for covalent cross-linking of protein-receptor complexes", J Am Chem Soc, 136:8411-7 (2014).
Gallagher, et al., "Rapid editing and evolution of bacterial genomes using libraries of synthetic DNA", Nature Protocols, 9(10):2301-16 (2014).
Gregg, et al., "Rational optimization of tolC as a powerful dual selectable marker for genome engineering", Nucleic Acids Research, 42(7):4779-90 (2014).
Heinemann, et al., "Enhanced phosphoserine insertion during *Escherichia coli* protein synthesis via partial UAG codon reassignment and release factor 1 deletion", FEBS Lett, 586:3716-22 (2012).
International Search Report for PCT/US2015/014841 dated Sep. 30, 2015.
Isaacs, et al., "Precise manipulation of chromosomes in vivo enables genome-wide codon replacement", Science, 333(6040):348-53 (2011).
Johnson, et al., "Residue-specific incorporation of non-canonical amino acids into proteins: recent developments and applications.", Curr Opin Chem Biol, 14:774-80 (2010).
Johnson, et al., "RF1 knockout allows ribosomal incorporation of unnatural amino acids at multiple sites", Nat Chem Biol, 7:779-86 (2011).
Kang, et al., "Evolution of iron(II)-finger peptides by using a bipyridyl amino acid" Chembiochem, 15:822-5 (2014).

Kirshenbaum, et al., "Biosynthesis of proteins incorporating a versatile set of phenylalanine analogues", Chembiochem, 3:235-7 (2002).
Ko, et al, "Pyrrolysyl-tRNA synthetase variants reveal ancestral aminoacylation function", FEBS Lett, 587:3243-8 (2013).
Kothakota, et al., "Biosynthesis of a Periodic Protein Containing 3-Thienylalanine: A Step Toward Genetically Engineered Conducting Polymers", J Am Chem Soc, 117:536-7 (1995).
Lajoie, et al., "Genomically recoded organisms expand biological functions", Science, 342: 357-60 (2013).
Lajoie, et al., "Probing the limits of genetic recoding in essential genes", Science, 342:361-3 (2013b).
Li, et al., "Biological applications of expanded genetic codes", Chembiochem, 15(16):2335-41 (2014).
Lim, et al., "Site-specific fatty acid-conjugation to prolong protein half-life in vivo", J Control Release, 170(2):219-25 (2013).
Link, et al., "Non-canonical amino acids in protein engineering", Curr Opin Biotechnol, 14:603-9 (2003).
Liu and Schultz, "Adding new chemistries to the genetic code", Annu. Rev. Biochem., 79:413-44 (2010).
Meyer, et al., "Quantification of the effects of chain length and concentration on the thermal behavior of elastin-like polypeptides", Biomacromolecules, 5:846-51 (2004).
Miyake-Stoner, et al., "Generating permissive site-specific unnatural aminoacyl-tRNA synthetases", Biochemistry, 49:1667-77 (2010).
Mizrahi, et al., "A Stiff Injectable Biodegradable Elastomer", Adv Funct Mater., 23(12):1527-33 (2013).
Mukai, et al., "Codon reassignment in the *Escherichia coli* genetic code", Nucleic Acids Res, 38:8188-95 (2010).
Nishi, et al., "Different effects of 4-hydroxyproline and 4-fluoroproline on the stability of collagen triple helix", Biochemistry, 44:6034-42 (2005).
O'Donoghue, et al., "Upgrading protein synthesis for synthetic biology", Nat Chem Biol, 9:594-8 (2013).
Park, et al., "Expanding the genetic code of *Escherichia coli* with phosphoserine", Science, 333:1151-4 (2011).
Pedelacq, et al., "Engineering and characterization of a superfolder green fluorescent protein", Nat Biotechnol, 24:79-88 (2006).
Presolski, et al., "Copper-Catalyzed Azide-Alkyne Click Chemistry for Bioconjugation", Cur Protoc Chem Biol.,, 3(4):153-62 (2011).
Schultz, et al., "A genetically encoded infrared probe", J Am Chem Soc, 128:13984-5 (2006).
Seitchik, et al., "Genetically encoded tetrazine amino acid directs rapid site-specific in vivo bioorthogonai ligation with trans-cyclooctenes", J Am Chem Soc, 134:2898-901 (2012).
Sharan, et al., "Recombineering: a homologous recombination-based method of genetic engineeri", Nat. Protoc., 4:206-23 (2009).
Stokes, et al., "Enhancing the utility of unnatural amino acid synthetases by manipulating broad substrate specificit", Mol Biosyst, 5:1032-8 (2009).
Strzegowski, et al., "Photornodulation of the inverse temperature transition of a modified elastin poly(pentapeptide)", J Am Chemical Soc., 116:813-814 (1994).
Tang, et al., "Fluorinated Coiled-Coil Proteins Prepared In Vivo Display Enhanced Thermal and Chemical Stability This work was supported by a grant from the U.S. Army Research Office. Y. Tang is supported by a Whitaker Graduate Research Fellowship. We thank Dr. Gary Hathaway for performing matrix-assisted laser desorption/ionization analyses", Angew Chem Int Ed Engl, 40:1494-1496 (2001).
Tian, et al., A general approach to site-specific antibody drug conjugates PNAS, 111:1766-71 (2014).
Tinberg, et al., "Computational design of ligand-binding proteins with high affinity and selectivity", Nature, 501:212-6 (2013).
Umehara, et al., "N-acetyl lysyl-tRNA synthetases evolved by a CcdB-based selection possess N-acetyl lysine specificity in vitro and in vivo", FEBS Lett, 586:729-33 (2012).
Wang, et al., "Addition of the keto functional group to the genetic code of *Escherichia coli*", PNAS, 100:56-61 (2003).
Wang, et al., "Programming cells by multiplex genome engineering and accelerated evolution", Nature, 460:894-8 (2009).
Wang, et al., "Unnatural amino acid mutagenesis of fluorescent proteins", Angew Chem Int Ed Engl, 51:10132-5 (2012).

(56) References Cited

OTHER PUBLICATIONS

Wu, et al., "Multiple site-selective insertions of noncanonical amino acids into sequence-repetitive polypeptides", Chembiochem, 14:968-78 (2013).

Yang, et al., "Biocompatible click chemistry enabled compartment-specific pH measurement inside *E. coli*", Nature communications, 5:4981 (2014).

Young, et al., "An enhanced system for unnatural amino acid mutagenesis in *E. coli*", J Mol Biol, 395:361-74 (2010).

Young, et al., "An evolved aminoacyl-tRNA synthetase with atypical polysubstrate specificity", Biochemistry, 50:1894-900 (2011).

Yuet, et al., "Chemical tools for temporally and spatially resolved mass spectrometry-based proteomics", Ann Biomed Eng, 42:299-311 (2014).

* cited by examiner

*FIG. 5N*

COMPOSITIONS AND METHODS OF USE THEREOF FOR MAKING POLYPEPTIDES WITH MANY INSTANCES OF NONSTANDARD AMINO ACIDS

CROSS-REFERENCE TO RELATED APPLICATIONS

This application is a 371 application of International Application No. PCT/US2015/014841 filed Feb. 6, 2015, which claims benefit of and priority to U.S. Provisional Application No. 61/936,507, entitled "Methods to create functionalized biopolymers containing many instances of nonstandard amino acids in genomically recoded organisms" filed Feb. 6, 2014, and where permissible is incorporated by reference in its entirety.

STATEMENT REGARDING FEDERALLY SPONSORED RESEARCH

This invention was made with government support under Grant N66001-12-C-4211 awarded by the National Institutes of Health. The government has certain rights in the invention.

REFERENCE TO SEQUENCE LISTING

The Sequence Listing submitted as a text file named "YU_6349_PCT_txt" created on May 19, 2015, and having a size of 159,928 bytes is hereby incorporated by reference.

FIELD OF THE INVENTION

The field of the invention generally relates to compositions and methods of manufacturing recombinant polypeptides including one or more iterations of one or more non-standard amino acids.

BACKGROUND OF THE INVENTION

Expansion of the genetic code by incorporation of nonstandard amino acids (nsAAs) into proteins has emerged as a powerful approach for template-based incorporation of over 100 nsAAs containing diverse chemical groups, including post-translational modifications, photocaged amino acids, bioorthogonal reactive groups, and spectroscopic labels (Liu, et al., *Annu Rev Biochem*, 79:413-44 (2010); Johnson, et al., *Curr Opin Chem Biol*, 14:774-80 (2010); O'Donoghue, et al., *Nat Chem Biol*, 9:594-8 (2013); Chin, et al., *Annu Rev Biochem*, (2014); Seitchik, et al., *J Am Chem Soc*, 134:2898-901 (2012)). For example, site-specific incorporation of nsAAs at a single position enables engineering of protein-drug conjugates (Tian, et al., *Proc Natl Acad Sci USA*, 111:1766-71 (2014), cross-linking proteins (Furman, et al., *J Am Chem Soc*, 136:8411-7 (2014), and enzymes with altered or improved function (Kang, et al., *Chembiochem*, 15:822-5 (2014); Wang, et al., *Angew Chem Int Ed Engl*, 51:10132-5 (2012)). Multi-site nsAA incorporation can further expand the function and properties of proteins and biomaterials by enabling synthesis of polypeptide polymers with programmable combinations of natural and nonstandard amino acids. However, multi-site nsAA incorporation has so far been limited by inefficiencies associated with the translation machinery and the cellular hosts in which the recombinant proteins are produced (Li, et al., *Chembiochem* (2014)).

Currently, there are two common approaches to recombinant protein expression with nsAAs. The first approach introduces an nsAA by complete amino acid replacement wherein a natural amino acid is substituted for a close synthetic analog (i.e., the nsAA) in an auxotrophic strain (Dougherty, et al., *Macromolecules*, 26:1779-1781 (1993)). This approach has been utilized extensively to tag, identify, and study newly synthesized proteomes in a variety of cell types (Dieterich, et al., *Proc Natl Acad Sci USA*, 103:9482-7 (2006); Yuet, et al., *Ann Biomed Eng*, 42:299-311 (2014)). In addition, multi-site incorporation of nsAAs using this method has generated biomaterials with improved stability (Tang, et al., *Angew Chem Int Ed Engl*, 40:1494-1496 (2001); Nishi, et al., *Biochemistry*, 44:6034-42 (2005)) biopolymers containing conductive chemical groups (Kothakota, et al., *Journal of the American Chemical Society*, 117:536-537 (1995)), and facilitated characterization of structural proteins (Bae, et al., *J Mol Biol*, 309:925-36 (2001)). However, complete amino acid replacement has drawbacks that limit its application. First, the chemical diversity introduced via nsAAs in this procedure is limited since the nsAA must be a close analog of the natural amino acid it replaces, a constraint that can be partially alleviated by mutations to the native translation machinery (Kirshenbaum, et al., *Chembiochem*, 3:235-7 (2002)). Second, the substitution of an nsAA excludes the use of the eliminated amino acid in the recombinant protein (Link, et al., *Curr Opin Biotechnol*, 14:603-9 (2003)) and replaces it in the entire proteome, causing growth defects which can reduce protein yields.

Alternatively, nsAAs can be incorporated via codon reassignment or frameshift codons using orthogonal translation systems (OTSs) consisting of an aminoacyl tRNA synthetases ("AARS") that is only able to charge a cognate tRNA, which is not aminoacylated by endogenous AARSs (Liu, et al., *Annu Rev Biochem*, 79:413-44 (2010); Chin, et al., *Annu Rev Biochem*, (2014)). Typically, a TAG stop codon (transcribed to UAG during mRNA synthesis) is assigned to the nsAA and the orthogonal tRNA anticodon is mutated to CUA for site-specific nsAA incorporation. Extensive work has demonstrated that AARS:tRNA pairs from divergent organisms such as *Methanocaldococcus jannaschii* and *Methanosarcina* species can be imported to bacterial hosts and used to generate OTSs for nsAA incorporation by plasmid library mutagenesis and iterative positive/negative selections (Liu, et al., *Annu Rev Biochem*, 79:413-44 (2010); Park, et al., *Science*, 333:1151-4 (2011); Umehara, et al., *FEBS Lett*, 586:729-33 (2012)). This approach enabled genetic code expansion to a wide variety of nsAAs (Liu, et al., *Annu Rev Biochem*, 79:413-44 (2010); Young, et al., *Biochemistry*, 50:1894-900 (2011)). However, several challenges have limited the impact of this technology to expression of proteins containing nsAAs incorporated into a single or few instances within a polypeptide chain (O'Donoghue, et al., *Nat Chem Biol*, 9:594-8 (2013); Li, et al., *Chembiochem* (2014)).

The first challenge for multi-site nsAA incorporation using codon-reassignment is competition between the orthogonal nsAA-tRNA$_{CUA}$ and essential translation machinery for the UAG codon (e.g., release factor 1, RF1), that reduces full-length protein production and limits the number of nsAAs that can be incorporated into a single protein (Johnson, et al., *Nat Chem Biol*, 7:779-86 (2011); Lajoie, et al., *Science*, 342: 357-60 (2013); Heinemann, et al., *FEBS Lett*, 586:3716-22 (2012); Mukai, et al., *Nucleic Acids Res*, 38:8188-95 (2010)). To address this, a genomically recoded organism (GRO) was created that recoded all instances of the TAG codon to the synonymous TAA codon in *E. coli* (Lajoie, et al., *Science*, 342: 357-60 (2013). This GRO permitted the deletion of RF1, and hence, elimination of translational termination at UAG codons. In this organism, TAG has been transformed from a nonsense codon (terminates translation) to a sense codon (incorporates amino acid of choice), provided the appropriate translation machinery is present (Lajoie, et al., *Science*, 342: 357-60 (2013); Isaacs, et al., *Science*, 333:348-53 (2011)).

Nevertheless, a second challenge to multi-site nsAA incorporation via codon reassignment is that the evolved AARSs show ~100- to 1000-fold reduced enzyme activity (O'Donoghue, et al., *Nat Chem Biol*, 9:594-8 (2013); Umehara, et al., *FEBS Lett*, 586:729-33 (2012)) compared with native translation machinery. This results in inefficient nsAA acylation by AARSs (Umehara, et al., *FEBS Lett*, 586:729-33 (2012); Wiltschi, et al., *Yeast*, 25:775-86 (2008); Nehring, et al., *PLoS One*, 7:e31992 (2012)) and subsequent low levels of nsAA-tRNA, reducing protein yields (Lajoie, et al., *Science*, 342: 357-60 (2013); Zaher, et al., *Cell*, 136:746-62 (2009); Odoi, et al., *PLoS One*, 8:e57035 (2013)). This effect is magnified when more than a single nsAA is encoded per protein (Johnson, et al., *Nat Chem Biol*, 7:779-86 (2011)). It is believed that current approaches rely on multi-copy plasmids for OTS overexpression (i.e., AARS and tRNA overexpression) to overcome enzyme inefficiency, which masks differences between modestly- and highly-active AARSs and prevents the identification of more efficient variants capable of multi-site nsAA incorporation. Therefore, there remains a need for improved compositions and methods for making polypeptides with multi-site nsAA incorporation.

It is an object of the invention to provide improved genomically recoded organisms (GRO) capable of multi-site nsAA incorporation.

It is another object of the invention to provide improved variant aminoacyl tRNA synthetases (AARS) and tRNA that can charge tRNA with a nonstandard amino acid.

It is another object of the invention to provide methods of making improved genomically recoded organism (GRO), aminoacyl tRNA synthetases (AARS), and tRNA.

It is another object of the invention to provide methods of making polypeptides including one or more non-standard amino acids, preferably two or more iterations of the non-standard amino acid or amino acids with a high purity and yield.

It is another object of the invention to provide polypeptides including one or more non-standard amino acids, preferably two or more iterations of the non-standard amino acid or amino acids.

SUMMARY OF THE INVENTION

It has been discovered that conventional approaches to making polypeptide including non-standard amino acids that utilize conventional orthogonal translation systems rely on multi-copy plasmids for overexpression (i.e., aminoacyl tRNA synthetases and tRNA overexpression) to overcome aminoacyl tRNA synthetase enzyme inefficiency. This inefficiency is compounded by increasing the number of iterations of the non-standard amino acid in the polypeptide. Under some circumstances, the number of iterations of the non-standard amino acid can overwhelm conventional systems, leading to prohibitively small yields of desire polypeptide.

Therefore, methods of evolving aminoacyl tRNA synthetases ("AARS") to alter or improve their specificity for an amino acid ligand and/or a cognate tRNA, improved AARS engineered according to the disclosed evolutionary methods, and host organisms having the improved AARS integrated into their genomes are provided. Methods of making polypeptides including one or more iterations of one or more non-standard amino acids utilizing some or all of the improved AARS compositions, AARS systems, and/or evolutionary methods are also provided. Furthermore, polypeptides including one or more iterations of one or more non-standard amino acids are also disclosed.

The compositions, systems, and/or methods disclosed herein enable the preparation of polypeptides having a greater number of iterations of non-standard amino acids, with a greater yield than the same or similar polypeptides made using conventional compositions, systems, and methods. In some embodiments, the polypeptides are ones that could not be made using conventional methods and reagents, or could not be made a sufficient yield to serve a practical purpose using conventional methods and reagents.

BRIEF DESCRIPTION OF THE DRAWINGS

FIGS. 4G and 411 are bar graphs showing the relative intensities of reporter peptides of ELP(10TAG)-GFP$_{MS}$ containing pAcF, produced by progenitor and evolved OTSs expressed on multi-copy plasmids in the GRO. Error bars represent confidence interval calculated at the 95% confidence level based on four technical replicates.

Figure 5N:
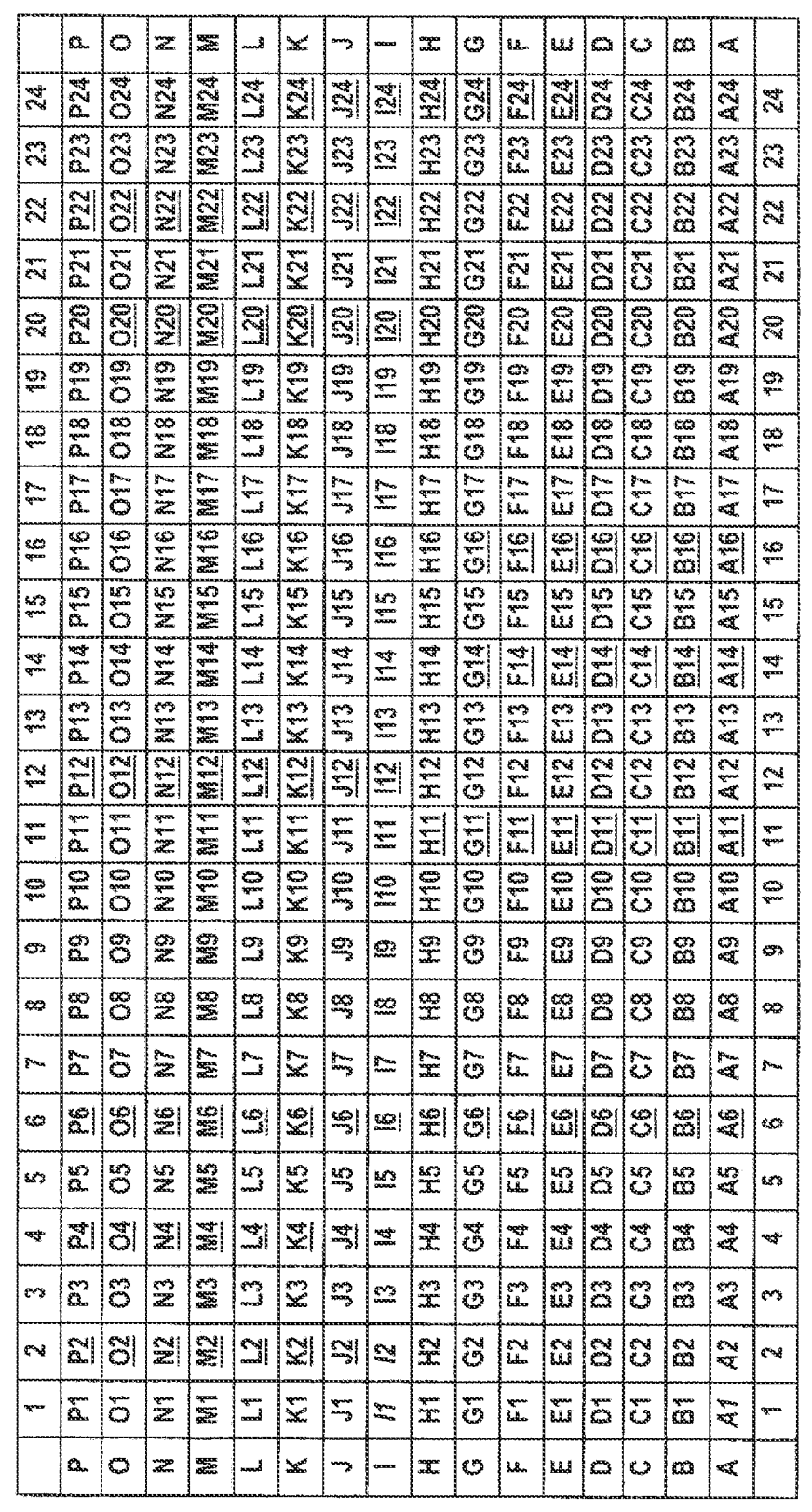

FIG. 5N is a diagram annotating the wells of the 384-well plates used for the experiments results of which are reported in FIGS. 5A-5M. Well numbers A1, A2, I1, and I2 (in italics) were set as control experiments with water; and wells with no nsAAs supplement indicated by underlining. Non-standard amino acids corresponding to each well designated in the graphs in FIGS. 5A-5M and the diagram in FIG. 5N are identified in Table 11 (column 1, "position").

DETAILED DESCRIPTION OF THE INVENTION

I. Definitions

Figure 1A:
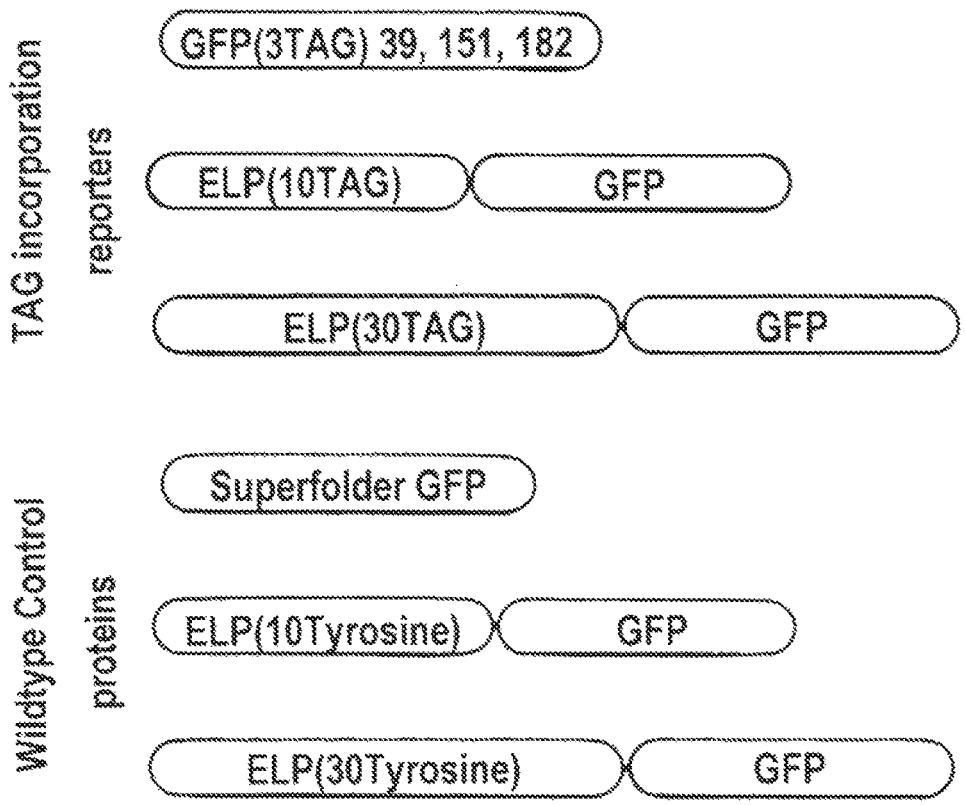
FIG. 1A is a series of schematic illustrations of reporter proteins for incorporation of three, ten and 30 nsAAs and equivalent control wild-type (WT) protein.

As used herein, the terms "transfer RNA" and "tRNA" refers to a set of genetically encoded RNAs that act during protein synthesis as adaptor molecules, matching individual amino acids to their corresponding codon on a messenger RNA (mRNA). In higher eukaryotes such as mammals, there is at least one tRNA for each of the 20 naturally occurring amino acids. In eukaryotes, including mammals, tRNAs are encoded by families of genes that are 73 to 150 base pairs long. tRNAs assume a secondary structure with four base paired stems known as the cloverleaf structure. The tRNA contains a stem and an anticodon. The anticodon is complementary to the codon specifying the tRNA's corresponding amino acid. The anticodon is in the loop that is opposite of the stem containing the terminal nucleotides. The 3' end of a tRNA is aminoacylated by a tRNA synthetase so that an amino acid is attached to the 3' end of the tRNA. This amino acid is delivered to a growing polypeptide chain as the anticodon sequence of the tRNA reads a codon triplet in an mRNA.

As used herein, the term "anticodon" refers to a unit made up of typically three nucleotides that correspond to the three bases of a codon on the mRNA. Each tRNA contains a specific anticodon triplet sequence that can base-pair to one or more codons for an amino acid or "stop codon." Known "stop codons" include, but are not limited to, the three codon bases, UAA known as ochre, UAG known as amber and UGA known as opal, which do not code for an amino acid but act as signals for the termination of protein synthesis. tRNAs do not decode stop codons naturally, but can be and have been engineered to do so. Stop codons are usually recognized by enzymes (release factors) that cleave the polypeptide as opposed to encode an AA via a tRNA.

As used herein, the term "suppressor tRNA" refers to a tRNA that alters the reading of a messenger RNA (mRNA) in a given translation system. For example, a non-sense suppressor tRNA can read through a stop codon.

As used herein, the term "aminoacyl tRNA synthetase (AARS)" refers to an enzyme that catalyzes the esterification of a specific amino acid or its precursor to one of all its compatible cognate tRNAs to form an aminoacyl-tRNA. These charged aminoacyl tRNAs then participate in mRNA translation and protein synthesis. The AARS show high specificity for charging a specific tRNA with the appropriate amino acid. In general, there is at least one AARS for each of the twenty amino acids.

As used herein, the term "residue" as used herein refers to an amino acid that is incorporated into a protein. The amino acid may be a naturally occurring amino acid and, unless otherwise limited, may encompass known analogs of natural amino acids that can function in a similar manner as naturally occurring amino acids.

As used herein, the terms "polynucleotide" and "nucleic acid sequence" refers to a natural or synthetic molecule including two or more nucleotides linked by a phosphate group at the 3' position of one nucleotide to the 5' end of another nucleotide. The polynucleotide is not limited by length, and thus the polynucleotide can include deoxyribonucleic acid (DNA) or ribonucleic acid (RNA).

As used herein, the term "gene" refers to a polynucleotide that encodes a protein or functional RNA molecule.

As used herein, the term "vector" refers to a polynucleotide capable of transporting into a cell another polynucleotide to which the vector sequence has been linked. The term "expression vector" includes any vector, (e.g., a plasmid, cosmid or phage chromosome) containing a gene construct in a form suitable for expression by a cell (e.g., linked to a transcriptional control element). "Plasmid" and "vector" are used interchangeably, as a plasmid is a commonly used form of vector.

As used herein, the term "operatively linked to" refers to the functional relationship of a nucleic acid with another nucleic acid sequence. Promoters, enhancers, transcriptional and translational stop sites, and other signal sequences are examples of nucleic acid sequences operatively linked to other sequences. For example, operative linkage of gene to a transcriptional control element refers to the physical and functional relationship between the gene and promoter such that the transcription of the gene is initiated from the promoter by an RNA polymerase that specifically recognizes, binds to and transcribes the DNA.

As used herein, the terms "transformation" and "transfection" refer to the introduction of a polynucleotide, e.g., an expression vector, into a recipient cell including introduction of a polynucleotide to the chromosomal DNA of the cell.

As used herein, the term "conservative variant" refers to a particular nucleic acid sequence that encodes identical or essentially identical amino acid sequences. Conservative substitution tables providing functionally similar amino acids are well known in the art. The following sets forth exemplary groups which contain natural amino acids that are "conservative substitutions" for one another. Conservative Substitution Groups 1 Alanine (A) Serine (S) Threonine (T); 2 Aspartic acid (D) Glutamic acid (E); 3 Asparagine (N) Glutamine (Q); 4 Arginine (R) Lysine (K); 5 Isoleucine (I) Leucine (L) Methionine (M) Valine (V); and 6 Phenylalanine (F) Tyrosine (Y) Tryptophan (W).

As used herein, the term "percent (%) sequence identity" or "homology" refers to the percentage of nucleotides or amino acids in a candidate sequence that are identical with the nucleotides or amino acids in a reference nucleic acid sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

As used herein, the term "transgenic organism" refers to any organism, in which one or more of the cells of the organism contains heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. Suitable transgenic organisms include, but are not limited to, bacteria, cyanobacteria, fungi, plants and animals. The nucleic acids described herein can be introduced into the host by methods known in the art, for example infection, transfection, transformation or transconjugation.

As used herein, the term "eukaryote" or "eukaryotic" refers to organisms or cells or tissues derived from these organisms belonging to the phylogenetic domain Eukarya such as animals (e.g., mammals, insects, reptiles, and birds), ciliates, plants (e.g., monocots, dicots, and algae), fungi, yeasts, *flagellates*, microsporidia, and protists.

As used herein, the term "prokaryote" or "prokaryotic" refers to organisms including, but not limited to, organisms of the Eubacteria phylogenetic domain, such as *Escherichia coli, Thermus thermophilus*, and *Bacillus stearothermophilus*, or organisms of the Archaea phylogenetic domain such as, *Methanococcus jannaschii, Methanobacterium thermoautotrophicum, Halobacterium* such as *Haloferax volcanii* and *Halobacterium* species NRC-1, *Archaeoglobus fulgidus, Pyrococcus furiosus, Pyrococcus horikoshii*, and *Aeuropyrum pernix*.

As used herein, the term "construct" refers to a recombinant genetic molecule having one or more isolated polynucleotide sequences. Genetic constructs used for transgene expression in a host organism include in the 5'-3' direction, a promoter sequence; a sequence encoding a gene of interest; and a termination sequence. The construct may also include selectable marker gene(s) and other regulatory elements for expression.

As used herein, the term "gene" refers to a DNA sequence that encodes through its template or messenger RNA a sequence of amino acids characteristic of a specific peptide, polypeptide, or protein. The term "gene" also refers to a DNA sequence that encodes an RNA product. The term gene as used herein with reference to genomic DNA includes intervening, non-coding regions as well as regulatory regions and can include 5' and 3' ends.

As used herein, the term "orthologous genes" or "orthologs" refer to genes that have a similar nucleic acid sequence because they were separated by a speciation event.

As used herein, the term "isolated" is meant to describe a compound of interest (e.g., nucleic acids) that is in an environment different from that in which the compound naturally occurs, e.g., separated from its natural milieu such as by concentrating a peptide to a concentration at which it is not found in nature. "Isolated" is meant to include compounds that are within samples that are substantially enriched for the compound of interest and/or in which the compound of interest is partially or substantially purified. Isolated nucleic acids are at least 60% free, preferably 75% free, and most preferably 90% free from other associated components.

As used herein, the term "cofactor", refers to a substance, such as a metallic ion or a coenzyme that must be associated with an enzyme for the enzyme to function. Cofactors work by changing the shape of an enzyme or by actually participating in the enzymatic reaction.

As used herein "G-C content" (or guanine-cytosine content) refers to the percentage of nitrogenous bases on a nucleic acid molecule, or fragment, section, or region thereof, that are either guanine or cytosine.

As used herein, the term "low stringency" refers to conditions that permit a polynucleotide or polypeptide to bind to another substance with little or no sequence specificity.

As used herein, the term "purified" and like terms relate to the isolation of a molecule or compound in a form that is substantially free (at least 60% free, preferably 75% free, and most preferably 90% free) from other components normally associated with the molecule or compound in a native environment.

As used herein, the term "pharmaceutically acceptable carrier" encompasses any of the standard pharmaceutical carriers, such as a phosphate buffered saline solution, water and emulsions such as an oil/water or water/oil emulsion, and various types of wetting agents.

As used herein, the term "translation system" refers to the components necessary to incorporate an amino acid into a growing polypeptide chain (protein). Key components of a translation system generally include amino acids, ribosomes, tRNAs, AARRS, EF-Tu, and mRNA. The components described herein can be added to a translation system, in vivo or in vitro, to incorporate amino acids into a protein.

As used herein, the term "orthogonal translation system (OTS)" refers to at least an AARS and paired tRNA that are both heterologous to a host or translational system in which they can participate in translation of an mRNA including at least one codon that can hybridize to the anticodon of the tRNA.

As used herein, the terms "recoded organism" and "genomically recoded organism (GRO)" in the context of codons refer to an organism in which the genetic code of the organism has been altered such that a codon has been eliminated from the genetic code by reassignment to a synonymous codon.

As used herein, the term "polyspecific" refers to an AARS that can accept and incorporate two or more different non-standard amino acids.

As used herein, the terms "protein," "polypeptide," and "peptide" refers to a natural or synthetic molecule comprising two or more amino acids linked by the carboxyl group of one amino acid to the alpha amino group of another. The term polypeptide includes proteins and fragments thereof. The polypeptides can be "exogenous," meaning that they are "heterologous," i.e., foreign to the host cell being utilized, such as human polypeptide produced by a bacterial cell. Polypeptides are disclosed herein as amino acid residue sequences. Those sequences are written left to right in the direction from the amino to the carboxy terminus.

As used herein, "standard amino acid" and "canonical amino acid" refer to the twenty amino acids that are encoded directly by the codons of the universal genetic code denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

As used herein, "non-standard amino acid (nsAA)" refers to any and all amino acids that are not a standard amino acid. A non-limiting list of non-standard amino acids can be found in Table 11. nsAA can those created by enzymes through posttranslational modifications; or those that are not found in nature and are entirely synthetic. In both classes, the nsAAs are made synthetically.

II. Systems and Methods for Making Polypeptides with Non-Standard Amino Acids

Compositions and systems for making polypeptides including non-standard amino acids are provided. As discussed in more detail below, the compositions and systems can include AARS with improved or alter specificity for their amino acid ligand(s) and/or cognate tRNA. The compositions also include host organisms, for example, *E. coli*, engineered to incorporate the AARS or an entire orthogonal translation system into its genome. Evolutionary methods for making AARS with tunable properties are also provided. It will be appreciated that the various compositions, systems and methods disclosed herein are modular in nature. Accordingly, the compositions, systems, and methods can stand alone, or can be used in combination, parallel, or tandem with conventional or other art recognized methods and utilities. For example, although host organism wherein improved AARS are incorporated into the genome are provided, these variant AARS can also be used in conventional methods that rely on plasmid borne or other non-integrated expression-based methods for making polypeptide. Likewise, methods of evolving an AARS to alter or improve its activity or specificity can stand alone as a method of creating new AARS, or can be linked to an overarching method of making polypeptides having one or more iterations of one or more non-standard amino acids.

A. Systems

Systems for making polypeptides including one or more iterations of one or more non-standard amino acids are provided. The systems typically include a host organism as well as an aminoacyl-tRNA synthetase (AARS) and paired transfer RNA (tRNA) pair (i.e., an orthogonal pair), and an mRNA encoding a polypeptide. The AARS, tRNA, and mRNA are typically heterologous to the host organism. In preferred embodiments, the host system is a genomically recoded organism (GRO). A GRO is an organism that has been recoded such that at least one codon is deleted from most, or preferable all, its iterations in the organism's genome. The heterologous tRNA can include an anticodon that recognizes the reduced or missing codon. The heterologous AARS is one that can charge it's paired heterologous tRNA with a non-standard amino acid. When a heterologous mRNA including at least one iteration of the GRO-deleted codon is expressed in the host in the presence of the non-standard amino acid, the non-standard amino acid is incorporated into the polypeptide by the heterologous tRNA during translation of the heterologous mRNA.

1. Host Organisms a. In Vivo Methods

When translation is carried out in vivo, using a genomically recoded organism (GRO) or other host organism, nucleic acids encoding the orthogonal AARS and tRNA are operably linked to one or more expression control sequences are introduced or integrated into cells or organisms. The heterolgous mRNA encoding the protein of interest is introduced or integrated into host cells or organisms, and can also be linked to an expression control sequence.

i. Genomically Recoded Organism (GRO)

The host can be a genomically recoded organism (GRO). The GRO can be transformed or genetically engineered to express the orthogonal AARS-tRNA pair and the mRNA of interest. As discussed in more detail below, the AARS-tRNA pair and mRNA of interest transformed or transfected into the host expressed extrachomasomally, for example by plasmid(s) or another vector(s) or an episome, or can be integrated into the host's genome. The GRO host organism prior to transfection or integration of the AARS-tRNA pair can be referred to as a precursor or parental GRO. Typically, the precursor GRO is a bacterial strain, for example, an *E. coli* bacterial strain, wherein a codon has been replaced by a synonymous codon. Because there are 64 possible 3-base codons, but only 20 canonical amino acids (plus stop codons), some amino acids are coded for by 2, 3, 4, or 6 different codons (referred to herein as "synonymous codons"). In a GRO, most or all of the iterations of a particular codon are replaced with a synonymous codon. The precursor strain of the GRO is recoded such at a least one codon is completely absent from the genome. Removal of a codon from the precursor GRO allows reintroduction of the deleted codon in a heterologous mRNA of interest. As discussed in more detail below, the reintroduced codon is typically dedicated to a non-standard amino acid, which in the presence of the appropriate orthogonal translation machinery, can be incorporated in the nascent peptide chain of during translation of the mRNA.

Different organisms often show particular preferences for one of the several codons that encode the same amino acid, and some codons are considered rare or infrequent. Preferably, the replaced codon is one that is rare or infrequent in the genome. The replaced codon can be one that codes for an amino acid (i.e., a sense codon) or a translation termination codon (i.e., a stop codon). GRO that are suitable for use as host or parental strains for the disclosed systems and methods are known in the art, or can be constructed using known methods. See, for example, Isaacs, et al., *Science*, 333, 348-53 (2011), Lajoie, et al., *Science* 342, 357-60 (2013), Lajoie, et al., *Science,* 342, 361-363 (2013).

Preferably, the replaced codon is one that codes for a rare stop codon. In a particular embodiment, the GRO is one in which all instances of the UAG (TAG) codon have been removed and replaced by another stop codon, and preferably wherein release factor 1 (RF1; terminates translation at UAG and UAA) has also been deleted, eliminating translational termination at UAG codons (Lajoie, et al., *Science* 342, 357-60 (2013)). In a particular embodiment, the host or precursor GRO is C321.Δ A [321 UAG→UAA conversions and deletion of prfA (encodes RF1)] (genome sequence at GenBank accession CP006698). This GRO allows the reintroduction of UAG codons in a heterologous mRNA, along with orthogonal translation machinery (i.e., aminoacyl-tRNA synthetases (aaRSs) and tRNAs as discussed in more detail below), to permit efficient and site specific incorporation of non-standard amino acids into protein encoded by the heterologous mRNA. That is, UAG has been transformed from a nonsense codon (terminates translation) to a sense codon (incorporates amino acid of choice), provided the appropriate translation machinery is present. UAG is a preferred codon for recoding because it is the rarest codon in *Escherichia coli* MG1655 (321 known instances) and a rich collection of translation machinery capable of incorporating non-standard amino acids has been developed for UAG (Liu and Schultz, *Annu. Rev. Biochem.,* 79:413-44 (2010), discussed in more detail below).

GRO can have two, three, or more codons replaced with a synonymous codon. Such GRO allow for reintroduction of the two, three, or more deleted codons in a heterologous mRNA of interest, each dedicated to a different non-standard amino acid. Such GRO can be used in combination with the appropriate orthogonal translation machinery to produce polypeptides having two, three, or more different non-standard amino acids.

ii. Other In Vivo Host Systems

Although the most preferred host organism is a GRO, it will be appreciated the methods and compositions disclosed herein can be adapted for use on other host organisms or in vitro. Other hosts and in vitro systems for translation are known in the art.

Suitable organisms include, but are not limited to, microorganisms such as bacteria transformed with recombinant bacteriophage, plasmid, or cosmid DNA expression vectors; yeast transformed with yeast expression vectors; insect cell systems infected with viral expression vectors (e.g., baculovirus); plant cell systems transformed with viral expression vectors (e.g., cauliflower mosaic virus, CaMV, or tobacco mosaic virus, TMV) or with bacterial expression vectors (e.g., Ti or pBR322 plasmids); or animal cell systems.

It will be understood by one of ordinary skill in the art that regardless of the system used (i.e. in vitro or in vivo), expression of genes encoding orthogonal AARS and tRNA will result in site specific incorporation of non-standard amino acids into the target polypeptides or proteins encoded by the specific heterologous mRNA transfected or integrated into the organism. Host cells are genetically engineered (e.g., transformed, transduced or transfected) with the vectors encoding orthogonal AARS, tRNA and heterologous mRNA which can be, for example, a cloning vector or an expression vector. The vector can be, for example, in the form of a plasmid, a bacterium, a virus, a naked polynucleotide, or a conjugated polynucleotide. The vectors are introduced into cells and/or microorganisms by standard methods including electroporation, infection by viral vectors, high velocity ballistic penetration by small particles with the nucleic acid either within the matrix of small beads or particles, or on the surface. Such vectors can optionally contain one or more promoter. A "promoter" as used herein is a DNA regulatory region capable of initiating transcription of a gene of interest.

Kits are commercially available for the purification of plasmids from bacteria, (see, e.g., GFX™ Micro Plasmid Prep Kit from GE Healthcare; STRATAPREP® Plasmid Miniprep Kit and STRATAPREP® EF Plasmid MIDIPREP Kit from Stratagene; GENELUTE™ HP Plasmid Midiprep and MAXIPREP Kits from Sigma-Aldrich, and, Qiagen plasmid prep kits and QIAfilter™ kits from Qiagen). The isolated and purified plasmids are then further manipulated to produce other plasmids, used to transfect cells or incorporated into related vectors to infect organisms. Typical vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems.

Prokaryotes useful as host cells include, but are not limited to, gram negative or gram positive organisms such as *E. coli* or *Bacilli*. In a prokaryotic host cell, a polypeptide may include an N-terminal methionine residue to facilitate expression of the recombinant polypeptide in the prokaryotic host cell. The N-terminal Met may be cleaved from the expressed recombinant polypeptide. Promoter sequences commonly used for recombinant prokaryotic host cell expression vectors include lactamase and the lactose promoter system.

Expression vectors for use in prokaryotic host cells generally comprise one or more phenotypic selectable marker genes. A phenotypic selectable marker gene is, for example, a gene encoding a protein that confers antibiotic resistance or that supplies an autotrophic requirement. Examples of useful expression vectors for prokaryotic host cells include those derived from commercially available plasmids such as the cloning vector pBR322 (ATCC 37017). pBR322 contains genes for ampicillin and tetracycline resistance and thus provides simple means for identifying transformed cells. To construct an expression vector using pBR322, an appropriate promoter and a DNA sequence are inserted into the pBR322 vector. Other commercially available vectors include, for example, T7 expression vectors from Invitrogen, pET vectors from Novagen and pALTER® vectors and PinPoint® vectors from Promega Corporation.

Yeasts useful as host cells include, but are not limited to, those from the genus *Saccharomyces, Pichia, K. Actinomycetes* and *Kluyveromyces*. Yeast vectors will often contain an origin of replication sequence, an autonomously replicating sequence (ARS), a promoter region, sequences for polyadenylation, sequences for transcription termination, and a selectable marker gene. Suitable promoter sequences for yeast vectors include, among others, promoters for metallothionein, 3-phosphoglycerate kinase (Hitzeman et al., J. Biol. Chem. 255:2073, (1980)) or other glycolytic enzymes (Holland et al., Biochem. 17:4900, (1978)) such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other suitable vectors and promoters for use in yeast expression are further described in Fleer et al., Gene, 107:285-195 (1991), in Li, et al., *Lett Appl Microbiol.* 40(5):347-52 (2005), Jansen, et al., *Gene* 344:43-51 (2005) and Daly and Hearn, *J. Mol. Recognit.* 18(2):119-38 (2005). Other suitable promoters and vectors for yeast and yeast transformation protocols are well known in the art.

Mammalian or insect host cell culture systems well known in the art can also be employed for producing proteins or polypeptides. Commonly used promoter sequences and enhancer sequences are derived from Polyoma virus, Adenovirus 2, Simian Virus 40 (SV40), and human cytomegalovirus. DNA sequences derived from the SV40 viral genome may be used to provide other genetic elements for expression of a structural gene sequence in a mammalian host cell, e.g., SV40 origin, early and late promoter, enhancer, splice, and polyadenylation sites. Viral early and late promoters are particularly useful because both are easily obtained from a viral genome as a fragment which may also contain a viral origin of replication. Exemplary expression vectors for use in mammalian host cells are well known in the art.

b. In vitro Transcription/Translation

In some embodiments, the nucleic acids encoding AARS and tRNA synthesized prior to translation of the target protein and are used to incorporate non-standard amino acids into a target protein in a cell-free (in vitro) protein synthesis system.

In vitro protein synthesis systems involve the use crude extracts containing all the macromolecular components (70S or 80S ribosomes, tRNAs, aminoacyl-tRNA synthetases, initiation, elongation and termination factors, etc.) required for translation of exogenous RNA. To ensure efficient translation, each extract must be supplemented with amino acids, energy sources (ATP, GTP), energy regenerating systems (creatine phosphate and creatine phosphokinase for eukaryotic systems, and phosphoenol pyruvate and pyruvate kinase for the *E. coli* lysate), and other co-factors ($Mg^{2+}$, $K^+$, etc.).

In vitro protein synthesis does not depend on having a polyadenylated RNA, but if having a poly(A) tail is essential for some other purpose, a vector may be used that has a stretch of about 100 A residues incorporated into the polylinker region. That way, the poly(A) tail is "built in" by the synthetic method. In addition, eukaryotic ribosomes read RNAs that have a 5' methyl guanosine cap more efficiently. RNA caps can be incorporated by initiation of transcription using a capped base analogue, or adding a cap in a separate in vitro reaction post-transcriptionally.

Suitable in vitro transcription/translation systems include, but are not limited to, the rabbit reticulocyte system, the *E. coli* S-30 transcription-translation system, the wheat germ based translational system. Combined transcription/translation systems are available, in which both phage RNA polymerases (such as T7 or SP6) and eukaryotic ribosomes are present. One example of a kit is the TNT® system from Promega Corporation.

2. Orthogonal Translation System

Translation systems include most or all of the translation machinery of the host organism and additionally include a heterologous aminoacyl-tRNA synthetase (AARS)-rRNA pair (also referred to as an orthogonal translation system (OTS)) that can incorporate one or more non-standard amino acids into a growing peptide during translation of the heterologous mRNA. AARS are enzymes that catalyze the esterification of a specific cognate amino acid or its precursor to one or all of its compatible cognate tRNAs to form an aminoacyl-tRNA. An AARS can be specific for a single amino acid or a non-standard amino acid, or can be polyspecific for two or more non-standard amino acids, canonical amino acids, or a combination thereof. The heterologous AARS used in the disclosed system typical can recognize, bind to, and transfer at least one non-standard amino acid to a cognate tRNA. Accordingly, the AARS can be selected by the practitioner based on the non-standard amino acid on interest. Some of the disclosed systems include two or more heterologous AARS.

tRNA is an adaptor molecule composed of RNA, typically about 76 to about 90 nucleotides in length that carries an amino acid to the protein synthetic machinery. Typically, each type of tRNA molecule can be attached to only one type of amino acid, so each organism has many types of tRNA (in fact, because the genetic code contains multiple codons that specify the same amino acid, there are many tRNA molecules bearing different anticodons which also carry the same amino acid). The heterologous tRNA used in the disclosed systems is one that can bind to the selected heterologous AARS and receive a non-standard amino acid to form an aminoacyl-tRNA. Because the transfer for the amino acid to the tRNA is dependent in-part on the binding of the tRNA to the AARS, these two components are typically selected by the practitioner based on their ability to interact with each other and participate in protein synthesis including the non-standard amino acid of choice in the host organism. Therefore, a selected heterologous AARS and tRNA are often referred to herein together as a heterologous AARS-tRNA pair, or an orthogonal translation system. Preferably, the heterologous AARS-tRNA pair does not cross-react with the existing host cell's pool of synthetases and tRNAs, or do so a low level (e.g., inefficiently), but is recognized by the host ribosome. Therefore, preferably the heterologous AARS cannot charge an endogenous tRNA with a non-standard amino acid (or does so a low frequency), and/or an endogenous AARS cannot charge the heterologous tRNA with a standard amino acid. Furthermore, preferably, the heterologous AARS cannot charge its paired heterologous tRNA with a standard amino acid (or does so at low frequency).

The heterologous tRNA also includes an anticodon that recognizes the codon of the codon in the heterologous mRNA that encodes the non-standard amino acid of choice. In the most preferred embodiment, the anticodon is one that hybridizes with a codon that is reduced or deleted in the host organism and reintroduced by the heterologous mRNA. For example, if the reduced or deleted codon is UAG (TAG), as in C321. Δ A, the heterologous tRNA anticodon is typically CUA.

The AARS-tRNA pair can be from an achaea, such as *Methanococcus maripaludis*, *Methanocaldococcus jannaschii*, *Methanopyrus kandleri*, *Methanococcoides burtonii*, *Methanospirillum hungatei*, *Methanocorpusculum labreanum*, *Methanoregula boonei*, *Methanococcus aeolicus*, *Methanococcus vannieli*, *Methanosarcina mazei*, *Methanosarcina barkeri*, *Methanosarcina acetivorans*, *Methanosaeta thermophila*, *Methanoculleus marisnigri*, *Methanocaldococcus vulcanius*, *Methanocaldococcus fervens*, or *Methanosphaerula palustris*, for can be variant evolved therefrom.

Suitable heterologous AARS-tRNA pairs for use in the disclosed systems and methods are known in the art. For example, Table 1 and the electronic supplementary information provided in Dumas, et al., *Chem. Sci.*, 6:50-69 (2015), provide non-natural amino acids that have been genetically encoded into proteins, the reported mutations in the AARS that enable their binding to the non-natural amino acid, the corresponding tRNA, and a host organism in which the translation system is operational. See also Liu and Schultz, *Annu. Rev. Biochem.*, 79:413-44 (2010) and Davis and Chin, *Nat. Rev. Mol. Cell Biol.*, 13:168-82 (2012), which provide additional examples of AARS-tRNA pairs which can be used in the disclosed systems and methods. Preferred AARS with improved activity and specificity for the specific non-naturally occurring amino acids are disclosed and described in more detail below.

The AARS and tRNA can be provided separately, or together, for example, as part of a single construct. In a particular embodiment, the AARS-tRNA pair is evolved from a *Methanocaldococcus jannaschii* aminoacyl-tRNA synthetase(s) (AARS)/suppressor tRNA pairs and suitable for use in an *E. coli* host organism. See, for example, Young, *J Mol. Biol.*, 395(2):361-74 (2010), which describes an OTS including constitutive and inducible promoters driving the transcription of two copies of a *M. jannaschii* AARS gene in combination with a suppressor tRNA(CUA)(opt) in a single-vector construct.

During protein synthesis, tRNAs with attached amino acids are delivered to the ribosome by proteins called elongation factors (EF-Tu in bacteria, eEF-1 in eukaryotes), which aid in decoding the mRNA codon sequence. If the tRNA's anticodon matches the mRNA, another tRNA already bound to the ribosome transfers the growing polypeptide chain from its 3' end to the amino acid attached to the 3' end of the newly delivered tRNA, a reaction catalyzed by the ribosome. Accordingly, the heterologous AARS-tRNA pair should be one that can be processed by the host organism's elongation factor(s). Additional or alternatively, the system can include additional or alternative elongation factor variants or mutants that facilitate delivery of the heterologous aminoacyl-tRNA to the ribosome.

It will also be appreciated that methods of altering the anticodon of tRNA are known in the art. Any suitable tRNA selected for use in the disclosed systems and methods can be modified to hybridize to any desired codon. For example, although many of the heterologous tRNA disclosed here and elsewhere have a CUA anticodon, CUA can be substituted for another stop anticodon (e.g., UUA or UCA), or anticodon for any desired sense codon. The tRNA anticodon can be selected based on the GRO and the sequence of the heterologous mRNA as discussed in more detail above.

The OTS can also include mutated EF-Tu, in addition to AARS and tRNA, especially for bulky and/or highly charged NSAAs (e.g., phosphorylated amino acids) (Park, et al., *Science*, 333:1151-4 (2011)).

B. Methods Making Polypeptides

GRO have been utilized in combination with a plasmid-based orthogonal translation system to translate a protein including three iterations of a non-standard amino acid (Lajoie, et al., Science, 342:357-360). However, the Examples below show that generally, as the number of iterations of non-standard amino acid increases, the yield of the protein decreases, even when the orthogonal translation system is overexpressed using a high copy number of expression plasmids. In some instances, expression of the protein of interest was too low to allow for purification. Expression was further reduced when the orthogonal systems was integrated into the host GRO's genome. It was subsequently discovered that at least one cause of this reduced yield is impaired binding between the heterologous AARS and the non-standard amino acid and/or its cognate tRNA which is compounds translation inefficiency with increasing iterations of the non-standard amino acid.

Accordingly, improved methods for incorporating one or more non-standard amino acids into a polypeptide are provided. The methods typically involve using an orthogonal AARS-tRNA pair in the translation process for a target polypeptide from heterologous mRNA of interest. As discussed above, the AARS preferentially aminoacylates its cognate tRNA with a non-naturally occurring amino acid. The resulting aminoacyl-tRNA recognizes at least one codon in the mRNA for the target protein, such as a stop codon. An elongation factor (such as EF-Tu in bacteria) mediates the entry of the amninoacyl-tRNA into a free site of the ribosome. If the codon-anticodon pairing is correct, the elongation factor hydrolyzes guanosine triphosphate (GTP) into guanosine diphosphate (GDP) and inorganic phosphate, and changes in conformation to dissociate from the tRNA molecule. The aminoacyl-tRNA then fully enters the A site, where its non-standard amino acid is brought near the P site's polypeptide and the ribosome catalyzes the covalent transfer of the non-standard amino acid onto the polypeptide. The resulting polypeptides can be isolated, purified, or otherwise enriched using methods known in the art, and discussed in more detail below.

In preferred embodiments, the heterologous AARS, its cognate tRNA, or more preferably both, are integrated into the host genome. Although suitable AARS are known in the art, in the most preferred embodiments, the AARS is a variant AARS that has improved binding to its cognate tRNA, its non-standard amino acid(s), or both compared to a known AARS. Exemplary variant AARS are discussed in more detail below.

The methods of making polypeptide are typically capable of producing polypeptides having a greater number of iterations of non-standard amino acids and/or a greater yield of the desired polypeptide than the same or similar polypeptide made using conventional compositions, systems, and methods. For example, previous attempts to incorporate more than one instance of an non-standard amino acids per protein in strains with no or attenuated RF1 activity showed at best 33% yield of WT protein when incorporating three instances of an non-standard amino acids into superfolder GFP 20.5 mg/L) (Wu, et al., *Chembiochem*, 14:968-78 (2013)) and 3% yield of WT when incorporating 10 instances of an NSAA into GFP (0.4 mg/L) produced in RF1 deficient, non-recoded *E. coli* (Johnson, et al., *Nat Chem Biol*, 7:779-86 (2011)).

Higher yield of the desired polypeptide can be measured as an increase in the amount of desired protein per total protein by weight or mass, or the amount of desired protein per culture volume, relative to the same polypeptide made using conventional methods and reagents. For example, in some embodiments, the yield is increased by at least 5, 10, 15, 20, 25, 50, 75, 100, 125, 150, 175, 200, 300, 400, or 500 percent. In some embodiments, the yield is at least 5, 10, 15, 20, 25, 50, 75, or 100 mg/L.

High purity of the desired polypeptide can be measured as at least 95% correct non-standard amino acid incorporated at the desired residue(s) relative to an undesired amino acid at the same residue. The methods are able to produce high yields of biopolymers with multiple nsAAs, and still maintain 95% purity. Purity can be determined using routine methods such as mass spectroscopy. Purity is largely achieved from two areas: properties of OTS to encode the desired/cognate nsAA while eliminating other nsAAs or natural amino acids; and conducting such experiments in GRO background with a dedicated codon free from interference/competition from native biomolecular components. The disclosed methods can achieve multi-site incorporation of nsAA and/or high purity of the desire polypeptide.

III. Methods of Evolving AARS

Methods of evolving AARS to improve AARS recognition of one or more non-standard amino acids, to improve AARS biomolecular interaction with a cognate tRNA, or a combination thereof are provided. Typically, the AARS is subjected to one or more rounds of mutagenesis, followed by at least one round of selection. The selection can be a negative selection, wherein cells are discarded or killed if they do not express an effective AARS. The selection can be a positive selection, wherein cells are selected based on expressing an improved AARS. The most preferred embodiments include both a negative selection and a positive selection. The methods can include one or more, and preferably include all of the following: OTS components integrated into genome; diversification (e.g., mutagenesis) performed directly at chromosomally integrated OTS in vivo; selections performed without manipulation of OTS constructs in/out of strains; and/or all done in GRO host. It will be appreciated that although the methods are described with respect to AARS, the methods can be adapted to evolve and select for improvements or alterations in other components of the translation system including, but not limited to, tRNA, EF-Tu, all RNA and protein components of the ribosome, etc.)

1. Selection of Residues to be Diversified

As discussed above, AARS bind to both an amino acid (refered to a amino acid ligand) and a tRNA and catalyzes the esterification of the amino acid ligand to the tRNA to form an aminoacyl-tRNA. Therefore, the amino acid binding pocket and the tRNA binding pocket contribute to be the specificity and activity of an AARS for specific amino acids and specific tRNAs, respectively. The methods disclosed herein typically include mutating by substitution, deletion, and/or insertion, the amino acid binding pocket, the tRNA binding pocket, or a combination thereof in a parent AARS. A number of heterologous AARS, their amino acid binding specificity, and their tRNA binding specificity are known in the art as discussed above, and can serve as the parent AARS for the methods of AARS evolution discussed herein.

In many cases, the domains of the known heterologous AARS have been mapped and/or crystalized in the presences of an amino acid, a tRNA, or both, to identify specific amino acid residues within the AARS that are important for binding between the AARS and its amino acid ligand and/or its cognate tRNA. Therefore, in the most preferred embodiments, the mutagenesis is targeted at amino acid residues of the parent AARS that are known to influence its binding to an amino acid ligand and/or its cognate tRNA. The methods of mutagenesis include mutating 1, 2, 3, 4, 5, 6, 7, 8, 9, 10, 11, 12, 13, 14, 15, 16, 17, 18, 19, 20, or more targeted amino acids residues of a parent AARS that are important for binding to its amino acid ligand, it cognate tRNA, or a combination thereof. In a particular embodiment exemplified in the working examples below, a *M. jannaschii* based AcF AARS (pAcFRS) that pairs with a tRNA$_{CUA}$ (Sharan, et al., *Nat. Protoc.*, 4:206-23 (2009)), was selected for mutagenesis. A previously reported crystal structure for the *M. jannaschii* TyrRS, the parent AARS of pAcFRS, was used to inform the diversification of twelve residues in the amino acid binding pocket surrounding the variable side chain of the non-standard amino acid, and five residues at the AARS-tRNA$_{CUA}$ anticodon recognition interface, that were mutated in various combinations to a create library of variant AARS with altered properties relative to the parental pAcFRS.

As discussed in more detail below, depending on the method of selection employed, the mutagenesis can be used to engineer new AARS with improved specificity and/or activity for an amino acid ligand not recognized by the parent AARS, improved specificity and/or activity for the cognate tRNA of the parent AARS, diversified specificity and/or activity for the amino acid ligand of the parent AARS, diversified specificity and/or activity for the cognate tRNA of the parent AARS, altered specificity and/or activity for the amino acid ligand of the parent AARS, altered specificity and/or activity for the cognate tRNA of the parent AARS, and combinations thereof. Specificity generally refers to ability of the AARS to bind one or more amino acid ligands and/or tRNAs. Higher specificity means binding to fewer amino acid ligands and/or few tRNAs. Activity generally refers to the efficiency or speed with which enzyme catalyzes the esterification of the amino acid ligand to the tRNA to form an aminoacyl-tRNA Therefore, the methods can used to enhance the performance the parent AARS, or to introduce a new function into the parent AARS. The methods can be used to tune the parent AARS to have specificity for one or more specific desired non-standard amino acids.

2. Methods of Mutagenesis

Mutagenesis can be carried out using any suitable means. Preferably, mutagenesis is carried out in vivo. Conventional methods typically carry out mutagenesis in vitro followed by transformation into a host, which results in dramatic (1000×) loss of library complexity. A heterologous precursor AARS is paired with a cognate tRNA and introduced into a population of host cells along with a heterologous nucleic acid (e.g., DNA, mRNA, etc.) encoding a polypeptide of interest including a least one non-standard amino acid. Preferably at least the AARS is integrated into the genome of the host cells. More preferably, both the AARS and the tRNA are integrated into the genome of the host cells. For example in some embodiments a DNA cassette including an AARS and optionally a cognate tRNA and selectable marker are introduced into the genome of the host cells. In a specific embodiment, the cassette includes an inducible AARS, a constitutive tRNA, and a tolC selection marker. Methods of making transgenic organisms are generally specific to each host organism and are known in the art. For example, DNA cassettes can be introduced into a known intergenic region of the genome of bacteria using λ Red recombination.

The mutagenesis can include making a library, preferably a diverse library of variant AARS and screening them for improved activity by positive and/or negative selection. The mutagenesis can be random, semi-random, targeted, or a combination thereof. Preferably, the mutagenesis includes substituting one or more specific residues in the amino acid binding domain, the tRNA binding domain or a combination thereof of the AARS. In the most preferred embodiments, the mutagenesis includes one or more rounds of MAGE-based evolution. MAGE refers to multiplex automated genome evolution, and generally includes introducing multiple nucleic acid sequences into one or more cells such that the entire cell culture approaches a state involving a set of changes to each genome or targeted region (Wang et al., Nature, 460:894 (2009)). The method can be used to generate one specific configuration of alleles or can be used for combinatorial exploration of designed alleles optionally including additional random, i.e., not-designed, changes. This can be used with any of a variety of devices that allow the cyclic addition of many DNAs in parallel in random or specific order, with or without use of one or more selectable markers.

Compositions and methods for carrying out MAGE are described in U.S. Pat. No. 8,153,432. Briefly, MAGE-based methods typically include introducing multiple nucleic acid sequences into a cell including the steps transforming or transfecting a cell(s) using transformation medium or transfection medium including at least one nucleic acid oligomer containing one or more mutations, replacing the transformation medium or transfection medium with growth medium, incubating the cell in the growth medium, and repeating the steps if necessary or desired until multiple nucleic acid sequences have been introduced into the cell. In some embodiments, the one or more nucleic acid oligomers is a pool of oligomers having a diversity of different random or non-random mutations at the location(s) of desired mutagenesis. Cells are transfected with a variety of combination of nucleotides leading to the formation of a diverse genomic library of mutants. The diversity of the library can be increased by increasing the number of MAGE cycles. The oligomers can be single-stranded DNA. In preferred embodiments, multiple mutations are generated in a chromosome or in a genome.

Genetic diversity of the mutants can be tuned by the number of cycles of mutagenesis. For example, increasing the number of cycles of mutagenesis generally increases the diversity of the library. In particular embodiments, a library is prepared by one or more cycles of MAGE, for example, 1, 2, 3, 4, 5, 6, 7, 8, 9, 10, 11, 12, 13, 14, 15, or more cycles, with or without intervening cycles of selection. In a particular embodiment, a library of mutants is prepared by, for example, between 1 and 50, between 3 and 15, between 5 and 9 cycles of MAGE. The cycles can occur without intervening rounds of selection to increase the diversity of library prior to selection. The methods can also modified to include additional or alternative steps to improve genetic diversity. See, for example, Carr, et al., *Nucleic Acids Research*, 1; 40(17):e132, 12 pages (2012), and Gregg, et al., *Nucleic Acids Research*, 42(7):4779-90 (2014).

Genetic diversity can also be tuned by selecting the number and diversity of the oligonucleotides introduced during any step of the mutagenesis processes. For example, in the working Examples discussed in more detail below, a MAGE protocol was designed to incorporate 1-5 oligonucleotides per clone. It will be appreciated that the number of oligonucleotides can be increased, that the oligonucleotides can include one or multiple mutations per oligonucleotide and therefore target multiple position (e.g., amino acid positions encoded by the target DNA); that the oligonucleotides can introduce various types of mutations (mismatches, insertions, deletions and with varying degrees of degeneracy (4N-A, T, G, C, 2 selected therefrom, or 3 selected therefrom) or specificity (N equals specific nt).

Figure 2A:
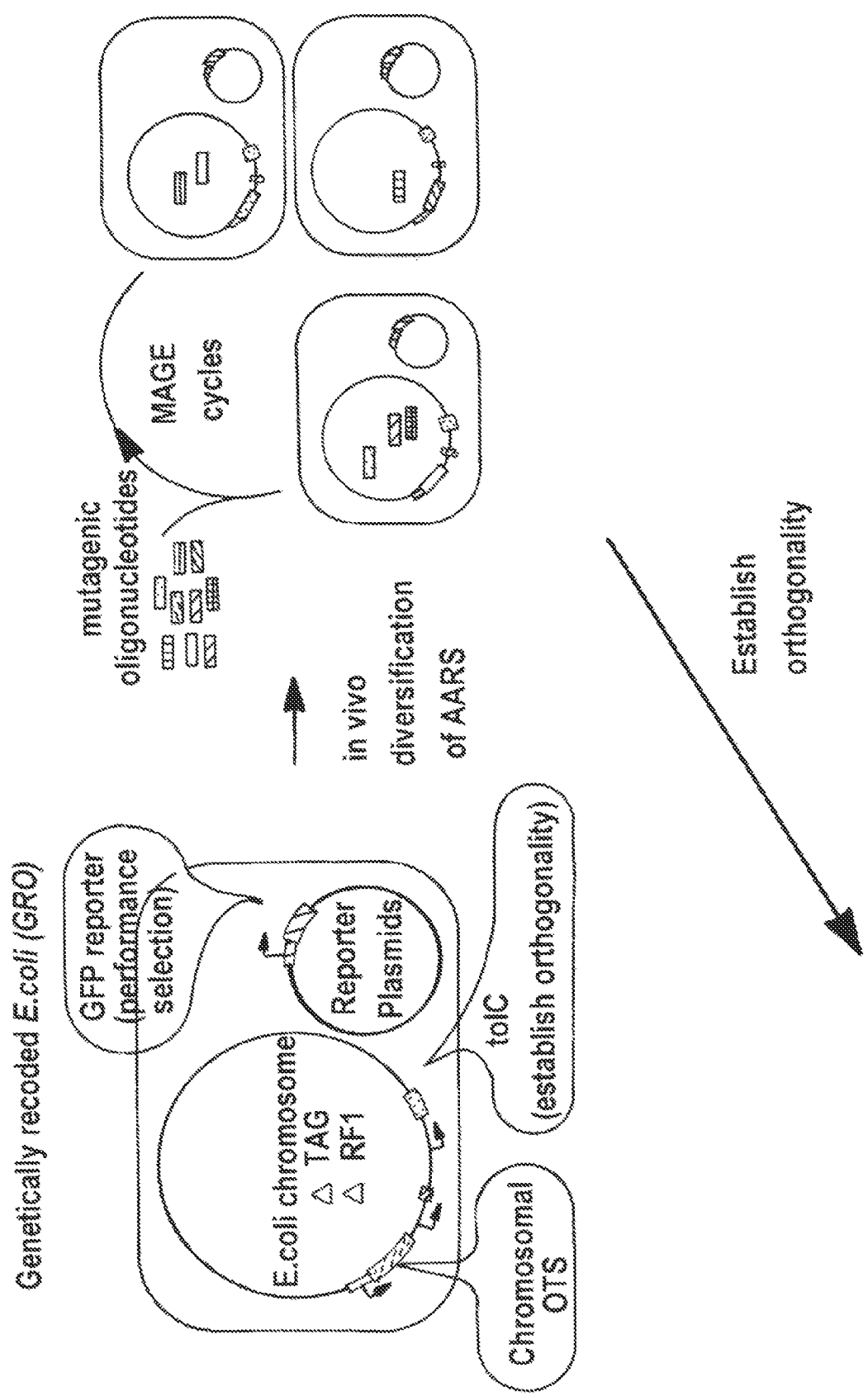
FIG. 2A is a schematic illustration of the platform developed for evolution of chromosomally integrated AARS variants: the GRO is engineered to contain a single chromosomal copy of the AARS for diversification using MAGE, a negative selection marker for removal of non-orthogonal OTSs (capable of incorporation of natural amino acids), and a GFP marker for fluorescence based identification and isolation of improved variants. Site-directed mutagenesis of chromosomally integrated translation components by MAGE generates a highly diversified population which is subsequently subjected to tolC and colicin E1 mediated negative selection in the absence of nsAAs. TAG suppression in GFP(3TAG) enables FACS of orthogonal AARS libraries in the presence of the desired nsAA to identify improved variants. The selected AARS variants are evaluated for multi-site nsAA incorporation, in vitro activity, and protein purity.
Figure 2A:
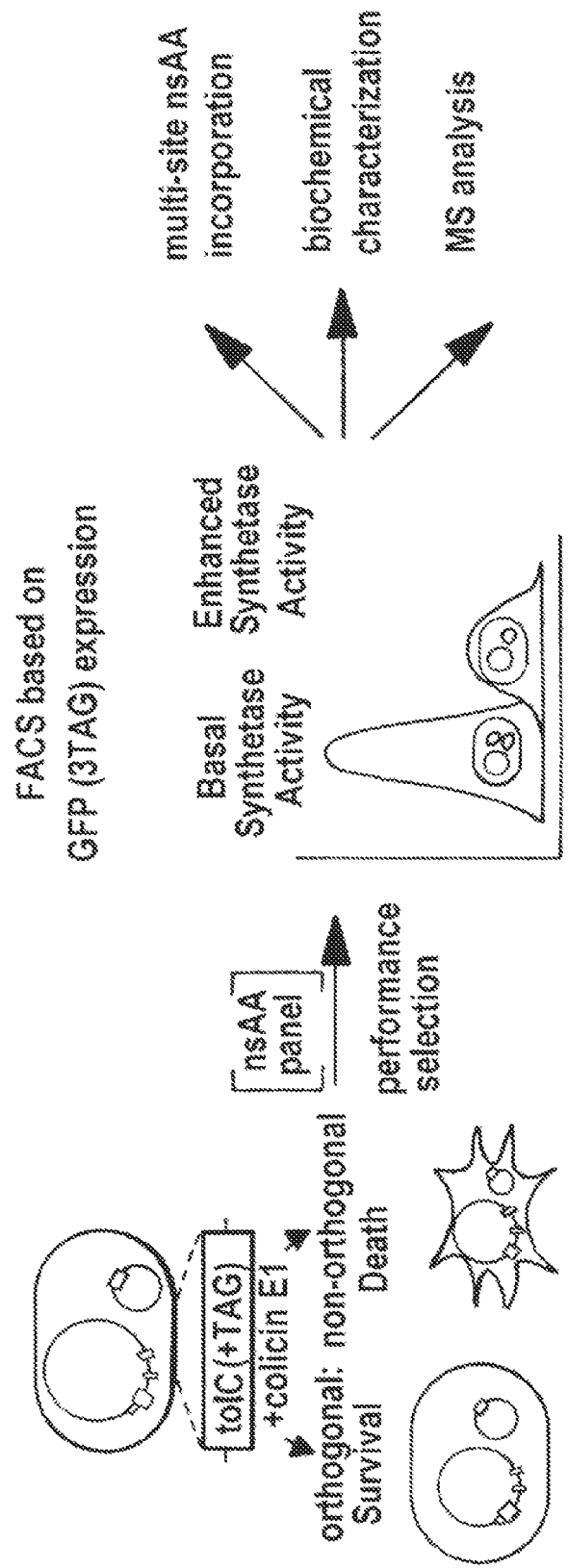

In general, MAGE experiments can be divided into three classes, characterized by varying degrees of scale and complexity: (i) many target sites, single genetic mutations; (ii) single target site, many genetic mutations; and (iii) many target sites, many genetic mutations. In the first class, MAGE has been used to recode all 321 instances of the TAG stop codon for the synonymous TAA codon using 321 discrete ssDNAs. This project yielded a strain of *E. coli* with only 63 'active' codons and a 64th 'blank' codon available for site-specific incorporation of nonstandard amino acids. In the second class, MAGE can be used to explore the effects of all possible amino acid substitutions at a single target locus. In such an experiment, it is possible, for example, to use a single degenerate ssDNA containing the NNN triplet at its center to introduce all possible amino acid substitutions. In the third class, MAGE has been used to construct diverse cell populations containing combinations of alleles across many loci involved in the biosynthesis of lycopene or aromatic amino acids. In this implementation, discrete oligos designed to knockout competing pathways by deletion can be mixed with degenerate oligos designed to randomize target positions in the coding sequence or regulatory regions of key pathway enzymes (FIG. 2). The highly diverse population resulting from a MAGE experiment can be used downstream to screen or select for mutants with a prescribed phenotype (e.g., overproduction of a metabolite or small molecule).

The use of MAGE for OTS optimization provides at least three advantages. First, MAGE permits the generation of sequence library sizes of $>10^9$, much larger than is possible with other in vivo randomization techniques. Second, MAGE can target multiple genetic components, enabling simultaneous co-evolution of all OTS components. Third, MAGE is an in vivo method, which permits the cell to adopt compensatory changes that will be critical for the isolation of optimized and highly efficient OTSs. This MAGE-based approach in GROs enables creation of more catalytically efficient OTSs for multi-site incorporation of nsAAs. Furthermore, this approach may be broadly used as a genetic platform to encode new chemically diverse naAAs.

Although MAGE-based mutagenesis is preferred, suitable alternative methods of mutagenesis which are well known in the art can be used to create a library of variants. Exemplary methods includes, but are not limited to, error prone PCR, PCR or overlap-elongation PCR with degenerate primers, custom DNA synthesis of degenerate DNA fragments encoding the library of interest.

3. Methods of Selection

The methods of evolution typically include selection of desirable AARS variants. Selection can include one or more cycles of negative selection, one or more cycles of positive selection, or a combination thereof. Selection can be integrated in between cycles of mutagenesis, reserved until after mutagenesis is complete, or a combination thereof. Negative selection can be before or after positive selection, or a combination thereof. Positive selection can be before or after negative selection, or a combination thereof. Therefore, selection can include any combination of iterative rounds of positive and/or negative selection.

a. Negative Selection

Negative selection generally refers to a process of reducing undesirable AARS variants from the library of AARS variants. For example, in some embodiments, negative selection includes reducing or removing AARS variants that have undesirable binding to an amino acid ligand(s), undesirable binding to a cognate tRNA, or reduced aminoacylation activity, etc.

Negative selection can be carried out using any suitable method known in the art. A particularly preferred method of negative selection when the host organism is bacteria such as *E. coli*, includes use of the tolC system. Recombineering with tolC is known in the art and described in, for example, DeVito, *Nucleic Acids Research*, 36(1):e4 (12 pages) (2008). Expression of TolC, an outermembrane protein in *E. coli*, confers resistance to toxic small molecules. Alternatively, in the absence of TolC, cells are tolerant to colincin E1. These attributes can be harnessed in both selection and counter-selection strategies.

An exemplary tolC-based negative selection strategy is outlined in the working Examples below. Briefly, tolC is mutated or deleted for the host organism. The tolC can be reintroduced into the organism as part of the heterologous expression construct. Codons capable of hybridizing with the heterologous cognate tRNA (e.g., TAG for $tRNA_{CUA}$, etc., can be inserted into permissive sites in the tolC cassette. Mutated AARS variants capable of mischarging the cognate tRNA with natural amino acids permit read-through of a tolC construct, rendering the organism sensitive to colicin E1. Thus, the negative selection marker is dormant unless colicin E1 is present, eliminating the need to replace or modify the cellular host for positive selection. Negative selection using this strategy can be carried out by culturing the host organism in the presence of colicin E1 for suitable period of time and selecting (e.g., collecting) the living clones.

Negative selection can also include Rec negative selection to remove variants that show activity toward the twenty canonical amino acids. Methods of selection are also discussed in Gallagher, et al., *Nature Protocols*, 9(10):2301-16 (2014) and Isaacs, et al., *Science*, 333(6040):348-53 (2011).

Particular embodiments include use of TolC alone or in combination with a nsAA-2 (e.g., pAzF) to select against and improve specificity for naAA-1 (e.g., pAcF).

b. Positive Selection

Positive selection generally refers to a process of choosing desirable AARS variants from the library of AARS variants. For example, in some embodiments, positive selection includes enriching, selecting, or identifying AARS variants that have improved binding to an amino acid ligand(s), improved binding to a cognate tRNA, or increased or improved aminoacylation activity, etc. In preferred embodiments, translation of a heterologous mRNA is carried out generally according to the methods discussed herein in the presence of at least one non-standard amino acid. The heterologous mRNA includes at least one codon that hybridizes with the anticodon of the heterologous tRNA. Therefore, the activity of isolated variant AARS can be assessed by biochemical and proteomic analysis, for example, the ability the variant AARS to make a protein including a non-standard amino acid. Suitable biochemical and proteomic analyses are well known in the art and can be adapted for use in the methods.

For example, in some embodiments, the heterologous mRNA can encode a protein that includes a detectable marker that is expressed when it is translated. A non-limiting example is green fluorescent protein (GFP), and the working Examples below illustrate how various proteins including GFP can be used to characterize translation. For example, the heterologous mRNA can include one or more codons recognized by the heterologous tRNA, and a variant can selected if GFP is detected (e.g., translated) in the host cell. The selection can be expression verse no expression (e.g., "yes" verse "no"), or can be qualitative, or quantitative. For example, in some embodiments, the variant AARS is selected if expression of the GFP is increased relative to the parent AARS. Methods of evaluating GFP expression by clones expressing a variant AARS are well known in the art and include, but are not limited to, microscopy, FACS, western blotting, etc.

In some embodiments, the heterologous mRNA includes an integer "n" from 1 to 100 iterations of a codon that hybridizes with the anticodon of the heterologous tRNA (i.e., encodes an integer "n" from 1 to 100 iterations of a non-standard amino acid). mRNAs encoding 3, 10, and 30 of a non-standard amino acid are used for positive selection in the Examples below. As discussed herein, due to inefficiencies in known orthogonal systems, translational systems commonly have difficulty translating full-length polypeptide having 10 or more iterations of a non-standard amino acid. Therefore, in some embodiments, a variant AARS is selected if it is quantitatively or qualitatively better that its parent AARS at facilitating translating a mRNA encoding a polypeptide having integer "n" from 1 to 100 iterations of a non-standard amino acid.

It will be appreciated that GFP is just one example of a marker that can be employed for selection variant AARS, and the selection method can be substituted with any other suitable means of measuring the incorporation of non-standard amino acids into a polypeptide encoded by the heterologous mRNA. Other exemplary markers that can be used for positive and/or negative selection include, but are not limited to, lacZ gene, which encodes β-galactosidase, dihydrofolate reductase (DHFR), thymidine kinase, and antibiotics such as neomycin, neomycin analog G418, hydromycin, chlorophenicol, zeocin, and puromycin. When such selectable markers are successfully transferred into a mammalian host cell or microorganism, the transformed mammalian host cell can survive if placed under selective pressure. There are two widely used distinct categories of selective regimes. The first category is based on a cell's metabolism and the use of a mutant cell line which lacks the ability to grow independent of a supplemented media. The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection.

4. Directed Evolution Strategies

As discussed above, the methods can be used to create and select AARS variants that have improved specificity and/or activity for a specific amino acid ligand, a specific cognate tRNA, or a combination thereof relative to the parent AARS. For example, when increased specificity and/or activity for a specific amino acid ligand is desired, the variant can be tested in the presence of the desire amino acid ligand, and optionally, separately in the presence other non-standard amino acids. The variant can be selected when the activity of the AARS (e.g., translation of the heterologous mRNA) is increased in the variant relative to the parent; when the activity of the AARS decreased in the variant relative to the parent; or a combination thereof. Such a selection criteria would result in a variant AARS with higher aminoacylation activity for a desired non-standard amino acid and/or reduced polyspecificity. In particular embodiments, a variant AARS is selected if it exhibits an integer "n" from 1 to 100 fold better aminoacylation for a selected non-standard amino acid compared to the parent AARS.

The methods can also be used to create and select variant AARS that have altered specificity and/or activity for a specific amino acid ligand, a specific cognate tRNA, or a combination thereof relative to the parent AARS. The Examples below show that the disclosed diversification-selection methods can be designed to alter the amino acid binding pocket of the AARS to both reject a specific non-standard amino acid and create a pocket capable of accepting a new, previously excluded, non-standard amino acid. For example, in some embodiments, an AARS can be mutated to form a variant library, followed by Rec negative selection and/or tolC negative selection in the presence of one or more of the undesirable non-standard amino acids to establish orthogonality toward the undesireable non-standard amino acid(s) in addition to the twenty canonical amino acids, followed by positive selection for increased activity for one or more desired non-standard amino acids. In some embodiments, the parent AARS is polyspecific and has some activity for both undesired and desired non-standard amino acids. The Examples below illustrate this strategy by evolving an AARS with exceptional specificity for pAzF to increase its specificity pAcF while excluding pAzF.

Any of the evolutionary strategies can include MAGE, as discussed above.

IV. Compositions for Making Polypeptides with Nonstandard Amino Acids

A. Variant AARS

Variant AARS obtaining according to the methods disclosed herein are also provided. The variant AARS typically have improved specificity and/or activity toward one or more non-standard amino acids and/or improved specificity and/or activity toward a paired tRNA relative to its parent AARS. Sequence variants can be substitutional, insertional and/or deletional variants. Insertions include amino and/or carboxyl terminal fusions as well as intrasequence insertions of single or multiple residues. Variants include, for example, hybrids of the mature parent AARS or a fragment thereof with polypeptides that are homologous with parent AARS or a fragment thereof. Fusions include amino or carboxy terminal fusions with heterologous proteins or fragment thereof, for example a signal sequence, purification tag, etc.

Insertions can also be introduced within the mature coding sequence of the parent AARS sequence. These, however, ordinarily will be smaller insertions than those of amino or carboxyl terminal fusions, on the order of one to four residues. Insertional sequence variants of parent AARS can be those in which one or more residues are introduced into a predetermined site in the parent AARS.

Deletion variants are characterized by the removal of one or more amino acid residues from the parent AARS sequence. For example, deletions or substitutions of potential proteolysis sites, e.g. Arg Arg, are accomplished, for example, by deleting one of the basic residues or substituting one by glutaminyl or histidyl residues. Variants ordinarily are prepared by mutagenesis of nucleotides in the DNA encoding the parent AARS, thereby producing DNA encoding the variant, and thereafter expressing the DNA in recombinant cell culture. Variant AARS fragments may also be prepared by in vitro synthesis. The variants can exhibit qualitative similar or different biological activity as the parent AARS, which can be measured according to biochemical and functional assays such as those disclosed herein.

Substitutional variants are those in which at least one residue sequence has been removed and a different residue inserted in its place. Owing to the degeneracy of the genetic code, "silent substitutions" (i.e., substitutions in a nucleic acid sequence which do not result in an alteration in an encoded polypeptide) are an implied feature of every nucleic acid sequence which encodes an amino acid. Similarly, conservative amino acid substitutions are also readily identified. Such conservative variations are a feature of each disclosed sequence. The substitutions which in general are expected to produce the greatest changes in parent AARS protein properties are those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine.

The site for introducing the mutation(s) may be predetermined or may be random. Furthermore, while the site(s) for introducing an amino acid sequence variation may be predetermined, the mutation per se need not be predetermined. For example, in order to optimize the performance of a mutation at a given site, random mutagenesis may be conducted at the target codon or region and the expressed variants screened for the optimal combination of desired activity. Techniques for making substitution mutations at predetermined sites in DNA having a known sequence are well known.

Substitutions are typically of single residues; insertions usually will be on the order of about from 1 to 10 residues; and deletions will range about from 1 to 30 residues. Substitutions, deletion, insertions or any combination thereof may be combined to arrive at a final construct. The mutations that will be made in the DNA encoding the variant must not place the sequence out of reading frame and preferably will not create complementary regions that could produce secondary mRNA structure.

A DNA isolate is understood to mean chemically synthesized DNA, cDNA or genomic DNA with or without the 3' and/or 5' flanking regions. DNA encoding AARS variants can be obtained by selecting and sequencing the expression construct in the host of the selected variant. DNA sequence(s) can also be deduced from the amino acid sequence of the variant. Accordingly, nucleic acid sequences encoding variant AARS are also provided.

The precise percentage of similarity between sequences that is useful in establishing sequence identity varies with the nucleic acid and protein at issue, but as little as 25% sequence similarity is routinely used to establish sequence identity. Higher levels of sequence similarity, e.g., at least 30%, 40%, 50%, 60%, 70%, 80%, 90%, 95% or 99% or more can also be used to establish sequence identity. Therefore, in some embodiments, the variant includes at least 30%, 40%, 50%, 60%, 70%, 80%, 90%, 95% or 99% or more sequence identity with the parent AARS.

Methods for determining sequence similarity percentages (e.g., BLASTP and BLASTN using default parameters) are generally available. Alignment of sequences for comparison can be conducted by many well-known methods in the art, for example, by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci.* USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), by the Gibbs sampling method (Chatterji and Pachter, *J Comput Biol.* 12(6):599-608 (2005)), by PSI-BLAST-ISS (Margelevicius and Venclovas, *BMC Bioinformatics* 21; 6:185 (2005)), or by visual inspection. One algorithm that is suitable for determining percent sequence identity and sequence similarity is the BLAST algorithm, which is described in Altschul et al., *J Mol. Biol.* 215:403-410 (1990). Software for performing BLAST analyses is publicly available through the National Center for Biotechnology Information (www.ncbi.nlm.nih.gov).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

In particular embodiments, the sequence identity between a parent AARS and a variant thereof is determined by global sequence alignment using software such as EMBOSS Needle. EMBOSS Needle reads two input sequences and writes their optimal global sequence alignment to file. It uses the Needleman-Wunsch alignment algorithm to find the optimum alignment (including gaps) of two sequences along their entire length (see, EMBOSS: the European Molecular Biology Open Software Suite. (2000 June) *Trends in genetics*: TIG 16 (6):276-7 PMID: 10827456; A new bioinformatics analysis tools framework at EMBL-EBI. (2010 July) *Nucleic acids research* 38 (Web Server issue):W695-9 PMID: 20439314; and Analysis Tool Web Services from the EMBL-EBI. (2013 July) *Nucleic acids research* 41 (Web Server issue):W597-600 PMID: 23671338.

B. Exemplary AARS Variants

Variant AARS of a parent *M. jannaschii* AARS referred to pAcF AARS (pAcFRS) (Young, et al., *J Mol Biol,* 395:361-74 (2010)) are provided. The amino acid sequence for pAcFRS is MDEFEMIKRNTSEIISEEELREVLKKDEKSALIGFEPSGKIHLGHYLQIKK MIDLQNAGF-DIIILLADLHAYLNQKGELDEIRKIGDYNKK-VFEAMGLKAKY VYGSEFQLDKDYTLNVYRLALKTTLKRARRSME-LIAREDENPKVAEVIYPI MQVNGCHYRGVDVAVG-GMEQRKIHMLARELLPKKVVCIHNPVLTGLDGEGK MSSSKGNFIAVDDSPEEIRAKIKKAYCPAGVVEGN-PIMEIAKYFLEYPLTI KRPEKFGGDLTVNSY-EELESLFKNKELHPMRLKNAVAEELIKILEPIRKRL (SEQ ID NO:1). A nucleic acid sequence encoding SEQ ID NO:1 is SEQ ID NO:16 (below).

The nucleic acid sequence for a cognate tRNA of SEQ ID NO:1 is CCGGCGGTAGTTCAGCAGGGCAGAACG-GCGGACTCTAAATCCGCATGGCAG GGGT-TCAAATCCCCTCCGCCGGACCA SEQ ID NO:28. This tRNA can also be a congnate tRNA for the variant AARS described in more detail below.

Variants of pAcFRS have one or more mutations relative to SEQ ID NO:1, and typically have altered specificity and/or activity toward one or more non-standard amino acids and/or altered specificity and/or activity toward a paired tRNA relative to the protein of SEQ ID NO:1. In some embodiments, the variant includes at least 30%, 40%, 50%, 60%, 70%, 80%, 90%, 95% or 99% or more sequence identity with the parent AARS, or a functional fragment thereof.

The variants typically have one or more substitution mutations in the non-standard amino acid (amino acid ligand) binding pocket of SEQ ID NO:1, the tRNA anticodon recognition interface of SEQ ID NO:1, or a combination thereof. For example, the variants can have a substitution mutation at one or more of amino acid positions 65, 107, 108, 109, 158, 159, 162, 167, 257, and 261 of SEQ ID NO:1 relative to the N-terminal methionine of SEQ ID NO:1.

Exemplary variants are provided below and have nsAA specificities at least as provided. The relative polyspecificities (or monospecificy) of each are discussed in more detail in the working Examples and FIGS. 5A-5M.

pAcFRS.1 (polyspecifity for at least pAcF, pAzF, StyA, 4IF, 4BrF, 4ClF, 4MeF, 4Cf3F, MeY, 4NO2F, 4BuF, BuY, 2NaA, PheF):

(SEQ ID NO: 2)
MDEFEMIKRNTSEIISEEELREVLKKDEKSALIGFEPSGKIHLGHYLQIK

KMIDLQNAGFDIIILLADLHAYLNQKGELDEIRKIGDYNKKVFEAMGLKA

KYVYGSEFQLDKDYTLNVYRLALKTTLKRARRSMELIAREDENPKVAEVI

YPIMQVNGCHYRGVDVDVGGMEQRKIHMLARELLPKKVVCIHNPVLTGLD

GEGKMSSSKGNFIAVDDSPEEIRAKIKKAYCPAGVVEGNPIMEIAKYFLE

YPLTIKRPEKFGGDLTVNSYEELESLFKNKELHPMRLKNAVAEELIKILE

PIRKRL;

pAcFRS.t1 (polyspecifity for at least pAc.F, pAzF, StyA):

(SEQ ID NO: 3)
MDEFEMIKRNTSEIISEEELREVLKKDEKSALIGFEPSGKIHLGHYLQIK

KMIDLQNAGEDIIILLADLHAYLNQKGELDEIRKIGDYNKKVFEAMGLKA

KYVYGSEFQLDKDYTLNVYRLALKTTLKRARRSMELIAREDENPKVAEVI

YPIMQVNGCHYRGVDVAVGGMEQRKIHMLARELLPKKVVCIHNPVLTGLD

GEGKMSSSKGNFIAVDDSPEEIRAKIKKAYCPAGVVEGNPIMEIAKYFLE

YPLTIKGPEKFGGDLTVNSYEELESLFKNKELHPMRLKNAVAEELIKILE

PIRKRL;

pAcFRS.t2 (polyspecifity for at least pAcF, pAzF, StyA):

(SEQ ID NO: 4)
MDEFEMIKRNTSEIISEEELREVLKKDEKSALIGFEPSGKIHLGHYLQIK

KMIDLQNAGFDIIILLADLHAYLNQKGELDEIRKIGDYNKKVFEAMGLKA

KYVYGSEFQLDKDYTLNVYRLALKTTLKRARRSMELIAREDENPKVAEVI

YPIMQVNGCHYRGVDVAVGGMEQRKIHMLARELLPKKVVCIHNPVLTGLD

GEGKMSSSKGNFIAVDDSPEEIRAKIKKAYCPAGVVEGNPIMEIAKYFLE

YPLTIKCPEKEGGDLTVNSYEELESLFKNKELHPMRLKNAVAEELIKILE

PIRKRL;

pAcFRS.1.t1 (polyspecifity for at least pAcF, pAzF, StyA, 4IF, 4BrF, 4ClF, 4MeF, 4Cf3F, MeY, 4NO2F, 4BuF, BuY, 2NaA, PheF):

(SEQ ID NO: 5)
MEFEMIKRNTSEIISEEELREVLKKDEKSALIGFEPSGKIHLGHYLQIK

KMIDLQNAGFDIIILLADLHAYLNQKGELDEIRKIGDYNKKVFEAMGLK

AKYVYGSEFQLDKDYTLNVYRLALKTTLKRARRSMELIAREDENPKVAE

VIYPIMQVNGCHYRGVDVDVGGMEQRKIHMLARELLPKKVVCIHNPVLT

GLDGEGKMSSSKGNFIAVDDSPEEIRAKIKKAYCPAGVVEGNPIMEIAK

YFLEYPLTIKGPEKFGGDLTVNSYEELESLFKNKELHPMRLKNAVAEEL

IKILEPIRKRL;

pAcFRS.1.t2 (polyspecifity for at least pAcF, pAzF, StyA, 4IF, 4BrF, 4ClF, 4MeF, 4Cf3F, MeY, 4NO2F, 4BuF, BuY, 2NaA, PheF):

(SEQ ID NO: 6)
MDEFEMIKRNTSEIISEEELREVLKKDEKSALIGFEPSGKIHLGHYLQIK

KMIDLQNAGFDIIILLADLHAYLNQKGELDEIRKIGDYNKKVFEAMGLKA

KYVYGSEFQLDKDYTLNVYRLALKTTLKRARRSMELIAREDENPKVAEVI

YPIMQVNGCHYRGVDVDVGGMEQRKIHMLARELLPKKVVCIHNPVLTGLD

GEGKMSSSKGNFIAVDDSPEEIRAKIKKAYCPAGVVEGNPIMEIAKYFLE

YPLTIKCPEKEGGDLTVNSYEELESLFKNKELHPMRLKNAVAEELIKILE

PIRKRL;

pAcFRS.2 (polyspecifity for at least pAcF, pAzF, StyA, 4IF, 4BrF, 4ClF, 4MeF, 4Cf3F, MeY, 4NO2F, 4BuF, BuY, 2NaA, PheF).

(SEQ ID NO: 7)
MDEFEMIKRNTSEIISEEELREVLKKDEKSALIGFEPSGKIHLGHYLQIK

KMIDLQNAGFDIIVLADLHAYLNQKGELDEIRKIGDYNKKVFEAMGLKA

KYVYGSEFQLDKDYTLNVYRLALKTTLKRARRSMELIAREDENPKVAEVI

YPIMQVNGCHYRGVDVDVGGMEQRKIHMLARELLPKKVVCIHNPVLTGLD

GEGKMSSSKGNFIAVDDSPEEIRAKIKKAYCPAGVVEGNPIMEIAKYFLE

YPLTIKRPEKFGGDLTVNSYEELESLEKNKELHPMRLKNAVAEELIKILE

PIRKRL;

pAcFRS.2.t1 (polyspecifity for at least pAcF, pAzF, StyA, 4IF, 4BrF, 4ClF, 4MeF, 4Cf3F, MeY, 4NO2F, 4BuF, BuY, 2NaA, PheF)

(SEQ ID NO: 8)
MDEFEMIKRNTSEIISEEELREVLKKDEKSALIGFEPSGKIHLGHYLQIK

KMIDLQNAGEDIIIVLADLHAYLNQKGELDEIRKIGDYNKKVFEAMGLKA

KYVYGSEFQLDKDYTLNVYRLALKTTLKRARRSMELIAREDENPKVAEVI

YPIMQVNGCHYRGVDVDVGGMEQRKIHMLARELLPKKVVCIHNPVLTGLD

GEGKMSSSKGNFIAVDDSPEEIRAKIKKAYCPAGVVEGNPIMEIAKYFLE

YPLTIKGPEKFGGDLTVNSYEELESLFKNKELHPMRLKNAVAEELIKILE

PIRKRL;

pAcFRS.2.t2 (polyspecifity for at least pAcF, pAzF, StyA, 4IF, 4BrF, 4ClF, 4MeF, 4Cf3F, MeY, 4NO2F, 4BuF, BuY, 2NaAPheF):

(SEQ ID NO: 9)
MDEFEMIKRNTSEIISEEELREVLKKDEKSALIGFEPSGKIHLGHYLQIK

KMIDLQNAGFDIIVLADLHAYLNQKGELDEIRKIGDYNKKVFEAMGLKA

KYVYGSEFQLDKDYTLNVYRLALKTTLKRARRSMELIAREDENPKVAEVI

YPIMQVNGCHYRGVDVDVGGMEQRKIHMLARELLPKKVVCIHNPVLTGLD

GEGKMSSSKGNFIAVDDSPEEIRAKIKKAYCPAGVVEGNPIMEIAKYFLE

YPLTIKCPEKEGGDLTVNSYEELESLFKNKELHPMRLKNAVAEELIKILE

PIRKRL;

pAzFRS.1 (specific for pAzF):

(SEQ ID NO: 10)
MDEFEMIKRNTSEIISEEELREVLKKDEKSALIGFEPSGKIHLGHYLQIK

KMIDLQNAGFDIIILLADLHAYLNQKGELDEIRKIGDYNKKVFEAMGLKA

KYVYGSEFQLDKDYTLNVYRLALKTTLKRARRSMELTAREDENPKVAEVI

YPIMQVNVMHYDGVDVYVGGMEQRKIHMLARELLPKKVVCIHNPVLTGLD

GEGKMSSSKGNFIAVDDSPEEIRAKIKKAYCPAGVVEGNPIMEIAKYFLE

YPLTIKRPEKFGGDLTVNSYEELESLFKNKELHPMRLKNAVAEELIKILE

PIRKRL;

pAzFRS.1.t1 (specific for pAzF):

(SEQ ID NO: 11)
MDEFEMIKRNTSEIISEEELREVLKKDEKSALIGFEPSGKIHLGHYLQIK

KMIDLQNAGFDIIILLADLHAYLNQKGELDEIRKIGDYNKKVFEAMGLKA

KYVYGSEFQLDKDYTLNVYRLALKTTLKRARRSMELIAREDENPKVAEVI

YPIMQVNVMHYDGVDVYVGGMEQRKIHMLARELLPKKVVCIHNPVLTGLD

GEGKMSSSKGNFIAVDDSPEEIRAKIKKAYCPAGVVEGNPIMMEIAKYFL

EYPLTIKGPEKFGGDLTVNSYEELESLFKNKELHPMRLKNAVAEELIKIL

EPIRKRL;

pAzFRS.1.t2 (specific for pAzF):

(SEQ ID NO: 12)
MDEFEMIKRNTSEIISEEELREVLKKDEKSALIGFEPSGKIHLGHYLQIK

KMIDLQNAGFDIIILLADLHAYLNQKGELDEIRKIGDYNKKVFEAMGLKA

KYVYGSEFQLDKDYTLNVYRLALKTTLKRARRSMELIAREDENPKVAEVI

YPIMQVNVMHYDGVDVYVGGMEQRKIHMLARELLPKKVVCIHNPVLTGLD

GEGKMSSSKGNFIAVDDSPEEIRAKIKKAYCPAGVVEGNPIMMEIAKYFL

EYPLTIKCPEKEGGDLTVNSYEELESLFKNKELHPMRLKNAVAEELIKIL

EPIRKRL;

pAzRS.2 (polyspecific for at least pAcF, pAzF, StyA, 4IF, 4BrF, 4ClF, 4MeF, 4Cf3F, MeY, 4NO2F, 4BuF, BuY, 2NaA, PheF):

(SEQ ID NO: 13)
MDEFEMIKRNTSEIISEEELREVLKKDEKSALIGFEPSGKIHLGHYLQIK

KMIDLQNAGFDIIILLADLHAYLNQKGELDEIRKIGDYNKKVFEAMGLKA

KYVYGSTYMLDKDYTLNVYRLALKTTLKRARRSMELIAREDENPKVAEVI

YPIMQVNGCHYRGVDVAVGGMEQRKIHMLARELLPKKVVCIHNPVLTGLD

GEGKMSSSKGNFIAVDDSPEEIRAKIKKAYCPAGVVEGNPIMEIAKYFLE

YPLTIKRPEKFGGDLTVNSYEELESLFKNKELHPMRLKNAVAEELIKILE

PIRKRL;

pAzRS.2.t1 (polyspecific for at least pAcF, pAzF, StyA, 4IF, 4BrF, 4ClF, 4MeF, 4Cf3F, MeY, 4NO2F, 4BuF, BuY, 2NaA, PheF):

(SEQ ID NO: 14)
MDEFEMIKRNTSEIISEEELREVLKKDEKSALIGFEPSGKIHLGHYLQIK

KMIDLQNAGFDIIILLADLHAYLNQKGELDEIRKIGDYNKKVFEAMGLKA

KYVYGSTYMLDKDYTLNVYRLALKTTLKRARRSMELIAREDENPKVAEVI

YPIMQVNGCHYRGVDVAVGGMEQRKIHMLARELLPKKVVCIHNPVLTGLD

GEGKMSSSKGNFIAVDDSPEEIRAKIKKAYCPAGVVEGNPIMEIAKYFLE

YPLTIKGPEKFGGDLTVNSYEELESLFKNKELHPMRLKNAVAEELIKILE

PIRKRL;

and pAzRS.2.t2 (polyspecific for at least pAcF, pAzF, StyA, 4IF, 4BrF, 4ClF, 4MeF, 4Cf3F, MeY, 4NO2F, 4BuF, BuY, 2NaA, PheF):

(SEQ ID NO: 15)
MDEFEMIKRNTSEIISEEELREVLKKDEKSALIGFEPSGKIHLGHYLQIK

KMIDLQNAGFDIIILLADLHAYLNQKGELDEIRKIGDYNKKVFEAMGLKA

KYVYGSTYMLDKDYTLNVYRLALKTTLKRARRSMELIAREDENPKVAEVI

YPIMQVNGCHYRGVDVAVGGMEQRKIHMLARELLPKKVVCIHNPVLTGLD

GEGKMSSSKGNFIAVDDSPEEIRAKIKKAYCPAGVVEGNPIMEIAKYFLE

YPLTIKCPEKEGGDLTVNSYEELESLFKNKELHPMRLKNAVAEELIKILE

PIRKRL.

The position and domain of the mutation in each of SEQ ID NO:2-15 relative to SEQ ID NO:1 is provided in Table 5 below. Variants having any combination of the mutations disclosed in Table 5 are also specifically provided. In some embodiments, the variant is a polypeptide including the amino acids of the non-standard amino acid (amino acid ligand) binding pocket of any of SEQ ID NO:2-15; a polypeptide including the amino acids of the tRNA anticodon recognition interface of any of SEQ ID NO:2-15; or a polypeptide including the non-standard amino acid (amino acid ligand) binding pocket and the amino acids of the tRNA anticodon recognition interface of any of SEQ ID NO:2-15. In some embodiments, the variant is a polypeptide including amino acids 65-261 of any of SEQ ID NO:2-15. All of SEQ ID NOS:1-15 are also specifically provided both with and without the N-terminal methionine.

C. Nucleic Acids

Polynucleotides encoding each of the proteins of SEQ ID NO:1-15, and fragments thereof are also disclosed. A specific, exemplary nucleic acid sequence encoding SEQ ID NO:1 is provided below as SEQ ID NO:16. Specific nucleic acid sequences encoding each of SEQ ID NO:2-15 can be derived by one of skill in the art by making suitable substitutions in SEQ ID NO:16. The polynucleotides can be isolated nucleic acids, incorporated into in a vector, or part of a host genome. The polynucleotides can also be part of a cassette including nucleic acids encoding other translational components such as a paired tRNA, selection marker, promoter and/or enhancer elements, integration sequences (e.g., homology arms), etc.

1. Promoters and Enhancers

Nucleic acids that are delivered to cells typically contain expression controlling systems. For example, the inserted genes in viral and retroviral systems usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

Therefore, polynucleotides encoding each of the proteins of SEQ ID NO:1-15 operably linked to an expression control sequence are also provided Suitable promoters are generally obtained from viral genomes (e.g., polyoma, Simian Virus 40 (SV40), adenovirus, retroviruses, hepatitis-B virus, and cytomegalovirus) or heterologous mammalian genes (e.g. beta actin promoter). Enhancer generally refers to a sequence of DNA that functions at no fixed distance from the transcription start site and can be either 5' or 3' to the transcription unit. Furthermore, enhancers can be within an intron as well as within the coding sequence itself. They are usually between 10 and 300 bp in length, and they function in cis. Enhancers function to increase transcription from nearby promoters. Enhancers also often contain response elements that mediate the regulation of transcription. Many enhancer sequences are now known from mammalian genes (globin, elastase, albumin, α-fetoprotein and insulin). However, enhancer from a eukaryotic cell virus are preferably used for general expression. Suitable examples include the SV40 enhancer on the late side of the replication origin, the cytomegalovirus early promoter enhancer, the polyoma enhancer on the late side of the replication origin, and adenovirus enhancers.

In certain embodiments the promoter and/or enhancer region can act as a constitutive promoter and/or enhancer to maximize expression of the region of the transcription unit to be transcribed. In certain constructs the promoter and/or enhancer region is active in all eukaryotic cell types, even if it is only expressed in a particular type of cell at a particular time. A preferred promoter of this type is the CMV promoter. In other embodiments, the promoter and/or enhancer is tissue or cell specific.

In certain embodiments the promoter and/or enhancer region is inducible. Induction can occur, e.g., as the result of a physiologic response, a response to outside signals, or as the result of artificial manipulation. Such promoters are well known to those of skill in the art. For example, in some embodiments, the promotor and/or enhancer may be specifically activated either by light or specific chemical events which trigger their function. Systems can be regulated by reagents such as tetracycline and dexamethasone. There are also ways to enhance viral vector gene expression by exposure to irradiation, such as gamma irradiation, or alkylating chemotherapy drugs.

Expression vectors used in eukaryotic host cells (yeast, fungi, insect, plant, animal, human or nucleated cells) may also contain sequences necessary for the termination of transcription which may affect mRNA expression. These regions are transcribed as polyadenylated segments in the untranslated portion of the mRNA encoding tissue factor protein. The 3' untranslated regions also include transcription termination sites. It is preferred that the transcription unit also contains a polyadenylation region. One benefit of this region is that it increases the likelihood that the transcribed unit will be processed and transported like mRNA. The identification and use of polyadenylation signals in expression constructs is well established. It is preferred that homologous polyadenylation signals be used in the transgene constructs.

2. Host Organisms

Host organisms whose genome is engineered to include a polynucleotide encoding any of SEQ ID NO:1-15, or a functional fragment thereof, are also provided. In a particularly preferred embodiment, the host organism is a GRO. Accordingly, genetically recoded organisms wherein a heterologous AARS, a heterologous tRNA, or a combination thereof is incorporated in the organism's genome are also provided. In some embodiments, the organism's genome includes a nucleic acid sequence encoding SEQ ID NO:1, a variant thereof, or a functional fragment of SEQ ID NO; 1 or a variant thereof. In particular embodiments, the organism's genome includes a nucleic acid sequence encoding the AARS variant of any one of SEQ ID NO:2-15, or a functional fragment thereof. The GRO can be bacteria, for example E. coli. In a particular embodiment, the E. coli is C321.Δ A.

Nucleic acids that are delivered to cells which are to be integrated into the host cell genome, typically contain integration sequences. These sequences are often viral related sequences, particularly when viral based systems are used. These viral intergration systems can also be incorporated into nucleic acids which are to be delivered using a non-nucleic acid based system of deliver, such as a liposome, so that the nucleic acid contained in the delivery system can be come integrated into the host genome. Techniques for integration of genetic material into a host genome are also known and include, for example, systems designed to promote homologous recombination with the host genome. These systems typically rely on sequence flanking the nucleic acid to be expressed that has enough homology with a target sequence within the host cell genome that recombination between the vector nucleic acid and the target nucleic acid takes place, causing the delivered nucleic acid to be integrated into the host genome. These systems and the methods necessary to promote homologous recombination are known to those of skill in the art.

An exemplary orthogonal translation system integration cassette including homology arms as well as nucleic acids sequences encoding pAcFRS and its cognate tRNA each operably linked to a promoter is provided as SEQ ID NO:17. Specific nucleic acid sequences encoding a corresponding integration cassette including each of SEQ ID NO:2-15 can be derived by one of skill in the art by making suitable substitutions in SEQ ID NO:17.

V. Polypeptides, Peptide Compositions, and Methods of Use Thereof

A. Polypeptides

Polypeptides including one or more iterations of one or more different non-standard amino acids are also provided. In preferred embodiments, the polypeptides are prepared using one or more of the variant AARS provided herein, and/or according to the methods of making polypeptides including non-standard amino acids provided herein.

The polypeptide can have any sequence dictated by the practitioner. As discussed herein, the practitioner can design a heterologous mRNA encoding the polypeptide can designed using a recoded codon (e.g., a stop codon such as UAG) to encode the non-standard amino acid. When the mRNA is expressed in a translation system in the presence of the non-standard amino acid, and the translation system includes an AARS that can aminoacylate a cognate tRNA having an anticodon that recognizes the recoded codon with the non-standard amino, the non-standard amino acid will be incorporated into the nascent peptide during translation of the mRNA.

The polypeptides can be monomeric or polymeric. A monomer is a molecule capable of reacting with identical or different molecules to form a polymer. Therefore, in some embodiments, the heterologous mRNA encodes a single subunit that can be part of a larger homomeric or heteromeric macromolecule. The compositions and methods can be used to produce sequence-defined polymers. In other embodiments, the mRNA encodes two or more subunits, for example, two or more repeats of a monomer. In some embodiments, the mRNA encodes a fusion protein including a sequence having at least one non-standard amino acid fused to a sequence of another protein of interest. Accordingly, the polypeptide including one or more non-standard amino acids can be part of a tag or a domain of a larger multiunit polypeptide. The polypeptide can include both standard and non-standard amino acids. In some embodiments, the biomolecule consists of a run of consecutive non-strandard amino acids, (e.g., 2, 3, 4, 5, 6, 7, 8, 9, 10, or more), or consists entirely of non-strandard amino acids. All iterations of non-standard amino acids can be the same, or the biomolecule can include combinations of two, three, four, or more non-standard amino acids. For example, the compositions can be used to create higher order combinations of monomers to create block polymers with more diverse chemistries.

As described above and exemplified below, the variant AARS and/or the improved methods of making polypeptides with non-standard amino acids described herein are particularly useful for preparing polypeptides with many (e.g., more than 3, more than 10, more than 15, more than 20, more than 25, more than 30, etc.), iterations of the non-standard amino acid. For example, the polypeptide can have any integer "n" from 1 to 500 of any non-standard amino acid. In some embodiments, "n" is more than 500. The compositions and methods allow for template-based biosynthesis of polymers of, in principle, any length including multiple instances of nonstandard amino acids. Polypeptides made using the disclosed variant AARS and/or methods exhibit higher yields and/or higher purities when compared to the same polypeptide produced by conventional translation-based methods and synthetic chemical methods.

The polypeptides can have any one or more non-standard amino acids. Exemplary non-standard amino acids that can be incorporated into the polypeptides disclosed herein are listed in Table 11. The non-standard amino acid or non-standard amino acid(s) are typically selected by the practitioner based on the side chain and the desired properties and/or use of the polypeptide as discussed in more detail below.

B. Methods of Using Polypeptides Including Non-Standard Amino Acids

Polypeptides engineered to include one or more iterations of one or more non-standard amino acids have far reaching uses. Over 100 non-standard amino acids have been described containing diverse chemical groups, including post-translational modifications, photocaged amino acids, bioorthogonal reactive groups, and spectroscopic labels (Liu, et al., *Annu Rev Biochem*, 79:413-44 (2010); Johnson, et al., *Curr Opin Chem Biol*, 14:774-80 (2010); O'Donoghue, et al., *Nat Chem Biol*, 9:594-8 (2013); Chin, et al., *Annu Rev Biochem*, (2014); Seitchik, et al., *J Am Chem Soc*, 134:2898-901 (2012) Davis and Chin, *Nature Reviews*, 13:168-182 (2012)). The use of the polypeptide is typically based on the nature of the polypeptide and the specific non-standard amino acid incorporated therein. Templates for polypeptides and methods of use thereof are known in the art. For example, site-specific incorporation of a non-standard amino acid at a single position enables engineering of protein-drug conjugates (Tian, et al., *Proc Natl Acad Sci USA*, 111:1766-71 (2014)), cross-linking proteins (Furman, et al., *J Am Chem Soc*, 136:8411-7 (2014)), and enzymes with altered or improved function (Kang, et al., *Chembiochem*, 15:822-5 (2014); Wang, et al., *Angew Chem Int Ed Engl*, 51:10132-5 (2012)). Multi-site non-standard amino acid incorporation can further expand the function and properties of proteins and biomaterials by enabling synthesis of polypeptide polymers with programmable combinations of natural and non-standard amino acids.

Limited to only one or a few instances of site-specific non-standard amino acid incorporation, most previous work have centered on tag and modify approaches or simple protein decorations. The disclosed compositions and methods allow for site-specific non-standard amino acid incorporation where multiple identical non-standard amino acids provide the dominant physical and biophysical properties to biopolymers, proteins and peptides. Multi-site non-standard amino acid incorporation also enable design and production of post-translationally modified proteins (e.g., kinases) for the study and treatment of disease or of new biologics (e.g., antibodies) with multiple instances of new chemical functionalities.

Other biomolecules include, but are not limited to, tunable materials, nanostructures, polypeptide-based therapeutics with new properties, industrial enzymes with new chemistries and properties, bio-sensors, drug delivery vehicles, adhesives, stimuli (e.g., metals-responsvie materials), anti-microbials, synthetic peptides with enhanced pharmacokinetic properties, and biologics.

C. Exemplary Polypeptides

1. Elastin-Like Proteins (ELPs)

ELPs are biopolymers composed of the pentapeptide repeat Val-Pro-Gly-Xaa-Gly (VPGXG) (SEQ ID NO:18), wherein "X" can be any standard or non-standard amino acid. ELPs are discussed in U.S. Pat. No. 6,852,834, which is specifically incorporated by reference herein in its entirety, and Tang, et al., *Angew Chem Int Ed Engl*, 40:1494-1496 (2001), Kothakota, Journal of the American Chemical Society, 117:536-537 (1995), and Wu, *Chembiochem* 14:968-78 (2013). They are monodisperse, stimuli-responsive, and biocompatible, making them attractive for applications like drug delivery and tissue engineering. Moreover, ELP properties can be precisely defined and genetically encoded, making them ideal candidates for expanded function via incorporation of multiple non-standard amino acids.

Accordingly, ELPs having the $(VPGXG)_n$ (SEQ ID NO:19), wherein "X" is a standard or non-standard amino acid, preferably a non-standard amino acid disclosed herein (e.g., a non-standard amino acid listed in Table 11, or 3,4-dihydroxyphenylalanine (DOPA)), and wherein "n" is an integer from 1 to 500, or more than 500 are disclosed. In specific embodiments, "X" is pAcF, pAzF, StyA, 4IF, 4BrF, 4ClF, 4MeF, 4Cf3F, MeY, $4NO_2F$, 4BuF, BuY, 2NaA, or PhF. In another embodiment, "X" is 3,4-dihydroxyphenylalanine (DOPA). For example, the ELP can be $(VPG(pAzF)G)_n$ (SEQ ID NO:113) or $(VPG(3,4-dihydroxyphenylalanine)G)_n$, wherein "n" is an integer from 1 to 500, or more than 500. In some embodiments, "n" is at least 5, at least 10, at least 15, at least 20, at least 25, at least 30, at least 35, at least 40, at least 45, or at least 50. In some embodiments, "n" is not more than 500, not more than 250, not more than 200, not more than 100, not more than 50, not more than 45, not more than 40, not more than 35, not more than 30, not more than 25, not more than 20, not more than 15, not more than 10, or not more than 5.

The ELPs can also be a fusion protein including one or more ELP domains fused to a one or more heterologous protein. The fusion protein can include linkers between the domains. ELP fusion proteins are exemplified below by fusion of an ELP polymer to GFP.

The ELPs can be made using the variant AARS disclosed herein and/or according to the methods of making polypeptides including non-standard amino acids disclosed herein. The ELPs disclosed herein can have more iterations of a non-standard amino acid, a higher purity (e.g., reduced heterogeneity), and/or a higher yield than ELPs made according to conventional methods.

2. Exemplary ELP Sequences

Exemplary ELP sequences are provided below.

ELP(10TAG):
MSKGPGVPGGGVPGAGVPGXGVPGGGVP-
GAGVPGXGVPGGGVPGAGVPGXG VPGGGVP-
GAGVPGXGVPGGGVPGAGVPGXGVPGGGVP-
GAGVPGXGVPGGGV
PGAGVPGXGVPGGGVPGAGVPGXGVPGGGVP-
GAGVPGXGVPGGGVPGAGVP GXG (SEQ ID NO:20), wherein "X" is non-standard amino acid, preferably a non-standard amino acid disclosed herein (e.g., a non-standard amino acid listed in Table 11, or 3,4-dihydroxyphenylalanine (DOPA)). In specific embodiments, "X" is pAcF, pAzF, StyA, 4IF, 4BrF, 4ClF, 4MeF, 4Cf3F, MeY, $4NO_2F$, 4BuF, BuY, 2NaA, or PhF. In another embodiment, "X" is 3,4-dihydroxyphenylalanine (DOPA).

ELP(10TAG)-GFP:
MSKGPGVPGGGVPGAGVPGXGVPGGGVP-
GAGVPGXGVPGGGVPGAGVPGXG VPGGGVP-
GAGVPGXGVPGGGVPGAGVPGXGVPGGGVP-
GAGVPGXGVPGGGV

PGAGVPGXGVPGGGVPGAGVPGXGVPGGGVP-GAGVPGXGVPGGGVPGAGVP GXGPGGGGSK-GEELFTGVVPILVELDGDVNGHKFSVRGEGEG-DATNGKLTL KFICTTGKLPVPWPTLVTTLTYGVQCFSRYPDHM-KRHDFFKSAMPEGYVQE RTISFKDDGTYKTRAEVK-FEGDTLVNRIELKGIDFKEDGNILGHKLEYNFN SHN-VYITADKQKNGIKANFKIRHNVEDGSVQLADHYQ QNTPIGDGPVLLPD NHYLSTQSVLSKDPNEKRDHM-VLLEFVTAAGITHGMDELYKGS (SEQ ID NO:21), wherein "X" is non-standard amino acid, preferably a non-standard amino acid disclosed herein (e.g., a non-standard amino acid listed in Table 11, or 3,4-dihydroxyphenylalanine (DOPA)). In specific embodiments, "X" is pAcF, pAzF, StyA, 4IF, 4BrF, 4ClF, 4MeF, 4Cf3F, MeY, 4NO$_2$F, 4BuF, BuY, 2NaA, or PhF. In another embodiment, "X" is 3,4-dihydroxyphenylalanine (DOPA).

ELP (30TAG):
MSKGPGVPGGGVPGAGVPGXGVPGGGVP-GAGVPGXGVPGGGVPGAGVPGXG VPGGGVP-GAGVPGXGVPGGGVPGAGVPGXGVPGGGVP-GAGVPGXGVPGGGV PGAGVPGXGVPGGGVPGAGVPGXGVPGGGVP-GAGVPGXGVPGGGVPGAGVP GXGVPGGGVP-GAGVPGXGVPGGGVPGAGVPGXGVPGGGVP-GAGVPGXGVPG GGVPGAGVPGXGVPGGGVPGAGVPGXGVPGGGVP-GAGVPGXGVPGGGVPGA GVPGXGVPGGGVP-GAGVPGXGVPGGGVPGAGVPGXGVPGGGVP-GAGVPGXG VPGGGVPGAGVPGXGVPGGGVP-GAGVPGXGVPGGGVPGAGVPGXGVPGGGV PGAGVPGXGVPGGGVPGAGVPGXGVPGGGVP-GAGVPGXGVPGGGVPGAGVP GXGVPGGGVP-GAGVPGXGVPGGGVPGAGVPGXGVPGGGVP-GAGVPGXG (SEQ ID NO:22), wherein "X" is non-standard amino acid, preferably a non-standard amino acid disclosed herein (e.g., a non-standard amino acid listed in Table 11, or 3,4-dihydroxyphenylalanine (DOPA)). In specific embodiments, "X" is pAcF, pAzF, StyA, 4IF, 4BrF, 4ClF, 4MeF, 4Cf3F, MeY, 4NO$_2$F, 4BuF, BuY, 2NaA, or PhF. In another embodiment, "X" is 3,4-dihydroxyphenylalanine (DOPA).

ELP(30TAG)-GFP:
MSKGPGVPGGGVPGAGVPGXGVPGGGVP-GAGVPGXGVPGGGVPGAGVPGXG VPGGGVP-GAGVPGXGVPGGGVPGAGVPGXGVPGGGVP-GAGVPGXGVPGGGV PGAGVPGXGVPGGGVPGAGVPGXGVPGGGVP-GAGVPGXGVPGGGVPGAGVP GXGVPGGGVP-GAGVPGXGVPGGGVPGAGVPGXGVPGGGVP-GAGVPGXGVPG GGVPGAGVPGXGVPGGGVPGAGVPGXGVPGGGVP-GAGVPGXGVPGGGVPGA GVPGXGVPGGGVP-GAGVPGXGVPGGGVPGAGVPGXGVPGGGVP-GAGVPGXG VPGGGVPGAGVPGXGVPGGGVP-GAGVPGXGVPGGGVPGAGVPGXGVPGGGV PGAGVPGXGVPGGGVPGAGVPGXGVPGGGVP-GAGVPGXGVPGGGVPGAGVP GXGVPGGGVP-GAGVPGXGVPGGGVPGAGVPGXGVPGGGVP-GAGVPGXGPGG GGSKGEELFTGVVPILVELDGDVNGHKFSVRGEGEG-DATNGKLTLKFICTT GKLPVPWPTLVTTLTYGVQCF-SRYPDHMKRHDFFKSAMPEGYVQERTISFK DDG-TYKTRAEVKFEGDTLVNRIELKGIDFKEDGNILGH KLEYNFNSHNVYI TADKQKNGIKANFKIRHN-VEDGSVQLADHYQQNT-PIGDGPVLLPDNHYLST QSVLSKDPNEKRDHMV-LLEFVTAAGITHGMDELYKGS (SEQ ID NO:23), wherein "X" is non-standard amino acid, preferably a non-standard amino acid disclosed herein (e.g., a non-standard amino acid listed in Table 11, or 3,4-dihydroxyphenylalanine (DOPA)). In specific embodiments, "X" is pAcF, pAzF, StyA, 4IF, 4BrF, 4ClF, 4MeF, 4Cf3F, MeY, 4NO$_2$F, 4BuF, BuY, 2NaA, or PhF. In another embodiment, "X" is 3,4-dihydroxyphenylalanine (DOPA).

ELP (10TAG)$_{MS}$:
MSKGPGKVPGAGVPGXGVPGVGKVP-GAGVPGXGVPGVGKVPGAGVPGXGVP GVGKVP-GAGVPGXGVPGVGKVPGAGVPGXGVPGVGKVP-GAGVPGXGVPGVG KVPGAGVPGXGVPGVGKVPGAGVPGXGVPGVGK-VPGAGVPGXGVPGVGKVP GAGVPGXG (SEQ ID NO:24), wherein "X" is non-standard amino acid, preferably a non-standard amino acid disclosed herein (e.g., a non-standard amino acid listed in Table 11, or 3,4-dihydroxyphenylalanine (DOPA)). In specific embodiments, "X" is pAcF, pAzF, StyA, 4IF, 4BrF, 4ClF, 4MeF, 4Cf3F, MeY, 4NO$_2$F, 4BuF, BuY, 2NaA, or PhF. In another embodiment, "X" is 3,4-dihydroxyphenylalanine (DOPA).

ELP(10TAG)-GFP$_{MS}$:
MSKGPGKVPGAGVPGXGVPGVGKVP-GAGVPGXGVPGVGKVPGAGVPGXGVP GVGKVP-GAGVPGXGVPGVGKVPGAGVPGXGVPGVGKVP-GAGVPGXGVPGVG KVPGAGVPGXGVPGVGKVPGAGVPGXGVPGVGK-VPGAGVPGXGVPGVGKVP GAGVPGXGVPGVG-PGGGGSKGEELFTGVVPILVELDGDVNGH-KFSVRGEGE GDATNGKLTLKFICTTGKLPVPWPTLVTTL-TYGVQCFSRYPDHMKRHDFFK SAMPEGYVQERTIS-FKDDGTYKTRAEVKFEGDTLVNRIELKGIDFKEDGNI LGHKLEYNFNSHNVYITADKQKNGIKANFKIRHN-VEDGSVQLADHYQQNTP IGDGPVLLPDNHYLSTQS-VLSKDPNEKRDHMVLLEFVTAAGITHGMDELYK GS (SEQ ID NO:25), wherein "X" is non-standard amino acid, preferably a non-standard amino acid disclosed herein (e.g., a non-standard amino acid listed in Table 11, or 3,4-dihydroxyphenylalanine (DOPA)). In specific embodiments, "X" is pAcF, pAzF, StyA, 4IF, 4BrF, 4ClF, 4MeF, 4Cf3F, MeY, 4NO$_2$F, 4BuF, BuY, 2NaA, or PhF. In another embodiment, "X" is 3,4-dihydroxyphenylalanine (DOPA).

ELP(30TAG)$_{MS}$:
MSKGPGKVPGAGVPGXGVPGVGKVP-GAGVPGXGVPGVGKVPGAGVPGXGVP GVGKVP-GAGVPGXGVPGVGKVPGAGVPGXGVPGVGKVP-GAGVPGXGVPGVG KVPGAGVPGXGVPGVGKVPGAGVPGXGVPGVGK-VPGAGVPGXGVPGVGKVP GAGVPGXGVPGVGKVP-GAGVPGXGVPGVGKVPGAGVPGXGVPGVGKVP-GAG VPGXGVPGVGKVPGAGVPGXGVPGVGKVP-GAGVPGXGVPGVGKVPGAGVPG XGVPGVGKVP-GAGVPGXGVPGVGKVPGAGVPG XGVPGVGKVP-GAGVPGXG VPGVGKVPGAGVPGXGVPGVGKVP-GAGVPGXGVPGVGKVPGAGVPGXGVPG V GKVP-GAGVPGXGVPGVGKVPGAGVPGXGVPGVGKVP-GAGVPGXGVPGVG KV PGAGVPGXGVPGVGKVPGAGVPGXGVPGVGKVP-GAGVPGXGVPGVGKVPGA GVPGXGVPGVGKVP-GAGVPGXG (SEQ ID NO:26), wherein "X" is non-standard amino acid, preferably a non-standard amino acid disclosed herein (e.g., a non-standard amino acid listed in Table 11, or 3,4-dihydroxyphenylalanine (DOPA)). In specific embodiments, "X" is pAcF, pAzF, StyA, 4IF, 4BrF, 4ClF, 4MeF, 4Cf3F, MeY, 4NO$_2$F, 4BuF, BuY, 2NaA, or PhF. In another embodiment, "X" is 3,4-dihydroxyphenylalanine (DOPA).

ELP(30TAG)-GFP$_{MS}$:
MSKGPGKVPGAGVPGXGVPGVGKVP-
GAGVPGXGVPGVGKVPGAGVPGXGVP GVGKVP-
GAGVPGXGVPGVGKVPGAGVPGXGVPGVGKVP-
GAGVPGXGVPGVG
KVPGAGVPGXGVPGVGKVPGAGVPGXGVPGVGK-
VPGAGVPGXGVPGVGKVP GAGVPGXGVPGVGKVP-
GAGVPGXGVPGVGKVPGAGVPGXGVPGVGKVP-
GAG
VPGXGVPGVGKVPGAGVPGXGVPGVGKVP-
GAGVPGXGVPGVGKVPGAGVPG XGVPGVGKVP-
GAGVPGXGVPGVGKVPGAGVPGXGVPGVGKVP-
GAGVPGXGV
PGVGKVPGAGVPGXGVPGVGKVP-
GAGVPGXGVPGVGKVPGAGVPGXGVPGV GKVP-
GAGVPGXGVPGVGKVPGAGVPGXGVPGVGKVP-
GAGVPGXGVPGVGKV
PGAGVPGXGVPGVGKVPGAGVPGXGVPGVGKVP-
GAGVPGXGVPGVGKVPGA GVPGXGVPGVGKVP-
GAGVPGXGVPGVGPGGGGSKGEELFTGVVPIL-
VELDG
DVNGHKFSVRGEGEGDATNGKLTLKFICTTGKLPVP-
WPTLVTTLTYGVQCF SRYPDHMKRHDFFKSAMP-
EGYVQERTISFKDDGTYKTRAEVKFEGDTLVNR
IELKGIDFKEDGNILGHKLEYNFNSHNVYITAD-
KQKNGIKANFKIRHNVED GSVQLADHYQQNT-
PIGDGPVLLPDNHYLSTQSVLSKDPNEKRDHMV-
LLEFV TAAGITHGMDELYKGS (SEQ ID NO:27), wherein "X" is non-standard amino acid, preferably a non-standard amino acid disclosed herein (e.g., a non-standard amino acid listed in Table 11, or 3,4-dihydroxyphenylalanine (DOPA)). In specific embodiments, "X" is pAcF, pAzF, StyA, 4IF, 4BrF, 4ClF, 4MeF, 4Cf3F, MeY, 4NO$_2$F, 4BuF, BuY, 2NaA, or PhF. In another embodiment, "X" is 3,4-dihydroxyphenylalanine (DOPA).

The polypeptides provided herein, including SEQ ID NO:20-27, are also specifically disclosed without the N-terminal methionine. The peptides provided herein are also provided as fragments of the full length sequence including, for example, at least 40%, 50%, 60%, 70, 80%, 90%, 95%, or 99% of the full-length sequence.

3. Exemplary Methods of Using ELPs

As with other polypeptides including one or more non-standard amino acids, uses for ELP include a wide range of medical and non-medical applications. The disclosed compositions and methods can be used to incorporate 30 or more non-standard amino acids into protein polymers, which has been previously shown to affect and direct polymer properties. Since ELPs undergo a sharp soluble-to-insoluble phase transition at their transition temperature (Tt), which depends on the ELP composition, ELP templates used for non-standard amino acid incorporation can be utilized as a scaffold for the design of smart biomaterials in which non-standard amino acid functionality can be translated to, for example, stimuli-responsiveness to light, electro-magnetic field, and various analytes. Multi-site nsAA incorporation into these and other protein-based biomaterials at high purity can modify and expand their chemical or physical properties to generate new materials.

Specific uses of ELPs are exemplified in the working Examples below. Polymers containing multiple instances of 3,4-dihydroxyphenylalanine (DOPA) amino acid were prepared. When the DOPA-ELPs were mixed with 2M Fe3+a viscose gel formed. Accordingly, formulations including DOPA-ELPs and Fe3+ are specifically provided. The formulations can be used in a wide range of biomedical applications, including, for example preparation of sustained release depots to mediate drug release for prolonged, yet tunable periods of time.

In another example, DOPA-ELPs were mixed with Ag nanoparticles. Accordingly, formulations including DOPA-ELPs and silver, preferably silver nanoparticles, are also specifically provided. The Examples below show that DOPA-ELP-AgNP hybrids have increased antimicrobial activity. Therefore, such formulations can be used in antimicrobial preparations and applications including but not limited to antimicrobial coatings, depots, wound dressing, etc.

Polypeptides including multiple instances of pAzF are also provided. The azide group of pAzF allows for the highly efficient copper-catalyzed azide-alkyne cycloaddition ("click") chemistry reaction with alkyne containing molecules. The pAzF-containing polypeptides can be functionalized with additional molecules by click addition using known methods. Suitable molecules include, but are not limited to, small molecules, proteins, etc. In some embodiments, the molecule is an active agent such a small molecule drug, and imaging agent, etc. In some embodiments, the molecule is a molecular linker that links the polypeptide to another molecule. The molecule can be any molecule with an alkyne capable of underdoing a click reaction with pAzF. The molecule can be a biomolecule.

In particular Examples below, polymers containing multiple instances of p-azidophenylalanine (pAzF) amino acid were prepared. In one Example, a fluorophore (Cy5.5) was conjugated to the pAzF creating a molecule with a detectable signal for imaging in vitro and in vivo.

In yet another example, click chemistry was used to conjugate palmitic acid-alkyne to azide group of pAzF ELPs. The resulting molecule improved BSA binding. Fatty acid conjugation to small molecules and peptides improves in vivo pharmacokinetics profile via albumin binding. Therefore, ELPs containing pAzF to conjugate multiple fatty acid molecules per protein can be used as a platform to further enhance albumin binding and enable tunable enhancement (as a function of the number of fatty acid molecules) of pharmacokinetics in vivo.

D. Compositions Including Polypeptides

1. Formulations

As discussed above, polypeptides including non-standard amino acids have a broad range of applications, including biomedical applications. Therefore, pharmaceutical compositions including a polypeptide having one or more iterations of one or more non-standard amino acids are provided. Pharmaceutical compositions containing peptides or polypeptides may be for administration by parenteral (intramuscular, intraperitoneal, intravenous (IV) or subcutaneous injection), transdermal (either passively or using iontophoresis or electroporation), or transmucosal (nasal, vaginal, rectal, or sublingual) routes of administration. The compositions may also be administered using bioerodible inserts and may be delivered directly to an appropriate lymphoid tissue (e.g., spleen, lymph node, or mucosal-associated lymphoid tissue) or directly to an organ or tumor. The compositions can be formulated in dosage forms appropriate for each route of administration.

a. Formulations for Parenteral Administration

In a preferred embodiment, the disclosed compositions, including those containing peptides and polypeptides, are prepared in an aqueous solution, and can be delivered to subject in need therefore, for example, by parenteral injection. The formulation may also be in the form of a suspension or emulsion. In general, pharmaceutical compositions are provided including effective amounts of a peptide or polypeptide, and optionally include pharmaceutically acceptable diluents, preservatives, solubilizers, emulsifiers, adjuvants and/or carriers. Such compositions include sterile water, buffered saline (e.g., Tris-HCl, acetate, phosphate), pH and ionic strength; and optionally, additives such as detergents and solubilizing agents (e.g., TWEEN® 20, TWEEN 80, Polysorbate 80), anti-oxidants (e.g., ascorbic acid, sodium metabisulfite), and preservatives (e.g., Thimersol, benzyl alcohol) and bulking substances (e.g., lactose, mannitol). Examples of non-aqueous solvents or vehicles are propylene glycol, polyethylene glycol, vegetable oils, such as olive oil and corn oil, gelatin, and injectable organic esters such as ethyl oleate. The formulations may be lyophilized and redissolved/resuspended immediately before use. The formulation may be sterilized by, for example, filtration through a bacteria retaining filter, by incorporating sterilizing agents into the compositions, by irradiating the compositions, or by heating the compositions.

b. Controlled Delivery Polymeric Matrices

Compositions including a polypeptide having one or more iterations of one or more non-standard amino acids can be administered in controlled release formulations. In some embodiments, the polypeptide is the controlled release agent and is used in combination with another active agent. Controlled release polymeric devices can be made for long term release systemically following implantation of a polymeric device (rod, cylinder, film, disk) or injection (microparticles). The matrix can be in the form of microparticles such as microspheres, where peptides are dispersed within a solid polymeric matrix or microcapsules, where the core is of a different material than the polymeric shell, and the peptide is dispersed or suspended in the core, which may be liquid or solid in nature. Unless specifically defined herein, microparticles, microspheres, and microcapsules are used interchangeably. Alternatively, the polymer may be cast as a thin slab or film, ranging from nanometers to four centimeters, a powder produced by grinding or other standard techniques, or even a gel such as a hydrogel. The matrix can also be incorporated into or onto a medical device to modulate an immune response, to prevent infection in an immunocompromised patient (such as an elderly person in which a catheter has been inserted or a premature child) or to aid in healing, as in the case of a matrix used to facilitate healing of pressure sores, decubitis ulcers, etc.

The matrices can be non-biodegradable or biodegradable matrices. These may be natural or synthetic polymers, although synthetic polymers are preferred due to the better characterization of degradation and release profiles. The polymer is selected based on the period over which release is desired. In some cases linear release may be most useful, although in others a pulse release or "bulk release" may provide more effective results. The polymer may be in the form of a hydrogel (typically in absorbing up to about 90% by weight of water), and can optionally be crosslinked with multivalent ions or polymers.

The matrices can be formed by solvent evaporation, spray drying, solvent extraction and other methods known to those skilled in the art. Bioerodible microspheres can be prepared using any of the methods developed for making microspheres for drug delivery, for example, as described by Mathiowitz and Langer, *J Controlled Release*, 5:13-22 (1987); Mathiowitz, et al., *Reactive Polymers,* 6:275-283 (1987); and Mathiowitz, et al., *J. Appl. Polymer Sci.,* 35:755-774 (1988).

Controlled release oral formulations may be desirable. Polypeptides can be incorporated into an inert matrix which permits release by either diffusion or leaching mechanisms, e.g., films or gums. Slowly disintegrating matrices may also be incorporated into the formulation. Another form of a controlled release is one in which the drug is enclosed in a semipermeable membrane which allows water to enter and push drug out through a single small opening due to osmotic effects. For oral formulations, the location of release may be the stomach, the small intestine (the duodenum, the jejunem, or the ileum), or the large intestine. Preferably, the release will avoid the deleterious effects of the stomach environment, either by protection of the active agent (or derivative) or by release of the active agent beyond the stomach environment, such as in the intestine. To ensure full gastric resistance an enteric coating (i.e, impermeable to at least pH 5.0) is essential.

The devices can be formulated for local release to treat the area of implantation or injection and typically deliver a dosage that is much less than the dosage for treatment of an entire body. The devices can also be formulated for systemic delivery. These can be implanted or injected subcutaneously.

c. Formulations for Enteral Administration

The polypeptides can also be formulated for oral delivery. Oral solid dosage forms are known to those skilled in the art. Solid dosage forms include tablets, capsules, pills, troches or lozenges, cachets, pellets, powders, or granules or incorporation of the material into particulate preparations of polymeric compounds such as polylactic acid, polyglycolic acid, etc. or into liposomes. Such compositions may influence the physical state, stability, rate of in vivo release, and rate of in vivo clearance of the present proteins and derivatives. See, e.g., Remington's Pharmaceutical Sciences, 21st Ed. (2005, Lippincott, Williams & Wilins, Baltimore, Md. 21201) pages 889-964. The compositions may be prepared in liquid form, or may be in dried powder (e.g., lyophilized) form. Liposomal or polymeric encapsulation may be used to formulate the compositions. See also Marshall, K. In: Modern Pharmaceutics Edited by G. S. Banker and C. T. Rhodes Chapter 10, 1979. In general, the formulation will include the active agent and inert ingredients which protect the polypeptide in the stomach environment, and release of the biologically active material in the intestine.

Liquid dosage forms for oral administration, including pharmaceutically acceptable emulsions, solutions, suspensions, and syrups, may contain other components including inert diluents; adjuvants such as wetting agents, emulsifying and suspending agents; and sweetening, flavoring, and perfuming agents.

2. Devices

In some embodiments, a polypeptide including one or more iterations of one or more non-standard amino acids is coated onto, or incorporate into, an object or device, for example a medical device. The device can be a device that is inserted into a subject transiently, or a device that is implanted permanently. In some embodiments, the device is surgical device.

Examples of medical devices include, but are not limited to, needles, cannulas, catheters, shunts, balloons, and implants such as stents and valves.

In some embodiments, the polypeptide can be formulated to permit its incorporation onto the medical device. In some embodiments the polypeptide inhibitor or pharmaceutical composition thereof is formulated by including it within a coating on the medical device. There are various coatings that can be utilized such as, for example, polymer coatings that can release an active agent over a prescribed time period. The polypeptide can be the polymer, the active agent, or both. The polypeptide can be embedded directly within the medical device. In some embodiments, the polypeptide is coated onto or within the device in a delivery vehicle such as a microparticle or liposome that facilitates its release and delivery. In some embodiments, the polypeptide is miscible in the coating.

In some embodiments, the medical device is a vascular implant such as a stent. Stents are utilized in medicine to prevent or eliminate vascular restrictions. The implants may be inserted into a restricted vessel whereby the restricted vessel is widened. The experience with such vascular implants indicates that excessive growth of the adjacent cells results again in a restriction of the vessel particularly at the ends of the implants which results in reduced effectiveness of the implants. If a vascular implant is inserted into a human artery for the elimination of an arteriosclerotic stenosis, intimahyperplasia can occur within a year at the ends of the vascular implant and results in renewed stenosis.

In some embodiments, the stents are coated or loaded with a composition including a polypeptide including one or more iterations or one or more non-standard polypeptides. Many stents are commercially available or otherwise know in the art.

EXAMPLES

Example 1: Whole Genome Recoding Improves Multi-Site nsAA Incorporation

Materials and Methods

Plasmid Construction

Plasmids bearing GFP-based reporter genes were constructed by insertion of reporter protein genes to a previously described plasmid harboring the gene coding for wild-type GFP, a colE1 origin of replication and a kanamycin resistance marker24. The genes encoding for GFP (3TAG) and superfolder GFP were chemically synthesized (IDT), and inserted in place of the existing wild-type GFP gene using the flanking restriction sites EcoRI and HindIII. The gene encoding for ELP(10TAG) or ELP(10Tyr) flanked by BseRI restriction sites, were chemically synthesized (GeneArt®, Life Technologies) and inserted sequentially (up to ELP(30TAG) and ELP(30Tyr)) into the BseRI restriction site located at the N-terminus of the GFP gene as described (Meyer, et al., *Biomacromolecules*, 3:357-67 (2002)). A DNA cassette encoding for a leader protein sequence ('MSKGP') was then inserted at the N-terminus of the ELP gene to optimize protein expression.

Plasmids bearing the OTS components were constructed by insertion of AARS genes to a plasmid harboring a p15A origin of replication and a chloramphenicol resistance marker (Lajoie, et al., *Science*, 342: 357-60 (2013), Young, et al., *J Mol Biol*, 395:361-74 (2010)). AARS genes were PCR-amplified from chromosomal templates and inserted sequentially in place of the progenitor pAcFRS gene using the flanking restriction sites BglII and SalI (for copy 1) and NdeI and PstI (for copy 2).

Analysis of GFP Expression by Intact Cell Fluorescence Measurements

Liquid cell cultures of strains harboring chromosomally integrated OTSs and GFP reporter plasmids were inoculated from frozen stocks and grown to confluence overnight. Cultures were then inoculated at 1:20 dilution in LBmin media supplemented with 30 µg/ml kanamycin. Strains were inoculated by addition of 1:20 confluent cell culture (grown overnight) and allowed to grow at 34° C. to an OD600 of 0.5-0.8 in a shaking plate incubator at 650 r.p.m (~3 h). AARS expression was then induced by the addition of 0.2% arabinose, GFP expression was induced by the addition of 60 ng/ul anhydrotetracycline, and the appropriate nsAA was added to a concentration of 1 mM. Cells were incubated at 34° C. for an additional 16 h. Liquid cell cultures of strains harboring plasmid-based OTSs and GFP or ELP-GFP reporter plasmids were inoculated from frozen stocks and grown to confluence overnight. Cultures were then inoculated at 1:20 dilution in 2×YT media supplemented with 30 µg/ml kanamycin and 20 µg/ml chloramphenicol. Strains were inoculated by addition of 1:20 confluent cell culture (grown overnight) and AARS expression was simultaneously induced by the addition of 0.2% arabinose, and the appropriate nsAA was added to a concentration of 1 mM. Cells were allowed to grow at 34° C. to an OD600 of 0.5-0.8 in a shaking plate incubator at 650 r.p.m (~3 h), reporter protein expression was then induced by the addition of 60 ng/ul anhydrotetracycline, and cells were incubated at 34° C. for an additional 16 h.

For 384 well plate-based assays, fluorescence and OD600 were directly measured following expression. For 96 well plate-based assays, cells were centrifuged at 4,000 g for 4 min. Supernatant medium was removed and cells were resuspended in PBS. This process was repeated twice with PBS. GFP fluorescence was measured on a Biotek spectrophotometric plate reader using excitation and emission wavelengths of 395 and 509 nm, respectively). Fluorescence signals were normalized by dividing the fluorescence counts by the OD600 reading. The nsAAs used in this study were purchased from Sigma-Aldrich (St. Louis, Mo.), Chemlmpex (Wood Dale, Ill.), and Bachem (Torrance, Calif.). Solutions of nsAAs (50 mM) were made in water or 50 mM NaOH; these stock solutions were diluted 50- or 100-fold (to 1 mM final concentration) into medium used for bacterial growth.

ELP Expression and Purification

Before batch expression, starter cultures (2 mL) of 2×YT media supplemented with 30 µg/mL kanamayacin and 20 µg/mL chloramphenicol were inoculated with transformed cells from a fresh agar plate or from stocks stored at −80° C., and incubated overnight at 34° C. while shaking at 250 rpm. Expression cultures (250 ml flasks containing 50 ml of 2×YT media, antibiotics, 0.2% arabinose and 1 mM of the nsAA) were inoculated with 0.5 ml of the starter culture and incubated at 34° C. for 4 h and then reporter protein expression was induced with 60 µg/mL anhydrotetracyclin.

Cells were harvested 24 h after inoculation by centrifugation at 4,000 g for 15 min at 4° C. The cell pellet was resuspended by vortex in ~1.5 mL PBS buffer and stored at −80° C. or immediately purified. For purification, resuspended pellets were lysed by ultrasonic disruption (9 cycles of 10 s sonication separated by 40 s intervals). Poly(ethyleneimine) (0.2 mL of 10% solution) was added to each lysed suspension before centrifugation at 15,000 g for 3 min to separate cell debris from the soluble cell lysate.

All ELP constructs were purified by a modified Inverse Transition Cycling (ITC) protocol consisting of multiple "hot" and "cold" spins using sodium citrate to trigger the phase transition. Before purification, the soluble cell lysate was incubated for 1-2 min at ~65° C. to denature native *E. coli* proteins. For "hot" spins, the ELP phase transition was triggered by adding sodium citrate to the cell lysate or the product of a previous cycle of ITC at a final concentration of ~0.5 M. The solutions were then centrifuged at 14,000 g for 3 min and the pellets were resuspended in PBS, followed by a 3-5 min "cold" spin performed without addition of sodium citrate to remove denatured contaminant. Additional rounds of ITC were carried out as needed until sufficient purification was achieved.

Protein concentration was calculated by measuring the OD280 of purified protein stocks according to the following extinction coefficients for ELP(30TAG)-GFP.

TABLE 1

Extinction Coefficients

| AA/nsAA | extinction coefficient ($M^{-1}$ $cm^{-1}$) |
|---|---|
| Tyr (WT protein) | 63,610 |
| pAcF | 82,510 |
| pAzF | 75,990 |
| BuY | 22,450 |
| 4CF3F | 19,027 |
| 4ClF | 20,905 |

DNA and Protein Sequences
A. DNA Sequence of OTS Integration Cassette.
Homology arms to the genomic integration site (at position 2434907-2434908 in the recoded E. coli C321.ΔA, CP006698.1, GI:54981157 are underlined).

(SEQ ID NO: 17)
TTTGCGTAGGGATTTCCTTCCCGCGCATCAATAAAAATGGCGCTGAAAAA

ACTTTTCATACTCCCGCCATTCAGAGAAGAAACCAATTGTCCATATTGCA

TCAGACATTGCCGTCACTGCGTCTTTTACTGGCTCTTCTCGCTAACCAAA

CCGGTAACCCCGCTTATTAAAAGCATTCTGTAACAAAGCGGGACCAAAGC

CATGACAAAAACGCGTAACAAAAGTGTCTATAATCACGGCAGAAAAGTCC

ACATTGATTATTTGCACGGCGTCACACTTTGCTATGCCATAGCATTTTTA

TCCATAAGATTAGCGGATCCTACCTGACGCTTTTTATCGCAACTCTCTAC

TGTTTCTCCATACCCGTTTTTTGGGCTAACAGGAGGAATTAGATCTATG

GACGAATTTGAAATGATAAAGAGAAACACATCTGAAATTATCAGCGAGGA

AGAGTTAAGAGAGGTTTTAAAAAAAGATGAAAAATCTGCTCTGATAGGTT

TTGAACCAAGTGGTAAAATACATTTAGGGCATTATCTCCAAATAAAAAAG

ATGATTGATTTACAAAATGCTGGATTTGATATAATTTATATTGTTGGCTGA

TTTACACGCCTATTTAAACCAGAAAGGAGAGTTGGATGAGATTAGAAAAA

TAGGAGATTATAACAAAAAAGTTTTTGAAGCAATGGGGTTAAAGGCAAAA

TATGTTTATGGAAGTGAATTCCAGCTTGATAAGGATTATACACTGAATGT

CTATAGATTGGCTTTAAAAACTACCTTAAAAAGAGCAAGAAGGAGTATGG

AACTTATAGCAAGAGAGGATGAAAATCCAAAGGTTGCTGAAGTTATCTAT

CCAATAATGCAGGTTAATGGTTGTCATTATAGGGGCGTTGATGTTGCTGT

TGGAGGGATGGAGCAGAGAAAAATACACATGTTAGCAAGGGAGCTTTTAC

CAAAAAAGGTTGTTTGTATTCACAACCCTGTCTTAACGGGTTTGGATGGA

GAAGGAAAGATGAGTTCTTCAAAAGGGAATTTTATAGCTGTTGATGACTC

TCCAGAAGAGATTAGGGCTAAGATAAAGAAAGCATACTGCCCAGCTGGAG

TTGTTGAAGGAAATCCAATAATGGAGATAGCTAAATACTTCCTTGAATAT

-continued

CCTTTAACCATAAAAAGGCCAGAAAAATTTGGTGGAGATTTGACAGTTAA

TAGCTATGAGGAGTTAGAGAGTTTATTTAAAAATAAGGAATTGCATCCAA

TGCGCTTAAAAAATGCTGTAGCTGAAGAACTTATAAAGATTTTAGAGCCA

ATTAGAAAGAGATTATAATAAGTCGACCATCATCATCATCATCATTGAGT

TTAAACGGTCTCCAGCTTGGCTGTTTTGGCGGATGAGAGAAGATTTTCAG

CCTGATACAGATTAAATCAGAACGCAGAAGCGGTCTGATAAAACAGAATT

TGCCTGGCGGCAGTAGCGCGGTGGTCCCACCTGACCCCATGCCGAACTCA

GAAGTGAAACGCCGTAGCGCCGATGGTAGTGTGGGGTCTCCCCATGCGAG

AGTAGGGAACTGCCAGGCATCAAATAAAACGAAAGGCTCAGTCGAAAGAC

TGGGCCTTGTTTGTGAGCTCCCGGTCATCAATCATAATTCCGCTTCGCAA

CATGTGAGCACCGGTTTATTGACTACCGGAAGCAGTGTGACCGTGTGCTT

CTCAAATGCCTGAGGCCAGTTTGCTCAGGCTCTCCCCGTGGAGGTAATAA

TTGACGATATGATCAGTGCACGGCTAACTAAGCGGCCTGCTGACTTTCTC

GCCGATCAAAAGGCATTTTGCTATTAAGGGATTGACGAGGGCGTATCTGC

GCAGTAAGATGCGCCCCGCATTCCGGCGGTAGTTCAGCAGGGCAGAACGG

CGGACTCTAAATCCGCATGGCAGGGGTTCAAATCCCCTCCGCCGGACCAA

ATTCGAAAAGCCTGCTCAACGAGCAGGCTTTTTTGCATGCTCGAGCAGCT

CAGGGTCGAATTTGCTTTCGTTGAGGCACATTAACGCCCTATGGCACGTA

ACGCCAACCTTTTGCGGTAGCGGCTTCTGCTAGAATCCGCAATAATTTTA

CAGTTTGATCGCGCTAAATACTGCTTCACCACAAGGAATGCAAATGAAGA

AATTGCTCCCCATTCTTATCGGCCTGAGCCTTTCTGGGTTCAGTTCGTTG

AGCCAGGCCGAGAACCTGATGCAAGTTTATCAGCAAGCACGCCTTAGTAA

CCCGGAATTGCGTAAGTCTGCCGCCGATCGTGATGCTGCCTTTGAAAAAA

TTAATGAAGCGCGCAGTCCATTACTGCCACAGCTAGGTTTAGGTGCAGAT

TACACCTATAGCAACGGCTACCGCGACGCGAACGGCATCAACTCTAACGC

GACCAGTGCGTCCTTGCAGTTAACTCAATCCATTTTTGATATGTCGAAAT

GGCGTGCGTTAACGCTGCAGGAAAAGCAGCAGGGATTCAGGACGTCACG

TATCAGACCGATCAGCAAACCTTGATCCTCAACACCGCGACCGCTTATTT

CAACGTGTTGAATGCTATTGACGTTCTTTCCTATACACAGGCACAAAAAG

AAGCGATCTACCGTCAATTAGATCAAACCACCCAACGTTTTAACGTGGGC

CTGGTAGCGATCACCGACGTGCAGAACGCCCGCGCACAGTACGATACCGT

GCTGGCGAACGAAGTGACCGCACGTAATAACCTTGATAACGCGGTAGAGC

AGCTGCGCCAGATCACCGGTAACTACTATCCGGAACTGGCTGCGCTGAAT

GTCGAAAACTTTAAAACCGACAAACCACAGCCGGTTAACGCGCTGCTGAA

AGAAGCCGAAAAACGCAACCTGTCGCTGTTACAGGCACGCTTGAGCCAGG

ACCTGGCGCGCGAGCAAATTCGCCAGGCGCAGGATGGTCACTTACCGACT

CTGGATTTAACGGCTTCTACCGGGATTTCTGACACCTCTTATAGCGGTTC

GAAAACCCGTGGTGCCGCTGGTACCCAGTATGACGATAGCAATATGGGCC

AGAACAAAGTTGGCCTGAGCTTCTCGCTGCCGATTTATCAGGGCGGAATG

GTTAACTCGCAGGTGAAACAGGCACAGTACAACTTTGTCGGTGCCAGCGA

GCAACTGGAAAGTGCCCATCGTAGCGTCGTGCAGACCGTGCGTTCCTCCT

-continued

TCAACAACATTAATGCATCTATCAGTAGCATTAACGCCTACAAACAAGCC

GTAGTTTCCGCTCAAAGCTCATTAGACGCGATGGAAGCGGGCTACTCGGT

CGGTACGCGTACCATTGTTGATGTGTTGGATGCGACCACCACGTTGTACA

ACGCCAAGCAAGAGCTGGCGAATGCGCGTTATAACTACCTGATTAATCAG

CTGAATATTAAGTCAGCTCTGGGTACGTTGAACGAGCAGGATCTGCTGGC

ACTGAACAATGCGCTGAGCAAACCGGTTTCCACTAATCCGGAAAACGTTG

CACCGCAAACGCCGGAACAGAATGCTATTGCTGATGGTTATGCGCCTGAT

AGCCCGGCACCAGTCGTTCAGCAAACATCCGCACGCACTACCACCAGTAA

CGGTCATAACCCTTTCCGTAACTGATGACGACGACGGGGAAGCTTAATTA

GCTGATCTAGAGGCATCAAATAAAACGAAAGGCTCAGTCGAAAGACTGGG

CCTTTCGTTTTATCTGTTGTTTGTCGGTGAACGCTCTCCTGAGTAGGACA

AATCCGCCGCCCTAGA<u>ATATTCAACGCCATCGACTTTTTATGCCTTTGCG</u>

<u>GCATCGGGCAATGCGT</u>.

B. DNA Sequence of 4TAG-tolC. In-Frame TAG Codons are Underlined.

(SEQ ID NO: 111)
ATGAAGAAATTGCTCCCCATTCTTATCGGCCTGAGCCTTTCTGGGTTCAG

TTCGTTGAGCCAGGCCGAGAACCTGATGCAAGTTTATCAGCAAGCACGCC

TTAGTAACCCGGAATTGCGTAAGTCTGCCGCCGATCGTGATGCTGCCTTT

GAAAAAATTAATGAAGCGCGCAGTCCATTACTGCCACAGCTAGGTTTAGG

TGCAGATTACACCTATAGCAACGGCTACCGCGACGCGAACGGCATCAACT

CTAACGCGACCAGTGCGTCCTTGCAGTTAACTCAATCCATTTTTGATATG

TCGAAATGGCGTGCGTTAACGCTGCAGGAAAAAGCAGCAGGGATTCAGGA

CGTCACGTATCAGACCGATCAGCAAACCTTGATCCTCAACACCGCGACCG

CTTATTTCAACGTGTTGAATGCTATTGACGTTCTTTCCTATACACAGGCA

CAAAAAGAAGCGATCTACCGTCAATTAGATCAAACCACCCAACGTTTTAA

CGTGGGCCTGGTAGCGATCACCGACGTGCAGAACGCCCGCGCACAGTACG

ATACCGTGCTGGCGAACGAAGTGACCGCACGTAATAACCTTGATAACGCG

GTAGAGCAGCTGCGCCAGATCACCGGTAACTACTATCCGGAACTGGCTGC

GCTGAATGTC<u>TAG</u>AACTTTAAAACC<u>TAG</u>AAACCACAGCCGGTTAACGCGC

TGCTGAAAGAAGCCGAAAAACGCAACCTGTCGCTGTTACAGGCACGCTTG

AGCCAGGACCTGGCGCGCGAGCAAATTCGCCAGGCGCAGGATGGTCACTT

ACCGACTCTGGATTTAACGGCTTCTACCGGGATTTCTGACACCTCTTATA

GCGGTTCGAAAACCCGTGGT<u>TAGTAG</u>GGTACCCAGTATGACGATAGCAAT

ATGGGCCAGAACAAAGTTGGCCTGAGCTTCTCGCTGCCGATTTATCAGGG

CGGAATGGTTAACTCGCAGGTGAAACAGGCACAGTACAACTTTGTCGGTG

CCAGCGAGCAACTGGAAAGTGCCCATCGTAGCGTCGTGCAGACCGTGCGT

TCCTCCTTCAACAACATTAATGCATCTATCAGTAGCATTAACGCCTACAA

ACAAGCCGTAGTTTCCGCTCAAAGCTCATTAGACGCGATGGAAGCGGGCT

ACTCGGTCGGTACGCGTACCATTGTTGATGTGTTGGATGCGACCACCACG

TTGTACAACGCCAAGCAAGAGCTGGCGAATGCGCGTTATAACTACCTGAT

TAATCAGCTGAATATTAAGTCAGCTCTGGGTACGTTGAACGAGCAGGATC

TGCTGGCACTGAACAATGCGCTGAGCAAACCGGTTTCCACTAATCCGGAA

AACGTTGCACCGCAAACGCCGGAACAGAATGCTATTGCTGATGGTTATGC

GCCTGATAGCCCGGCACCAGTCGTTCAGCAAACATCCGCACGCACTACCA

CCAGTAACGGTCATAACCCTTTCCGTAACTGA.

C. DNA Sequence of Superfolder GFP with Three TAG Sites (GFP(3TAG)).

In-frame TAG codons are underlined.

(SEQ ID NO: 112)
ATGAGCAAGGGCGAAGAACTGTTTACGGGCGTGGTGCCGATTCTGGTGGA

ACTGGATGGTGATGTCAATGGTCACAAATTCAGCGTGCGCGGCGAAGGTG

AAGGCGATGCAACC<u>TAG</u>GGTAAACTGACGCTGAAGTTTATTTGCACCACG

GGTAAACTGCCGGTTCCGTGGCCGACCCTGGTCACCACGCTGACGTATGG

TGTTCAGTGTTTCAGTCGTTACCCGGATCACATGAAACGCCACGACTTTT

TCAAGTCCGCGATGCCGGAAGGTTATGTCCAAGAACGTACCATCTCATTT

AAAGATGACGGCACCTACAAAACGCGCGCCGAAGTGAAATTCGAAGGTGA

TACGCTGGTTAACCGTATTGAACTGAAAGGCATCGATTTTAAGGAAGACG

GTAATATTCTGGGCCATAAACTGGAATATAACTTCAATTCGCACAACGTG

<u>TAG</u>ATCACCGCAGATAAGCAGAAGAACGGTATCAAGGCTAACTTCAAGAT

CCGCCATAATGTGGAAGATGGCAGCGTTCAACTGGCCGACCAC<u>TAG</u>CAGC

AAAACACCCCGATTGGTGATGGCCCGGTCCTGCTGCCGGACAATCATTAC

CTGAGCACGCAGTCTGTGCTGAGTAAAGATCCGAACGAAAAGCGTGACCA

CATGGTCCTGCTGGAATTCGTGACCGCGGCCGGCATCACGCACGGTATGG

ACGAACTGTATAAAGGCTCA.

D. DNA Sequence of the Progenitor pAcFRS Used as a Basis for Synthetase Evolution in this Study.

(SEQ ID NO: 16)
ATGGACGAATTTGAAATGATAAAGAGAAACACATCTGAAATTATCAGCGA

GGAAGAGTTAAGAGAGGTTTTAAAAAAAGATGAAAAATCTGCTCTGATAG

GTTTTGAACCAAGTGGTAAAATACATTTAGGGCATTATCTCCAAATAAAA

AAGATGATTGATTTACAAAATGCTGGATTTGATATAATTATATTGTTGGC

TGATTTACACGCCTATTTAAACCAGAAAGGAGAGTTGGATGAGATTAGAA

AAATAGGAGATTATAACAAAAAAGTTTTTGAAGCAATGGGGTTAAAGGCA

AAATATGTTTATGGAAGTGAATTCCAGCTTGATAAGGATTATACACTGAA

TGTCTATATTGGCTTTAAAAACTACCTTAAAAAGAGCAAGAAGGAGTA

TGGAACTTATAGCAAGAGAGGATGAAAATCCAAAGGTTGCTGAAGTTATC

TATCCAATAATGCAGGTTAATGGTTGTCATTATAGGGGCGTTGATGTTGC

TGTTGGAGGGATGGAGCAGAGAAAAATACACATGTTAGCAAGGGAGCTTT

TACCAAAAAAGGTTGTTTGTATTCACAACCCTGTCTTAACGGGTTTGGAT

GGAGAAGGAAAGATGAGTTCTTCAAAAGGGAATTTTATAGCTGTTGATGA

-continued
```
CTCTCCAGAAGAGATTAGGGCTAAGATAAAGAAAGCATACTGCCCAGCTG

GAGTTGTTGAAGGAAATCCAATAATGGAGATAGCTAAATACTTCCTTGAA

TATCCTTTAACCATAAAAAGGCCAGAAAAATTTGGTGGAGATTTGACAGT

TAATAGCTATGAGGAGTTAGAGAGTTTATTTAAAAATAAGGAATTGCATC

CAATGCGCTTAAAAAATGCTGTAGCTGAAGAACTTATAAAGATTTTAGAG

CCAATTAGAAAGAGATTATAATAA.
```

TABLE 2

Amino acid sequence of proteins used in this study

| Protein name | Amino acid sequence (* denotes the TAG codon encoding for nsAAs) |
|---|---|
| GFP(3TAG) | SKGEELFTGVVPILVELDGDVNGHKFSVRGEGEGDAT\*GKLTLKFICTTGKLPVPWPTLVTTLTYGVQCFSRYPDHMKRHDFFKSAMPEGYVQERTISFKDDGTYKTRAEVKFEGDTLVNRIELKGIDFKEDGNILGHKLEYNFNSHNV\*ITADKQKNGIKANFKIRHNVEDGSVQLADH\*QQNTPIGDGPVLLPDNHYLSTQSVLSKDPNEKRDHMVLLEFVTAAGITHGMDELYKGS (SEQ ID NO: 29). |
| GFP-WT | SKGEELFTGVVPILVELDGDVNGHKFSVRGEGEGDATNGKLTLKFICTTGKLPVPWPTLVTTLTYGVQCFSRYPDHMKRHDFFKSAMPEGYVQERTISFKDDGTYKTRAEVKFEGDTLVNRIELKGIDFKEDGNILGHKLEYNFNSHNVYITADKQKNGIKANFKIRHNVEDGSVQLADHYQQNTPIGDGPVLLPDNHYLSTQSVLSKDPNEKRDHMVLLEFVTAAGITHGMDELYKGS (SEQ ID NO: 30). |
| ELP(10TAG)-GFP | SKGPG(VPGGGVPGAGVPG*G)$_{10}$PGGGG-(GFP-WT) (SEQ ID NO: 31). |
| ELP(10Tyr)-GFP | SKGPG(VPGGGVPGAGVPGYG)$_{10}$PGGGG-(GFP-WT) (SEQ ID NO: 32). |
| ELP(30TAG)-GFP | SKGPG(VPGGGVPGAGVPG*G)$_{30}$PGGGG-(GFP-WT) (SEQ ID NO: 33). |
| ELP(30Tyr)-GFP | SKGPG(VPGGGVPGAGVPGYG)$_{30}$PGGGG-(GFP-WT) (SEQ ID NO: 34). |
| ELP(10TAG)-GFP$_{MS}$ | SKGPG(KVPGAGVPG*GVPGVG)$_{10}$PGGGG-(GFP-WT) (SEQ ID NO: 35). |

Results

Experiments were designed to characterize the ability of a known OTS34 to incorporate three, ten and 30 nsAAs per protein in the GRO. nsAA incorporation (at three UAGs) was previously characterized in the GRO and demonstrated reduced natural suppression and elimination of protein truncation in this strain compared with WT or other RF1 deficient strains (Lajoie, et al., *Science*, 342: 357-60 (2013)). In this study, three fluorescent protein standards were constructed: a superfolder GFP (Pedelacq, et al., *Nat Biotechnol*, 24:79-88 (2006)) containing three TAG codons at positions 39, 151 and 182 (GFP(3TAG)), and two ELP-GFP fusion proteins where the ELP construct is fused to the N-terminus of superfolder GFP and contains 10 (ELP(10TAG)-GFP) or 30 (ELP(30TAG)-GFP) TAG codons. The TAG codons were positioned at the guest residue of the ELP sequence in every third pentapeptide repeat, and control (wild-type, WT) proteins with no TAGs were similarly constructed (FIG. 1A). Next, the GRO24 were co-transformed with the plasmid containing a reporter gene and an OTS plasmid (Young, et al., *J Mol Biol*, 395:361-74 (2010)) containing an AARS:tRNA pair previously engineered for incorporation of p-acetyl-L-phenylalanine (pAcF), that is also able to incorporate p-azido-L-phenylalanine (pAzF) (Young, et al., *Biochemistry*, 50:1894-900 (2011)).

Figure 1B:
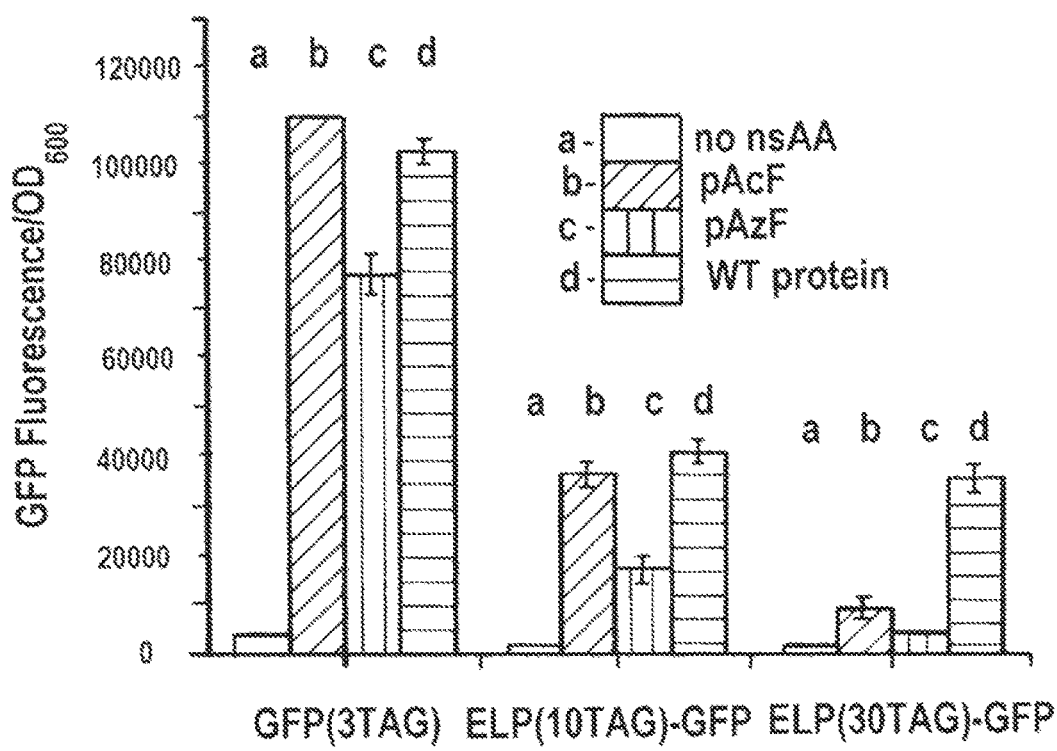
FIG. 1B is bar graph showing GFP fluorescence (/OD600) in wildtype and reporter protein incorporating no non-standard amino acids, or three, ten, or 30 pAcF or pAzF, in a single protein by the plasmid-based *M. jannaschii* derived pAcF OTS in the GRO.

Although a reduction in the fluorescence signal intensity for ELP-GFP fusion protein compared with GFP (with no ELP fusion), all fusion proteins resulted in quantifiable signals. GFP fluorescence assays indicated that multi-site pAcF incorporation in the recoded strain produced 110%, 87% and 25% of pAcF containing GFP(3TAG), ELP(10TAG)-GFP and ELP(30TAG)-GFP fluorescence, respectively, and 75%, 32% and 6% of pAzF containing GFP(3TAG), ELP(10TAG)-GFP and ELP(30TAG)-GFP compared to WT-proteins (FIG. 1B). Similarly, the yield of purified ELP(30TAG)-GFP containing pAcF expressed in small batch cultures was 18% and 8% compared to expression of WT protein in the GRO or parent (non-recoded) strain, respectively (Table 3). The yield of pAzF containing ELP(30TAG)-GFP in the GRO was too low to allow for purification. Based on these results additional experiments were designed to determine if further evolution of the OTSs could enhance the yield of polypeptides containing multiple instances of pAcF or pAzF.

TABLE 3

Yield of purified ELP(30TAG)-GFP expressed in the GRO by various OTSs in the presence of nsAAs.

| OTS | Yield (mg/L) | nsAA | strain |
|---|---|---|---|
| pAcFRS* | 3.04 ± 1.4 | pAcF | Non-recoded *E. coli* |
| WT-TyrRS** | 38.7 ± 4.3 | pAcF | Non-recoded *E. coli* |
| pAcFRS | 10.5 ± 5.5 | pAcF | GRO |
| pAcFRS | N.D.*** | pAzF | GRO |
| pAzFRS | N.D.*** | pAzF | GRO |
| pAcFRS.1.t1 | 52.6 ± 6.3 | pAcF | GRO |
| pAzFRS.2.t1 | 39.05 ± 3.4 | pAcF | GRO |
| pAzFRS.2.t1 | 41.9 ± 6 | pAzF | GRO |
| pAcFRS.2.t1 | 64.5 ± 9.7 | BuY | GRO |
| pAcFRS.2.t1 | 53 ± 5.4 | 4CF3F | GRO |
| pAzFRS.2.t1 | 48.2 ± 11.2 | 4ClF | GRO |
| WT-TyrRS** | 67.7 ± 6.2 | No nsAA | GRO |
| WT-TyrRS** | 58.7 ± 5 | pAcF | GRO |
| WT-TyrRS** | 61.4 ± 10.1 | pAzF | GRO |

*Expression too low to allow sufficient purification for A280 measurement, therefore protein quantity was estimated based on fluorescence of semi-purified protein extracts.
**WT ELP(30Tyrosine)-GFP proteins contain no TAGs and were expressed using *E. coli* native translation machinery. However, expression of ELP(30Tyrosine)-GFP was measured in the presence of pAcF or pAzF to assess for potential toxic effects of these nsAAs on protein expression.
***N.D.: expression too low to allow purification of reporter protein via ITC.

Data is reported as mean±s.d. calculated from purification of three independently grown cultures.

Example 2: Chromosomal Integration of an OTS Highlights Enzyme Inefficiency

Materials and Methods

Assembly of OTS Integration Cassette

To generate an OTS integration cassette, previously published 34 p-acetyl-L-phenylalanine AARS (pAcFRS) gene downstream of the araBAD promoter, a constitutive tRNACUA under the control of the proK promoter and a tolC expression cassette were amplified using primers containing genomic homology regions or terminal sequence overlaps for Gibson Assembly (Gibson, et al., *Nature Methods*, 6:343-U41 (2009)). The integration cassette was then assembled using Gibson Assembly® Master Mix (New England Biolabs) according to the manufacturer instructions. The OTS integration cassette was then amplified by PCR consisting of 2 µl of the of Gibson Assembly product, 10 pmol each of sense and antisense DNA primers, 50 µl, Hot-Start HiFi Mastermix enzyme (Kapa Biosystems) and water for a final volume of 100 µL. The PCR reaction conditions were 95° C. for 2 min for initial denaturation, followed by 30 cycles at 98° C. for 30 s, 65° C. for 30 s and 72° C. for 5 min. The resulting PCR product visualized on a 1% agarose gel stained with SYBR® Safe DNA stain (Invitrogen) and the correct size band was excised and purified using a gel extraction kit (Qiagen). Genomic integration of OTS cassette to the GRO (*E. coli* C321.ΔA, CP006698.1, GI:54981157) was performed with 100 ng of the DNA cassette as described (Murphy, et al., *Journal of Bacteriology*, 180:2063-2071 (1998)). Colonies were screened for correct integration by colony-PCR and verified by Sanger sequencing.

Results

Figure 1C:
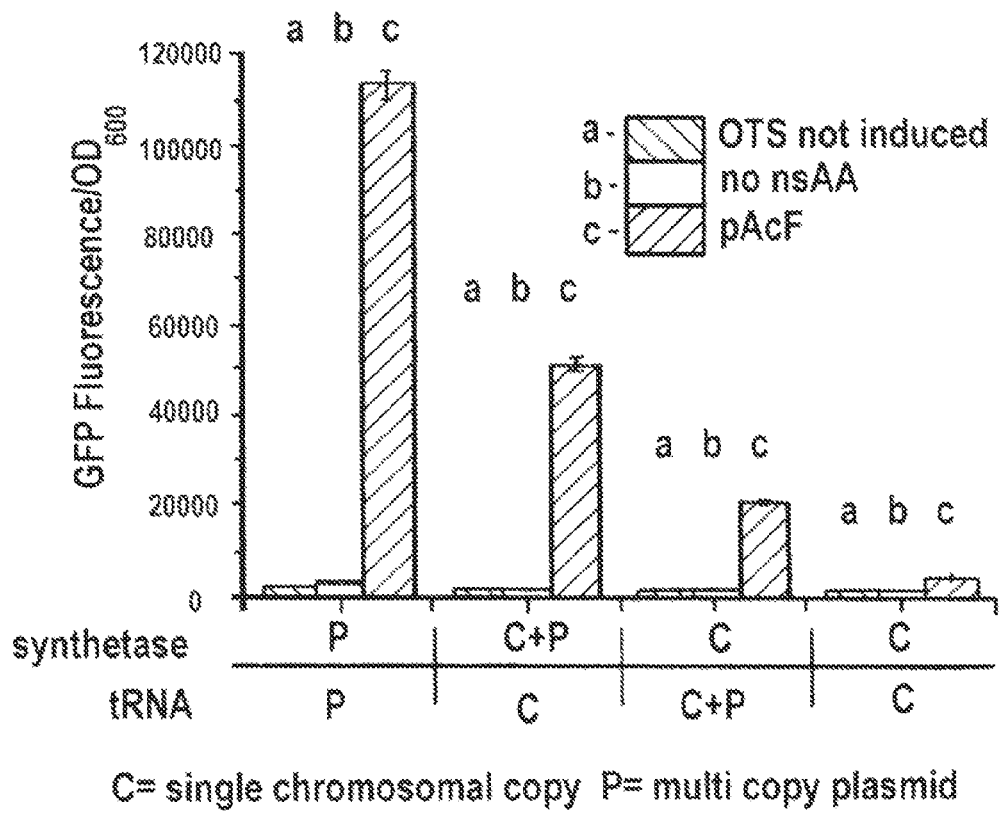
FIG. 1C is a bar graph showing production of superfolder GFP (GFP fluorescence/OD600)) containing three TAG sites (GFP(3TAG)) by pAcFRS and tRNA$_{CUA}$ expressed by plasmid or chromosomal integration and compared to controls (without OTS, and no nsAA).
Figure 1D:
FIG. 1D is a schematic illustration of a DNA cassette based on a previously published OTS plasmid (Young, et al., *J. Mol. Biol.* 395, 361-74 (2010)) for chromosomal integration and subsequent MAGE evolution. The illustrated cassette includes a *M. jannaschii* based p-acetyl-L-phenylalanine AARS (pAcFRS) gene downstream of the araBAD promoter, a constitutive tRNA$_{CUA}$ under the control of the proK promoter, and a tolC selection marker.

A GRO strain containing a chromosomally integrated OTS (AARS:tRNA pair) was constructed to enable MAGE-based evolution of the AARS and to characterize the performance of an OTS in this context. Toward this end, a DNA cassette based on the pAcF OTS plasmid above (Young, et al., *J Mol Biol*, 395:361-74 (2010)) was assembled, consisting of an inducible *M. jannaschii* based pAcF AARS (pAc-FRS), a constitutive tRNACUA, and a tolC selection marker (FIG. 1D). This DNA cassette was genomically integrated using λRed recombination (Sharan, et al., *Nat Protoc*, 4:206-23 (2009)) in a known intergenic region in the GRO. Subsequently, TAG codons were inserted by MAGE in four permissive sites in the tolC cassette, to enable negative selection (see sequences above).

Next, the effect of varying AARS (i.e., pAcFRS) and tRNA$_{CUA}$ concentration on GFP(3TAG) production in the GRO was analyzed. The reduction in copy number caused by genomic integration of the OTS resulted in a ~20 fold decrease in the yield of GFP(3TAG) in the RF1 deficient GRO, highlighting the impaired efficiency of this OTS (FIG. 1C). Individually increasing either pAcFRS or tRNA$_{CUA}$ concentration by supplementation with plasmids resulted in partial restoration of GFP(3TAG) expression (FIG. 1C), indicating impaired binding of pAcFRS to pAcF and to its cognate tRNA$_{CUA}$. This is possible because the MjTyrRS from which the pAcFRS was originally evolved natively recognizes the GUA anticodon (Young, et al., *J Mol Biol*, 395:361-74 (2010)). These results indicate that elevated levels of pAcFRS and tRNA$_{CUA}$ expression are needed to compensate for their reduced enzymatic activity.

Example 3: Evolution of Orthogonal Translation Systems In Vivo

Materials and Methods

MAGE Evolution of OTSs

Liquid cell cultures were inoculated from colonies grown at 30° C. to mid-logarithmic growth (optical density at 600 nm of ~0.7) in a shaking incubator. To induce expression of the lambda-red recombination proteins (Exo, Beta and Gam), cell cultures were shifted to 42° C. for 15 min and then immediately chilled on ice. In a 4° C. environment, 1 ml of cells was centrifuged at 16,000 g for 30 s. Supernatant medium was removed and cells were resuspended in milli-Q water. The cells were spun down, the supernatant was removed, and the cells were washed a second time. After a final 30 s spin, supernatant water was removed and oligos prepared at a concentration of 5-6 µM in DNAase-free water were added to the cell pellet. The oligos/cells mixture was transferred to a pre-chilled 1 mm gap electroporation cuvette (Bio-Rad) and electroporated under the following parameters: 1.8 kV, 200V and 25 mF. LB-min medium (3 ml) was immediately added to the electroporated cells. The cells were recovered from electroporation and grown at 30° C. for 3-3.5 h. Once cells reached mid-logarithmic growth they were used in additional MAGE cycles, isolated, or assayed for genotype and/or phenotype analysis.

Negative Selection

Following the last MAGE cycle, cultures were immediately resuspended in 1 ml of LB-min medium containing 0.2% arabinose and colicin E1. After 8 hours of incubation at 34° C., cells were transferred to 3 ml of LB-min medium, grown to an OD600 of 1.0 in a shaking incubator at 250 r.p.m, and frozen in glycerol.

Flow Cytometry Analysis and Cell Sorting

GFP expression was induced as above. Following ~16 h of induction, cells were washed in PBS and diluted 1:100 in PBS. Cell fluorescence analysis and sorting was performed using a FACS-Aria flow cytometer (BD-Biosciences) and FACS Diva software. Sorted fractions were recovered for 1 h in 0.5-1 ml LBmin media before small aliquots were plated on LBmin plates supplemented with 30 µg/ml kanamycin for individual colony analysis. The remaining mixed culture was grown to confluence in LBmin media with 30 µg/ml Kanamycin and frozen at −80° C. to maintain diversity.

AARS Expression and Purification

The genes of pAcFRS variants were cloned into pET15a and transformed into Rosetta cells for expression. For each variant, the expression strain was grown on 500 ml of LB media supplemented with 100 µg/ml ampicillin at 37° C. to an OD600 of 0.6-0.8 and the protein expression was induced by the addition of 0.5 mM isopropyl β-D-thiogalactopyranoside. Cells were incubated at 30° C. for an additional 3 h and harvested by centrifugation at 5000×g for 10 min at 4° C. The cell paste was suspended in 15 ml of lysis buffer [50 mM Tris (pH 7.5), 300 mM NaCl, 20 mM imidazole] and lysed by sonication. The crude extract was centrifuged at 30,000×g for 30 min at 4° C. The soluble fraction was loaded onto a column containing 2 ml of Ni-NTA resin (Qiagen) previously equilibrated with 20 ml lysis buffer. The column was washed with 20 ml lysis buffer, and the bound protein was then eluted with 2 ml of 50 mM Tris (pH 7.5), 300 mM NaCl, 300 mM imidazole. Purified proteins were dialyzed with 50 mM HEPES-KOH (pH 7.5), 50 mM KCl, 1 mM DTT and 50% glycerol, and stored at −80° C. for further studies.

Results

Figure 2B:
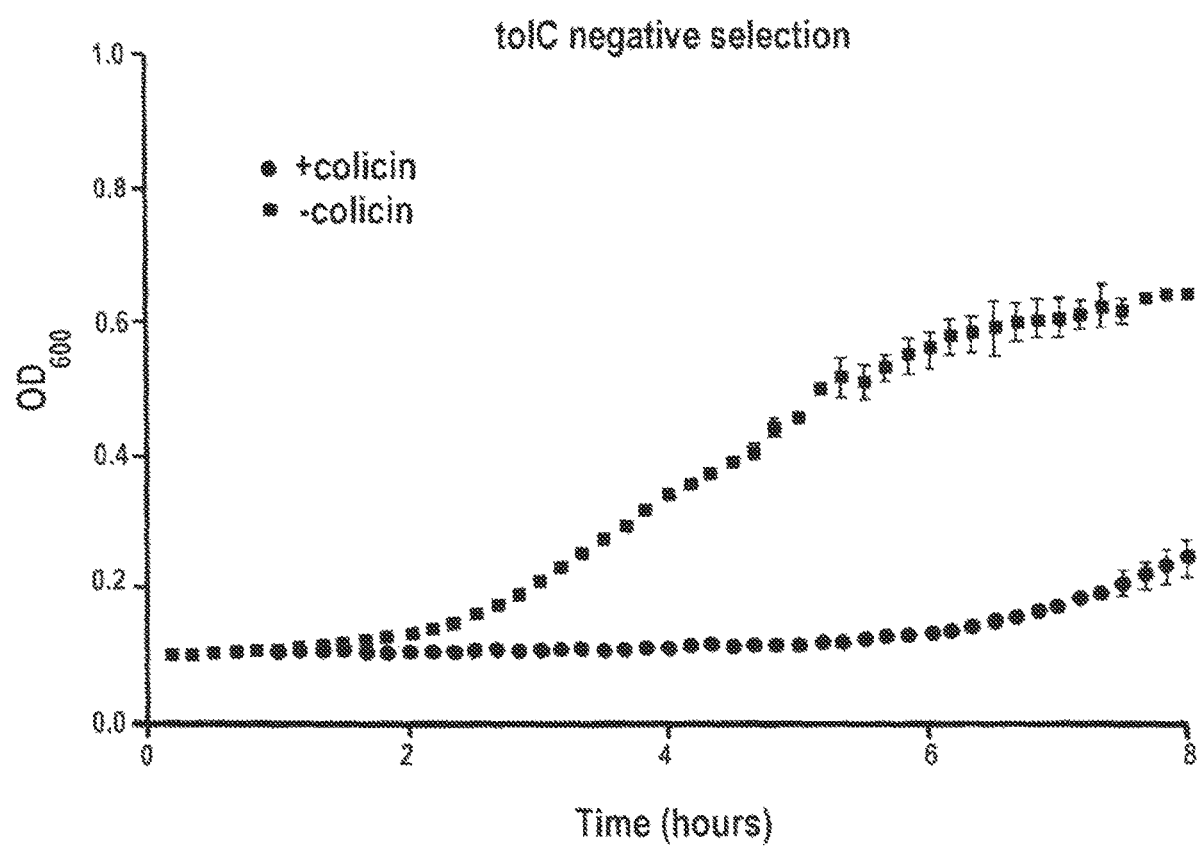
FIG. 2B is a graph showing TolC based negative selection in the presence of pAcF and the induced pAcF-OTS as measured by OD600 over time (hours) of *E. coli* grown in the presence or absence of colicin. The pAcF-OTS incorporates pAcF in all 4 UAG codons in the tolC transcript, full tolC protein is expressed and cells are rendered susceptible to the toxin colicin E1, demostrating the principle of using tolC as a negative selection marker to eliminate promiscuous OTSs.

MAGE was previously shown to generate a genomic library of ribosome binding site sequences, in which genetic diversity can be increased simply by increasing the number of MAGE cycles (Wang, et al., *Nature*, 460:894-8 (2009)). Here, a MAGE-based platform was developed for evolution of protein (i.e., AARS) function in vivo to alter molecular recognition of ligands (e.g., nsAA) and domains that govern bimolecular interactions (e.g., AARS-tRNA interface). The platform included the construction of a GRO strain containing a chromosomal OTS and negative and positive selection markers to enable evolution by continuous rounds of diversification and selection (FIG. 2A). To generate an AARS library via MAGE, a pool of synthetic ssDNA oligonucleotides was designed to mutagenize the selected amino acid targets, and five rounds of MAGE were employed to diversify the library. The resulting cell population was then subjected to a tolC-based negative selection step (DeVito, et al., *Nucleic Acids Research*, 36 (2008)) wherein mutated AARS variants capable of mischarging tRNA$_{CUA}$ with natural amino acids permitted read-through of a tolC construct containing four TAG sites, rendering the organism sensitive to colicin E1 (FIG. 2B). Thus, the negative selection marker is dormant unless colicin E1 is present, eliminating the need to replace or modify the cellular host for positive selection.

The remaining orthogonal library was subsequently screened for improved GFP(3TAG) production in the presence of either pAcF or pAzF. AARS variants with improved performance were then isolated from the heterogeneous population by FACS. Finally, biochemical and proteomic analyses were performed and the resulting isolated variants were evaluated for their ability to produce proteins containing up to 30 instances of pAcF or pAzF, as well as 236 other nsAAs. This workflow was designed for streamlined selection of diversified populations or further diversification of selected mutants to improve or tune the properties of selected AARSs for a variety of nsAAs (FIG. 2A).

Example 4: Evolution of Chromosomally Integrated AARSs Variants with Improved Efficiency Materials and Methods
ATP-PPi Exchange Assay
A 25 µl ATP-PPi exchange reaction contained the following components: 100 mM HEPES-KOH (pH 7.5), 30 mM KCl, 10 mM $MgCl_2$, 2 mM DTT, 2 mM KF, 2 mM NaPPi, 5 mM ATP, 5 mM enzyme, 2 µCi/µl of [γ-32P]-labeled ATP (PerkinElmer) and varied concentrations of amino acids (0.25, 0.5, 1.25, 2.5, 5, 10, and 20 mM, respectively). The reactions were incubated at 37° C. Time points were taken at 2 minutes, 5 minutes and 10 minutes by plotting 1 µl aliquots from the reaction immediately to the PEI-cellulose plates (Merck). For each reaction, 1 µl of blank reaction mixture containing no enzymes was set as background. The reaction mixtures were separated on the plates in 1 M urea and 1 M monopotassium phosphate. The plates were then scanned in a Molecular Dynamics Storm 860 phosphorimager (Amersham Biosciences). The ratio of ATP to PPi was determined to monitor reaction progress. The kinetic constants were derived from plotting initial velocity of a series of reactions that contained varied concentrations of amino acids. The data were analyzed by GraFit 5.0 (Erithacus Software).

tRNA Transcription and Purification
Template plasmid containing tRNA gene was purified with the plasmid maxi kit (Qiagen), and 100 µg of plasmid was digested with BstNI (New England Biolabs). The BstNI digested template DNA was purified by phenol chloroform extraction, followed by ethanol precipitation and resolved in double distilled water. A His-tagged T7 RNA polymerase was purified over column of Ni-NTA resin according to manufacturer's instructions (Qiagen). The transcription reaction [40 mM Tris (pH 8); 4 mM each of UTP, CTP, GTP, and ATP at pH 7.0; 22 mM MgCl2; 2 mM spermidine; 10 mM DTT; 6 µg pyrophosphatase (Roche Applied Science); 60 µg/mL BstNI digested DNA template, approximately 0.2 mg/ml T7 RNA polymerase] was performed in 10 ml reaction volumes for overnight at 37° C. The tRNA was purified on 12% denaturing polyacrylamide gel containing 8 M urea and TBE buffer (90 mM Tris, 90 mM boric acid, 2 mM EDTA). UV shadowing illuminates the pure tRNA band, which is excised and extracted three times with 1M sodium acetate pH 5.3 at 4° C. The tRNA extractions were then ethanol precipitated, dissolved in RNase-free distilled water, pooled, and finally desalted using a Biospin 30 column (BioRad). The ratio of aminoacylated tRNA to total tRNA was determined to monitor reaction progress.

tRNA Folding and P32 Labeling
The tRNA was refolded by heating to 100° C. for 5 min and slow cooling to room temperature. At 65° C., $MgC_{12}$, was added to a final concentration of 10 mM to aid folding. A His-tagged CCA adding enzyme was purified over column of Ni-NTA resin according to manufacturer's instructions (Qiagen). 16 µM folded tRNA in 50 mM Tris (pH 8.0), 20 mM $MgCl_2$, 5 mM DTT and 50 µM NaPPi was incubated at room temperature for 1 hour with approximately 0.2 mg/ml CCA-adding enzyme and 1.6 µCi/µl of [α-32P]-labeled ATP (PerkinElmer). The sample was phenol/chloroform extracted and then passed over a Bio-spin 30 column (Bio-Rad) to remove excess ATP.

Aminoacylation Assay
A 20 µl aminoacylation reaction contained the following components: 50 mM HEPES-KOH (pH 7.2), 25 mM KCl, 10 mM $MgCl_2$, 5 mM DTT, 10 mM ATP, 25 µg/ml pyrophosphatase (Roche Applied Science), 2 mM amino acids. All plateau tRNA aminoacylation levels were determined at 37° C. according to the reactions conditions described above with 500 nM enzyme, 5 µM unlabeled tRNA plus 100 nM 32P-labeled tRNA. Time points were taken at 5 minutes, 20 minutes and 60 minutes by removing 2 µl aliquots from the reaction and immediately quenching the reaction into an ice-cold 3 µl quench solution [0.66 µg/µl nuclease P1 (Sigma) in 100 mM sodium citrate (pH 5.0)]. For each reaction, 2 µl of blank reaction mixture containing no enzymes was added to the quench solution as the start time point. The nuclease P1 mixture was then incubated at room temperature for 30 min and 1 µl aliquots were spotted on PEI-cellulose plates (Merck) and developed in running buffer containing 5% acetic acid and 100 mM ammonium acetate. Radioactive spots for AMP and AA-AMP (representing free tRNA and aminoacyl-tRNA, respectively) were separated and then visualized and quantified by phosphor imaging by a Molecular Dynamics Storm 860 phosphorimager (Amersham Biosciences). The ratio of aminoacylated tRNA to total tRNA was determined to monitor reaction progress.

Synthetic Degenerate ssDNA Oligonucleotides
These oligos were utilized in the evolution of the AARS nsAA binding pocket (top) and the AARS-tRNA interface (bottom). Single-stranded DNA Oligonucleotides were purchased from Integrated DNA Technologies (IDT) with two phosphothioate bonds at the 5' (as denoted by *). The degenerate base n represents all four bases, while k represents G/T.

TABLE 4

Degenerate ssDNA MAGE oligonucleotides used in this study

| Targeted Residues in nsAA binding pocket | Oligonucleotide sequence |
|---|---|
| L32, G34 | a*a*gagttaagagaggttttaaaaaaagatgaaaaatctgctnnka tannktttgaaccaagtggtaaaatacatttagggcattatctcc (SEQ ID NO: 36) |
| L65, A67 | a*g*atgattgatttacaaaatgctggatttgatataattatannkttgn nkgatttacacgcctatttaaaccagaaaggagagttggatg (SEQ ID NO: 37) |

TABLE 4-continued

Degenerate ssDNA MAGE oligonucleotides used in this study

| | |
|---|---|
| E107, F108, Q109 | t*t*tttgaagcaatggggttaaaggcaaaatatgtttatggaagtnn knnknnkcttgataaggattatacactgaatgtctatagattgg (SEQ ID NO: 38) |
| Y151 | a*a*aagagcaagaaggagtatggaacttatagcaagagaggatg aaaatccaaaggttgctgaagttatcnnkccaataatgcaggttaat (SEQ ID NO: 39) |
| G158, C159, R162, A167 | c*c*aataatgcaggttaatnnknnkcattatnnkggcgttgatgtt nnkgttggagggatggagcagagaaaaatacacatgttagcaagg (SEQ ID NO: 40) |

| Targeted Residues in tRNA binding interface | Oligonucleotide sequence |
|---|---|
| R257, F261 | a*g*ctaaatacttccttgaatatcctttaaccataaaannkccagaaa aannkggtggagatttgacagttaatagctatgaggagttaga (SEQ ID NO: 41) |
| H283, M 285, R286 | t*a*tgaggagttagagagtttatttaaaaataaggaattgnnkccan nknnkttaaaaaatgctgtagctgaagaacttataaagatttta (SEQ ID NO: 42) |

Results

Figure 3A:
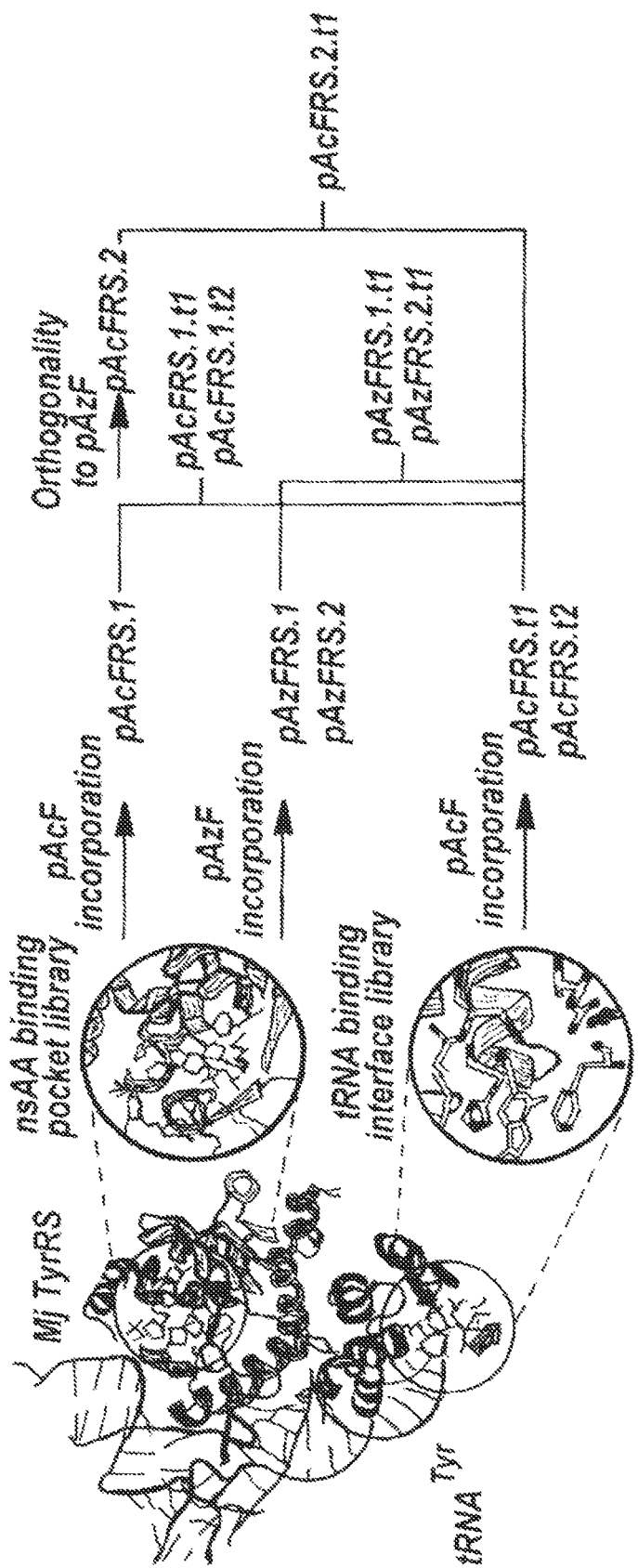
FIG. 3A is a crystal structure of MjTyrRS in complex with tRNA$_{CUA}$ and tyrosine. Insets highlight the amino acid binding pocket and the tRNA$_{CUA}$ anticodon binding interface with a schematic representation of the libraries generated from pAcFRS (a mutant of the MjTyrRS) and AARS variants isolated following each library diversification and selection steps.

To expand upon the diversity of AARS libraries created in previous studies (Wang, et al., *Proc Nad Acad Sci USA*, 100:56-61 (2003); Chin, et al., *J Am Chem Soc*, 124:9026-7 (2002)) and enable selection of AARS variants for pAcF, pAzF, and potentially other nsAAs, a previously reported crystal structure for the *M. jannaschii* TyrRS was used to inform the diversification of 12 residues in the amino acid binding pocket surrounding the variable side chain of the nsAA sites (compared with typically 6 or less residues (Park, et al., *Science*, 333:1151-4 (2011); Wang, et al., *Proc Natl Acad Sci USA*, 100:56-61 (2003); Schultz, et al., *J Am Chem Soc*, 128:13984-5 (2006)), with few exceptions targeting 9 residues (Cooley, et al., *Biochemistry* (2014); Miyake-Stoner, et al., *Biochemistry*, 49:1667-77 (2010)), and five residues at the AARS-tRNA$_{CUA}$ anticodon recognition interface (FIG. 3A). Synthetic degenerate ssDNA oligonucleotides were designed to randomize the residues in the nsAA binding pocket and AARS-tRNACUA binding interface separately (Table 4) to distinguish between improved nsAA binding as opposed to tRNA$_{CUA}$ recognition.

Orthogonal AARS libraries generated following MAGE and subsequent negative selection contained 29% and 43% mutated cells after five or nine MAGE cycles, respectively, with incorporation of 1-5 oligonucleotides per clone (Table 6). The diversified populations were screened by induction of GFP(3TAG) in the presence of pAcF or pAzF and two rounds of FACS were performed to isolate cells with improved AARS activity. The resulting subpopulations were plated to isolate and analyze individual colonies, and mutations in the AARS sequence of the selected variant were determined by Sanger sequencing. To verify that increased activity did not result from mutations to the host cell or other changes associated with the evolution process, the specific identified mutations were re-introduced (via MAGE) into the AARS in a clean GRO strain and repeated the evaluation of AARS activity in these strains.

The nsAA binding library was screened for enhanced GFP(3TAG) production in the presence of pAcF or pAzF and improved pAcFRS and pAzFRS variants were isolated (FIG. 3A, and Table 5 for a list of annotations and corresponding mutations).

Figure 3B:
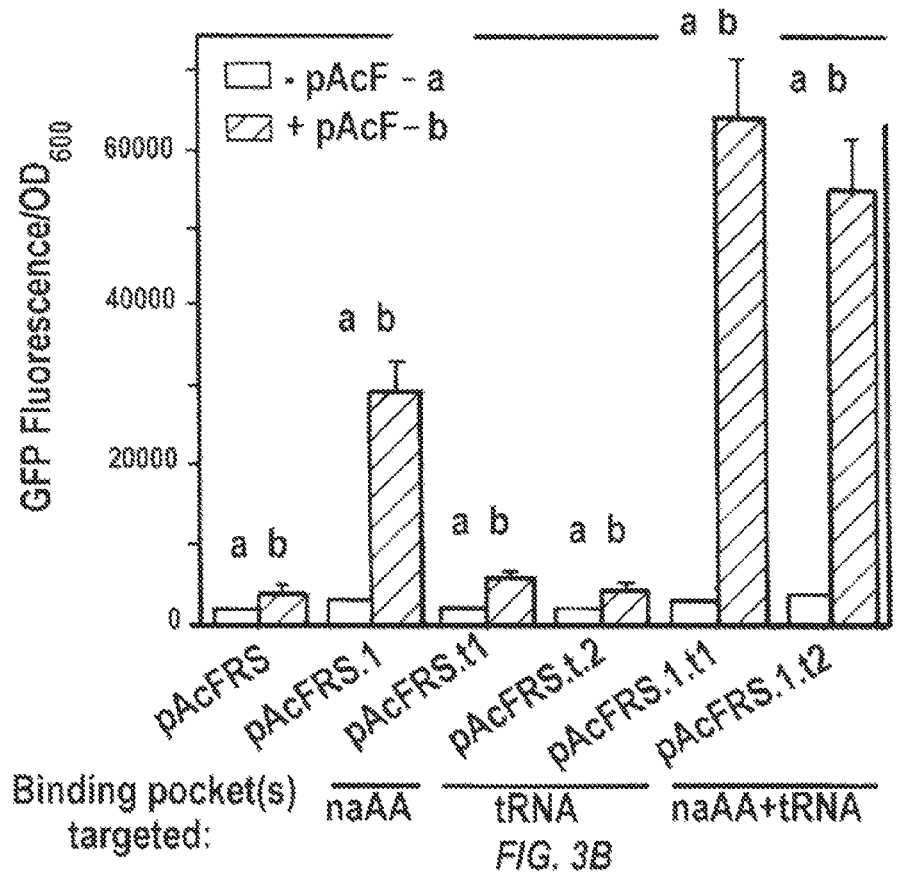
FIGS. 3B and 3C are bar graphs showing pAcFRS (3B) and pAzFRS variants (3C) assayed by GFP (3TAG) fluorescence (OD600).
Figure 3C:
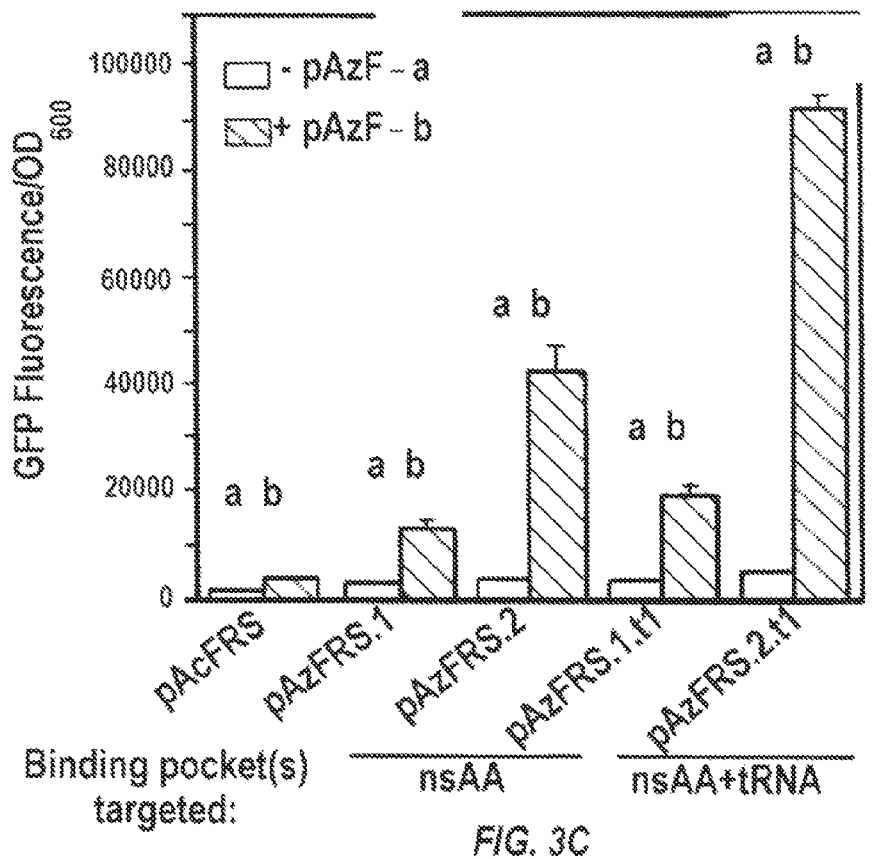

Individual colonies selected after FACS revealed a variant for improved pAcF incorporation (pAcFRS.1, A167D)) capable of ~8 fold higher GFP(3TAG) production compared with the progenitor enzyme, pAcFRS34 (FIG. 3B). In addition, individual colony analysis of sorted populations revealed two top variants for pAzF incorporation (pAzFRS.1 and pAzFRS.2, [D158V, I159M, L162D, A167Y] and [E107T, F108Y, Q109M] mutations, respectively) capable of producing ~3.5- and ~12-fold more GFP (3TAG) than the progenitor enzyme (FIG. 3c).

Similarly, screening of the library for AARS-tRNA$_{CUA}$ binding optimization (screened for enhanced GFP(3TAG) production with pAcF) revealed two mutants, pAcFRS.t1 and pAcFRS.t2 ([R257G] or [R257C, F261E] mutations, respectively), both exhibiting ~1.5 fold higher GFP(3TAG) production as compared to the progenitor enzyme (FIG. 3B). Mutations isolated for nsAA binding and tRNA binding via MAGE were combined, which produced variants pAcFRS.1.t1, pAcFRS.1.t2, pAzFRS.1.t1, and pAzFRS.2.t1. The chromosomally integrated variants harboring mutations for improved pAcF or pAzF and tRNA$_{CUA}$ binding resulted in a more than additive ~17-(pAcFRS.1.t1), ~15-(pAcFRS.1.t2), ~5.5-(pAzFRS.1.t1) and ~25-(pAzFRS.2.t1) fold increase in GFP(3TAG) production compared with the progenitor enzyme (FIG. 3b-c). Furthermore, correct incorporation of pAcF or pAzF into all three sites in GFP(3TAG) was confirmed by mass spectrometry (Table 7). In vitro biochemical analysis of nsAA aminoacylation and tRNA charging confirmed increased activity of the evolved variants compared with the progenitor enzyme (Tables 8 and 9). Amino acid activation increased 5.34-, 3.32-, and 2.02-fold for pAcFRS.1.t1, pAzFRS.1.t1 and pAzFRS.2.t1 respectively. Similarly, tRNA charging increased 9.58-, 3.29-, and 8.17-fold for pAcFRS.1.t1, pAzFRS.1.t1 and pAzFRS.2.t1 respectively

TABLE 5

Annotations of specific mutations in AARS variants (mutations in evolved synthetases are annotated with respect to the progenitor pAcFRS variant)

| Annotation | Mutant | Evolved for nsAA/tRNA |
|---|---|---|
| pAcFRS | pAcFRS (Young, et al., *J Mol Biol*, 395: 361-74 (2010)) | — |
| pAzFRS | pAzFRS (Schultz, et al., *J Am Chem Soc*, 128: 13984-5 (2006)) | — |
| pAcFRS.1 | A167D | pAcF |
| pAcFRS.t1 | R257G | tRNA |
| pAcFRS.t2 | R257C, F261E | tRNA |

TABLE 5-continued

Annotations of specific mutations in AARS variants (mutations in evolved synthetases are annotated with respect to the progenitor pAcFRS variant)

| Annotation | Mutant | Evolved for nsAA/tRNA |
|---|---|---|
| pAcFRS.1.t1 | A167D, R257G | pAcF + tRNA |
| pAcFRS.1.t2 | A167D, R257C, F261E | pAcF + tRNA |
| pAzFRS.1 | D158V, I159M, L162D, A167Y | pAzF |
| pAzFRS.1.t1 | D158V, I159M, L162D, A167Y, R257G | pAzF + tRNA |
| pAzFRS.1.t2 | D158V, I159M, L162D, A167Y, R257C, F261E | pAzF + tRNA |
| pAzFRS.2 | E107T, F108Y, Q109M | pAzF |
| pAzFRS.2.t1 | E107T, F108Y, Q109M, R257G | pAzF + tRNA |
| pAzFRS.2.t2 | E107T, F108Y, Q109M, R257C, F261E | pAzF + tRNA |
| pAcFRS.2 | L65V, A167D | pAcF |
| pAcFRS.2.t1 | L65V, A167D, R257G | pAcF + tRNA |
| pAcFRS.2.t2 | L65V, A167D, R257C, F261E | pAcF + tRNA |

TABLE 6

MAGE Results

| Strain | # of MAGE cycles | # of clones analyzed | # of unique clones identified | % unique clones | # of clones with observed n = 1-5 recombination events | | | | |
|---|---|---|---|---|---|---|---|---|---|
| | | | | | 1 | 2 | 3 | 4 | 5 |
| GRO | 5 | 254 | 75 | 29% | 47 | 18 | 7 | 1 | 2 |
| | 9 | 286 | 122 | 43% | 83 | 33 | 3 | 2 | 1 |
| | 15 | 285 | 80 | 28% | 49 | 22 | 7 | 2 | 0 |
| ECNR2 | 5 | 271 | 171 | 63% | 67 | 52 | 23 | 19 | 10 |
| | 9 | 279 | 200 | 72% | 80 | 60 | 46 | 10 | 4 |
| | 15 | | | | | | | | |

TABLE 7

Confirmation of nsAA incorporation in GFP(3TAG) via mass spectrometry

| Mutant | nsAA | Theoretical amu | Experimental amu |
|---|---|---|---|
| Progenitor pAcFRS | pAcF | 27726.88 | 27724.27 |
| pAcFRS.1.t1 | pAcF | 27726.88 | 27724.92 |
| pAcFRS.2.t1 | pAcF | 27726.88 | 27725.21 |
| pAzFRS.1.t1 | pAzF | 27723.88 | 27722.06 |

Theoretical amu for WT SF-GFP=27648.83; Δ(WT, pAcF)=78.05 amu; Δ(WT, pAzF)=75.05 amu. Calculated mass accuracy (based on known standards)=0.3 ppm

TABLE 8

Pyrophosphate exchange kinetics of amino acids activation by progenitor (pAcFRS), and evolved pAcFRS and pAzFRS variants.

| nsAA | Annotation | $k_{cat}$ (×10$^{-2}$ s$^{-1}$) | $K_{m, nsAA}$ (mM) | $k_{cat}/K_{m, nsAA}$ (s$^{-1}$ M$^{-1}$) | Fold change |
|---|---|---|---|---|---|
| Tyrosine | WTmjYRS | 52.2 ± 4.1 | 0.076 ± 0.030 | 6868 | 1007 |
| pAcF | pAcFRS | 5.01 ± 0.48 | 7.34 ± 1.62 | 6.82 | 1 |
| | pAcFRS.1 | 6.84 ± 0.64 | 2.16 ± 0.72 | 31.7 | 4.64 |
| | pAcFRS.t1 | 6.92 ± 1.27 | 9.17 ± 3.67 | 7.54 | 1.11 |
| | pAcFRS.t2 | 6.67 ± 1.27 | 8.59 ± 3.23 | 7.76 | 1.14 |
| | pAcFRS.1.t1 | 6.12 ± 0.74 | 1.68 ± 0.78 | 36.4 | 5.34 |
| | pAcFRS.1.t2 | 6.30 ± 0.46 | 1.69 ± 0.44 | 37.3 | 5.47 |
| | pAzFRS.1 | ND | ND | ND | ND |
| | pAzFRS.1.t1 | ND | ND | ND | ND |
| | pAcFRS.2 | 5.28 ± 0.79 | 3.13 ± 1.73 | 16.9 | 2.48 |
| | pAcFRS.2.t1 | 5.43 ± 0.54 | 2.81 ± 0.89 | 19.3 | 2.84 |
| pAzF | pAcFRS | 4.45 ± 0.13 | 3.04 ± 0.27 | 14.6 | 1 |
| | pAzFRS.2 | 4.13 ± 0.86 | 1.25 ± 0.11 | 33.0 | 2.26 |
| | pAzFRS.2.t1 | 4.14 ± 0.23 | 1.40 ± 0.35 | 29.5 | 2.02 |
| | pAzFRS.1 | 4.61 ± 0.18 | 1.18 ± 0.21 | 39.1 | 2.68 |
| | pAzFRS.1.t1 | 4.79 ± 0.67 | 0.99 ± 0.13 | 48.4 | 3.32 |
| | pAcFRS.1 | 3.50 ± 0.20 | 1.74 ± 0.39 | 20.1 | 1.37 |
| | pAcFRS.1.t1 | 3.65 ± 0.62 | 1.49 ± 0.11 | 24.5 | 1.68 |
| | pAcFRS.2 | 4.08 ± 0.20 | 6.40 ± 0.78 | 6.38 | 0.44 |
| | pAcFRS.2.t1 | 4.22 ± 0.45 | 6.59 ± 1.70 | 6.40 | 0.44 |

*ND: Not detected. The means and standard deviations were calculated in triplicates.

TABLE 9

Kinetic parameters of tRNA aminoacylation by progenitor (pAcFRS), and evolved pAcFRS and pAzFRS variants.

| nsAA | Annotation | $k_{cat}$ ($\times 10^{-3}$ s$^{-1}$) | $K_{m, tRNA}$ (μM) | $k_{cat}/K_{m, tRNA}$ (s$^{-1}$ M$^{-1}$) | Fold change |
|---|---|---|---|---|---|
| Tyrosine | WTmjYRS | 130 ± 22 | 23 ± 3 | 5652 | 774 |
| pAcF | pAcFRS | 0.25 ± 0.04 | 34 ± 6 | 7.3 | 1 |
| | pAcFRS.1 | 1.21 ± 0.24 | 36 ± 7 | 33.6 | 4.60 |
| | pAcFRS.t1 | 0.22 ± 0.02 | 17 ± 3 | 12.9 | 1.77 |
| | pAcFRS.t2 | 0.27 ± 0.07 | 29 ± 3 | 9.3 | 1.27 |
| | pAcFRS.1.t1 | 1.12 ± 0.14 | 16 ± 4 | 70.0 | 9.58 |
| | pAcFRS.1.t2 | 1.03 ± 0.06 | 27 ± 3 | 38.1 | 5.22 |
| | pAzFRS.1 | ND | ND | ND | ND |
| | pAzFRS.1.t1 | ND | ND | ND | ND |
| | pAcFRS.2 | 0.58 ± 0.09 | 31 ± 7 | 18.7 | 2.56 |
| | pAcFRS.2.t1 | 0.54 ± 0.15 | 18 ± 2 | 30.0 | 4.10 |
| pAzF | pAcFRS | 0.23 ± 0.03 | 34 ± 7 | 6.2 | 1 |
| | pAzFRS.2 | 0.73 ± 0.06 | 32 ± 11 | 22.8 | 3.67 |
| | pAzFRS.2.t1 | 0.71 ± 0.13 | 14 ± 3 | 50.7 | 8.17 |
| | pAzFRS.1 | 0.46 ± 0.18 | 38 ± 5 | 9.2 | 1.48 |
| | pAzFRS.1.t1 | 0.49 ± 0.17 | 24 ± 3 | 20.4 | 3.29 |
| | pAcFRS.1 | 0.65 ± 0.20 | 31 ± 9 | 20.9 | 3.38 |
| | pAcFRS.1.t1 | 0.63 ± 0.12 | 16 ± 1 | 39.3 | 6.33 |
| | pAcFRS.2 | 0.18 ± 0.02 | 33 ± 8 | 5.5 | 0.88 |
| | pAcFRS.2.t1 | 0.22 ± 0.05 | 24 ± 7 | 9.2 | 1.47 |

*ND: Not detected. The means and standard deviations were calculated in triplicates.

Example 5: Evolution of Chromosomally Integrated AARSs Variants with Tunable nsAA Specificities

Materials and Methods
Non-Standard Amino Acids

TABLE 10 nsAA Library used in this Study

| Class | Side Chain Property | Type of Amino acid analogs | Numbers of nsAAs |
|---|---|---|---|
| Class I | Ia: Aliphatic Non-polar | Glycine, Alanine, Valine, Leucine, and Isoleucine | 43 |
| | Ib: Aliphatic Polar and Sulfur containing | Serine, Threonine, Aspartate, Asparagine, Glutamate, Glutamine, Lysine, Arginine, Cysteine and Methionine | 87 |
| Class II | Aromatic[b] | Tyrosine, Phenylalanine, Histidine and Tryptophan | 121 |
| Class III | Cyclic | Proline | 7 |

Classification of nsAA Library used in this Study[a]

[a]298 members are in the nsAA library (included 20 natural amino acids)

[b]Aromatic amino acids contain 107 Phe analogs, 25 Tyr analog, 11 His analog and 18 Trp Analog including 40 repeated entries (Phe and Tyr analogs). The Phe/Tyr analogs in the library were chosen based on the chemical structures of Phe analogs encoded by evolved MjTyrRS/tRNA$^{Tyr}_{CUA}$ and MmPylRS/tRNA$^{Pyl}_{CUA}$ pairs.

TABLE 11

List of nonstandard amino acids used in this study

| Position | Name | NAA Name | IUPAC Name | CAS Number |
|---|---|---|---|---|
| A1 | Control | — | — | — |
| B1 | CbzK | N$^\varepsilon$-Carbobenzoxy-L-lysine | (S)-2-Amino-6-(phenylmethoxycarbonyl amino)hexanoic acid | 1155-64-2 |
| C1 | mK | N$^\varepsilon$-Methyl-L-lysine hydrochloride | (S)-2-Amino-6-(methylamino)hexanoic acid hydrochloride | 7622-29-9 |
| D1 | 2mK | N$^\varepsilon$,N$^\varepsilon$-Dimethyl-L-lysine hydrochloride | (S)-2-Amino-6-(dimethylamino)hexanoic acid hydrochloride | 2259-86-1 |
| E1 | 3mK | N$^\varepsilon$,N$^\varepsilon$,N$^\varepsilon$-Trimethyl-L-lysine chloride | (S)-2-Amino-6-(trimethylamino)hexanoic acid chloride | 55528-53-5 |
| F1 | AcK | N$^\varepsilon$-Acetyl-L-lysine | (S)-2-Amino-6-(acetylamino)hexanoic acid | 692-04-6 |
| G1 | NicoK | N$^\varepsilon$-Nicotinyl-L-lysine | (S)-2-Amino-6-(nicotinylamino)hexanoic acid | 158276-23-4 |
| H1 | AlocK | N$^\varepsilon$-Allyloxycarbonyl-L-lysine | (S)-2-Amino-6-(allyloxycarbonyl amino)hexanoic acid | 6298-03-9 |

TABLE 11-continued

List of nonstandard amino acids used in this study

| Position | Name | NAA Name | IUPAC Name | CAS Number |
|---|---|---|---|---|
| I1 | Control | — | — | — |
| J1 | 2BrF | L-2-Bromo phenylalanine | (S)-2-amino-3-(2-bromophenyl)propanoic acid | 42538-40-9 |
| K1 | 2IF | L-2-Iodo phenylalanine | (S)-2-amino-3-(2-iodophenyl)propanoic acid | 167817-55-2 |
| L1 | 2MeF | L-2-Methyl phenylalanine | (S)-2-amino-3-(2-methylphenyl)propanoic acid | 80126-53-0 |
| M1 | 2CF3F | L-2-Trifluoromethyl phenylalanine | (S)-2-amino-3-(2-trifluoromethylphenyl)propanoic acid | 119009-47-1 |
| N1 | 3BrF | L-3-Bromo phenylalanine | (S)-2-amino-3-(3-bromophenyl)propanoic acid | 82311-69-1 |
| O1 | 3ClF | L-3-Chloro phenylalanine | (S)-2-amino-3-(3-chlorophenyl)propanoic acid | 80126-51-8 |
| P1 | 2CBF | L-2-Carbamoyl phenylalanine | (S)-2-amino-3-(2-carbamoyl phenyl)propanoic acid | — |
| A2 | Control | — | — | — |
| B2 | 34MeF | L-3,4-Dimethoxyl phenylalanine | (S)-2-amino-3-(3,4-dimethoxyphenyl)propanoic acid | 32161-30-1 |
| C2 | 24NiF | L-2,4-Dinitro phenylalanine | (S)-2-amino-3-(2,4-dinitrophenyl) propanoic acid | 49607-21-8 |
| D2 | ZY | O-Carbobenzoxy-L-tyrosine | (S)-2-amino-3-(4-(((benzyloxy)carbonyl)oxy)phenyl)propanoic acid | 21106-04-7 |
| E2 | 35BrY | L-3,5-Dibromo tyrosine | (S)-2-amino-3-(3,5-dibromo-4-hydroxyphenyl)propanoic acid | 300-38-9 |
| F2 | 26ClBzY | O-2,6-Dichlorobenzyl-L-tyrosine | (S)-2-amino-3-(4-((2,6-dichlorobenzyl)oxy)phenyl)propanoic acid | 40298-69-9 |
| G2 | FOH | L-β-Phenyllactic acid | (S)-2-hydroxy-3-phenylpropanoic acid | 20312-36-1 |
| H2 | 26FF | L-2,6-Difluoro phenylalanine | (S)-2-amino-3-(2,6-difluorophenyl)propanoic acid | 33787-05-2 |
| I2 | Control | — | — | — |
| J2 | — | — | — | — |
| K2 | — | — | — | — |
| L2 | — | — | — | — |
| M2 | — | — | — | — |
| N2 | — | — | — | — |
| O2 | — | — | — | — |
| P2 | — | — | — | — |
| A3 | 2ClZK | N$^\varepsilon$-2-Chloro-carbobenzoxy-L-lysine | (S)-2-Amino-6-(2-chlorobenzyl amino)hexanoic acid | 42390-97-6 |
| B3 | BocK | N$^\varepsilon$-(tert-butoxycarbonyl)-L-lysine | (S)-2-Amino-6-(tert-butoxycarbonyl amino)hexanoic acid | 2418-95-3 |
| C3 | ForK | N$^\varepsilon$-Formyl-L-lysine | (S)-2-Amino-6-(formylamino) hexanoic acid | 1190-48-3 |
| D3 | 4NO2K | N$^\varepsilon$-4-Nitro-carbobenzoxy-L-lysine | (S)-2-Amino-6-(4-nitro carbobenzoxy amino)hexanoic acid | 3557-90-2 |
| E3 | 5OHK | 5-Hydroxylsine | (2S,5R)-2,6-diamino-5-hydroxyhexanoic acid | 30528-11-1 |
| F3 | BioK | N$^\varepsilon$-Biotinyl-L-lysine | (S)-2-Amino-6-(5-((3aS,4S,6aR)-2-oxohexahydro-1H-thieno[3,4-d]imidazol-4-yl)pentanoyl amino)hexanoic acid | 576-19-2 |
| G3 | AcNH2K | DL-2-Acetylamino-6-N-Boc-amino-4-hexynoic acid•DCHA | 2-acetamido-6-((tert-butoxycarbonyl)amino)hex-4-ynoic acid•DCHA | 90102-79-7 |

TABLE 11-continued

List of nonstandard amino acids used in this study

| Position | Name | NAA Name | IUPAC Name | CAS Number |
|---|---|---|---|---|
| H3 | TosK | N$^\varepsilon$-p-Tosyl-L-lysine | (S)-2-Amino-6-(4-tosylamino)hexanoic acid | 2130-76-9 |
| I3 | 3IF | 3-Iodo-L-phenylalanine | (S)-2-amino-3-(3-iodophenyl)propanoic acid | 20846-39-3 |
| J3 | 3MeF | 3-Methyl-L-phenylalanine | (S)-2-amino-3-(3-methylphenyl)propanoic acid | 114926-37-3 |
| K3 | 3MeOF | 3-Methoxy-L-phenylalanine | (S)-2-amino-3-(3-methoxyphenyl)propanoic acid | 33879-32-2 |
| L3 | 3CF3F | 3-Trifluoromethyl-L-phenylalanine | (S)-2-amino-3-(3-trifluoromethylphenyl)propanoic acid | 14464-68-7 |
| M3 | 3CNF | 3-Cyano-L-phenylalanine | (S)-2-amino-3-(3-cyanophenyl)propanoic acid | 57213-48-6 |
| N3 | 3NO2F | 3-Nitro-L-phenylalanine | (S)-2-amino-3-(3-nitrophenyl)propanoic acid | 19883-74-0 |
| O3 | 4ClF | 4-Chloro-L-phenylalanine | (S)-2-Amino-3-(4-chlorophenyl)propanoic acid | 14173-39-8 |
| P3 | 4BrF | 4-Bromo-L-phenylalanine | (S)-2-Amino-3-(4-bromophenyl)propanoic acid | 24250-84-8 |
| A4 | b2BrF | L-2-Bromo-β-phenylalanine | (S)-3-amino-3-(2-bromophenyl)propanoic acid | 275826-34-1 |
| B4 | aMeF | α-Methyl-L-phenylalanine | (S)-2-amino-2-methyl-3-phenylpropanoic acid | 23239-35-2 |
| C4 | aMe4FF | α-Methyl-L-4-fluorophenylalanine | (S)-2-amino-3-(4-fluorophenyl)-2-methylpropanoic acid | 130855-57-1 |
| D4 | g3MeBzP | (R)-γ-(3-Methylbenzyl)-L-proline•HCl | (2S,4R)-4-(3-methylbenzyl)pyrrolidine-2-carboxylic acid hydrochloride | 1049734-52-2 |
| E4 | 4FF | L-4-Fluoro phenylalanine | (S)-2-amino-3-(4-fluorophenyl)propanoic acid | 1132-68-9 |
| F4 | HOaF | α-Phenyllactic acid | 2-hydroxy-2-methyl-3-phenylpropanoic acid | 515-30-0 |
| G4 | 2FF | L-2-Fluoro phenylalanine | (S)-2-amino-3-(2-fluorophenyl)propanoic acid | 19883-78-4 |
| H4 | 24ClF | L-2,4-Dichloro phenylalanine | (S)-2-amino-3-(2,4-dichlorophenyl)propanoic acid | 111119-36-9 |
| I4 | 2NapA | 3-(2-Naphthyl)-L-alanine | (S)-2-Amino-3-(naphthalen-2-yl)propanoic acid | 58438-03-2 |
| J4 | — | — | — | — |
| K4 | — | — | — | — |
| L4 | — | — | — | — |
| M4 | — | — | — | — |
| N4 | — | — | — | — |
| O4 | — | — | — | — |
| P4 | — | — | — | — |
| A5 | AmAdP | L-2-Aminoadipic acid | (S)-2-aminohexanedioic acid | 1118-90-7 |
| B5 | FmocK | N$^\varepsilon$-(Fmoc)-L-lysine | (S)-2-Amino-6-(9H-fluoren-9-yl)methoxy)carbonylamino)hexanoic acid | 84624-28-2 |
| C5 | HomoR | L-Homoarginine | (S)-2-Amino-6-(carbamimidoyl amino)hexanoic acid | 156-86-5 |
| D5 | TFAK | N$^\varepsilon$-(Trifluoroacetyl)-L-lysine | (S)-2-Amino-6-(trifluoroacetylamino)hexanoic acid | 10009-20-8 |
| E5 | HomoCit | L-Homocitrulline | (S)-2-Amino-6-(carbamoylamino)hexanoic acid | 1190-49-4 |

TABLE 11-continued

List of nonstandard amino acids used in this study

| Position | Name | NAA Name | IUPAC Name | CAS Number |
|---|---|---|---|---|
| F5 | MeR | N$^\omega$-methyl-L-arginine hydrochloride | (2S)-2-amino-5-[(N'-methylcarbamimidoyl)amino]pentanoic hydrochloride | 156706-47-7 |
| G5 | NO2R | N$^\omega$-Nitro-L-arginine | (2S)-2-amino-5-[[amino(nitramido)methylidene]amino]pentanoic acid | 2149-70-4 |
| H5 | TosR | N$^\omega$-p-Tosyl-L-arginine | (2S)-2-amino-5-[[amino-[(4-methylphenyl)sulfonylamino]methylidene]amino]pentanoic acid | 4353-32-6 |
| I5 | 4IF | L-4-Iodo phenylalanine | (S)-2-amino-3-(4-iodophenyl)propanoic acid | 24250-85-9 |
| J5 | 4MeF | L-4-Methyl phenylalanine | (S)-2-amino-3-(4-methylphenyl)propanoic acid | 1991-87-3 |
| K5 | oMeY | L-4-Methoxy phenylalanine | (S)-2-amino-3-(4-methoxyphenyl)propanoic acid | 6230-11-1 |
| L5 | 4CF3F | L-4-Trifluoromethyl phenylalanine | (S)-2-amino-3-(4-trifluorormethylphenyl)propanoic acid | 114926-38-4 |
| M5 | 4NO2F | L-4-Nitro phenylalanine | (S)-2-amino-3-(4-nitrophenyl)propanoic acid | 949-99-5 |
| N5 | 4NH2F | L-4-Amino phenylalanine | (S)-2-amino-3-(4-aminophenyl)propanoic acid | 2410-24-4 |
| O5 | 4tBuF | L-4-tert-butyl phenylalanine | (S)-2-amino-3-(4-(tert-butyl)phenyl)propanoic acid | 82372-74-5 |
| P5 | 4BzoF | L-4-benzoyl phenylalanine | (S)-2-amino-3-(4-benzoylphenyl)propanoic acid | 104504-45-2 |
| A6 | — | — | — | — |
| B6 | — | — | — | — |
| C6 | — | — | — | — |
| D6 | — | — | — | — |
| E6 | — | — | — | — |
| F6 | — | — | — | — |
| G6 | — | — | — | — |
| H6 | — | — | — | — |
| I6 | — | — | — | — |
| J6 | — | — | — | — |
| K6 | — | — | — | — |
| L6 | — | — | — | — |
| M6 | — | — | — | — |
| N6 | — | — | — | — |
| O6 | — | — | — | — |
| P6 | — | — | — | — |
| A7 | Cit | L-Citrulline | (S)-2-amino-5-ureidopentanoic acid | 372-75-8 |
| B7 | Orn | L-Ornithine | (S)-2,5-diaminopentanoic acid | 70-26-8 |
| C7 | AcmC | S-(acetamidomethyl)-L-cysteine | 3-(acetamidomethyl sulfanyl)-2-aminopropanoic acid | 19647-70-2 |
| D7 | BzS | O-Benzyl-L-serine | (2R)-2-amino-3-phenylmethoxypropanoic acid | 4726-96-9 |
| E7 | PhtOrn | N$^\delta$-Phthaloyl-L-ornithine hydrochloride | (S)-2-amino-5-(isoindolin-2-yl)pentanoic acid hydrochloride | — |
| F7 | AlStA | 3-Styryl-L-alanine | (S,E)-2-amino-5-phenylpent-4-enoic acid | 267650-37-3 |
| G7 | BzC | S-benzyl-L-cysteine | (2R)-2-amino-3-benzylsulfanylpropanoic acid | 3054-01-1 |
| H7 | ONBC | S-(2-nitrobenzyl)-L-cysteine | (2R)-2-amino-3-(2-nitrobenzyl)sulfanylpropanoic acid | — |

TABLE 11-continued

List of nonstandard amino acids used in this study

| Position | Name | NAA Name | IUPAC Name | CAS Number |
|---|---|---|---|---|
| I7 | 4CNF | 4-Cyano-L-phenylalanine | (S)-2-Amino-3-(4-cyanophenyl)propanoic acid | 167479-78-9 |
| J7 | THY | L-Thyroxine | (S)-2-Amino-3-(4-(4-hydroxy-3,5-diiodophenoxy)-3,5-diiodophenyl)propanoic acid | 51-48-9 |
| K7 | 34ClF | 3,4-Dichloro-L-phenylalanine | (S)-2-Amino-3-(3,4-dichlorophenyl)propanoic acid | 52794-99-7 |
| L7 | 34FF | 3,4-Difluoro-L-phenylalanine | (S)-2-Amino-3-(3,4-difluorophenyl)propanoic acid | 31105-90-5 |
| M7 | 245FF | 2,4,5-Trifluoro-L-phenylalanine | (S)-2-Amino-3-(2,4,5-trifluorophenyl)propanoic acid | 749847-57-2 |
| N7 | 345FF | 3,4,5-Trifluoro-L-phenylalanine | (S)-2-Amino-3-(3,4,5-trifluorophenyl)propanoic acid | 646066-73-1 |
| O7 | 35FF | 3,5-Difluoro-L-phenylalanine | (S)-2-Amino-3-(3,5-difluorophenyl)propanoic acid | 31105-91-6 |
| P7 | F5F | Pentafluoro-L-phenylalanine | (S)-2-Amino-3-(perfluorophenyl)propanoic acid | 138109-65-6 |
| A8 | 4OHP | L-3-Phenyllactic acid | (S)-2-Hydroxy-3-phenylpropanoic acid | 20312-36-1 |
| B8 | MttN | N$^\gamma$-4-Methyltrityl-L-asparagine | (2S)-2-Amino-4-oxo-4-(diphenyl(p-tolyl)methyl amino)butanoic acid | 144317-20-4 |
| C8 | gBzP | (R)-γ-(benzyl)-L-proline | (2S,4R)-4-Benzylpyrrolidine-2-carboxylic acid | — |
| D8 | ForW | N$^{in}$-Formyl-L-tryptophan hydrochloride | (S)-2-Amino-3-(1-formyl-1H-indol-3-yl)propanoic acid hydrochloride | 38023-86-8 |
| E8 | 5BrW | 5-Bromo-L-tryptophan | (S)-2-Amino-3-(5-bromo-1H-indol-3-yl)propanoic acid | 25197-99-3 |
| F8 | 6BrW | 6-Bromo-DL-tryptophan | 2-Amino-3-(6-bromo-1H-indol-3-yl)propanoic acid | 33599-61-0 |
| G8 | BocW | N$^{in}$-tert-Butoxycarbonyl-L-tryptophan | (S)-2-Amino-3-(1-tert-butoxycarbonyl-1H-indol-3-yl)propanoic acid | 146645-63-8 |
| H8 | 5FW | 5-Fluoro-DL-tryptophan | 2-Amino-3-(5-fluoro-1H-indol-3-yl)propanoic acid | 154-08-5 |
| I8 | 3MeOF | 3-Methoxy-L-phenylalanine | (S)-2-Amino-3-(3-methoxyphenyl)propanoic acid | 33879-32-2 |
| J8 | 3CF3F | 3-Trifluoromethyl-L-phenylalanine | (S)-2-Amino-3-(3-trifluoromethylphenyl)propanoic acid | 14464-68-7 |
| K8 | 3CNF | 3-Cyano-L-phenylalanine | (S)-2-amino-3-(3-cyanophenyl)propanoic acid | 57213-48-6 |
| L8 | 3NO2F | 3-Nitro-L-phenylalanine | (S)-2-Amino-3-(3-nitrophenyl)propanoic acid | 19883-74-0 |
| M8 | 4ClF | 4-Chloro-L-phenylalanine | (S)-2-Amino-3-(4-chlorophenyl)propanoic acid | 14173-39-8 |
| N8 | 4BrF | 4-Bromo-L-phenylalanine | (S)-2-Amino-3-(4-bromophenyl)propanoic acid | 24250-84-8 |
| O8 | 4IF | L-4-Iodo phenylalanine | (S)-2-Amino-3-(4-iodophenyl)propanoic acid | 24250-85-9 |
| P8 | 4MeF | L-4-Methyl phenylalanine | (S)-2-Amino-3-(4-methylphenyl)propanoic acid | 1991-87-3 |
| A9 | NovF | L-2-Amino-5-phenylpentanoic acid | (S)-2-Amino-5-phenylpentanoic acid | 62777-25-7 |

TABLE 11-continued

List of nonstandard amino acids used in this study

| Position | Name | NAA Name | IUPAC Name | CAS Number |
|---|---|---|---|---|
| B9 | CaMeC | S-(Carboxymethyl)-L-cysteine | (2S)-2-Amino-3-(carboxymethylsulfanyl)propanoic acid | 50698-76-5 |
| C9 | AmEtC | S-(Aminoethyl)-L-cysteine | (S)-2-Amino-3-(2-aminoethylsulfanyl)-propionic acid | 2936-69-8 |
| D9 | 6FW | 6-Fluoro-DL-tryptophan | 2-Amino-3-(6-fluoro-1H-indol-3-yl)propanoic acid | 7730-20-3 |
| E9 | 7AzW | L-7-Azatryptophan | (S)-2-Amino-3-(1H-pyrrolo[2,3-b]pyridin-3-yl)propanoic acid | 1137-00-4 |
| F9 | 7MeW | 7-Methyl-DL-tryptophan | 2-Amino-3-(7-methyl-1H-indol-3-yl)propanoic acid | 17332-70-6 |
| G9 | 5MeW | 5-Methyl-L-tryptophan | (S)-2-Amino-3-(5-methyl-1H-indol-3-yl)propanoic acid | 154-06-3 |
| H9 | HyQuA | 3-(2-Oxo-1,2-dihydro-4-quinolinyl)alanine hydrochloride monohydrate | (S)-2-Amino-3-(2-oxo-1,2-dihydroquinolin-4-yl)propanoic acid hydrochloride monohydrate | 5162-90-3 |
| I9 | K | L-Lysine | (2S)-2,6-Diaminohexanoic acid | 56-87-1 |
| J9 | P | L-Proline | (2S)-Pyrrolidine-2-carboxylic acid | 147-85-3 |
| K9 | E | L-Glutamic acid | (2S)-2-Aminopentanedioic acid | 56-86-0 |
| L9 | N | L-Asparagine | (2S)-2,4-Diamino-4-oxobutanoic acid | 70-47-3 |
| M9 | D | L-Aspartic acid | (2S)-2-Aminobutanedioic acid | 56-84-8 |
| N9 | A | L-Alanine | (2S)-2-Aminopropanoic acid | 56-41-7 |
| O9 | G | Glycine | 2-Aminoacetic acid | 56-40-6 |
| P9 | M | L-Methionine | (2S)-2-amino-4-methylsulfanylbutanoic acid | 63-68-3 |
| A10 | 4MeW | 4-Methyl-DL-tryptophan | 2-Amino-3-(4-methyl-1H-indol-3-yl)propanoic acid | 1954-45-6 |
| B10 | 5MeOW | 5-Methoxy-L-tryptophan | (S)-2-amino-3-(5-methoxy-1H-indol-3-yl)propanoic acid | 4350-09-8 |
| C10 | 5OHW | 5-hydroxy-L-tryptophan | (S)-2-amino-3-(5-hydroxy-1H-indol-3-yl)propanoic acid | 4350-09-8 |
| D10 | HOW | DL-Indole-3-lactic acid | 2-hydroxy-3-(1H-indol-3-yl)propanoic acid | 1821-52-9 |
| E10 | 5MeW | 5-Methyl-L-tryptophan | (S)-2-amino-3-(5-methyl-1H-indol-3-yl)propanoic acid | 154-06-3 |
| F10 | 7BrW | 7-Bromo-DL-tryptophan | 2-Amino-3-(7-bromo-1H-indol-3-yl)propanoic acid | 852391-45-8 |
| G10 | CycL | Cycloleucine | 1-Aminocyclopentane-1-carboxylic acid | 52-52-8 |
| H10 | AmCaEtK | N$^\delta$-(2-amino-2-carboxyethyl)-L-lysine | (2S)-2-Amino-6-[(2-amino-3-hydroxy-3-oxopropyl)amino]hexanoic acid | 18810-04-3 |
| I10 | oMeY | L-4-Methoxy phenylalanine | (S)-2-Amino-3-(4-methoxyphenyl)propanoic acid | 6230-11-1 |
| J10 | 4CF3F | L-4-Trifluoromethyl phenylalanine | (S)-2-Amino-3-(4-trifluorormethylphenyl)propanoic acid | 114926-38-4 |
| K10 | 4NO2F | L-4-Nitro phenylalanine | (S)-2-Amino-3-(4-nitrophenyl)propanoic acid | 949-99-5 |
| L10 | 4NH2F | L-4-Amino phenylalanine | (S)-2-Amino-3-(4-aminophenyl)propanoic acid | 2410-24-4 |
| M10 | 4tBuF | L-4-tert-butyl phenylalanine | (S)-2-Amino-3-(4-(tert-butyl)phenyl)propanoic acid | 82372-74-5 |
| N10 | 4BzoF | L-4-benzoyl phenylalanine | (S)-2-Amino-3-(4-benzoylphenyl)propanoic acid | 104504-45-2 |

TABLE 11-continued

List of nonstandard amino acids used in this study

| Position | Name | NAA Name | IUPAC Name | CAS Number |
|---|---|---|---|---|
| O10 | 4CNF | 4-Cyano-L-phenylalanine | (S)-2-Amino-3-(4-cyanophenyl)propanoic acid | 167479-78-9 |
| P10 | THY | L-Thyroxine | (S)-2-Amino-3-(4-(4-hydroxy-3,5-diiodophenoxy)-3,5-diiodophenyl)propanoic acid | 51-48-9 |
| A11 | — | — | — | — |
| B11 | — | — | — | — |
| C11 | — | — | — | — |
| D11 | — | — | — | — |
| E11 | — | — | — | — |
| F11 | — | — | — | — |
| G11 | — | — | — | — |
| H11 | — | — | — | — |
| I11 | V | L-Valine | (2S)-2-Amino-3-methylbutanoic acid | 72-18-4 |
| J11 | I | L-Isoleucine | (2S,3S)-2-Amino-3-methylpentanoic acid | 73-32-5 |
| K11 | S | L-Serine | (2S)-2-Amino-3-hydroxypropanoic acid | 56-45-1 |
| L11 | C | L-Cysteine | (2R)-2-Amino-3-sulfanylpropanoic acid | 52-90-4 |
| M11 | Q | L-Glutamine | (2S)-2,5-Diamino-5-oxopentanoic acid | 56-85-9 |
| N11 | T | L-Threonine | (2S,3R)-2-Amino-3-hydroxybutanoic acid | 72-19-5 |
| O11 | R | L-Arginine | (2S)-2-Amino-5-(diaminomethylideneamino)pentanoic acid | 74-79-3 |
| P11 | Y | L-Tyrosine | (2S)-2-Amino-3-(4-hydroxyphenyl)propanoic acid | 60-18-4 |
| A12 | dHONoR | ω-Hydroxy-nor-L-arginine | (S)-2-Amino-4-(2'-hydroxyguanidino)butyric acid | 189302-40-7 |
| B12 | BHOMeA | α-Hydroxyisobutyric acid | 2-Hydroxy-2-methylpropanoic acid | 209-848-8 |
| C12 | Tr42ThibP | (±)-trans-4-(2-Thienyl)pyrrolidine-3-carboxylic acid hydrochloride | (3R,4R)-4-(Thiophen-2-yl)pyrrolidine-3-carboxylic acid hydrochloride | — |
| D12 | DetG | Di-ethylglycine | 2-Amino-2-ethylbutanoic acid | 2566-29-22 |
| E12 | DBuG | Di-n-butylglycine | 2-Amino-2-butylhexanoic acid | 7597-66-2 |
| F12 | N3A | Azido-L-alanine hydrochloride | (S)-2-Amino-3-azidopropanoic acid hydrochloride | 105661-40-3 |
| G12 | aMeL | α-Methyl-L-leucine | (S)-2-Amino-2,4-dimethylpentanoic acid | 105743-53-1 |
| H12 | gAbn | γ-Aminobutyric acid | 4-Aminobutyric acid | 56-12-2 |
| I12 | — | — | — | — |
| J12 | — | — | — | — |
| K12 | — | — | — | — |
| L12 | — | — | — | — |
| M12 | — | — | — | — |
| N12 | — | — | — | — |
| O12 | — | — | — | — |
| P12 | — | — | — | — |
| A13 | PrpG | L-Propargylglycine | (S)-2-Aminopent-4-ynoic acid | 23235-01-0 |
| B13 | DehL | L-4,5-Dehydroleucine | (S)-2-amino-4-methylpent-4-enoic acid | 87392-13-0 |
| C13 | CynA | Cyano-L-aianine | (S)-2-Amino-3-cyanopropanoic acid | 6232-19-5 |
| D13 | HomoL | L-Homoleucine hydrochloride | (S)-3-Amino-5-methylhexanoic acid hydrochloride | 96386-92-4 |
| E13 | DPrG | Di-n-propylglycine | 4-Aminoheptane-4-carboxylic acid | 2566-31-6 |
| F13 | OMeS | O-Methyl-L-serine | (2S)-2-Amino-3-methoxypropanoic acid | 32620-11-4 |
| G13 | AllG | L-Allylglycine | (S)-2-Amino-4-pentenoic acid | 16338-48-0 |

TABLE 11-continued

List of nonstandard amino acids used in this study

| Position | Name | NAA Name | IUPAC Name | CAS Number |
| --- | --- | --- | --- | --- |
| H13 | HomoC | L-Homocysteine | (S)-2-Amino-4-mercaptobutyric acid | 6027-13-0 |
| I13 | F | L-Phenylalanine | (S)-2-Amino-3-phenylpropionic acid | 63-91-2 |
| J13 | H | L-Histidine | (2S)-2-Amino-3-(1H-imidazol-5-yl)propanoic acid | 71-00-1 |
| K13 | W | L-Tryptophan | (2S)-2-Amino-3-(1H-indol-3-yl)propanoic acid | 73-22-3 |
| L13 | L | L-Leucine | (2S)-2-Amino-4-methylpentanoic acid | 61-90-5 |
| M13 | HomoS | L-Homoserine | (S)-2-Amino-4-hydroxybutyric acid | 672-15-1 |
| N13 | MetG | γ-Methallyl glycine | (E)-but-2-en-1-ylglycine | 28024-56-8 |
| O13 | tertL | L-tert-Leucine | (S)-2-Amino-3,3-dimethylbutanoic acid | 20859-02-3 |
| P13 | bAla | β-Alanine | 3-Aminopropanoic acid | 107-95-9 |
| A14 | — | — | — | — |
| B14 | — | — | — | — |
| C14 | — | — | — | — |
| D14 | — | — | — | — |
| E14 | — | — | — | — |
| F14 | — | — | — | — |
| G14 | — | — | — | — |
| H14 | aMeH | DL-α-Methylhistidine dihydrochloride | 2-Amino-3-(1H-imidazol-4-yl)-2-methyl propanoic acid dihydrochloride | 32381-18-3 |
| I14 | tBuY | O-tert-Butyl-L-tyrosine | (S)-2-Amino-3-(4-(tert-butoxy)phenyl)propanoic acid | 18822-59-8 |
| J14 | 4AcF | L-4-Acetyl phenylalanine | (S)-3-(4-Acetylphenyl)-2-aminopropanoic acid | 122555-04-8 |
| K14 | OAcY | O-Acetyl-L-tyrosine | (S)-3-(4-Acetoxyphenyl)-2-aminopropanoic acid | 6636-22-2 |
| L14 | 4CAF | L-4-Carbamoyl phenylalanine | (S)-2-Amino-3-(4-carbamoylphenyl)propanoic acid | 223593-04-2 |
| M14 | 4PhF | L-4-Phenyl phenylalanine | (S)-3-([1,1'-Biphenyl]-4-yl)-2-aminopropanoic acid | 155760-02-4 |
| N14 | 4NH2F | L-4-Amino phenylalanine | (S)-2-Amino-3-(4-aminophenyl)propanoic acid | 2410-24-4 |
| O14 | 34MeOF | L-3,4-Dimethoxy phenylalanine | (S)-2-Amino-3-(3,4-dimethoxyphenyl)propanoic acid | 32161-30-1 |
| P14 | 24NiF | L-2,4-Dinitro phenylalanine | (S)-2-Amino-3-(2,4-dinitrophenyl) propanoic acid | 49607-21-8 |
| A15 | OxM | L-Methionine sulfoxide | (2S)-2-Amino-4-(methylsulfinyl)butanoic acid | 86631-49-4 |
| B15 | 2OxM | L-Methionine sulfone | (S)-2-Amino-4-(methylsulfonyl)butanoic acid | 7314-32-1 |
| C15 | BzD | γ-Benzyl-L-aspartate | (S)-2-Amino-4-(benzyloxy)-4-oxobutanoic acid | 2177-63-1 |
| D15 | AzL | 4-Azaleucine | 2-Amino-3-(dimethylamino)propanoic acid | 4746-36-5 |
| E15 | tBuA | L-α-tert-Butylglycine | (S)-2-Amino-3,3-dimethylbutanoic acid | 20859-02-3 |
| F15 | tBuC | S-tert-Butyl-L-cysteine hydrochloride | (S)-2-amino-2-(tert-butylthio)acetic acid hydrochloride | 2481-09-6 |
| G15 | ClA | β-Chloroalanine | (R)-2-Amino-3-chloropropanoic acid | 2731-73-9 |
| H15 | Eth | L-Ethionine | (S)-2-Amino-4-(ethylthio)butyric acid | 13073-35-3 |
| I15 | bHdL | β-Hydroxy-L-leucine | (2S,3R)-(+)-2-Amino-3-hydroxy-4-methylpentanoic acid | 10148-71-7 |
| J15 | Nov | L-Norvaline | (S)-2-Aminopentanoic acid | 6600-40-4 |

TABLE 11-continued

List of nonstandard amino acids used in this study

| Position | Name | NAA Name | IUPAC Name | CAS Number |
|---|---|---|---|---|
| K15 | aMeE | α-Methyl-L-glutamic acid | (S)-2-Amino-2-methylpentanedioic acid | 6208-95-3 |
| L15 | CF3L | 5,5,5-Trifluoro-L-leucine | (2S)-2-amino-5,5,5-trifluoro-4-methylpentanoic acid | 372-22-5 |
| M15 | 2FF | L-2-Fluoro phenylalanine | (S)-2-Amino-3-(2-fluorophenyl)propanoic acid | 19883-78-4 |
| N15 | 4FF | L-4-Fluoro phenylalanine | (S)-2-Amino-3-(4-fluorophenyl)propanoic acid | 1132-68-9 |
| O15 | NoL | L-Norleucine | (S)-2-aminohexanoic acid | 327-57-1 |
| P15 | bAmBua | β-aminobutric acid | 3-Aminobutanoic acid | 541-48-0 |
| A16 | — | — | — | — |
| B16 | — | — | — | — |
| C16 | — | — | — | — |
| D16 | — | — | — | — |
| E16 | — | — | — | — |
| F16 | — | — | — | — |
| G16 | — | — | — | — |
| H16 | 4N3F | L-4-Azido phenylalanine | (S)-2-Amino-3-(4-azidophenyl)propanoic acid | 33173-53-4 |
| I16 | OZY | O-Benzyl-L-tyrosine | (S)-2-amino-3-(4-(benzyloxy)phenyl)propanoic acid | 16652-64-5 |
| J16 | 35BrY | 3,5-Dibromo-L-tyrosine | (S)-2-Amino-3-(3,5-dibromo-4-hydroxyphenyl)propanoic acid | 300-38-9 |
| K16 | 26ClBzY | O-2,6-Dichlorobenzyl-L-tyrosine | (S)-2-amino-3-(4-((2,6-dichlorobenzyl)oxy)phenyl)propanoic acid | 40298-69-9 |
| L16 | 26FF | L-2,6-Difluoro phenylalanine | (S)-2-Amino-3-(2,6-difluorophenyl)propanoic acid | 33787-05-2 |
| M16 | FOH | L-β-Phenyllactic acid | (S)-2-Hydroxy-3-phenylpropanoic acid | 20312-36-1 |
| N16 | b2BrF | (S)-2-Bromo-β-phenylalanine | (S)-3-Amino-3-(2-bromophenyl)propionic acid | 275826-34-1 |
| O16 | aMeF | α-Methyl-L-phenylalanine | (S)-2-Amino-2-methyl-3-phenylpropanoic acid | 23239-35-2 |
| P16 | aMe4FF | α-Methyl-4-fluoro-phenylalanine | (S)-2-Amino-3-(4-fluorophenyl)-2-methylpropanoic acid | 130855-57-1 |
| A17 | 4OHP | 4-Hydroxyproline | (2S)-4-Hydroxypyrrolidine-2-carboxylic acid | 618-27-9 |
| B17 | PyroE | L-Pyroglutamic acid | (S)-5-oxopyrrolidine-2-carboxylic acid | 98-79-3 |
| C17 | 1MeH | 1-Methyl-L-hsitidine | (S)-2-Amino-3-(1-methyl-1H-imidazol-4-yl)propanoic acid | 332-80-9 |
| D17 | 3MeH | 3-Methyl-L-hsitidine | (2S)-2-Amino-3-(1-methyl-1H-imidazol-5-yl)propanoic acid | 368-16-1 |
| E17 | BzH | Benzyl-L-histidine | (2S)-2-amino-3-(1-benzylimidazol-4-yl)propanoic acid | 16832-24-9 |
| F17 | 4ThzA | 3-(4-Thiazolyl)-L-alanine | (S)-2-amino-3-(thiazol-4-yl)propanoic acid | 119433-80-6 |
| G17 | 2ThzA | β-(2-Thiazolyl)-DL-alanine | 2-Amino-3-(thiazol-2-yl)propanoic acid | 1596-65-2 |
| H17 | 2PyA | 3-(2'-Pyridyl)-L-alanine | (S)-2-Amino-3-(pyridin-2-yl)propanoic acid | 37535-51-6 |
| I17 | aHdL | 2-Hydroxy-L-Leucine | (R)-2-Amino-2-hydroxy-4-methylpentanoic acid | 65242-70-8 |
| J17 | TriAzA | 1,2,4-Triazole-Alanine | 2-Amino-3-(1H-1,2,3-triazol-4-yl)propanoic acid | 678980-89-7 |
| K17 | gMeE | 5-Methyl-L-glutamic acid | (S)-2-amino-5-methoxy-5-oxopentanoic acid | 1499-55-4 |
| L17 | AllG | L-Allylglycine | (S)-2-Amino-4-pentenoic acid | 16338-48-0 |

TABLE 11-continued

List of nonstandard amino acids used in this study

| Position | Name | NAA Name | IUPAC Name | CAS Number |
|---|---|---|---|---|
| M17 | aMeS | α-Methyl-L-Serine | (S)-2-amino-3-hydroxy-2-methylpropanoic acid | 16820-18-1 |
| N17 | bHdNoV | β-hydroxy-L-Norvaline | (2S)-2-amino-3-hydroxypentanoic acid | 34042-00-7 |
| O17 | CycL | Cycloleucine | 1-Aminocyclopentane-1-carboxylic acid | 52-52-8 |
| P17 | bE | β-Glutamic acid | 3-Aminopentanedioic acid | 1948-48-7 |
| A18 | 4NHBocF | L-4-Bocamino phenylalanine | (S)-2-Amino-3-(4-((tert-butoxycarbonyl)amino)phenyl)propanoic acid | 74578-48-6 |
| B18 | 24FF | L-2,4-Difluoro phenylalanine | (S)-2-Amino-3-(2,4-difluorophenyl)propanoic acid | 31105-93-8 |
| C18 | 24MeF | L-2,4-Dimethyl phenylalanine | (S)-2-Amino-3-(2,4-dimethylphenyl)propanoic acid | 259726-56-2 |
| D18 | 245FF | 2,4,5-Trifluoro-L-phenylalanine | (S)-2-Amino-3-(2,4,5-trifluorophenyl)propanoic acid | 749847-57-2 |
| E18 | 24MeF | L-2,4-Dimethyl phenylalanine | (S)-2-Amino-3-(2,4-dimethylphenyl)propanoic acid | 259726-56-2 |
| F18 | AnilideE | L-Glutamic acid γ-anilide | (S)-2-Amino-5-anilide-5-oxopentanoic acid | 5963-60-0 |
| G18 | 4CO2F | L-4-carboxy-phenylalanine | (S)-4-(2-Amino-2-carboxyethyl)benzoic acid | 22976-70-1 |
| H18 | QuinolyA | 3-(2-Quinoyl)-L-alanine | (S)-2-amino-3-(quinolin-2-yl)propanoic acid | 161513-46-8 |
| I18 | g3MeBzP | (R)-γ-(3-Methylbenzyl)-L-proline hydrocloride | (2S,4R)-4-(3-methylbenzyl)pyrrolidine-2-carboxylic acid hydrochloride | 1049734-52-2 |
| J18 | 4FF | L-4-Fluoro phenylalanine | (S)-2-Amino-3-(4-fluorophenyl)propanoic acid | 1132-68-9 |
| K18 | aMePhG | α-Methyl-L-phenylglycine | S-2-Methylphenylglycine | 1004980-56-6 |
| L18 | 2FF | L-2-Fluoro phenylalanine | (S)-2-Amino-3-(2-fluorophenyl)propanoic acid | 19883-78-4 |
| M18 | 24ClF | L-2,4-Dichloro phenylalanine | (S)-2-Amino-3-(2,4-dichlorophenyl)propanoic acid | 111119-36-9 |
| N18 | 24ClF | L-2,4-Dichloro phenylalanine | (S)-2-Amino-3-(2,4-dichlorophenyl)propanoic acid | 111119-36-9 |
| O18 | 24FF | L-2,4-Difluoro phenylalanine | (S)-2-Amino-3-(2,4-difluorophenyl)propanoic acid | 31105-93-8 |
| P18 | 3NH2Y | L-3-Aminotyrosine | (S)-2-Amino-3-(3-amino-4-hydroxyphenyl)propanoic acid | 300-34-5 |
| A19 | 3PyA | 3-(3'-Pyridyl)-L-alanine | (S)-2-Amino-3-(pyridin-3-yl)propanoic acid | 64090-98-8 |
| B19 | 4PyA | 3-(4'-Pyridyl)-L-alanine | (S)-2-Amino-3-(pyridin-4-yl)propanoic acid | 37535-49-2 |
| C19 | 3BzThiA | 3-Benzothienyl-L-alanine | (S)-2-Amino-3-(benzo[b]thiophen-3-yl)propanoic acid | 72120-71-9 |
| D19 | 2FUA | β-(2-Furyl)-L-alanine | (S)-2-Amino-3-(furan-2-yl)propanoic acid | 127682-08-0 |
| E19 | Cyc5A | 3-Cyclopentane-L-alanine | (S)-2-Amino-3-cyclopentylpropanoic acid | 99295-82-6 |
| F19 | BrThiA | L-2-(5-Bromothienyl)alanine | (S)-2-amino-3-(2-bromothiophen-3-yl)propanoic acid | 154593-58-5 |
| G19 | DL3ThiA | 3-(3-Thienyl)-DL-alanine | 2-Amino-3-(thiophen-3-yl)propanoic acid | 3685-48-1 |
| H19 | 3ThiA | 3-(3-Thienyl)-L-alanine | (S)-2-Amino-3-(thiophen-3-yl)propanoic acid | 3685-51-6 |
| I19 | gMeE | 5-Methyl-L-glutamic acid | (S)-2-amino-5-methoxy-5-oxopentanoic acid | 1499-55-4 |

TABLE 11-continued

List of nonstandard amino acids used in this study

| Position | Name | NAA Name | IUPAC Name | CAS Number |
|---|---|---|---|---|
| J19 | DiAmPAC | 2,6-Diaminopimelic acid | (2R,6R)-2,6-diaminoheptanedioic acid | 583-93-7 |
| K19 | HomoS | L-Homoserine | (S)-2-Amino-4-hydroxybutyric acid | 672-15-1 |
| L19 | g4NiAnE | L-Glutamic acid γ-(p-nitroanilide) hydrochloride | (S)-(5-amino-1-hydroxy-1,5-dioxopentan-2-yl)-(4-nitrophenyl)azanium | 67953-08-6 |
| M19 | ClA | β-chloroalanine | (R)-2-Amino-3-chloropropanoic acid | 2731-73-9 |
| N19 | gAnilE | L-Glutamic acid γ-anilide | (S)-2-Amino-5-anilide-5-oxopentanoic acid | 5963-60-0 |
| O19 | tBuY | O-tert-Butyl-L-tyrosine | (S)-2-Amino-3-(4-(tert-butoxy)phenyl)propanoic acid | 18822-59-8 |
| P19 | 4AcF | L-4-Acetyl phenylalanine | (S)-3-(4-Acetylphenyl)-2-aminopropanoic acid | 122555-04-8 |
| A20 | OtBuE | L-Glutamic acid γ-tert-butyl ester | (2S)-2-Amino-5-[(2-methylpropan-2-yl)oxy]-5-oxopentanoic acid | 2419-56-9 |
| B20 | OClAnE | L-Glutamic acid γ-2-chloroanilide | (S)-2-Amino-5-(2-chloroanilide)-5-oxepentanoic acid | 200616-97-3 |
| C20 | OEtE | L-Glutamic acid γ-ethyl ester | (4S)-4-Amino-5-ethoxy-5-oxopentanoic acid | 1119-33-1 |
| D20 | 4NH2MeF | L-4-Aminomethyl-phenylalanine | (S)-2-Amino-3-(4-(aminomethyl)phenyl)propanoic acid | 150338-20-8 |
| E20 | IPrQ | N<sup>δ</sup>-Isopropyl-L-glutamine | (2S)-2-amino-5-oxo-5-(propan-2-lamino)pentanoic acid | 4311-12-0 |
| F20 | NapQ | L-Glutamic acid γ-(α-naphthylamide) | (2S)-5-amino-2-(naphthalen-1-ylamino)-5-oxopentanoic acid | 28401-75-4 |
| G20 | StBuC | S-(tert-butylthio)-L-cysteine | (S)-2-Amino-3-tert-butyldisulfanylpropanoic acid | 30044-51-0 |
| H20 | CaMeC | S-(carboxymethyl)-L-cysteine | (S)-2-Amino-3-(carboxymethylsulfanyl)propanoic acid | 638-23-3 |
| I20 | — | — | — | — |
| J20 | — | — | — | — |
| K20 | — | — | — | — |
| L20 | — | — | — | — |
| M20 | — | — | — | — |
| N20 | — | — | — | — |
| O20 | — | — | — | — |
| P20 | 4N3F | L-4-Azido phenylalanine | (S)-2-Amino-3-(4-azidophenyl)propanoic acid | 33173-53-4 |
| A21 | 2ThiA | 3-(2-Thienyl)-L-alanine | (S)-2-amino-3-(thiophen-2-yl)propanoic acid | 22951-96-8 |
| B21 | ThiS | DL-β-(2-Thienyl)serine | 2-Amino-3-hydroxy-3-(thiophen-2-yl)propanoic acid | 32595-59-8 |
| C21 | mY | m-Tyrosine | (S)-2-Amino-3-(3-hydroxyphenyl)propanoic acid | 587-33-7 |
| D21 | MIN | L-Minosine | (S)-2-Amino-3-(3-hydroxy-4-oxopyridin-1(4H)-yl)propanoic acid | 500-44-7 |
| E21 | 3IY | L-3-Iodotyrosine | (S)-2-Amino-3-(4-hydroxy-3-iodophenyl)propanoic acid | 2751-18-0 |
| F21 | 3NO2Y | L-3-Nitrotyrosine | (S)-2-Amino-3-(4-hydroxy-3-nitrophenyl)propanoic acid | 621-44-3 |
| G21 | 3ClY | L-3-Chlorotyrosine | (S)-2-Amino-3-(3-chloro-4-hydroxyphenyl)propanoic acid | 7423-93-0 |
| H21 | 3FY | L-3-Fluorotyrosine | (S)-2-Amino-3-(3-fluoro-4-hydroxyphenyl)propanoic acid | 7423-96-3 |

TABLE 11-continued

List of nonstandard amino acids used in this study

| Position | Name | NAA Name | IUPAC Name | CAS Number |
|---|---|---|---|---|
| I21 | 2tBuG | L-α-tert-Butylglycine | (S)-2-Amino-3,3-dimethylbutyric acid | 20859-02-3 |
| J21 | aMeH | DL-α-Methylhistidine dihydrochloride | 2-Amino-3-(1H-imidazol-4-yl)-2-methylpropanoic acid dihydrochloride | 32381-18-3 |
| K21 | gHdMaE | L-γ-Glutamyl hydroxamate | (2S)-5-Amino-2-(hydroxyamino)-5-oxopentanoic acid | 1955-67-5 |
| L21 | AllG | L-Allylgiycine | (S)-2-Amino-4-pentenoic acid | 16338-48-0 |
| M21 | Aib | 2-Methylalanine | 2-amino-2-methylpropanoic acid | 62-57-7 |
| N21 | OAcY | O-Acetyl-L-tyrosine | (S)-3-(4-Acetoxyphenyl)-2-aminopropanoic acid | 6636-22-2 |
| O21 | Abu | L-2-Aminobutyric acid | (S)-2-Aminobutanoic acid | 1492-24-6 |
| P21 | AlloI | L-allo-Isoleucine | (2S,3R)-2-Amino-3-methylpentanoic acid | 1509-34-8 |
| A22 | 4MeBzC | S-(4-Methylbenzyl)-L-cysteine | (S)-2-Amino-3-(phenylmethylsulfanyl)propanoic acid | 3054-01-1 |
| B22 | OCHexE | L-Glutamic acid γ-cyclohexyl ester | (S)-2-Amino-5-(cyclohexyloxy)-5-oxopentanoic acid | 112471-82-6 |
| C22 | 4MeOBzC | S-(4-Methoxybenzyl)-L-cysteine | (S)-2-Amino-3-[(4-methoxyphenyl)methyl-sulfanyl]propanoic acid | 2544-31-2 |
| D22 | OBzE | L-Glutamic acid γ-benzyl ester | (S)-2-amino-5-(benzyloxy)-5-oxopentanoic acid | 1676-73-9 |
| E22 | FmocC | S-9-Fluorenylmethyl-L-cysteine hydrochloride | (S)-2-Amino-3-(9H-fluoren-9-ylmethylsulfanyl)-propionic acid hydrochloride | 84888-34-6 |
| F22 | OBzY | O-Benzyl-L-tyrosine | (S)-2-amino-3-(4-(benzyloxy)phenyl)propanoic acid | 16652-64-5 |
| G22 | 2SHH | 2-Thio-L-histidine | (S)-2-amino-3-(2-thioxo-2H-imidazol-4-yl)propanoic acid | 63789-18-5 |
| H22 | 24NiF | L-2,4-Dinitro phenylalanine | (S)-2-Amino-3-(2,4-dinitrophenyl) propanoic acid | 49607-21-8 |
| I22 | — | — | — | — |
| J22 | — | — | — | — |
| K22 | — | — | — | — |
| L22 | — | — | — | — |
| M22 | — | — | — | — |
| N22 | — | — | — | — |
| O22 | — | — | — | — |
| P22 | — | — | — | — |
| A23 | 3NH2Y | L-3-Aminotyrosine | (S)-2-Aamino-3-(3-amino-4-hydroxyphenyl)propanoic acid | 300-34-5 |
| B23 | 2CNF | L-2-Cyano phenylalanine | (S)-2-Amino-3-(2-cyanophenyl)propanoic acid | 263396-42-5 |
| C23 | 1NapA | 3-(1-Naphthyl)-L-alanine | (S)-2-Amino-3-(naphthalen-1-yl)propanoic acid | 55516-54-6 |
| D23 | Cha | β-Cyclohexyl-L-alanine | (S)-2-Amino-3-cyclohexylpropanoic acid | 27527-05-5 |
| E23 | PheG | L-Phenylglycine | (S)-2-Amino-2-phenylacetic acid | 2935-35-5 |
| F23 | HomoF | L-Homophenylalanine | (S)-2-Amino-4-phenylbutanoic acid | 943-73-7 |
| G23 | Cyc3A | H-β-Cyclopropyl-L-Alanine | (S)-2-Amino-3-cyclopropylpropanoic acid | 102735-53-5 |
| H23 | 2ClF | L-2-Chloro phenylalanine | (S)-2-Amino-3-(2-chlorophenyl)propanoic acid | 103616-89-3 |

TABLE 11-continued

List of nonstandard amino acids used in this study

| Position | Name | NAA Name | IUPAC Name | CAS Number |
|---|---|---|---|---|
| I23 | TrtC | S-Trityl-L-cysteine | (2R)-2-amino-3-(triphenylmethylthio)propanoic acid | 2799-07-7 |
| J23 | TrtH | $N^\tau$-trityl-L-histidine | (2S)-2-Amino-3-[1-(triphenylmethyl)-4-imidazolyl]propanoic acid | 35146-32-8 |
| K23 | AllG | L-Allylglycine | (S)-2-Amino-4-pentenoic acid | 16338-48-0 |
| L23 | 4CAF | L-4-Carbamoyl phenylalanine | (S)-2-Amino-3-(4-carbamoylphenyl)propanoic acid | 223593-04-2 |
| M23 | 4PhF | L-4-Phenyl phenylalanine | (S)-3-([1,1'-Biphenyl]-4-yl)-2-aminopropanoic acid | 155760-02-4 |
| N23 | 4NH2F | L-4-Amino phenylalanine | (S)-2-Amino-3-(4-aminophenyl)propanoic acid | 2410-24-4 |
| O23 | AcmC | S-(acetamidomethyl)-L-cysteine | 3-(Acetamidomethyl sulfanyl)-2-aminopropanoic acid | 19647-70-2 |
| P23 | Alb | Albizziin | (S)-2-Amino-3-ureidopropionic acid | 1483-07-4 |
| A24 | 2CNF | L-2-Cyano phenylalanine | (S)-2-Amino-3-(2-cyanophenyl)propanoic acid | 263396-42-5 |
| B24 | Dab | L-2,4-Diaminobutyric acid dihydrochloride | (2S)-2,4-Diaminobutanoic acid dihydrochloride | 1883-09-6 |
| C24 | PbfR | $N^\omega$-(2,2,4,6,7-Pentamethyldihydro-benzofuran-5-sulfonyl)-L-arginine | (2S)-2-Amino-5-[[amino-[(2,2,4,6,7-pentamethyl-3H-1-benzofuran-5-yl)sulfonyl amino]methylidene]amino]pentanoic acid | 200115-86-2 |
| D24 | Z2R | $N^\omega,N^{\omega'}$-Di-carbobenzyloxy-L-arginine | (2S)-2-Amino-5-{[(benzyloxy)carbonyl]({[(benzyloxy)carbonyl]amino}methanimidoyl)amino}pentanoic acid | 4125-79-5 |
| E24 | — | — | — | — |
| F24 | — | — | — | — |
| G24 | — | — | — | — |
| H24 | — | — | — | — |
| I24 | — | — | — | — |
| J24 | — | — | — | — |
| K24 | — | — | — | — |
| L24 | 4tBuF | L-4-tert-butyl phenylalanine | (S)-2-amino-3-(4-(tert-butyl)phenyl)propanoic acid | 82372-74-5 |
| M24 | CbzK | $N^\varepsilon$-Carbobenzoxy-L-lysine | (S)-2-Amino-6-(phenylmethoxycarbonyl amino)hexanoic acid | 1155-64-2 |
| N24 | NicoK | $N^\varepsilon$-Nicotinyl-L-lysine hydrochloride | (S)-2-Amino-6-(nicotinylamino)hexanoic acid hydrochloride | 158276-23-4 |
| O24 | AcK | $N^\varepsilon$-Acetyl-L-lysine | (S)-2-Amino-6-(acetylamino)hexanoic acid | 692-04-6 |
| P24 | TFAK | $N^\varepsilon$-(Trifluoroacetyl)-L-lysine | (S)-2-Amino-6-(trifluoroacetylamino)hexanoic acid | 10009-20-8 |

Results

To expand the diversity and function of proteins and polypeptide-based biomaterials, efficient AARSs must be developed for nsAAs harboring a variety of chemical groups. Since several of the AARS variants described to date have been demonstrated to accept and incorporate numerous nsAAs (Young, et al., *Biochemistry*, 50:1894-900 (2011); Stokes, et al., *Mol Biosyst*, 5:1032-8 (2009)) (a property termed polyspecificity (Young, et al., *Biochemistry*, 50:1894-900 (2011)), the polyspecificity of each of the chromosomally integrated AARS variants was investigated by assaying GFP(3TAG) production in the presence of pAcF or pAzF (FIG. 3D) as well as with 236 other nsAAs (Tables 10 and 11) (Ko, et al, *FEBS Lett*, 587:3243-8 (2013)). These assays revealed polyspecificity in each of the variants with the exception of pAzFRS.1 and pAzFRS.1.t1, which demonstrated exceptional specificity toward pAzF with almost complete exclusion of any other nsAA (FIGS. 5B-5M). In vitro biochemical analysis validated the observed selectivity of pAzFRS.1.t1 for pAzF and complete exclusion of pAcF and showed a 5 fold decrease in aminoacylation and 2.8 fold decreases in tRNA charging for pAzF compared with pAcF by pAcFRS.2.t1 (Tables 8-9).

Next, customized diversification-selection experiments were designed to alter the nsAA binding pocket to reject a specific nsAA would create a pocket capable of accepting new, previously excluded, nsAAs. In these assays, an additional round of evolution was performed to increase the specificity of pAcFRS.1 toward pAcF while excluding pAzF. pAcFRS.1 was subjected to five additional MAGE cycles with an oligonucleotide pool designed to preserve the [A167D] mutation, which is responsible for the improved activity of pAcFRS.1, and to randomize the remaining eleven sites in the nsAA binding pocket. This library was subjected to tolC negative selection in the presence of pAzF, establishing orthogonality toward pAzF in addition to the twenty canonical amino acids. The remaining orthogonal library was screened for improved GFP(3TAG) in the presence of pAcF and cells expressing high levels of GFP were isolated via two rounds of FACS. Individual colony sequencing revealed that the sorted population was enriched in an AARS mutant (pAcFRS.2, [L65V, A167D] mutations).

Figure 3D:
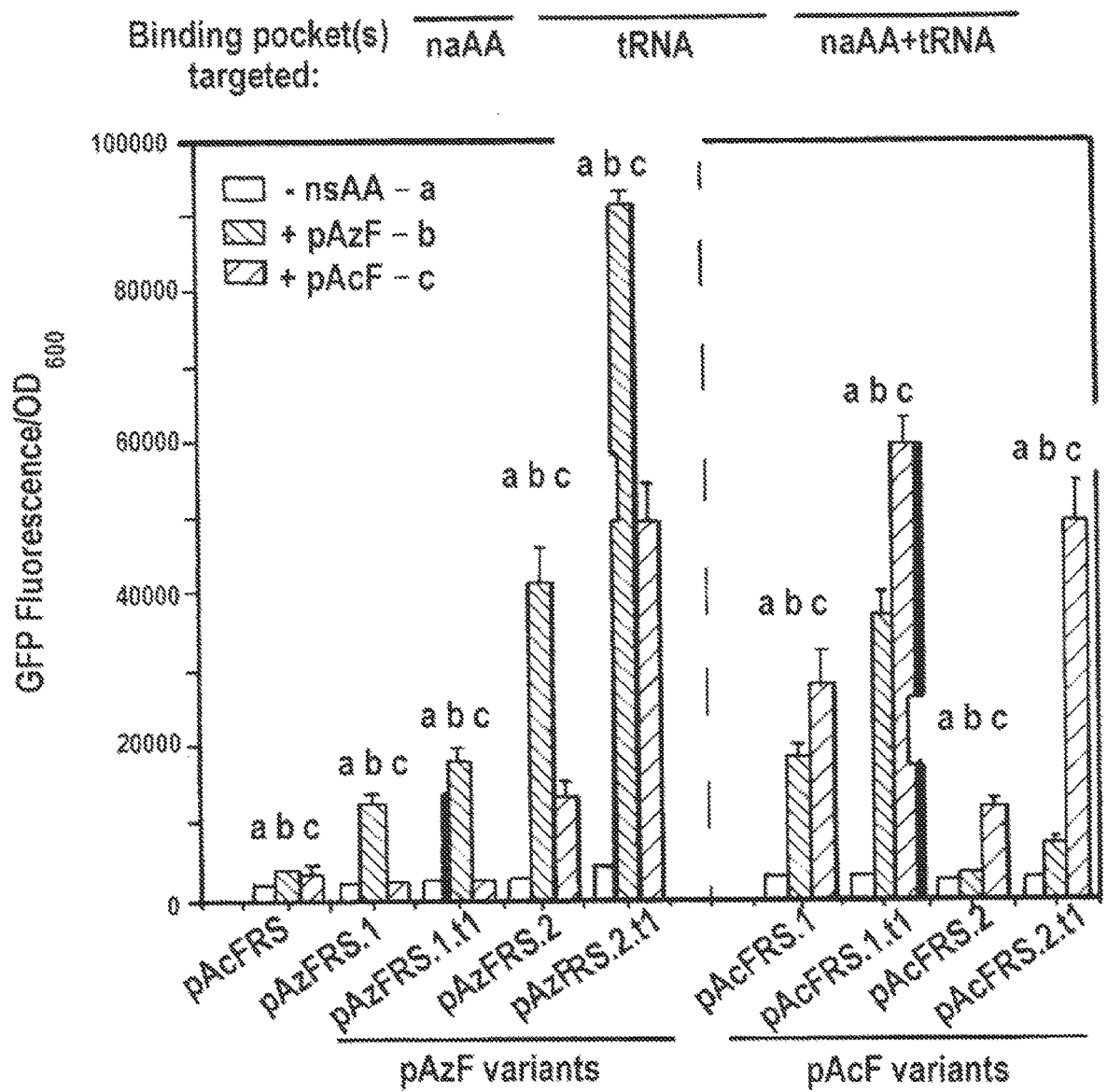
FIG. 3D is a bar graph showing pAcFRS and pAzFRS variants specificities for pAcF, pAzF as assayed by GFP(3TAG) fluorescence. Error bars represent s.d. from the values of three technical replicates. Data shown is representative of at least three independent experiments.

Comparison of GFP(3TAG) expression in the presence of pAcF or pAzF confirmed an increase in selectivity for pAcFRS.2 and pAcFRS.2.t1 toward pAcF over pAzF (FIG. 3D). In addition, the increased activity of this new variant was validated by in vitro biochemical analysis (Tables 8-9). Upon polyspecificity analysis of chromosomally integrated progenitor (pAcFRS), first generation (pAcFRS.1.t1) and second generation (pAcFRS.2.t1) AARSs, it was discovered that altering the binding pocket to exclude pAzF resulted in the selection of a variant that efficiently incorporated nsAAs not incorporated by other variants. A AARS-nsAA specificity heat map based on the results indicated that each of the 14 different nsAAs can be incorporated at high efficiency by selecting the appropriate AARS variant (Table 12).

TABLE 12

Nonstandard amino acids (nsAAs) that generated significant fluorescent signals in the nsAA library screening experiments.

| nsAA No. | nsAA name | Positions |
| --- | --- | --- |
| 1 | pAcF | 19; J14 (repeat) |
| 2 | pAzF | H16; P20 (repeat) |
| 3 | StyA | F7 |
| 4 | 4IF | I5; O8 (repeat) |
| 5 | 4BrF | P3; N8 (repeat) |
| 6 | 4ClF | O3; M8 (repeat) |
| 7 | 4MeF | J5; P8 (repeat) |
| 8 | 4CF3F | L5; J10 (repeat) |
| 9 | MeY | K5; I10 (repeat) |
| 10 | 4NO2F | M5; K10 (repeat) |
| 11 | 4BuF | O5; M10 (repeat); L24 (repeat) |
| 12 | BuY | I14; O19 (repeat) |
| 13 | 2NaA | I4 |
| 14 | PhF | M14; M23 (repeat) |

TABLE 13

Chemical structures of non-standard amino acids that generated significant fluorescent signals in the nsAA library screening experiments.

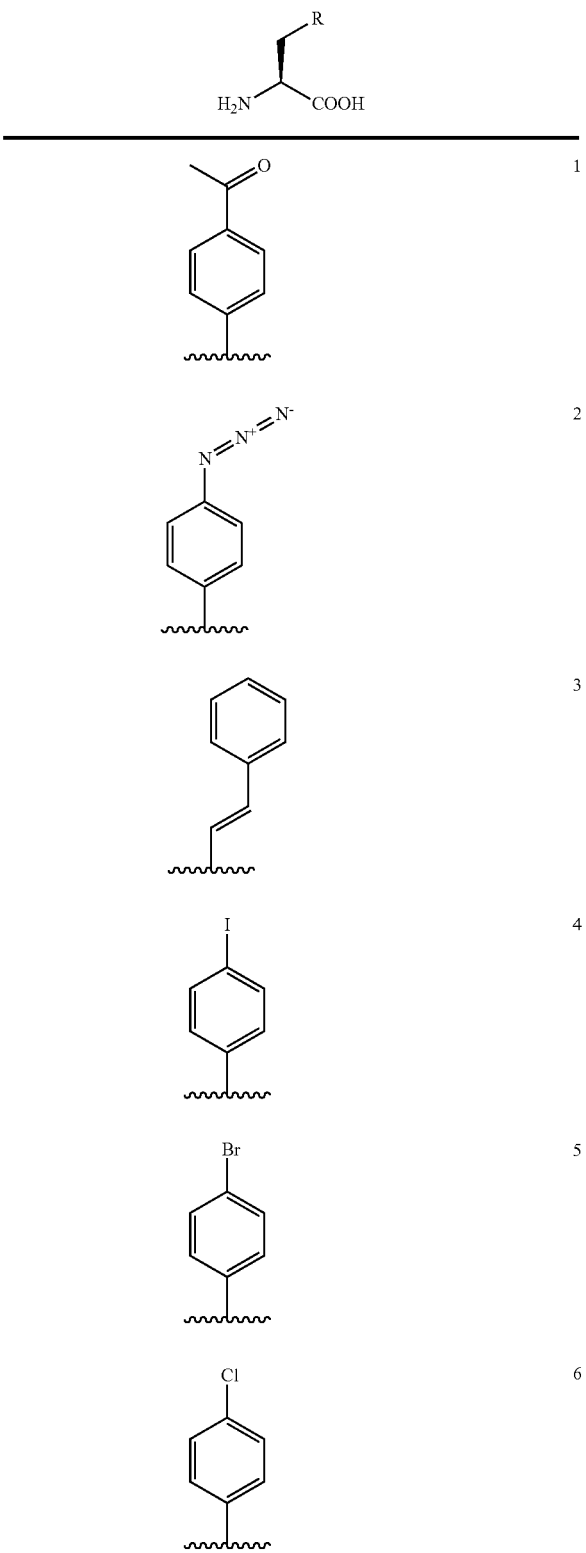

TABLE 13-continued

Chemical structures of non-standard amino acids that generated significant fluorescent signals in the nsAA library screening experiments.

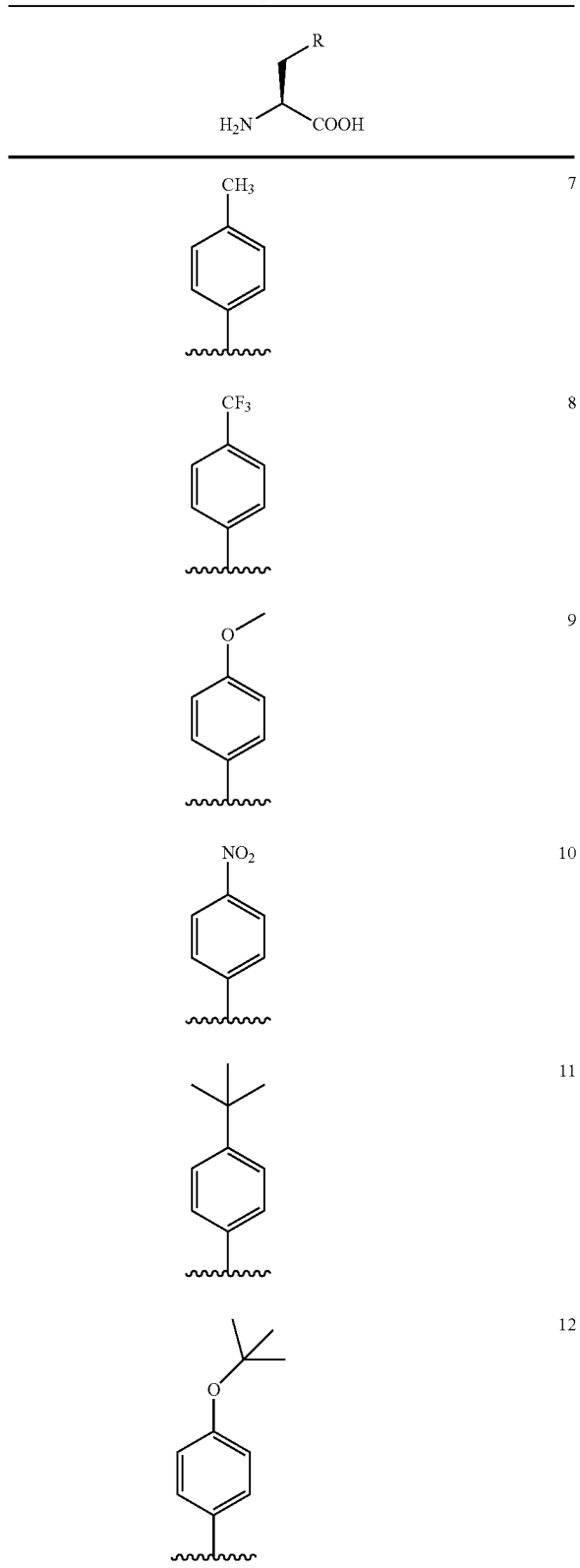

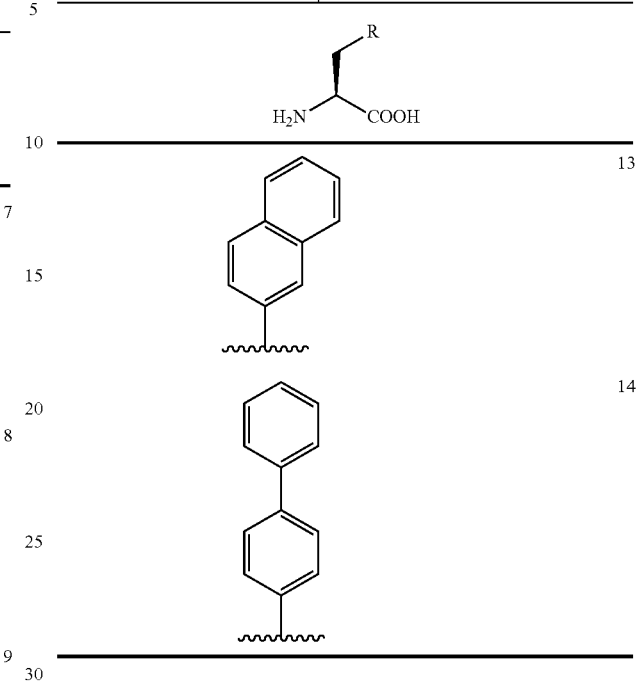

Example 6: Evolved AARSs Enable Efficient and Accurate Incorporation of Many nsAAs Per Protein Materials and Methods Intact Mass Measurements of GFP(3TAG)

Intact mass measurements were performed by electrospray MS on an Agilent 6550 QTOF instrument after external calibration. Samples were dissolved in 0.1% formic acid in water and 3% acetonitrile and infused at a flow rate of 0.6 ml/min onto a gradient from 3% Acetonitrile w/0.1% formic acid in water to 90% Acetonitrile w/0.1% formic acid in water through a Poroshell 300SB-C18, 2.1×75, 5 mm column, over 10 minutes. Spectra deconvolution was performed with Agilent MassHunter Qualitative Analysis software v. B.06.00 Bioconfirm Intact mass module using the maximum entropy deconvolution algorithm.

Shotgun Discovery Proteomic Analysis and Quantitation of nsAA Incorporation by MRM Reagents Tris base (Tris), hydrochloric acid (HCL), 1-propanol, dimethyl sulfoxide (DMSO), methyl stearate, sodium deoxycholate and iodoacetamide (IAA) were obtained from Sigma Aldrich (St. Louis, Mo.). Dithiothretitol (DTT) and ethylenediaminetetraacetic acid disodium salt (EDTA) was from American Bioanalytical (Natick, Mass.). The acid labile surfactant II (ALS II) was from Protea Biosciences (Morgantown, W. Va.). ALS II stock solutions were prepared fresh at a concentration of 5% (w/v) using a mixture of 1:1 (v/v) 100 mM Tris-HCl pH=8.0 and methanol. Trifluoroacetic acid (TFA) and concentrated formic acid (FA) were from Burdick and Jackson (Morristown, N.J.). Premixed HPLC grade water and acetonitrile (ACN) containing 0.1% FA was from Fisher Scientific (Pittsburgh, Pa.). CaCl$_2$ was from J. T. Baker (Phillipsburg, N.J.). Lysyl Endopeptidase (LysC) was obtained from Wako Chemicals (Richmond, Va.) as a lyophilized powder. Sequencing grade modified trypsin (0.5 mg/µl) was from Promega Madison, Wis.). Stable isotope labeled peptides for absolute quantitation were obtained from JPT Technologies (Berlin, Germany) as a lyophilized powder.

Protein Digestion

Purified ELP-GFP protein was dissolved by vortex in protein solubilization buffer (15 mM Tris-HCl, 1.5 mM EDTA, pH=8.5) and the protein concentration was determined by $UV_{280}$. Solubilization buffer was then added to adjust the concentration of the protein stock solutions to 2.0 µg/µl. For protein digestion, 12.5 µl of this solution (25 µg) was supplemented with 3.125 µl freshly prepared digestion buffer 5×. The composition of the digestion buffer 5× was: 50 mM Tris-HCl pH=8.5, 5 mM EDTA, 50 mM DTT and 2.5% (w/v) freshly prepared acid labile surfactant II (ALS II). Proteins were thermally denatured in a heat block at 95° C. for 5 min and the reaction was then quenched on ice. To alkylate the cysteines, 2.5 µl of 1 M Tris-HCl buffer (pH=8.5) and 5.83 µl freshly prepared 100 mM IAA solution were added. The reaction proceeded for 30 min at room temperature and in the dark. Excess IAA was quenched with 0.875 µl of 200 mM aqueous DTT solution. Next, 1.25 µl LysC enzyme solution, prepared at $7.0 \times 10^{-4}$ activity units/µl in water, were added and protein was digested for 4 h at 37° C. in an incubator without shaking. The digest was supplemented with 157.77 µl 105.6 mM Tris-HCl pH=8.5 buffer containing 5.28 mM $CaCl_2$. For digestion with trypsin, 3.6 µl sequencing grade porcine trypsin (Promega), provided as solution with 0.5 µg/µl trypsin, was added and digestion proceeded for 15 h at 37° C. in an incubator without shaking. The digest was quenched by adding 15.63 µl 20% TFA solution. The pH value of the digest was tested with pH indicator paper to ensure that the pH value was between a value of 1 and 2 to ensure efficient cleavage conditions for ALSII. Detergent was hydrolyzed for 15 min at 23° C. and peptides were desalted using $C_{18}$ UltraMicroSpin columns (The Nest Group, Southborough, Mass.) following the instructions provided with the columns. Eluted peptides solutions were dried in a vacuum centrifuge which was operated at 45° C. The dried peptides were then dissolved by vortex in 11 µl peptide solvent consisting of 2:3:7 by volume 70% FA, 1-propanol and 0.5% acetic acid. The peptide concentration was determined by $UV_{280}$ enabling equal loading for LC-MS. Peptide stock solutions were frozen at −80° C. until use. For shotgun proteomic analysis, peptide stock solutions were diluted to a concentration of 60 ng/µl in 3:8 by volume 70% formic acid 0.1 TFA and 5 µl corresponding to 300 ng total peptides were injected for each analysis.

Standard and Sample Preparation for MRM Quantitation of ELP-GFP Peptides

The C-terminally labeled stable isotope labeled peptides (lysine ($^{13}C_6{}^{15}N_2$) or arginine ($^{13}C_6{}^{15}N_4$)) VPGAGVP-GYGVPGVGK, VPGAGVPGFGVPGVGK and FEGDTLVNR were obtained as a lyophilized powder supplied as 1 nmol aliquots. Peptides were dissolved in 30% acetonitrile 0.1% formic acid at a concentration of 20 pmol/µl. Standards were then combined to obtain a master mix with 6.666 pmol/µl of each peptide. Dilution of peptide standards and protein digest for MRM was performed in Agilent polypropylene sample vials with MRM solvent consisting of 100 ng/µl sodium deoxycholate in 3:7 by volume DMSO/0.1% formic acid. Calibration of the instrument was performed with a 11 point calibration curve with 0, 1, 2, 5, 10, 20, 50, 100, 200, 500 and 1000 fmol peptide injected. Peptide stock solutions from the digestion of ELP-GFP were prepared at 5 ng/µl in MRM solvent containing 50 fmol/µl of the stable isotope labeled peptides. MRM solvent blank injections between sample injections and quality control standards analyzed before and after sample injection ensured consistent performance of the MRM platform.

MRM Assay Development

Shotgun discovery data from the analysis of stable isotope labeled peptides and ELP-GFP digests were imported into Skyline[2] software v. 2.5 to extracted suitable transitions for MRM quantitation of peptides. A detailed description of this workflow will be reported somewhere else[3]. Briefly, at least 3 transitions were extracted for peptides reporting incorporation of natural and unnatural amino acids at the position of the stop codon. The reporter peptide had the generic formula VPGAGVPGXGVPGVGK with X designating the position of the stop codon. Any amino acid identified in the shotgun discovery runs was included in the assay specifically the amino acids: W, F, H, Q, Q-1 (deamidated Q) K, I, L, P, S, G, K, R and NSAA pAcF and pAzF. Optimized transitions for these peptides corresponding to fragment ions y10, y5 and b5 are provided in Table 18. Additional peptides were included in the MRM assay notably truncated reporter peptides (resulting from the cleavage of K or R at X by trypsin) and peptides SAMPEGYVQER and FEGDTLVNR which were used for quantitation of GFP (see Table 18 for details). All collision energies (CE) were calculated in silico with Skyline software according to the instrument specific formula: CE=0.051*m/z−15.563 and CE=0.037*m/z−9.784 for doubly and triply charged precursor ions, respectively[4]. The final method consisted of 83 transitions with 20 ms dwell time for each transition and an overall cycle time of 1.927 s.

Mass Spectrometry

Shotgun proteomics analysis of peptides was performed by LC-MS/MS on a Orbitrap Velos mass spectrometer[5] using at top 10 higher energy collisional dissociation (HCD) method for peptide sequencing. Online nano electrospray was performed in positive ionization mode with a spray voltage of 1.8 kV. The temperature of the ion transfer capillary was 270° C. and the S-lens RF voltage was set to 55%. Internal lock-mass calibration was performed with methyl stearate (m/z=299.294457) supplied to a custom reservoir in the ion source as described[6]. Survey full scan spectra were collected over the mass range from m/z 300-1700 using a resolving power (R) of 30000. Fragment ion spectra were collected at R=7500. Target values for ion accumulation were $1 \times 10^6$ and $3 \times 10^5$ for precursor and fragment ion scans respectively and the maximum allowed ion accumulation time for survey scans was 500 ms. The ion selection threshold for HCD was 5000 counts, the maximum allowed accumulation time for MS/MS was 250 ms and the normalized HCD collision energy was 35%. Dynamic exclusion criteria were set as follows: Unknown charge states or precursors with a charge state of 1 were excluded, the exclusion list size was 500 and the exclusion duration was 60 s. Nano liquid chromatography was performed as described earlier with the following minor modifications. The trap column consisted of a 360 µm OD and 150 µm ID fused silica capillary terminated with a 1 mm Kasil frit manufactured according to the instruction of a commercially available Kasil fit kit (Next Advance, Averill Park, N.Y.). The trap column was packed to a length of 30 mm using MAGIC $C_{18}$AQ resin (Bruker Daltonics, Fremont, Calif.) consisting of 3 µm particles with 200 Å pore size. The analytical column was prepared in-house by slurry packing a 75 µm ID PicoFrit column (New Objectives, Woburn, Mass.) with 1.9 µm diameter Reprosil-Pur 120 C18-AQ $C_{18}$ particles (Dr. Maisch GmBH, Ammerbuch, Germany) to a length of 20 cm using methanol as the packing solvent. A 90 min method and a 120 min method was used for peptide separation. Gradient conditions for the 90 min protocol have been described earlier[7]. The gradient program for the 120 min method was as follows: (min/% B) 0.0/5.0, 0.1/5.0, 15.0/11.0, 75.0/25.0, 98.0/50.0, 99.0/95.0 104.0/95.0, 106.0/5.0, 120.0/5.0.

Multiple reaction monitoring (MRM) for peptide quantitation was performed on an Agilent model 6490 triple quadrupole instrument equipped with a ChipCube ion source. The ions source was operated at 200° C. with a spray voltage of 1880 V. Nitrogen and compressed air were supplied at flow rates of 11 and 5 L/min respectively. The Fragmentor voltage was 380 V and the cell accelerator voltage was 5 V. The mass resolving quadrupoles were operated at unit resolution and the offset of the electron multiplier was 350 V. All MRM experiments were performed with a dwell time of 20 ms for each peptide transition and the overall cycle time of the method was 1927 ms. This ensured collection of at least 10 data points across peaks. The HPLC system consisted of a temperature controlled Agilent model 1260 HiP micro AS autosampler an Agilent 1260 cap pump, used for rapid loading of samples onto the trap column, and a Agilent model 1260 nano pump for gradient elution of peptides. The autosampler was operated at 4° C. and the injection volume was 1 µl for all analyses. The ChipCube was operated with a sample flush volume of 8 µl. The carryover function was activated performing 2 wash cycles, one with 20% B and one with 80% eluent B between subsequent injections. Peptides were separated on a Polaris-HR-Chip $3C_{18}$ chip (Agilent) consisting of a 360 nl trap column and a 75 µm ID×150 mm analytical column packed with 3 µm Polaris $C_{18}$ particles. Eluent A and B were 0.1% formic acid and 0.1% formic acid in 90% acetonitrile respectively. The flow rate was 1.5 µl/min for sample trapping and 0.4 µl/min for gradient elution of peptides. The following optimized linear gradient program was used for peptide separation: (min/% B) 0.0/2.0, 1.0/12.0, 16.0/25.0, 18.5/30.0, 20.0/85.0, 23.0/2.0 28.0/2.0.

Bioinformatics

Spectra from shotgun discovery experiments were matched with MaxQuant[8] version 1.4.1.2 using the default search parameters and using E. coli database EcoCyc[9] v. 17 combined with a custom database for identification of the ELP-GFP protein. The custom database contained 20 ELP-GFP protein sequences each representing the incorporation of any of the 20 natural amino acids for a given database entry at any of the 10 UAG stop codons in the ELP-GFP protein. A detailed description of this workflow will be provided somewhere else[3]. Variable custom modifications for natural amino acids were specified to detect incorporation of the nsAA. The composition and monoisotopic masses for the modifications were the following: pAcF, delta H2C2 on Y, +26.101565 Da; pAzF, delta N3H(−1) on F, +41.00140 Da and pAzF_am, delta HN on F, +15.01090 Da. pAzF is a degradation product of pAzF. Additional variable modifications for the searches were oxidation (M) and deamidation (N/Q). Carbamidomethyl(C) was specified as a fixed modification. The enzyme specificity was Trypsin/P and only fully tryptic peptides were considered while allowing up to 3 missed cleavages. The precursor mass tolerance was 4.5 ppm and the fragment ion mass tolerance was 20 ppm for all searches. Proteins and peptides were reported after removing reverse database hits in Perseus software[10] v. 1.4.0.20. The false discovery rate for protein and peptide identifications was 1% for all experiments.

Analysis of MRM data was performed using the Agilent Quantitative Analysis software v. B.06.00 SP01 considering one quantifier ion and up to 2 additional qualifier transitions for each peptide. The ratio between the quantifier and the qualifier ion intensity (see Tables 18 and 19) was required to be within 20% of the ratio determined from the analysis of stable isotope labeled peptide standards. The Agile peak picking algorithm was used for peak integration only considering peaks exceeding a minimum signal/noise ratio of 9. Peak integration was manually verified to ensure consistent peak integration. Quantitation of peptides was performed with a weighted (1/x) quadratic calibration function that ignored the origin. Data was exported to Microsoft Excel for normalization with the spiked internal standard peptide and plotting of the data.

Results

Figure 4A:
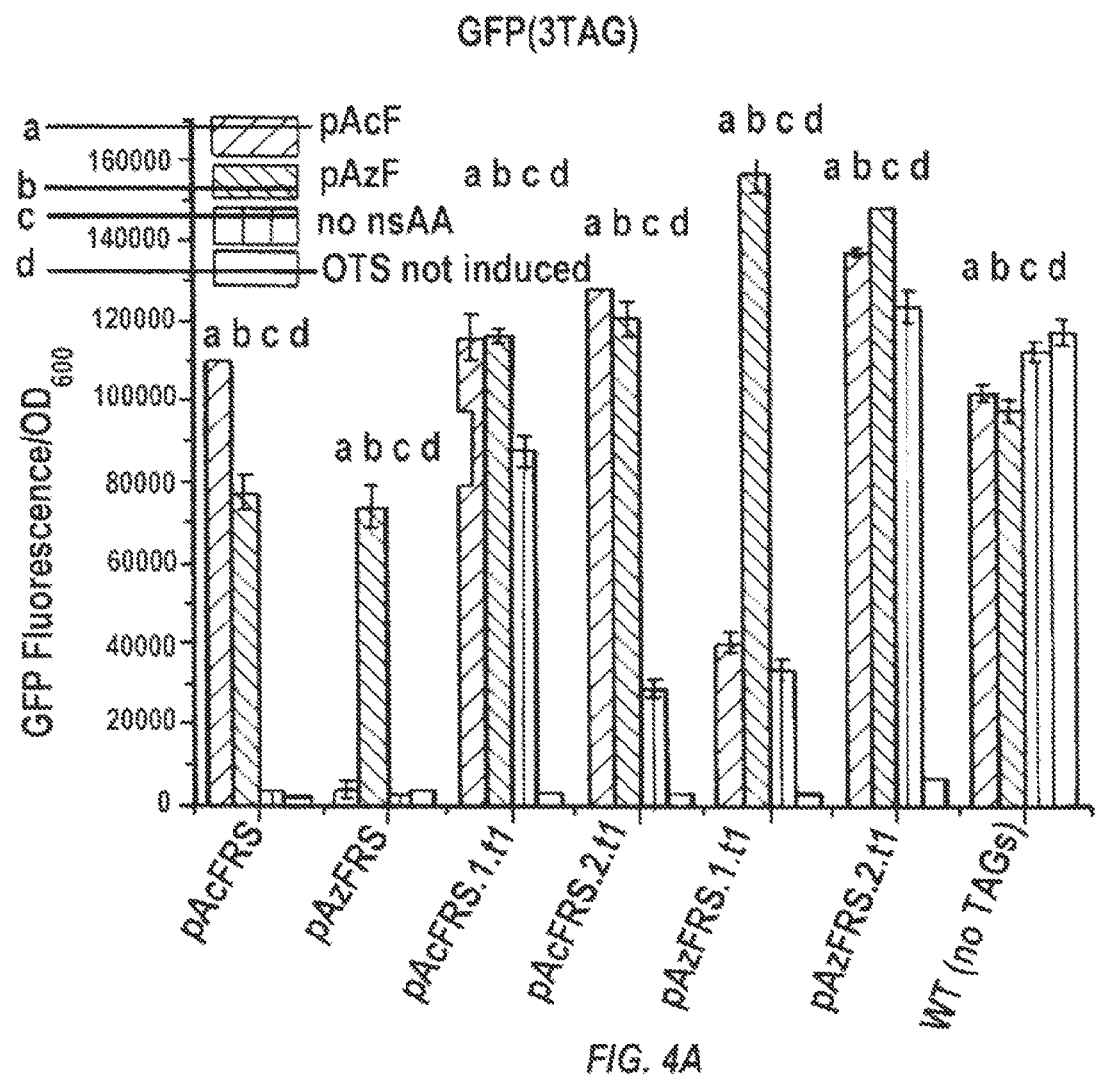
FIGS. 4A-4C are bar graphs showing the production of GFP(3TAG) (FIG. 4A), ELP(10TAG)-GFP (FIG. 4B) and ELP(30TAG)-GFP (FIG. 4C) by progenitor and evolved OTSs expressed on multi-copy plasmids in the GRO compared with WT (no TAG) proteins. Error bars represent s.d. from the values of three technical replicates. Data shown is representative of at least three independent experiments.
Figure 4B:
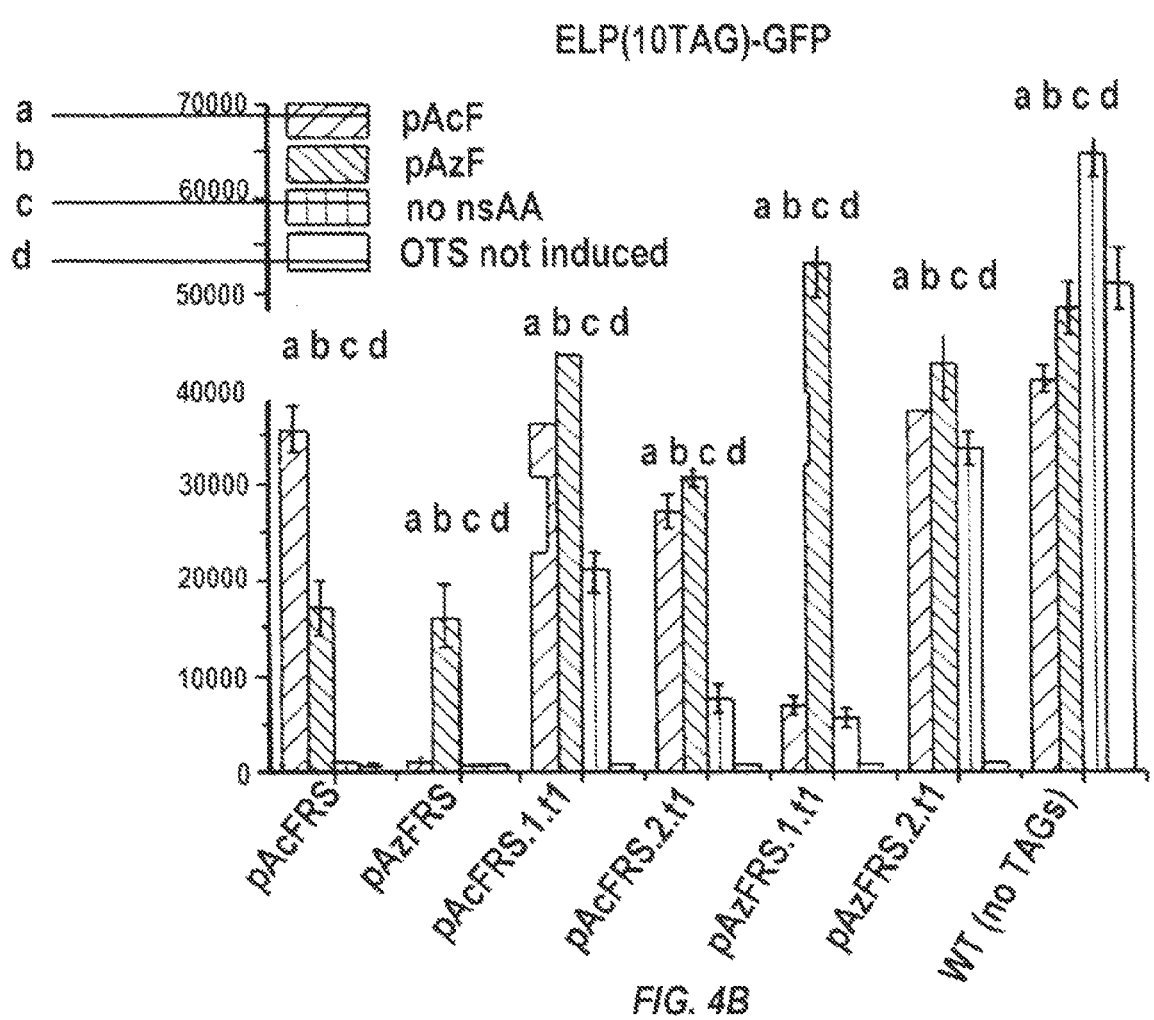
Figure 4C:
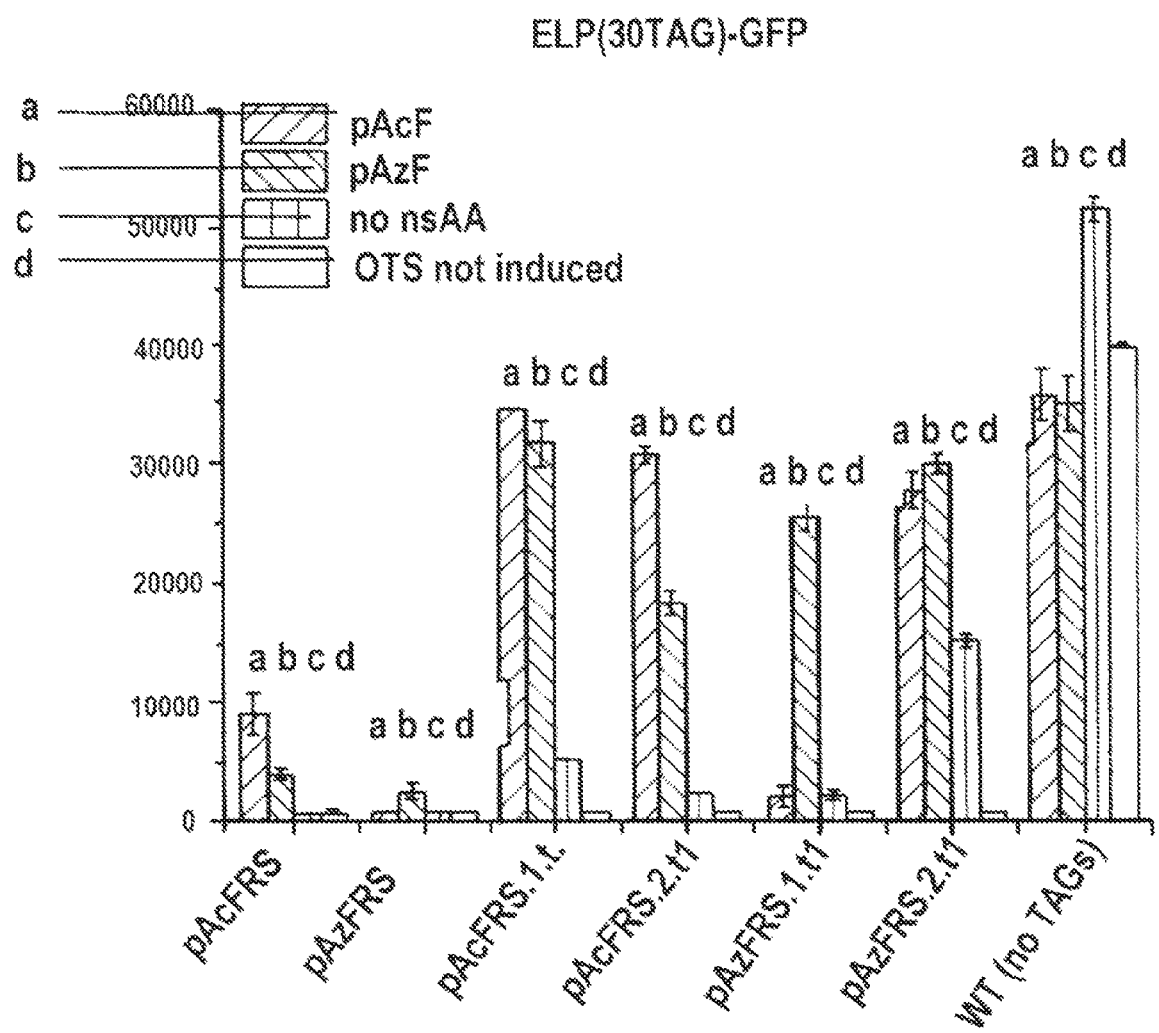
Figure 4D:
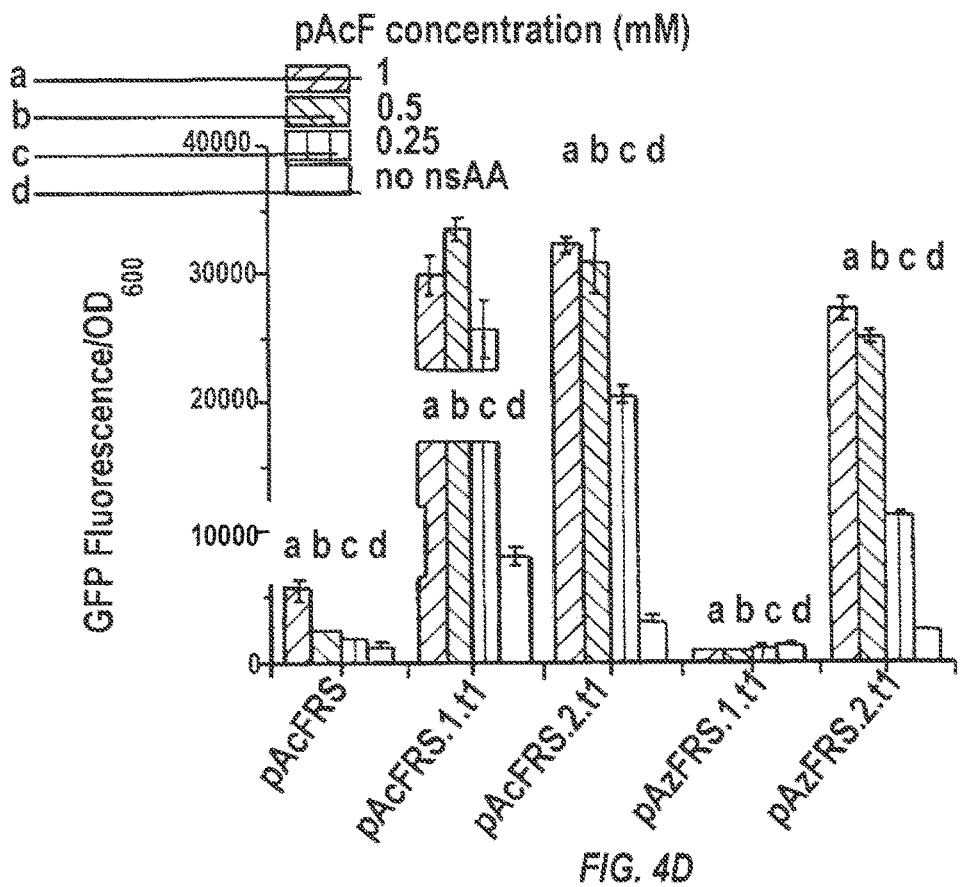
FIGS. 4D and 4E are bar graphs showing production of GFP by pAcFRS (FIG. 4D) and pAzFRS (FIG. 4E) variants at different concentrations of pAcF (FIG. 4D) and pAzF (FIG. 4E). Data shown is the average of two independent experiments each with three technical replicates.
Figure 4E:
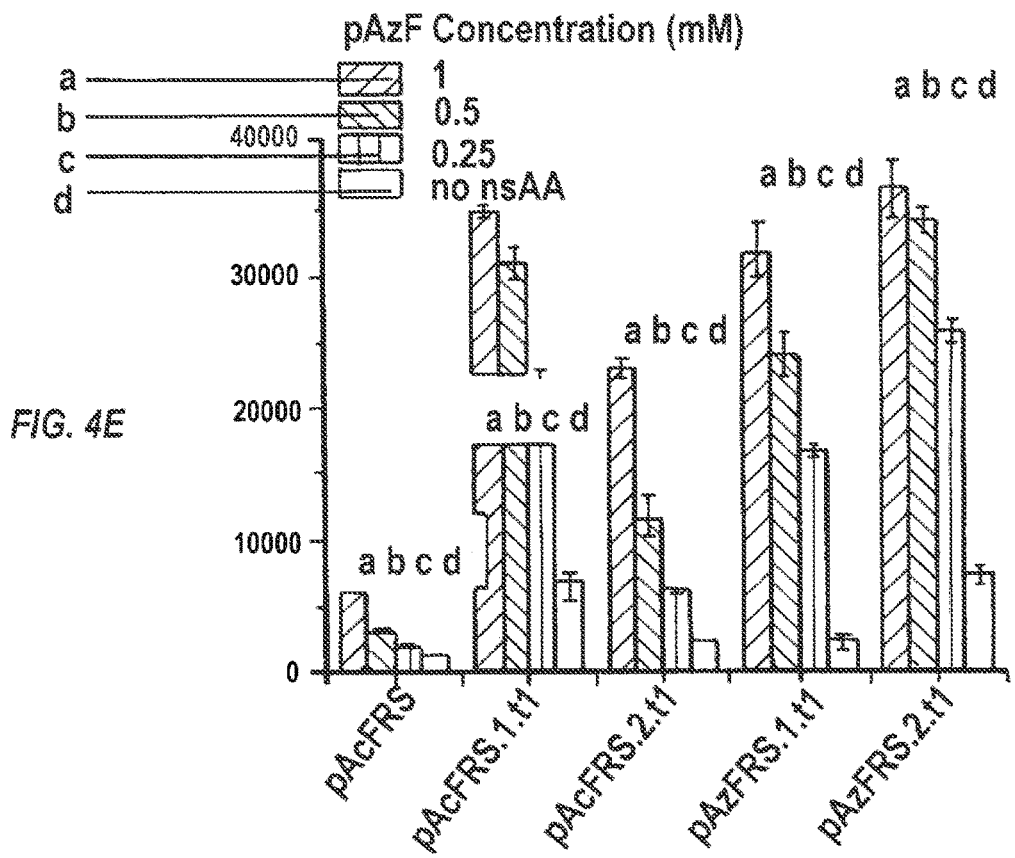
Figure 6:
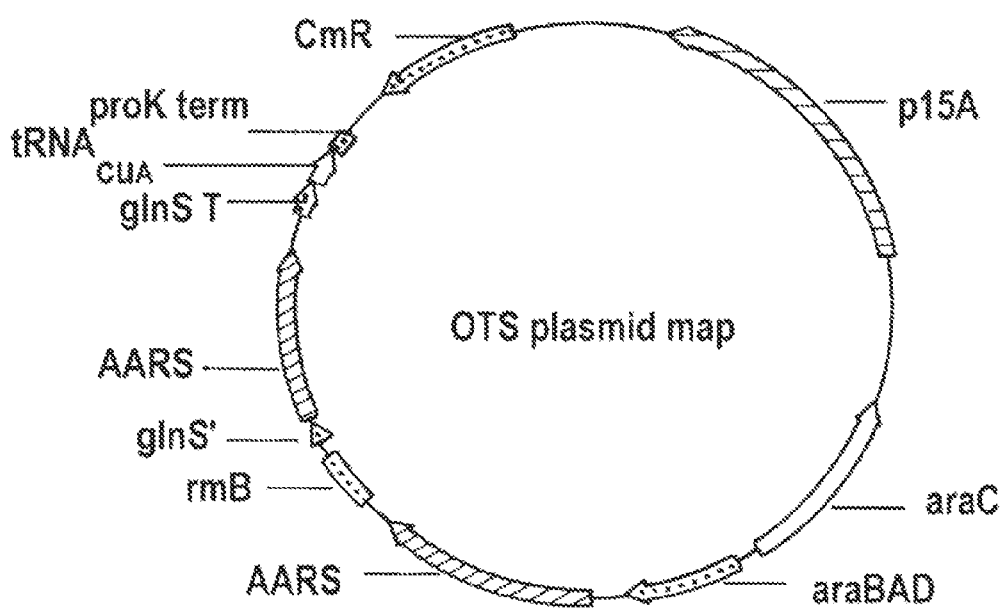
FIG. 6 is a Plasmid map of the OTS plasmids constructed for each AARS variants.

To evaluate whether the evolved AARSs can improve multi-site nsAA incorporation, the GRO were transformed with episomal versions of each OTS variant (FIG. 6) and a plasmid carrying the reporter protein with three, ten, or 30 TAGs, or WT equivalents. Plate-based fluorescence analysis indicated increased incorporation of either pAcF or pAzF for all of the evolved OTSs by the evolved OTSs for expression of GFP(3TAG) up to 1.1- or 2-fold with pAcF or pAzF, for expression of ELP(10TAG)-GFP up to 1.1- or 3.2-fold with pAcF or pAzF, and for expression of ELP(30TAG)-GFP up to 4- or 7-fold with pAcF or pAzF (FIG. 4A-4C). Purification of ELP(30TAG)-GFP containing pAcF expressed by the GRO in small batch cultures revealed a 5-fold increase in protein production of up to 54 mg/L or >90% of WT-protein expression under similar conditions, as well as high-yield expression of ELP(30TAG)-GFP containing pAzF (~35 mg/L, compared with extremely low yields generated by progenitor pAcFRS or pAzFRS, that could not be purified) (Table 3). In addition, the production of ELP(30TAG)-GFP was evaluated in the presence of up to 4-fold reduced concentrations of pAcF or pAzF. This analysis reveals that several of the enzyme variants are capable of efficient production of ELP(30TAG)-GFP with 0% or <20% loss in protein yield with 2-fold or 4-fold reduced pAcF concentration, respectively, or with <5% or <30% loss in protein yield with 2-fold or 4-fold reduced pAzF concentration, respectively. Importantly, the evolved OTSs outperform the progenitor synthetase at all nsAA concentrations.

Next, the ability of the plasmid-based OTSs to produce ELP(30TAG)-GFP was evaluated with a panel of 14 nsAAs. A fluorescence assay indicates increased production of ELP (30TAG)-GFP by select AARS variants for every nsAA in this panel compared with the progenitor pAcFRS, and purification of ELP(30TAG)-GFP containing select nsAAs confirms high yield (48-65 mg/L) production of these biopolymers. This analysis also reveals that while the pAzFRS.1.t1 maintains stringent specificity for pAzF, the specificity of variant pAcFRS.2.t1 for pAcF over pAzF decreases when expressed on a multi-copy plasmid. Importantly, these results demonstrate that the ELP-GFP fusion protein resolves previously encountered issues of misfolding and aggregation caused by multi-site nsAA incorporation in the GFP open reading frame (Johnson, et al., Nat Chem Biol, 7:779-86 (2011)), while retaining the ability to assay chemically diverse nsAA incorporation by GFP fluorescence.

When expressed on multi-copy plasmids in the absence of nsAAs, all of the evolved variants generate an increase in protein production compared with the progenitor enzyme (FIG. 4A-4C), which may indicate incorporation of natural amino acids. Accordingly, the plasmid-based, but not the chromosomal-based, variants fail the negative selection step by producing full-length tolC containing 4 TAGs in the absence of nsAAs. However, protein production in the absence of nsAAs decreases with increasing number of TAGs, indicating reduced efficiency of natural amino acid incorporation compared with nsAA incorporation. Similarly, time-course analysis of GFP(3TAG) or ELP(30TAG)-GFP expression reveal reduced rate of protein production in the absence of the nsAA, indicating that incorporation of the nsAA is favored over natural amino acids.

Figure 4F:
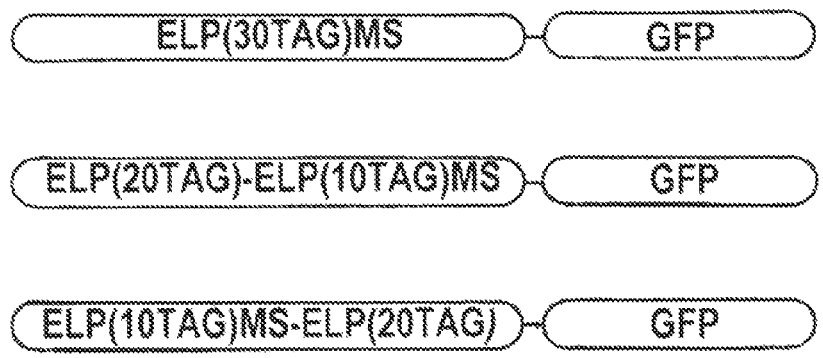
FIG. 4F is a series of schematic illustrations of reporter proteins for incorporation of 30 nsAAs.
Figure 4G:
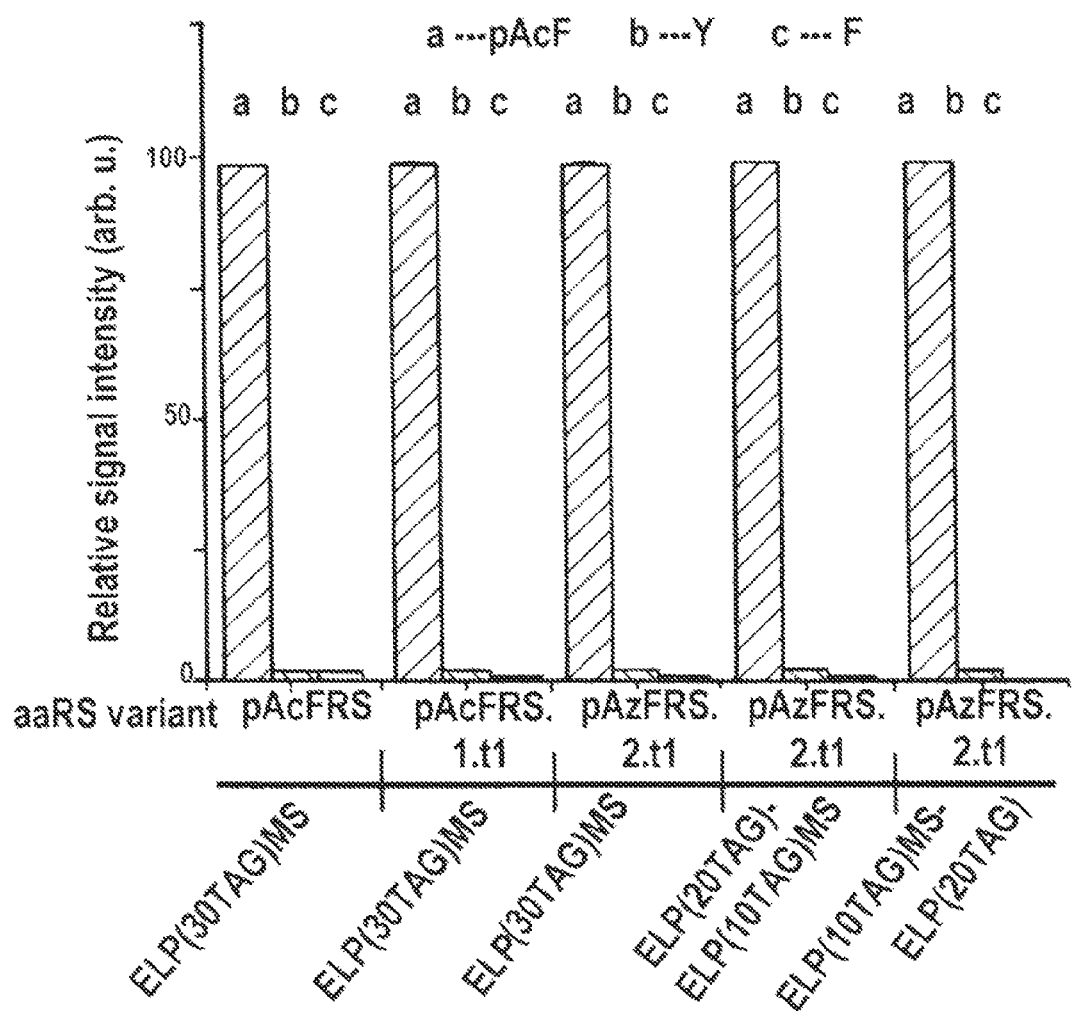
Figure 4H:
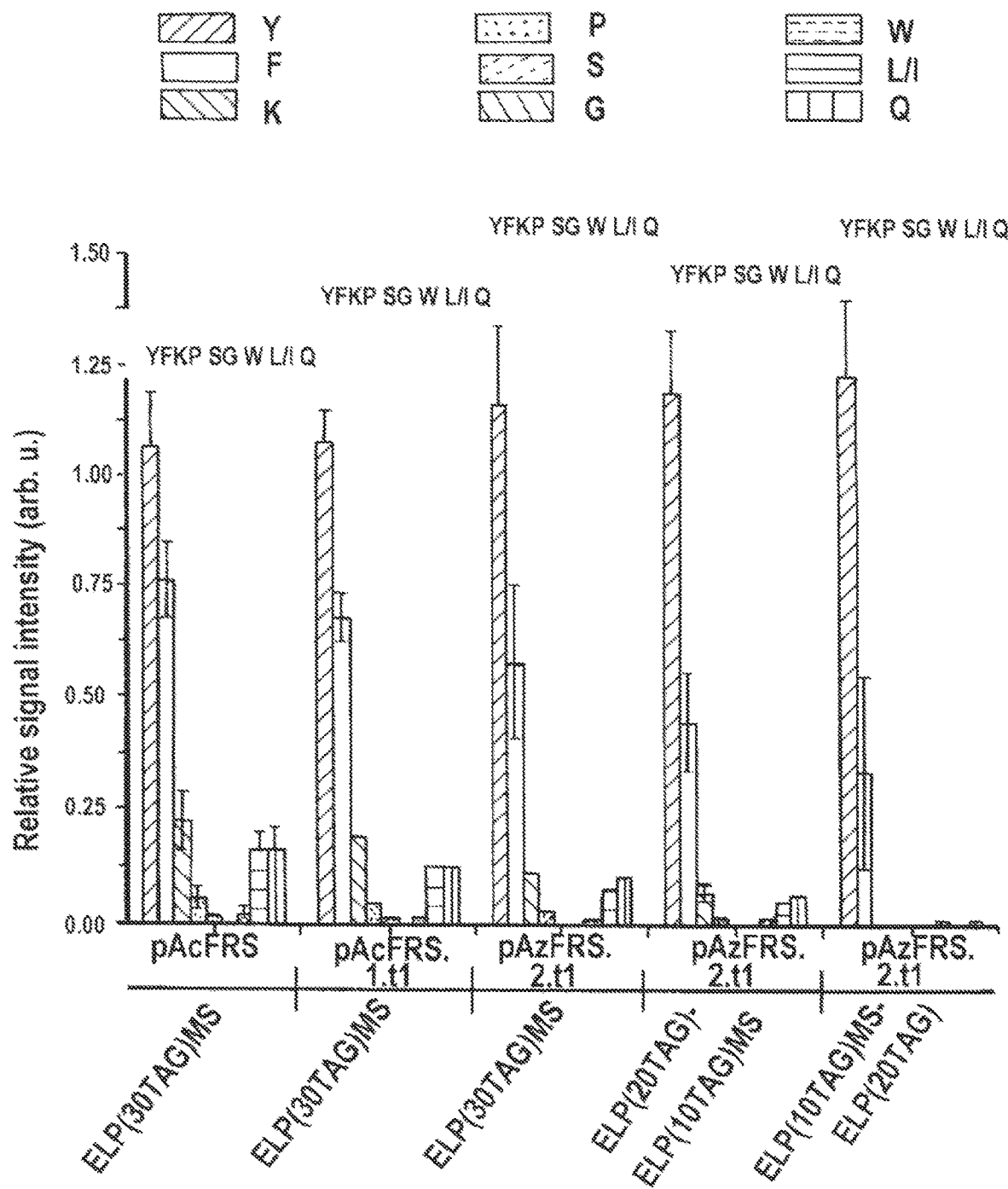
Figure 5A:
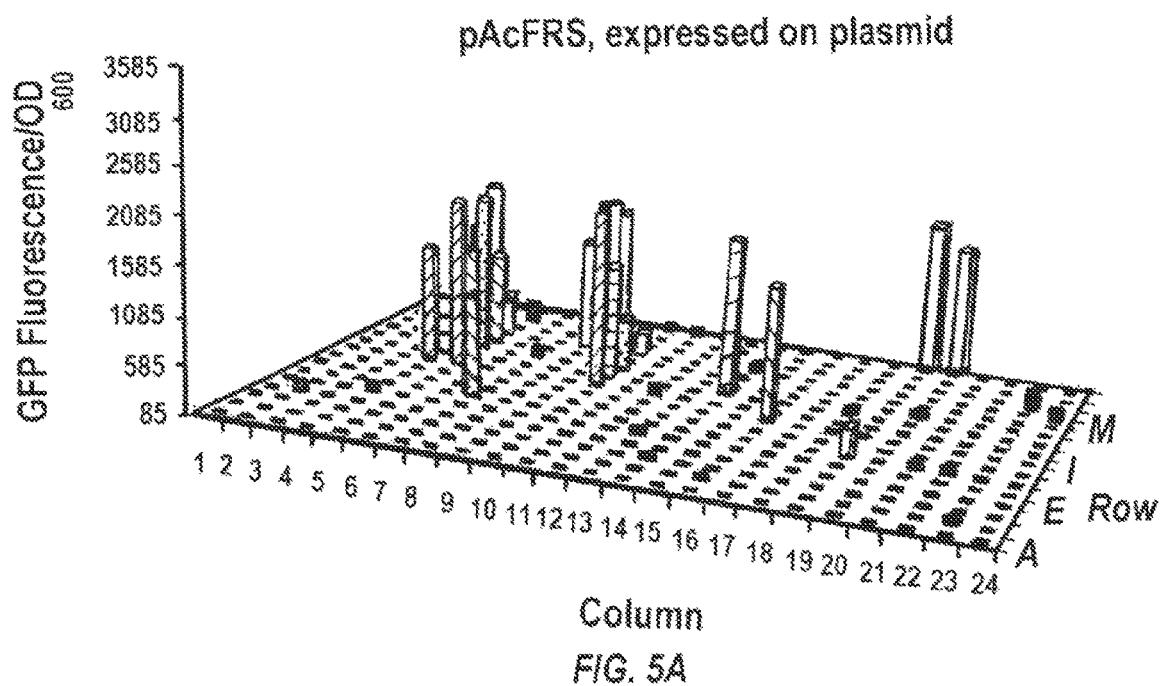
FIGS. 5A-5M are bar graphs showing the relative GFP (3TAG) fluorescence for each of the indicated progenitor (pAcFRS (expressed on plasmid) in 5A; pAcFRS (chromosomally integrated) in 5B)) and evolved AARS (pCnFRS (chromosomally integrated) in 5C; R257G (chromosomally integrated) in 5D; R257C, F261E (chromosomally integrated) in 5E; A167D (chromosomally integrated) in 5F; A167D, R257G (chromosomally integrated) in 5G; D158V, I159M, L162D, A167Y (chromosomally integrated) in 5H; D158V, I159M, L162D, A167Y, R257G (chromosomally integrated) in 5I; E107T, F108Y, Q109M (chromosomally integrated) in 5J; E107T, F108Y, Q109M, R257G (chromosomally integrated) in 5K; L56V, A167D (chromosomally integrated) in 5L; and L56V, A167D, R257G (chromosomally integrated) in 5M) in the presence of each of the non-standard amino acids listed in Table 11.
Figure 5B:
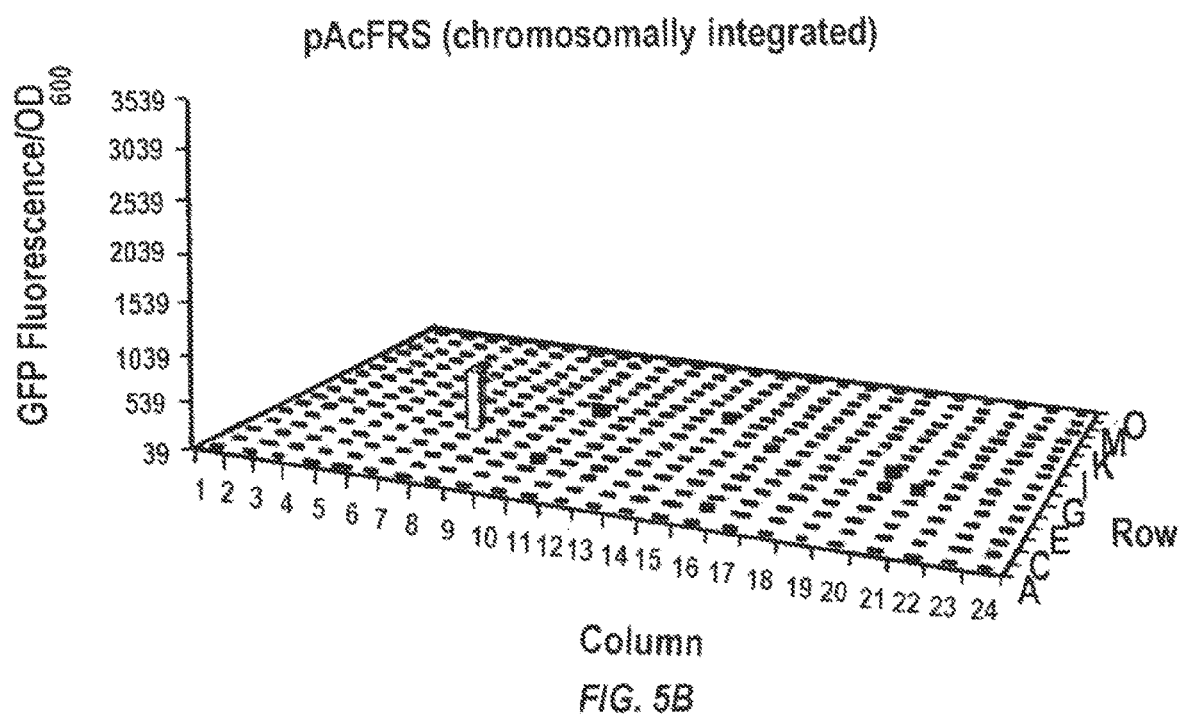
Figure 5C:
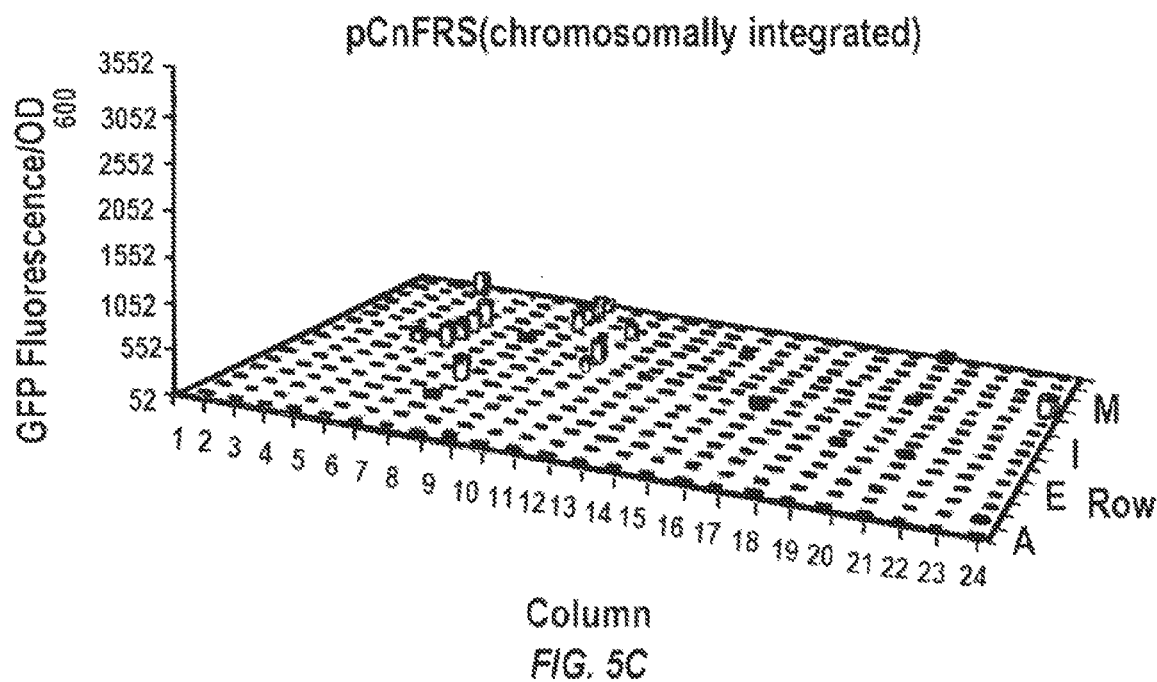
Figure 5D:
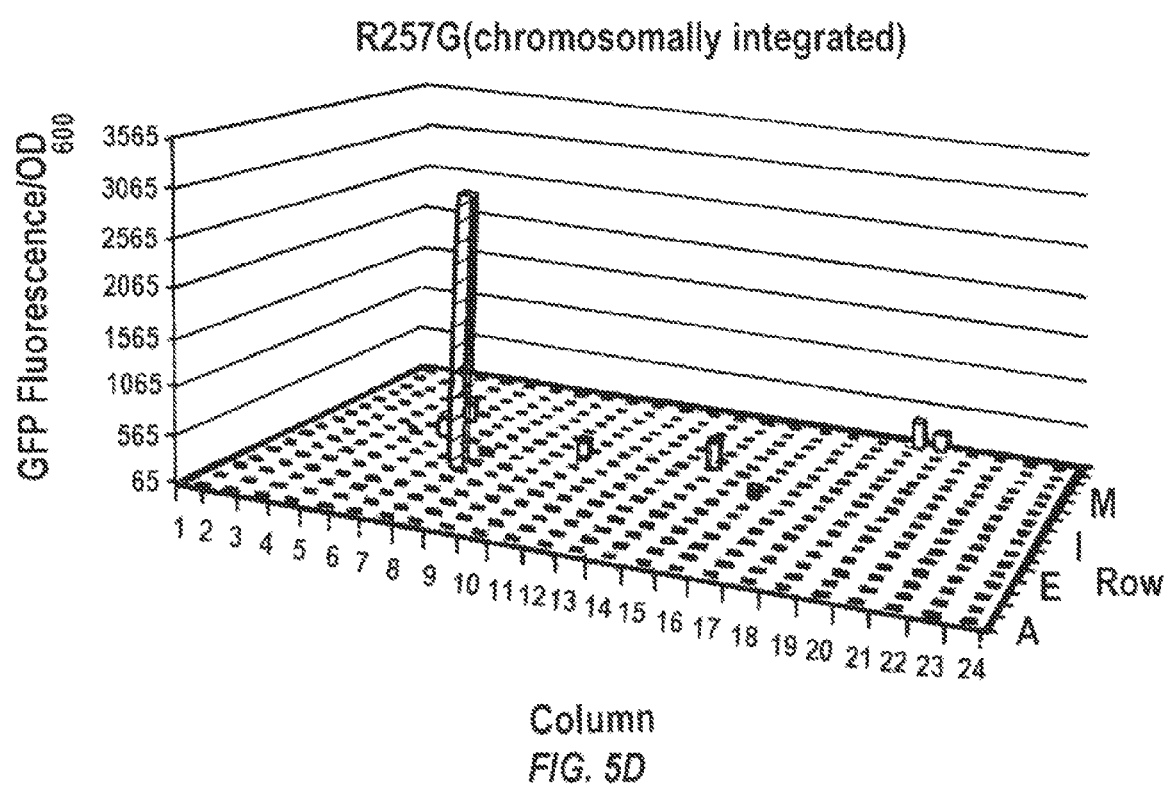
Figure 5E:
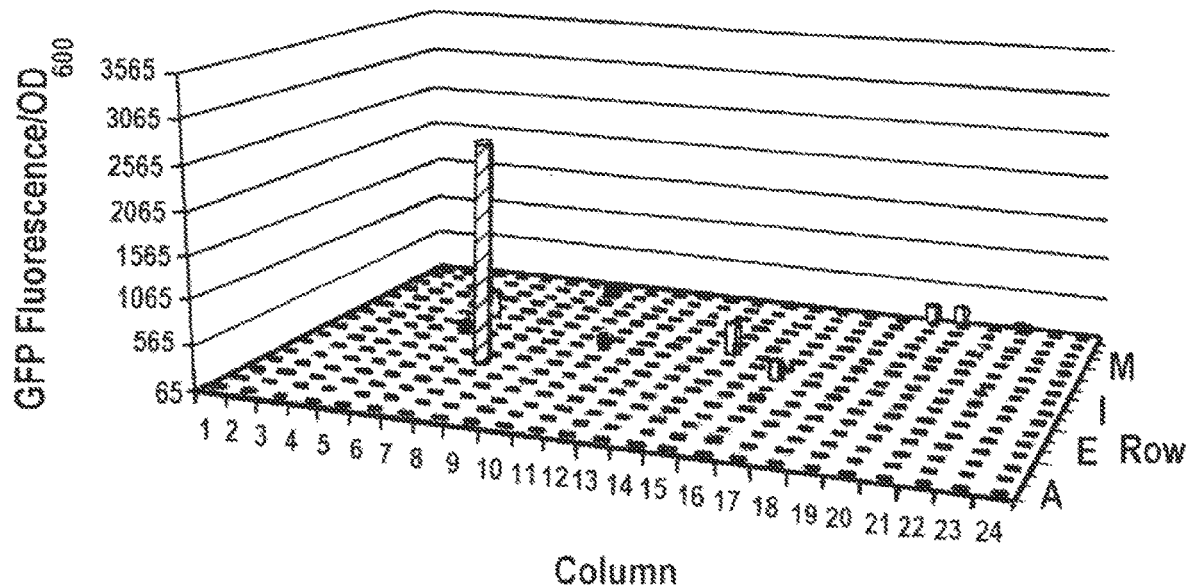
Figure 5F:
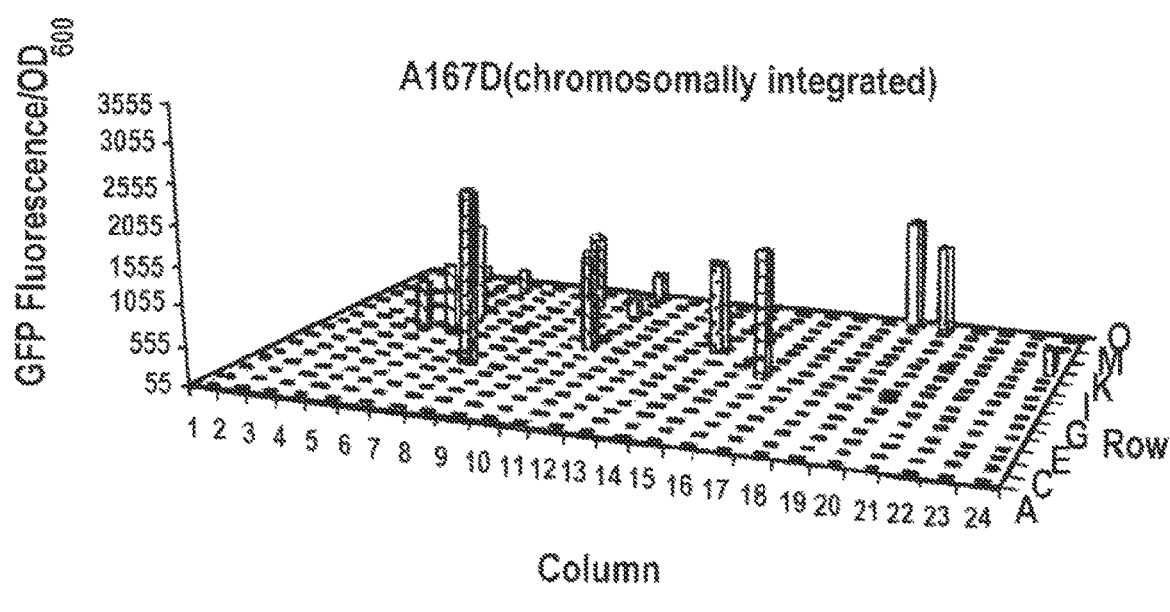
Figure 5G:
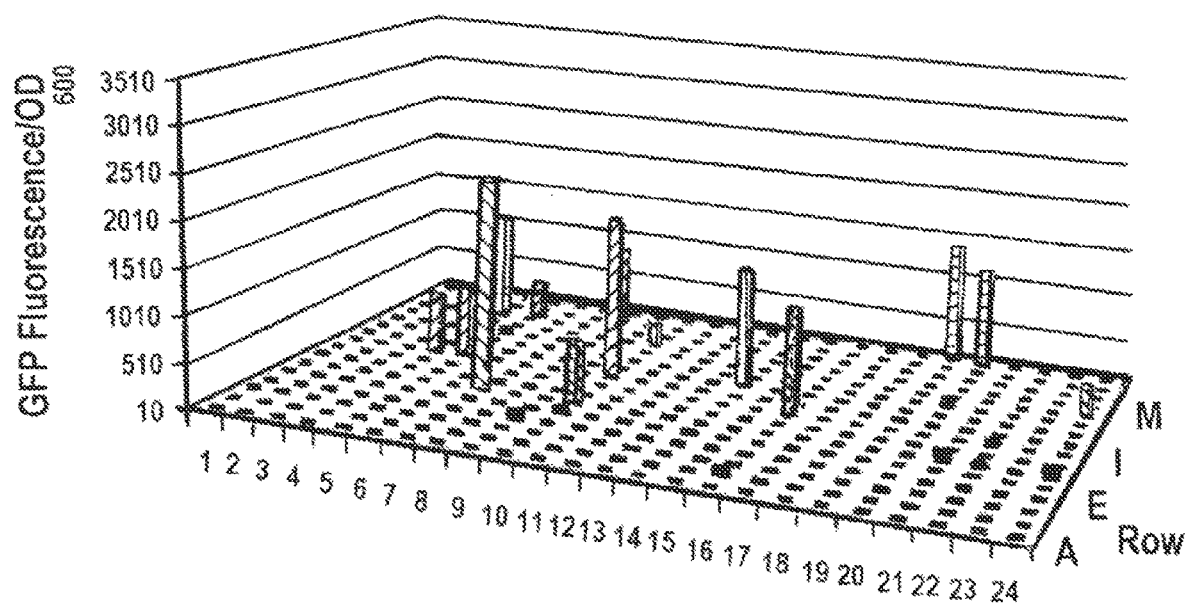
Figure 5H:
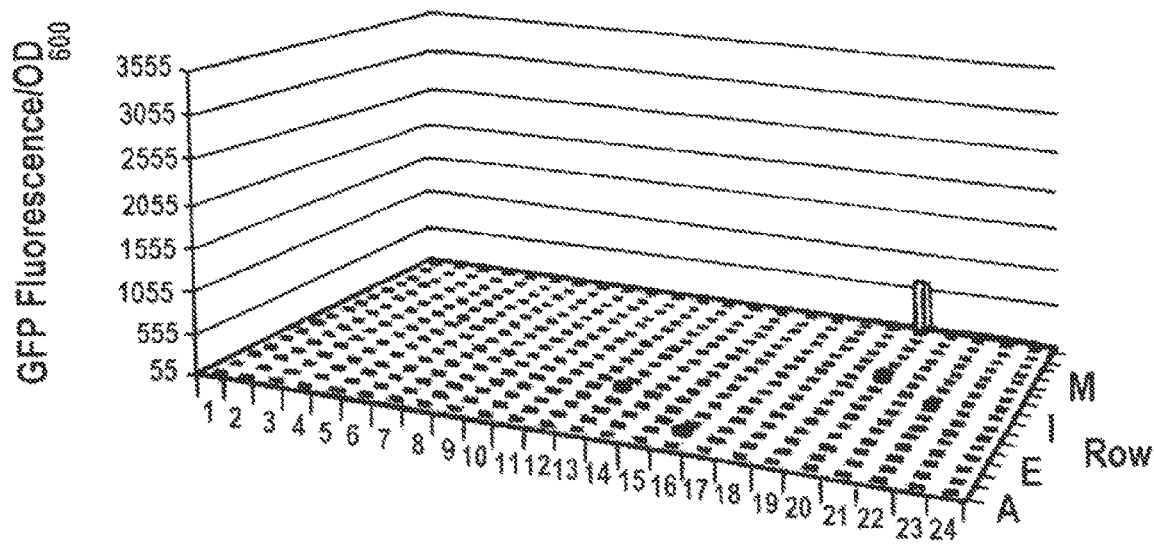
Figure 5I:
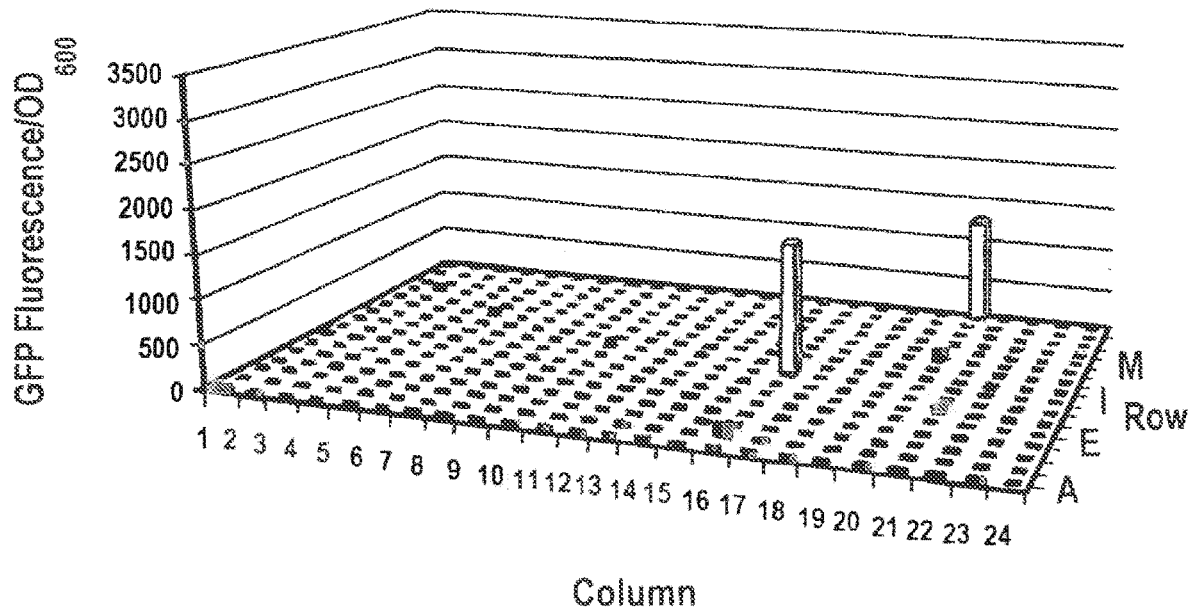
Figure 5J:
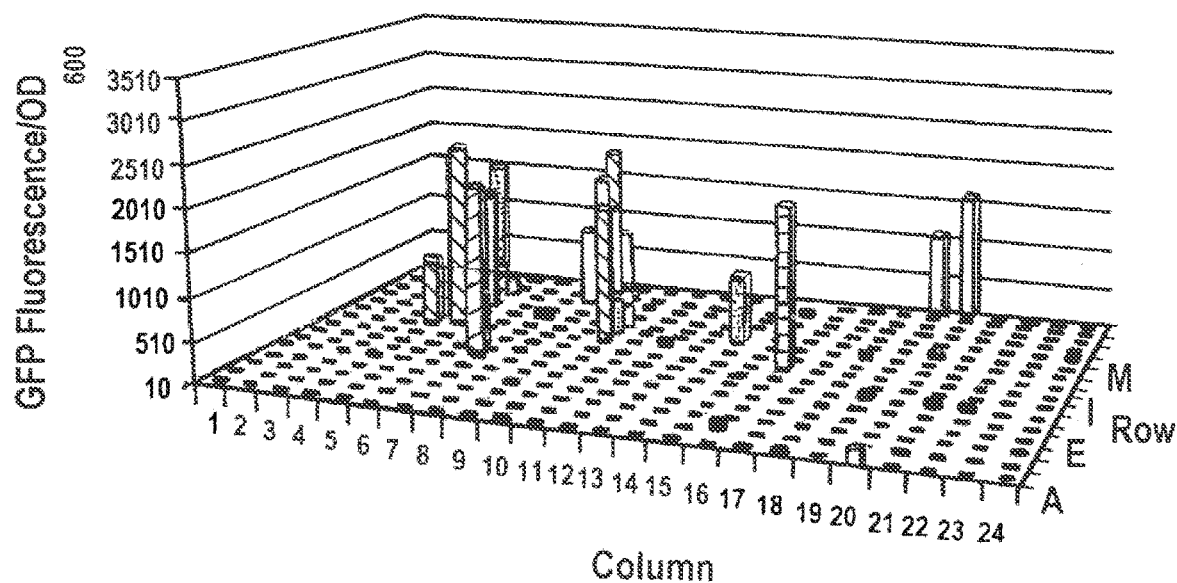
Figure 5K:
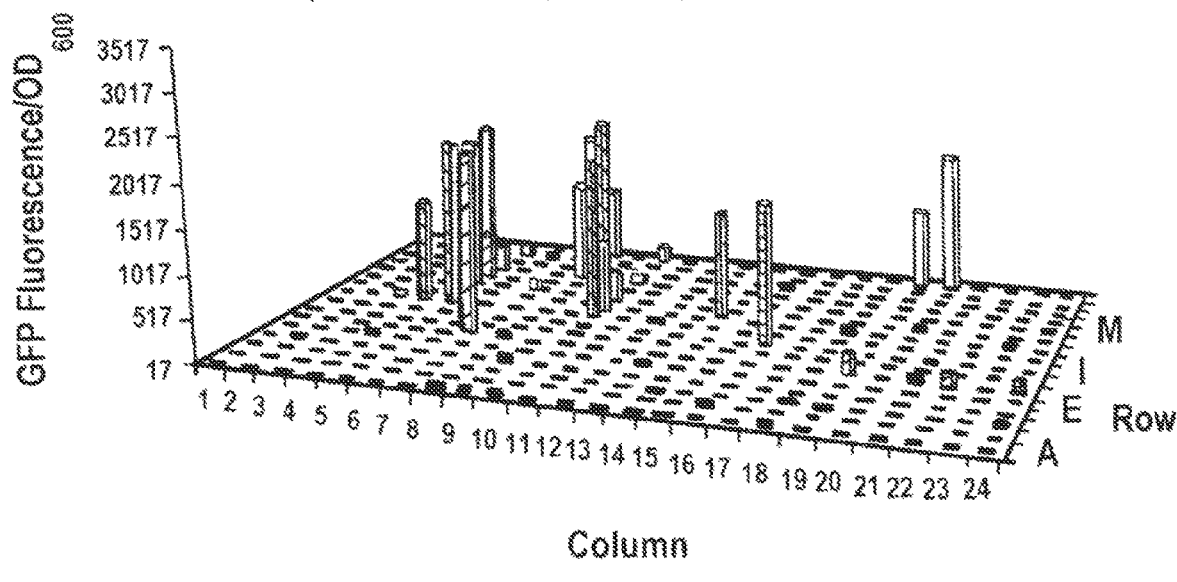
Figure 5L:
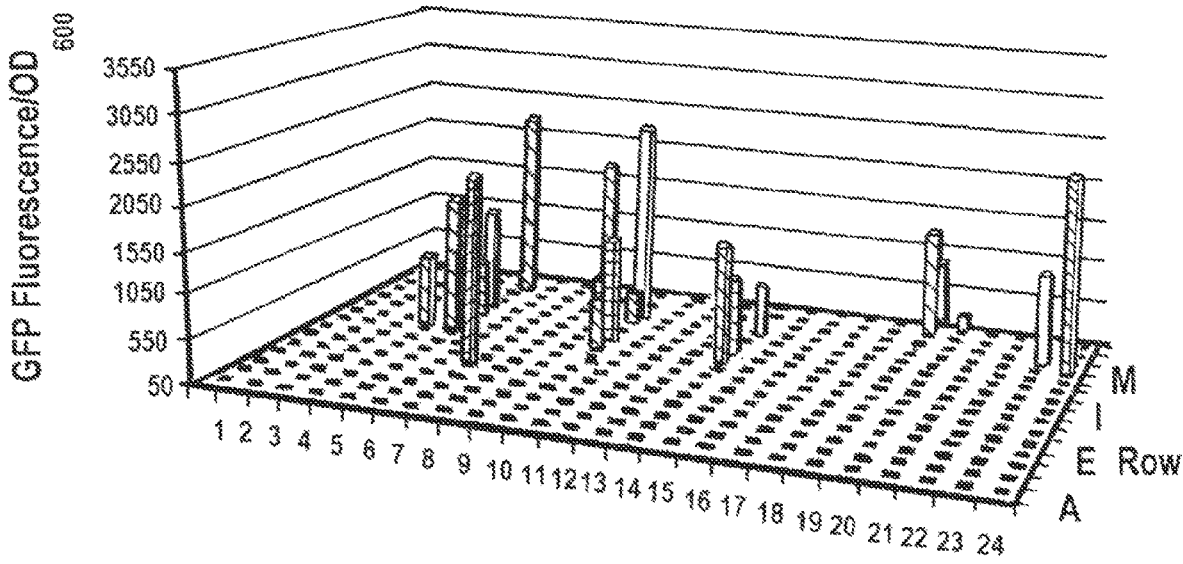
Figure 5M:
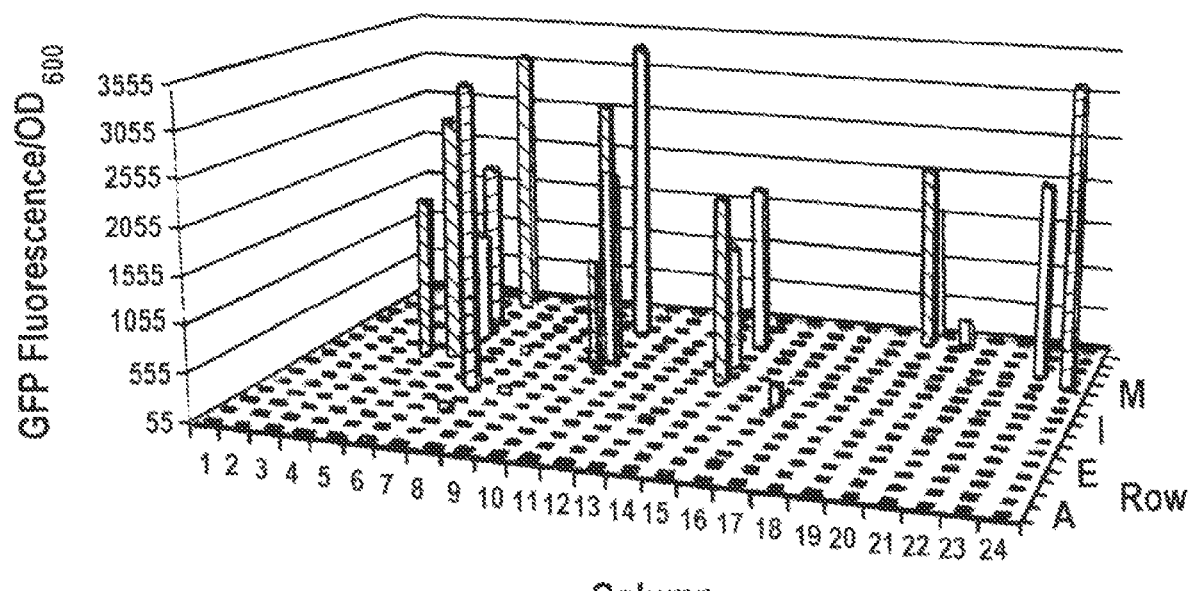

A multiple reaction monitoring (MRM) based-mass spectrometry assay was employed to examine and assay the fidelity of multi-site nsAA incorporation by the plasmid based variants (Lajoie, et al., Science, 342: 357-60 (2013); Aerni, et al., NAR IN PRESS). The most efficient variants (pAcFRS.1.t1 and pAzFRS.2.t1) and multi-site incorporation in ELP(10TAG)-GFP and ELP(30TAG)-GFP, and the effect of TAG codon position (i.e., at the N- or C-terminus) on nsAA incorporation accuracy were examined. New reporters termed ELP(10TAG)-GFP$_{MS}$, ELP(30TAG)-GFP$_{MS}$, were constructed to facilitate examination of nsAA incorporation accuracy throughout the 10TAG or 30TAG polymer chain. Additional reporters ELP(10TAG)$_{MS}$-ELP (20TAG), ELP(20TAG)-ELP(10TAG)$_{MS}$, and ELP(10TAG)-ELP(10TAG)$_{MS}$-ELP(10TAG) were also constructed to facilitate examination of the TAG codon position with respect to the N-terminus on nsAA incorporation accuracy (FIG. 4F). All proteins expressed with good yields with the exception of ELP(10TAG)-ELP(10TAG)MS-ELP(10TAG) which did not express. Shotgun LC-MS/MS analysis was carried out to inform MRM assay development (Tables 14 and 15). While the shotgun assay cannot be used to quantify the amount of pAcF or natural amino acid containing peptides, it informs of the most prevalent amino acids incorporated at the TAG codons. To accurately quantify the accuracy of nsAA incorporation, MRM analysis of pAcF incorporation by pAcFRS, pAcFRS.1.t1, and pAzFRS.2.t1 was performed, and indicated that these OTSs incorporate pAcF at >95% of the peptides for all constructs examined (FIG. 4H-4I). In addition, we found that nsAA incorporation accuracy is independent of TAG codon position with respect to the protein N-terminus, and is also independent of any local mRNA differences such as proximity to the GFP mRNA or to ELP(10TAG) mRNA.

Analysis of nsAA incorporation accuracy was similarly performed for pAzF incorporation in ELP(10TAG)-GFP$_{MS}$ by pAzFRS.1.t1, which indicated similar magnitudes of misincorporation as in pAcF containing samples (Table 14-15). Low levels of K, P, S, G, W, L/I and Q (FIG. 4H-4I) were observed. A striking decrease in near cognate suppression and mischarging events of K, P, L/I, and Q content in proteins produced by pAcFRS.1.t1 and pAzFRS.2.t1, but not in pAzFRS.1.t1 was also observed.

In addition, ELP(10TAG)-GFP$_{MS}$ expressed in the presence of the evolved pAcFRS and pAcF and the GFP-derived peptides FEGDTLVNR and SAMPEGYVQER were examined for pAcF incorporation at the phenylalanine (F) and Tyrosine (Y) positions underlined (as F and Y as most structurally similar to pAcF and therefore more likely to mischarge). In previous shotgun analysis detection of misincorporation was demonstrated at levels greater or equal to 0.01%, given that misincorporation of methionine, proline, and glutamine could be identified at 0.01% or greater at TAG codons. Next methods (Aerni, et al., NAR IN PRESS) were adapted to generate a searchable database by which pAcF could be identified, in an unbiased fashion, at the FEGDTLVNR and SAMPEGYVQER peptides. The results of this analysis revealed only F and Y incorporation in these peptides with no misincorporation of pAcF, indicating that misincorporation is below the level of detection and likely to be less than 0.01%; if it exists at all. Since misincoprotation of pAcF was not detected at two different positions in GFP, it was concluded that missincorporation is less likely to occur at native proteins that express at levels lower that ELP-GFP and that the levels of pAcF in the cell cannot compete with native Y and F AARS aminoacylation, confirming that the system is orthogonal as designed. Further testing of the fitness of the GRO expressing the progenitor and evolved OTS confirmed that no fitness effects can be detected due to misincorporation of pAcF by native synthetases at non-TAG codons. Taken together, these results show that the selected AARS variants are capable of orthogonal, efficient, multi-site nsAA incorporation demonstrated by high yields while maintaining purity and cell viability.

Tables 14 and 15 show a summary of shotgun proteomic data of the mass spectrometry friendly ELP(10TAG)-GFP$_{MS}$ expressed in the GRO strain without nsAAs (Table 14) or with pAcF (Table 15). The number of instances a peptide was sequenced was recorded. The highest scoring peptide is shown for each peptide is identified.

Tables 16-17 the absolute quantitation of F and Y incorporation in ELP(10TAG)-GFP$_{MS}$ELPs containing 10 or 30 TAGs. The concentration of GFP protein and the reporter peptides for Y and F was determined by absolute quantitation using MRM-based mass spectrometry using stable isotope labeled peptides for calibration. The data was corrected considering the relative abundance of isotopes in the stable isotope labeled calibration standard and the natural peptide respectively. The concentration of the NSAA's pAcF and pAzF was calculated assuming that % NSAA=100%−Y %−F %. Confidence intervals (CI) were calculated at the 95% confidence level. N=4 unless mentioned otherwise.

Table 18 shows the optimized MRM method used for quantitation of ELP-GFP peptides by MRM.

TABLE 14

Sequence and signal intensities of peptides identified in shotgun proteomics analysis of ELP(10TAG)-GFP$_{MS}$ GRO strain without nsAAs

| NSAA | Sequence | Instances of peptide sequenced | Calculated mass Da | Mass error ppm | Andromeda score |
|---|---|---|---|---|---|
| None | VPGAGVPGEGVPGVGK (SEQ ID NO: 43) | 1 | 1375.7460 | −0.83 | 76.358 |
| None | VPGAGVPGFGVPGVGK (SEQ ID NO: 44) | 6 | 1393.7718 | −3.01 | 118.76 |

TABLE 14-continued

Sequence and signal intensities of peptides identified in shotgun proteomics analysis of ELP(10TAG)-GFP$_{MS}$ GRO strain without nsAAs

| NSAA | Sequence | Instances of peptide sequenced | Calculated mass Da | Mass error ppm | Andromeda score |
|---|---|---|---|---|---|
| None | VPGAGVPGFGVPGVGKVPGAGVPGFGVPGVGK (SEQ ID NO: 45) | 1 | 2769.5330 | −0.07 | 39.795 |
| None | VPGAGVPGGGVPGVGK (SEQ ID NO: 46) | 1 | 1303.7248 | 0.33 | 95.428 |
| None | *GVPGVGK (SEQ ID NO: 47) | 1 | 612.3595 | −0.17 | 77.906 |
| None | VPGAGVPGLGVPGVGK (SEQ ID NO: 48) | 1 | 1359.7874 | −1.39 | 128.21 |
| None | VPGAGVPGPGVPGVGK (SEQ ID NO: 49) | 1 | 1343.7561 | −0.97 | 98.337 |
| None | VPGAGVPGQGVPGVGK (SEQ ID NO: 50) | 1 | 1374.7619 | −0.82 | 95.264 |
| None | VPGAGVPGSGVPGVGK (SEQ ID NO: 51) | 1 | 1333.7354 | 0.14 | 77.664 |
| None | VPGAGVPGWGVPGVGK (SEQ ID NO: 52) | 1 | 1432.7827 | −0.15 | 92.039 |
| None | GPGKVPGAGVPGYGVPGVGK (SEQ ID NO: 53) | 1 | 1748.9574 | 0.65 | 62.94 |
| None | SKGPGKVPGAGVPGYGVPGVGK (SEQ ID NO: 54) | 2 | 1964.0843 | −0.01 | 47.499 |
| None | VPGAGVPGYGVPGVGK (SEQ ID NO: 55) | 13 | 1409.7667 | −1.79 | 124.51 |
| None | VPGAGVPGYGVPGVGKVPGAGVPGYGVPGVGK (SEQ ID NO: 56) | 2 | 2801.5228 | 0.03 | 39.388 |

*C terminal fragment reporting incorporation of K or R.

TABLE 15

Sequence and signal intensities of peptides identified in shotgun proteomics analysis of ELP(10TAG)-GFP$_{MS}$ GRO strain with pAcF

| NSAA | Sequence | Instances of peptide sequenced | Calculated mass Da | Mass error ppm | Andromeda score |
|---|---|---|---|---|---|
| pAcF | VPGAGVPGFGVPGVGK (SEQ ID NO: 57) | 1 | 1393.7718 | 0.10 | 118.24 |
| pAcF | VPGAGVPGM(ox)GVPGVGK (SEQ ID NO: 58) | 1 | 1393.7388 | −1.96 | 71.933 |
| pAcF | VPGAGVPGPGVPGVGK (SEQ ID NO: 59) | 1 | 1343.7561 | −0.37 | 80.746 |
| pAcF | VPGAGVPGpAcFGVPGVGK (SEQ ID NO: 60) | 15 | 1435.7823 | −4.02 | 127.79 |
| pAcF | VPGAGVPGQGVPGVGK (SEQ ID NO: 61) | 1 | 1374.7619 | −0.23 | 91.812 |
| pAcF | VPGAGVPGYGVPGVGK (SEQ ID NO: 62) | 2 | 1409.7667 | −1.27 | 98.592 |

TABLE 16

Absolute quantitation of F and Y in ELP(10TAG)-GFP$_{MS}$

| AARS variant | nsAA added | Y | 95% CI | F | 95% CI | pAcF (Y) | 95% CI |
|---|---|---|---|---|---|---|---|
| pAcFRS | pAcF | 1.37 | 0.07 | 0.36 | 0.03 | 98.26 | 0.08 |
| pAcFRS.1.t1 | pAcF | 2.42 | 0.15 | 0.26 | 0.04 | 97.32 | 0.18 |
| pAzFRS.2.t1 | pAcF | 2.08 | 0.17 | 2.45 | 0.18 | 95.47 | 0.23 |
| pAzFRS.1.t1* | pAzF | 0.13 | 0.02 | 3.34 | 0.15 | — | — |
| pAzFRS.2.t1 | No nsAA | 50.15 | 7.10 | 55.35 | 6.62 | −5.50 | 13.69 |

*N = 3

TABLE 17

Absolute quantitation of F and Y in ELPs with 30 TAGs

| AARS variant | Construct | nsAA added | Y | 95% CI | F | 95% CI | pAcF | 95% CI |
|---|---|---|---|---|---|---|---|---|
| pAcFRS | ELP(30TAG)-GFP$_{MS}$ | pAcF | 1.14 | 0.27 | 0.55 | 0.13 | 98.31 | 0.29 |
| pAcFRS.1.t1 | ELP(30TAG)-GFP$_{MS}$ | pAcF | 1.53 | 0.22 | 0.29 | 0.08 | 98.18 | 0.16 |
| pAzFRS.2.t1 | ELP(30TAG)-GFP$_{MS}$ | pAcF | 1.78 | 0.34 | 2.87 | 0.50 | 95.35 | 0.16 |
| pAzFRS.2.t1 | ELP(20TAG)-ELP(10TAG)$_{MS}$-GFP | pAcF | 2.17 | 0.34 | 3.25 | 0.14 | 94.58 | 0.92 |
| pAzFRS.2.t1 | ELP(10TAG)$_{MS}$-ELP(20TAG)-GFP | pAcF | 2.19 | 0.29 | 3.74 | 0.15 | 94.06 | 0.67 |

*N = 3

TABLE 18

Optimized transitions used for quantitation of ELP-GFP peptides by MRM.

| Peptide | SEQ ID NO: | Int. Std. | Precursor Ion m/z | Fragment Ion m/z | Collision energy V |
|---|---|---|---|---|---|
| VPGAGVPGY[+26.0]GVPGVGKlight | 63 | No | 718.90 | 956.52 | 21.1 |
| VPGAGVPGY[+26.0]GVPGVGK.light | 63 | No | 718.90 | 457.28 | 21.1 |
| VPGAGVPGY[+26.0]GVPGVGK.light | 63 | No | 718.90 | 382.21 | 21.1 |
| VPGAGVPGF[+41.0]GVPGVGK.light | 64 | No | 718.39 | 955.51 | 21.1 |
| VPGAGVPGF[+41.0]GVPGVGK.light | 64 | No | 718.39 | 457.28 | 21.1 |
| VPGAGVPGF[+41.0]GVPGVGK.light | 64 | No | 718.39 | 382.21 | 21.1 |
| VPGAGVPGWGVPGVGK.light | 65 | No | 717.40 | 953.52 | 21 |
| VPGAGVPGWGVPGVGK.light | 65 | No | 717.40 | 457.28 | 21 |
| VPGAGVPGWGVPGVGK.light | 65 | No | 717.40 | 382.21 | 21 |
| VPGAGVPGYGVPGVGK.heavy | 66 | Yes | 709.90 | 938.52 | 20.4 |
| VPGAGVPGYGVPGVGK.heavy | 66 | Yes | 709.90 | 465.29 | 20.4 |
| VPGAGVPGYGVPGVGK.heavy | 66 | Yes | 709.90 | 382.21 | 20.4 |
| VPGAGVPGYGVPGVGK.light | 67 | No | 705.89 | 930.50 | 20.4 |
| VPGAGVPGYGVPGVGK.light | 67 | No | 705.89 | 457.28 | 20.4 |
| VPGAGVPGYGVPGVGK.light | 67 | No | 705.89 | 382.21 | 20.4 |
| VPGAGVPGF[+15.0]GVPGVGK.light | 68 | No | 705.40 | 929.52 | 20.4 |
| VPGAGVPGF[+15.0]GVPGVGK.light | 68 | No | 705.40 | 457.28 | 20.4 |
| VPGAGVPGF[+15.0]GVPGVGK.light | 68 | No | 705.40 | 382.21 | 20.4 |
| VPGAGVPGFGVPGVGK.heavy | 69 | Yes | 701.90 | 922.52 | 20 |
| VPGAGVPGFGVPGVGK.heavy | 69 | Yes | 701.90 | 465.29 | 20 |
| VPGAGVPGFGVPGVGK.heavy | 69 | Yes | 701.90 | 382.21 | 20 |

TABLE 18-continued

Optimized transitions used for quantitation of ELP-GFP peptides by MRM.

| Peptide | SEQ ID NO: | Int. Std. | Precursor Ion m/z | Fragment Ion m/z | Collision energy V |
|---|---|---|---|---|---|
| VPGAGVPGFGVPGVGK.light | 70 | No | 697.89 | 914.51 | 20 |
| VPGAGVPGFGVPGVGK.light | 70 | No | 697.89 | 457.28 | 20 |
| VPGAGVPGFGVPGVGK.light | 70 | No | 697.89 | 382.21 | 20 |
| VPGAGVPGHGVPGVGK.light | 71 | No | 692.89 | 904.50 | 19.8 |
| VPGAGVPGHGVPGVGK.light | 71 | No | 692.89 | 457.28 | 19.8 |
| VPGAGVPGHGVPGVGK.light | 71 | No | 692.89 | 382.21 | 19.8 |
| VPGAGVPGQ[+1.0]GVPGVGK.light | 72 | No | 688.88 | 896.48 | 19.6 |
| VPGAGVPGQ[+1.0]GVPGVGK.light | 72 | No | 688.88 | 457.28 | 19.6 |
| VPGAGVPGQ[+1.0]GVPGVGK.light | 72 | No | 688.88 | 382.21 | 19.6 |
| VPGAGVPGKGVPGVGK.light | 73 | No | 688.41 | 895.54 | 19.5 |
| VPGAGVPGKGVPGVGK.light | 73 | No | 688.41 | 457.28 | 19.5 |
| VPGAGVPGKGVPGVGK.light | 73 | No | 688.41 | 382.21 | 19.5 |
| VPGAGVPGQGVPGVGK.light | 74 | No | 688.39 | 895.50 | 19.5 |
| VPGAGVPGQGVPGVGK.light | 74 | No | 688.39 | 457.28 | 19.5 |
| VPGAGVPGQGVPGVGK.light | 74 | No | 688.39 | 382.21 | 19.5 |
| VPGAGVPGIGVPGVGK.light | 75 | No | 680.90 | 880.53 | 19.2 |
| VPGAGVPGLGVPGVGK.light | 76 | No | 680.90 | 880.53 | 19.2 |
| VPGAGVPGIGVPGVGK.light | 75 | No | 680.90 | 457.28 | 19.2 |
| VPGAGVPGLGVPGVGK.light | 76 | No | 680.90 | 457.28 | 19.2 |
| VPGAGVPGIGVPGVGK.light | 75 | No | 680.90 | 382.21 | 19.2 |
| VPGAGVPGLGVPGVGK.light | 76 | No | 680.90 | 382.21 | 19.2 |
| VPGAGVPGPGVPGVGK.light | 77 | No | 672.89 | 864.49 | 18.8 |
| VPGAGVPGPGVPGVGK.light | 77 | No | 672.89 | 457.28 | 18.8 |
| VPGAGVPGPGVPGVGK.light | 77 | No | 672.89 | 382.21 | 18.8 |
| VPGAGVPGSGVPGVGK.light | 78 | No | 667.87 | 854.47 | 18.5 |
| VPGAGVPGSGVPGVGK.light | 78 | No | 667.87 | 457.28 | 18.5 |
| VPGAGVPGSGVPGVGK.light | 78 | No | 667.87 | 382.21 | 18.5 |
| VPGAGVPGGGVPGVGK.light | 79 | No | 652.87 | 824.46 | 17.7 |
| VPGAGVPGGGVPGVGK.light | 79 | No | 652.87 | 457.28 | 17.7 |
| VPGAGVPGGGVPGVGK.light | 79 | No | 652.87 | 382.21 | 17.7 |
| SAMPEGYVQER.heavy | 80 | Yes | 638.80 | 987.48 | 16.8 |
| SAMPEGYVQER.heavy | 80 | Yes | 638.80 | 890.42 | 16.8 |
| SAMPEGYVQER.heavy | 80 | Yes | 638.80 | 761.38 | 16.8 |
| SAMPEGYVQER.heavy | 80 | Yes | 638.80 | 494.24 | 16.8 |
| SAMPEGYVQER.light | 81 | No | 633.79 | 977.47 | 16.8 |
| SAMPEGYVQER.light | 81 | No | 633.79 | 880.42 | 16.8 |
| SAMPEGYVQER.light | 81 | No | 633.79 | 751.37 | 16.8 |

TABLE 18-continued

Optimized transitions used for quantitation of ELP-GFP peptides by MRM.

| Peptide | SEQ ID NO: | Int. Std. | Precursor Ion m/z | Fragment Ion m/z | Collision energy V |
|---|---|---|---|---|---|
| SAMPEGYVQER.light | 81 | No | 633.79 | 489.24 | 16.8 |
| FEGDTLVNR.heavy | 82 | Yes | 530.77 | 784.42 | 11.3 |
| FEGDTLVNR.heavy | 82 | Yes | 530.77 | 612.37 | 11.3 |
| FEGDTLVNR.heavy | 82 | Yes | 530.77 | 398.24 | 11.3 |
| FEGDTLVNR.light | 83 | No | 525.76 | 774.41 | 11.3 |
| FEGDTLVNR.light | 83 | No | 525.76 | 602.36 | 11.3 |
| FEGDTLVNR.light | 83 | No | 525.76 | 388.23 | 11.3 |
| VPGAGVPGR.light | 84 | No | 405.24 | 710.39 | 5.1 |
| VPGAGVPGR.light | 84 | No | 405.24 | 635.35 | 5.1 |
| VPGAGVPGR.light | 84 | No | 405.24 | 613.34 | 5.1 |
| VPGAGVPGR.light | 84 | No | 405.24 | 578.33 | 5.1 |
| VPGAGVPGR.light | 84 | No | 405.24 | 556.32 | 5.1 |
| VPGAGVPGR.light | 84 | No | 405.24 | 485.28 | 5.1 |
| VPGAGVPGR.light | 84 | No | 405.24 | 481.28 | 5.1 |
| VPGAGVPGR.light | 84 | No | 405.24 | 428.26 | 5.1 |
| VPGAGVPGK.light | 85 | No | 391.23 | 682.39 | 4.4 |
| VPGAGVPGK.light | 85 | No | 391.23 | 585.34 | 4.4 |
| VPGAGVPGK.light | 85 | No | 391.23 | 528.31 | 4.4 |
| VPGAGVPGK.light | 85 | No | 391.23 | 382.21 | 4.4 |
| VPGAGVPGK.light | 85 | No | 391.23 | 341.70 | 4.4 |
| GVPGVGK.light | 86 | No | 307.19 | 457.28 | 0.1 |
| GVPGVGK.light | 86 | No | 307.19 | 360.22 | 0.1 |
| GVPGVGK.light | 86 | No | 307.19 | 311.17 | 0.1 |
| GVPGVGK.light | 86 | No | 307.19 | 303.20 | 0.1 |

TABLE 19

MRM transitions used for quantitation of peptides with Agilent MassHunter Quantitative Analysis software.

| Peptide | SEQ ID NO: | Transition used for quantitation | Retention time min |
|---|---|---|---|
| GVPGVGK.light | 87 | 307.2 → 457.3 | 6.7 |
| VPGAGVPGK.light | 88 | 391.2 → 341.7 | 7.199 |
| VPGAGVPGR.light | 89 | 405.2 → 485.3 | 9.2 |
| SAMPEGYVQER.heavy | 90 | 638.8 → 494.2 | 9.2 |
| SAMPEGYVQER.light | 91 | 633.8 → 489.2 | 9.4 |
| FEGDTLVNR.light | 92 | 525.8 → 774.4 | 10.2 |
| FEGDTLVNR.heavy | 93 | 530.8 → 784.4 | 10.2 |

TABLE 19-continued

MRM transitions used for quantitation of peptides with Agilent MassHunter Quantitative Analysis software.

| Peptide | SEQ ID NO: | Transition used for quantitation | Retention time min |
|---|---|---|---|
| VPGAGVPGF[+15.0]GVPGVGK.light | 94 | 705.4 → 929.5 | 10.2 |
| VPGAGVPGQGVPGVGK.light | 95 | 688.4 → 895.5 | 11.04 |
| VPGAGVPGKGVPGVGK.light | 96 | 688.4 → 895.5 | 11.225 |
| VPGAGVPGQ[+1.0]GVPGVGK.light | 97 | 688.9 → 896.5 | 11.285 |
| VPGAGVPGPGVPGVGK.light | 98 | 672.9 → 864.5 | 12.445 |
| VPGAGVPGSGVPGVGIClight | 99 | 667.9 → 854.5 | 13 |
| VPGAGVPGGGVPGVGK.light | 100 | 652.9 → 824.5 | 13.9 |
| VPGAGVPGYGVPGVGK.light | 101 | 705.9 → 930.5 | 14.1 |
| VPGAGVPGYGVPGVGK.heavy | 102 | 709.9 → 938.5 | 14.1 |
| VPGAGVPGWGVPGVGK.light | 103 | 717.4 → 953.5 | 14.407 |
| VPGAGVPGHGVPGVGK.light | 104 | 692.9 → 904.5 | 15.751 |
| VPGAGVPGLGVPGVGK.light | 105 | 680.9 → 880.5 | 17.1 |
| VPGAGVPGIGVPGVGK.light | 106 | 680.9 → 880.5 | 17.2 |
| VPGAGVPGY[+26.0]GVPGVGK.light | 107 | 718.9 → 956.5 | 17.2 |
| VPGAGVPGFGVPGVG1Clight | 108 | 697.9 → 914.5 | 17.938 |
| VPGAGVPGFGVPGVGK.heavy | 109 | 701.9 → 922.5 | 18.2 |
| VPGAGVPGF[+41.0]GVPGVGK.light | 110 | 718.4 → 955.5 | 21.1 |

Example 7: Incorporating Non-Standard Amino Acids Changes the Properties of an Elastin-Like Protein Materials and Methods Elastin-like polypeptides containing 10 instances of DOPA were expressed in GROs as discussed above, using a previously described orthogonal translation system (Alfonta, et al., *J Am Chem Soc.*, 125(48):14662-3 (2003)).

To assay for DOPA-mediated biopolymer-nanoparticle adhesion, DOPA-ELPs (containing 10 instances of DOPA as above) and control tyrosine-ELPs were pre-incubated with silver nanoparticles (AgNP, 10 nm diameter), and assayed for antimicrobial activity.

Results

Petroleum-based products have limited chemical complexity, motivating the production of new chemicals and materials with expanded chemical, biological, and structural properties for demanding applications in electronics, environmental protection, aerospace, medicine, etc. Evolution has designed natural biopolymers such as elastin, collagen, silk and keratin with a range of strength, elasticity, and stability. For example, keratin is composed of peptides that self-assemble into coiled-coil units that form fibers with overlapping units. The fibers are ultimately stabilized by crosslinking, effectively forming a single covalent molecule. The folding of the peptides imparts stability and the crosslinking imparts great strength. Most natural biomaterials, and their versatile functional attributes, arise from the hierarchical assembly and crosslinking of a limited set of protein building blocks. Consequently, biomaterial diversity is actually quite limited.

Increasingly demanding biomedical and biotechnological endeavors require sophisticated materials that can respond to multiple environmental cues, interact with biological systems, template compound assemblies, and direct the growth and differentiation of cells and tissues. Such complex behaviors and properties can be generated by combining biologically derived materials with various chemically synthesized, inorganic or man-made materials to create hybrid materials with new functions. One route to the creation of such hybrid materials is by introduction of non-standard amino acids (NSAAs) into protein based materials.

Precise, template-directed polymerization of proteins is unmatched by chemical methods, but their composition is largely constrained to the 20 canonical amino acids. However, a primary challenge to producing affection function onto protein polymers via NSAAs is that multiple NSAAs must be incorporated in specific arrangements to generate and fine-tune the desired properties.

Until now, the ability to site-specifically incorporate more than a single NSAA per protein has been limited due to partial reassignment of the DNA triplet (codon) used to incorporate the NSAAs. Most commonly, the amber stop codon (TAG) is reassigned for site specific NSAA incorporation. In bacteria, this approach leads to competition between $tRNA_{CUA}$ and release factor 1 (RF1), dramatically reducing the yields of NSAA-containing protein. To address this, a genomically recoded organism (GRO) was created in which all amber stop codons have been converted to synonymous TAA codons, permitting deletion of RF1 and providing an optimized cellular platform for NSAA incorporation via the newly dedicated amber codon. The methods and compositions can be used to predictably design, synthesize and assay desired properties of bio-inspired materials containing many instances of non-standard amino acids (NSAAs).

NSAAs spans vast structural and functional diversity, is unattainable through synthetic chemistry and cannot be synthesized using existing biological chemistry. NSAAs that elaborate basic biomaterial structure with pendant moieties (e.g., L-DOPA, see below) are highly desirable. These NSAAs, when site-specifically incorporated multiple identical times per protein (>30), provide the dominant physical and biophysical properties to biopolymers. For example, 3,4-dihydroxyphenylalanine (DOPA), an important component of mussel adhesive proteins, has been previously shown to bind a variety of biomedically important materials including many metals, Teflon, crystals and carbon nanotubes. Therefore, multi-site incorporation of DOPA in protein-based materials can be used to create hybrid materials with biological function and biocompatibility, combined with magnetic, electronic and therapeutic properties endowed by the various inorganic or synthetic materials. In this example, genomically recoded organisms were utilized to enable multi-site incorporation of DOPA residues into a stimuli responsive protein polymer, and demonstrate that DOPA incorporation imparts an adhesive functionality that enable the protein to bind various materials to generate a composite with new properties.

ELPs are artificial biopolymers composed of the pentapeptide repeat Val-Pro-Gly-Xaa-Gly (VPGXG). They are monodisperse, stimuli-responsive, and biocompatible, making them attractive for applications like drug delivery and tissue engineering. Moreover, ELP properties can be precisely defined and genetically encoded, making them ideal candidates for expanded function via incorporation of multiple NSAAs. For example, "adhesive" NSAAs (e.g., L-DOPA (L-3,4-dihydroxyphenylalanine), which adheres tightly to a number of different surfaces, including metals) mixed with nonpolar amino acids (e.g., isoleucine or a fluorinated analog) to produce a film that confers hydrophobicity to a metal or ceramic surface. Producing such a material, which could form a molecular monolayer, could easily be practical—a peptide layer of beta sheet would only require about 10 grams of material to coat a battleship.

Figure 7:
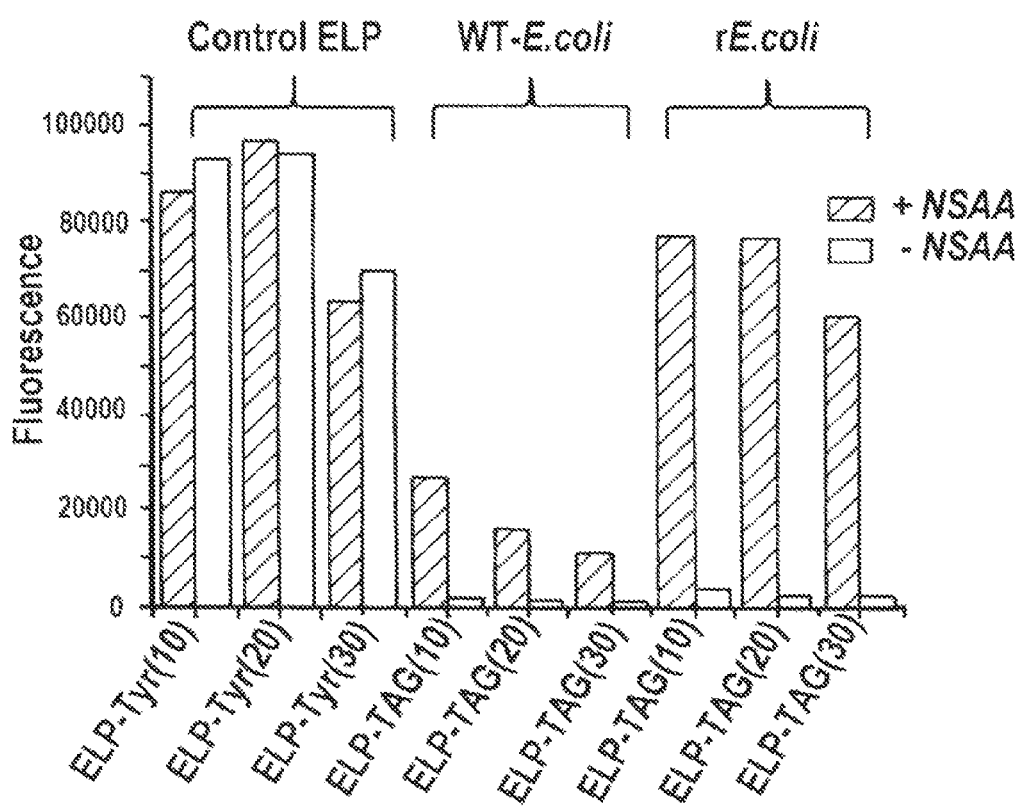
FIG. 7 is a bar graph showing production in GROs of GFP-protein polymers (fluorescence) containing up to 30 NSAAs as compared with tyrosine control and NSAA proteins expressed in WT-E. coli.

As illustrated and discussed in more detail in the Examples above, using genomically recoded organisms, protein polymers can be expressed containing at least 30 (likely many more) instances of NSAAs with minimal loss in yield (FIG. 7). This contrasts with previous studies, which showed at best 60% reduction in yield when incorporating three instances of an NSAA and 97% reduction in yield when incorporating 10 instances of an NSAA into GFP produced in RF1 deficient, non-recoded *E. coli*. See FIG. 7, which illustrates that high yield production in GROs of protein polymers containing up to 30 NSAAs as compared with tyrosine control and NSAA proteins expressed in WT-*E. coli*.

Similarly, a recombinant ELP containing 10 instances of 3,4-dihydroxyphenylalanine (DOPA) was produced. Upon mixing (by pipette) of DOPA-ELPs with 2M $Fe^{3+}$ (Mizrahi, et al., *Adv Funct Mater.*, 23(12):1527-33 (2013)), a viscose gel is immediately formed. This result indicates that DOPA-ELP formulations can be co-injected with $Fe^{3+}$ to generate genetically encoded sustained release depots to mediate drug release for prolonged, yet tunable periods of time.

Next, the ability of DOPA-ELPs to bind silver nanoparticles (AgNP, 10 nm diameter) was investigated. Silver nanoparticles have unique optical, electrical, and thermal properties and are being incorporated into products that range from photovoltaics to biological and chemical sensors. An increasingly common application is the use of silver nanoparticles for antimicrobial coatings, and many textiles, keyboards, wound dressings, and biomedical devices now contain silver nanoparticles that continuously release a low level of silver ions to provide protection against bacteria. As the diameter of the AgNP increases, the peak plasmon resonance shifts to longer wavelengths and broadens.

Additionally, UV-Visible spectroscopy provides a mechanism to monitor how the nanoparticles change over time. When silver nanoparticles aggregate, the metal particles become electronically coupled and this coupled system has a different SPR than the individual particles.

Figure 8:
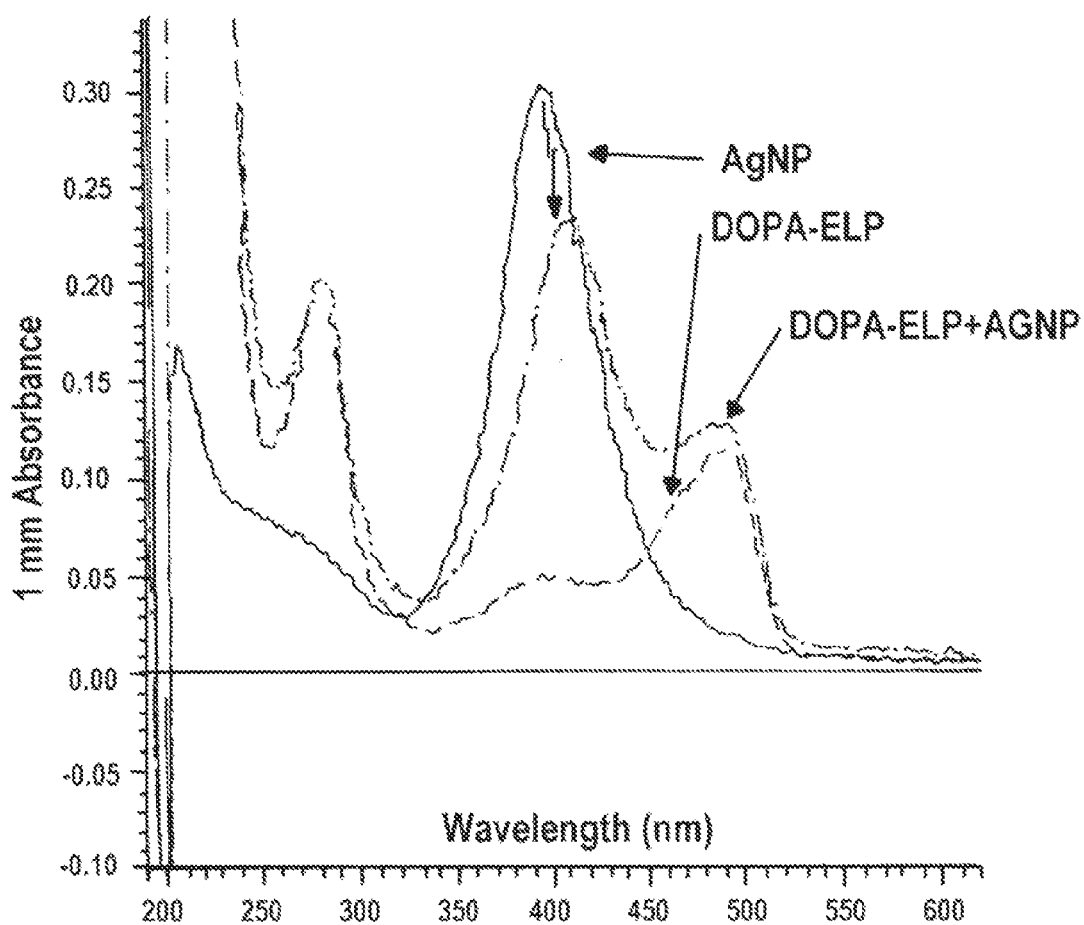
FIG. 8 is a UV-VIS spectragram of the nanoparticles before and after the addition of DOPA-ELP.

Therefore, to monitor DOPA-ELP binding to AgNP, the UV-VIS spectra of the nanoparticles was monitored before and after the addition of the DOPA-ELP. A 5 nm shift in the peak position (from 395 to 400 nM) indicates binding of DOPA-ELP to the AgNP (FIG. 8).

Figure 9:
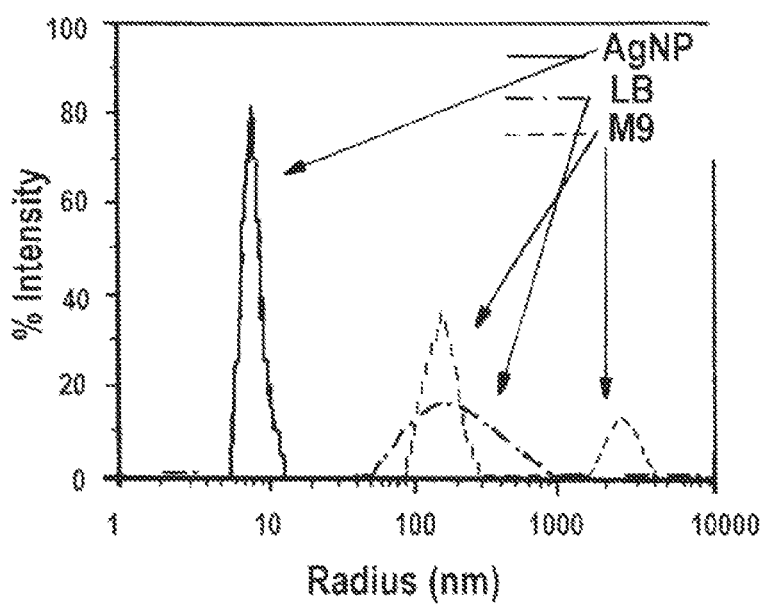
FIG. 9 is a plot showing hydrodynamic size of Ag nanoparticles measured by dynamic light scattering (DLS) (Radius (nm)).

Next the effect of DOPA-ELP on the stability of AgNP in salt solutions was examined. AgNPs are knows to destabilize and aggregate in the presence of various ions, including chloride ions. To determine the aggregation properties of AgNPs in buffered media (LB, M9), the effective size of the particles was measured via dynamic light scattering (DLS). Stabilized AgNPs (in Sodium citrate buffer) display a diameter of ~16 nm caused by minor hydration shell around the 10 nm particle. In contrast, AgNPs form large aggregates in LB and in M9, as evidenced by the change of solution color and hydrodynamic size measured by DLS (FIG. 9).

Figure 10A:
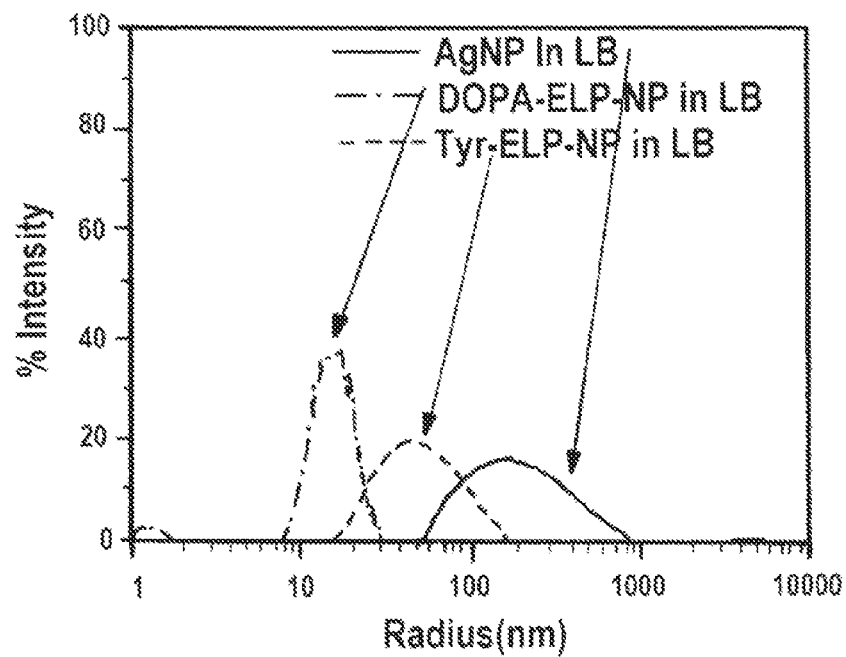
FIGS. 10A-10B are plots showing stabilization of AgNP by DOPA-ELP as a function of hydrodynamic size of Ag nanoparticles measured by dynamic light scattering (DLS) (Radius (nm)) in LB (10A) and M9 (10B) media.
Figure 10B:
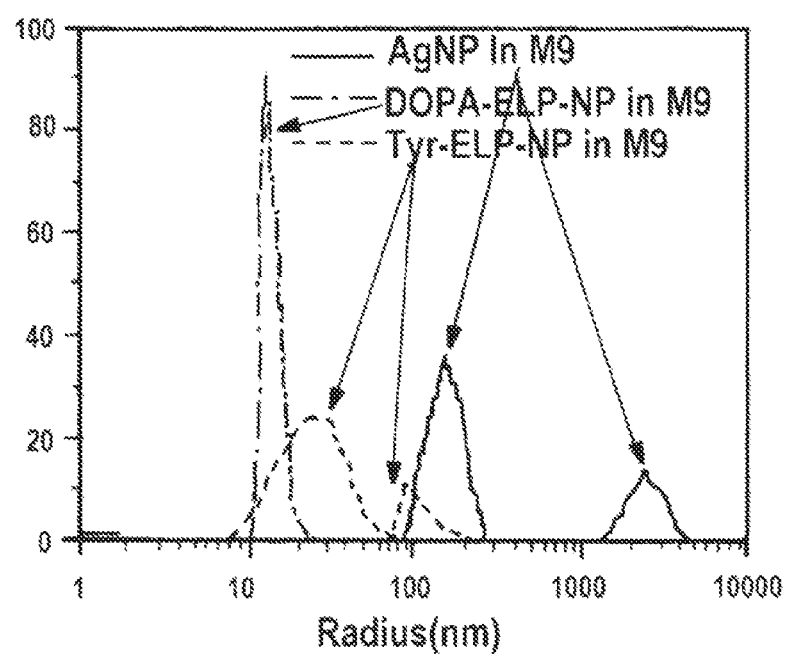
Figure 10C:
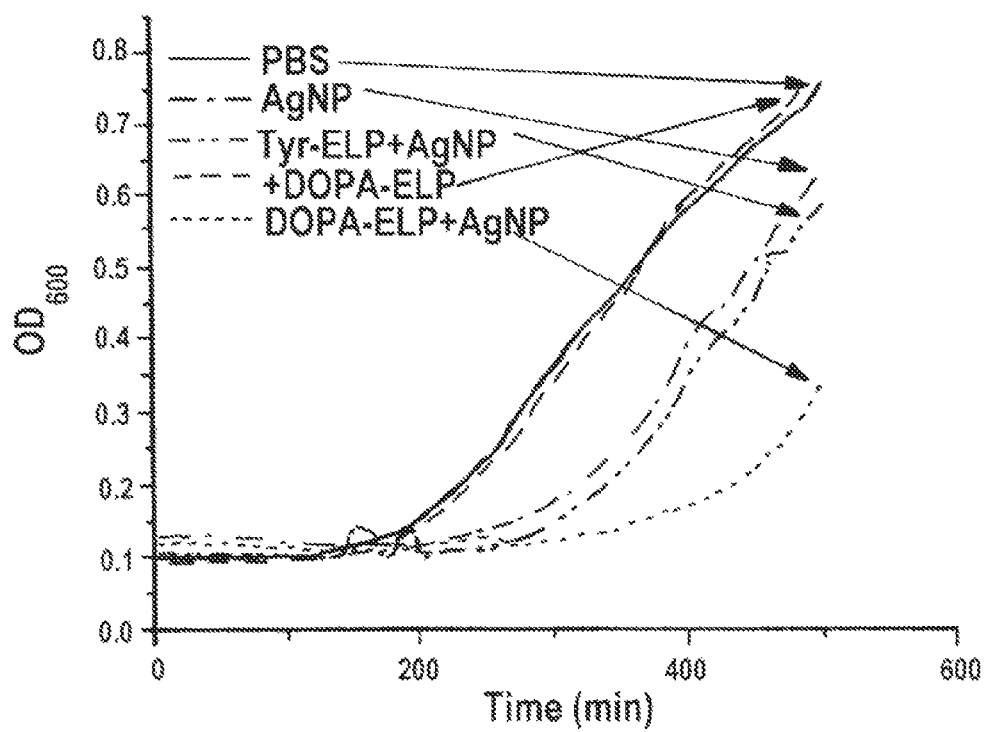
FIG. 10C is a line graph showing the bacterial growth curve (OD600) for control (PBS), AgNP only, Tyr-ELP+AgNP, DOPA-ELP+AgNP, and DOPA-ELP only.

In contrast, hybridizations with DOPA-ELPs prevent AgNP aggregation, and stabilize the NPs in solution. This stabilizing effect directly translates to increased antimicrobial activity of the ELPDOPA-AgNP hybrids, compared with both free AgNPs and control assemblies of ELP-tyrosine-AgNP. Increased AgNP stability in solution is believed to increase the antimicrobial activity as evidenced by the increase in lag time of the bacterial growth curve in the presence of ELP-DOPA-AgNP (FIG. 10A-10C). In conclusion, the resulting DOPA-ELP-AgNP hybrids bind and stabilize the AgNPs in solution by preventing aggregation which typically causes decreased antimicrobial activity, and exhibit increased antimicrobial activity, as compared with free AgNPs or control tyrosine-ELP-AgNP hybrids.

These results indicate that DOPA-ELPs can be used to bind, stabilize and improve the properties of nanoparticles in solution. As such, DOPA-ELP-NP hybrids are broadly applicable to a variety of biomedical and biotechnological applications including but not limited to:

1. Complexes with various antimicrobial metals, with or without additional antibiotics or antimicrobial peptides to overcome multi-drug resistance in bacteria.
2. Complexes with various cytotoxic metals to target, image and treat cancer.
3. Complexes with magnetic materials for guided drug delivery, imaging and sensing and creating magnetic-responsive biomaterials.
4. Complexes with conductive material, such as carbon nanotubes, to create conductive scaffolds, sensors antimicrobial surfaces.

Furthermore:
1. Multi-site incorporation of NSAAs in high yields was not possible using previous stateof-the-art methods and strains (i.e. not genomically recoded organisms).

2. Multi-site incorporation of DOPA has not been previously described in recombinantly produced protein based biopolymers.
3. Functionalization and stabilization of NPs has not been previously described with DOPAproteins.
4. Increase in antimicrobial activity of AgNPs by coating with DOPA-ELPs has not been previously described. To the contrary, previous studies suggest that NP coating decrease NP activity.
5. Functionalization of DOPA-ELPs that also possess strong adhesive properties when exposed to metals (e.g., iron)

Example 8: Multi-Site In-Vitro and In-Vivo Fluorophore Conjugation Improves Signal Generation Materials and Methods
Results As discussed and exemplified in detail above, elastin-like polypeptides containing 30 instances of pAzF were expressed in GROs using an orthogonal translation system evolved for efficient incorporation of pAzF. The azide group allows for the highly efficient copper-catalyzed azide-alkyne cycloaddition ("click") chemistry reaction with alkyne containing molecules. At optimized ratios, azide functional groups present in the ELPs are able to react to completion with Cy5.5 fluorophore bearing an alkyne group (Presolski, et al., *Current protocols in chemical biology*, 3(4):153-62 (2011)). A click reaction with the sizable (~600 Da) Cy 5.5 fluorophore, resulted in a distribution of different size polymers when the ratio of alkyne:azide is <1 (hence, there are not enough fluorophore molecules to react with every azide group) and is represented by a smear on an SDS-PAGE gel. In contrast, at optimal ratios (i.e., an alkyne to azide ration >1) the click reaction ran to completion resulting in a single, sharp band that indicates a homogenous polymer containing 30 instances of pAzF-Cy5.5 conjugates.

A similar "click" reaction can be conducted in vivo (i.e., intracellular) (Yang, et al., *Nature communications*, 5:4981 (2014)), wherein the presence of multiple pAzF functionalities can increase the signal generated and can thus be used for more efficient, detectable signal for imaging in vivo (intracellular) molecules and events. In an vivo "click" reaction (Yang, et al., *Nature communications*, 5:4981 (2014)) between an ELP containing 1 or 30 pAzF groups and an Alexa488 fluorophore bearing an alkyne group, multi-site pAzF incorporation results in a detectable signal of labeled ELP molecules, in contrast to the weak (undetectable) signal of an ELP with 1 pAzF molecule.

Example 9: Multi-Site Fatty Acid Conjugation for Improved Albumin Binding

Materials and Methods
Results

As discussed and exemplified in detail above, elastin-like polypeptides containing 30 instances of pAzF were expressed in GROs using an orthogonal translation system evolved for efficient incorporation of pAzF. In this Example, the Azide functional group was utilized for efficient "click" reaction with fatty acids (e.g., palmitic acid) bearing an alkyne group. It is well known that fatty acid conjugation to small molecules and peptides improves in vivo pharmacokinetics profile via albumin binding (Lim, et al., *Journal of controlled release*, 170(2):219-25 (2013)). ELPs containing pAzF were utilized to conjugate multiple fatty acid molecules per protein to further enhance albumin binding and enable tunable enhancement (as a function of the number of fatty acid molecules) of pharmacokinetics in vivo.

Figure 11:
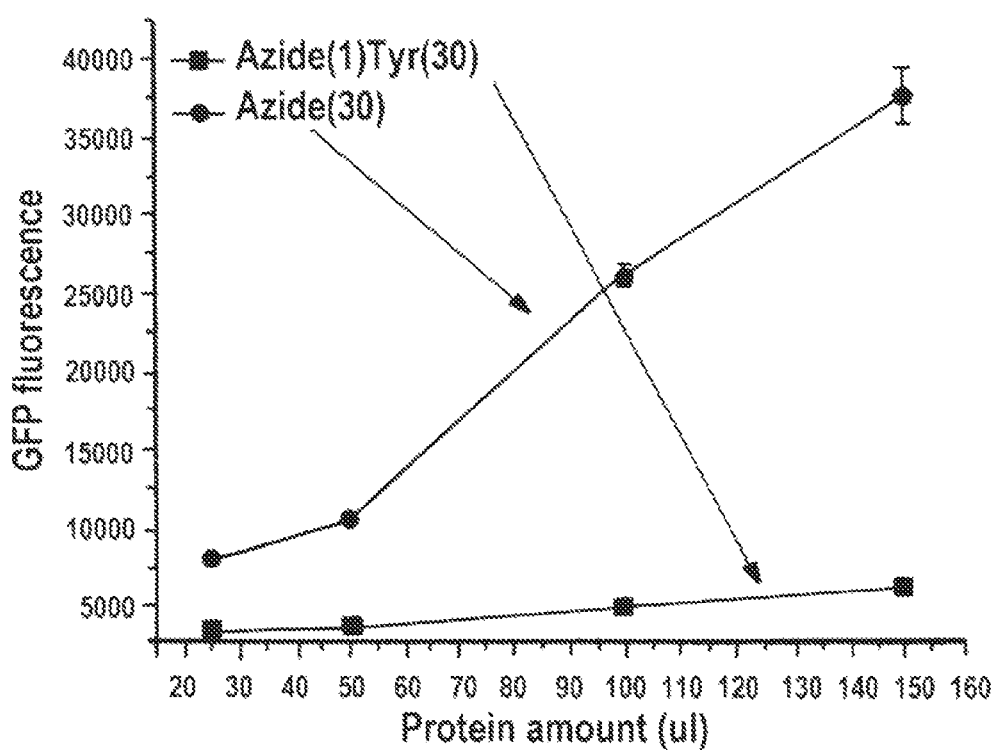
FIG. 11 is a line graph showing BSA binding of fatty acid decorated ELPs (represented as GFP fluorescence) as a function of protein amount (µl) for Azide(1)Tyr(30) (one fatty acid conjugate) and Azide(30) (30 fatty acid conjugates) containing proteins.

A 'click' reaction resulted in incorporation of 30 azide groups via the pAzF nsAA in ELP(30TAG)-GFP with a palmitic acid fatty acid bearing the compatible alkyne group. When supplied with insufficient amounts of alkyne (a ratio of 0.125, 0.25 and 0.5 alkyne:azide), a partial shift was observed as well as a "smear" of the protein band that signifies stochastic reaction of less than 30 sites. In contrast, when sufficient alkyne was supplied, a sharp band is apparent with a consistent size shift compared with the unreacted control. Next, ELP-GFP containing either 30 azide groups or a single azide group and 30 tyrosine groups were contacted with BSA coated agarose beads. The beads were subsequently washed and the amount of protein bound to the beads was measured via GFP fluorescence. The results are illustrated in FIG. 11.

These experiments demonstrate efficient conjugation of palmitic acid-alkyne to ELPs containing 30 pAzF nsAAs, at optimized ratios (i.e., alkyne:azide >1) and improved BSA binding of ELPs containing 1 vs. 30 pAzF instances to albumin coated agarose beads. These results indicate that an increase in the number of fatty acid molecules per protein chain can mediate improved albumin binding in vivo and will result in improved pharmacokinetic profile.

In summary, Examples 1-9 illustrate the development and implementation of a platform for the evolution of AARS variants capable of multi-site nsAA incorporation in proteins. This platform is facilitated by the application of MAGE to the evolution of chromosomally integrated AARSs in a GRO strain which contains a dedicated codon for nsAA incorporation integrated with positive/negative selection markers. Utilizing MAGE, combinatorial genomic libraries were rapidly generated by targeting multiple and distal genetic loci within the target protein. While libraries of chromosomally integrated genes can be generated with other approaches (e.g., recombineering), the low rate of recombination achieved with these methods and limited ability for multi-site mutagenesis in vivo results in a reduction in library complexity (Wang, et al., *Nature*, 460:894-8 (2009)).

Here, AARS mutagenesis by MAGE enabled simultaneous targeting of an expanded number of residues in the nsAA binding pocket (12, compared with 6 residues typically targeted (Young, et al., *Biochemistry*, 50:1894-900 (2011); Wang, et al., *Proc Natl Acad Sci USA*, 100:56-61 (2003); Chin, et al., *J Am Chem Soc*, 124:9026-7 (2002)). This expanded library facilitated the selection of several efficient AARSs for the incorporation of a variety of nsAAs—all from a single diversified population—a direct result of the increased number of targeted residues since several of the mutated residues in these variants were not included in previous screens (Chin, et al., *J Am Chem Soc*, 124:9026-7 (2002); Schultz, et al., *J Am Chem Soc*, 128: 13984-5 (2006)). These diverse libraries also enabled the isolation of enzymes with tunable substrate specificities including a pAzFRS variant (pAzFRS.1) that is both more efficient and more specific for pAzF than previously reported pAzFRSs. Second, although the full diversity of the library was not explored in a single evolution (i.e., diversification and selection) experiment (~$10^{15}$ for 12 targets in the amino acid binding pocket), continuous diversification and selection was performed by increasing the number of MAGE cycles, changing the mutagenic ssDNA pool, or targeting of different areas in the AARS (i.e., the nsAA or tRNA binding site). Alternatively, library diversity can be modified by simply changing the conditions applied during negative selection (e.g., by adding pAzF during negative selection to vary the nsAA binding site), without the need for plasmid reconstruction and retransformation and resultant loss of library diversity since all selection markers are present in the cell. It is believed that the modular nature of this in vivo evolution methodology can facilitate multiplexed and automated evolution and isolation of diverse AARS-nsAA pairs, and that this strategy can be applied to improve and alter the properties of many other proteins or pathways in vivo.

The evolution of a chromosomally integrated AARS, whose expression level is lower than conventional plasmid-based systems, is an additional distinction in the workflow that enabled the isolation of variants with improved efficiency of nsAA incorporation. Expression of AARS variants from multi-copy plasmids largely mask the differences between low-, modestly-, and highly-active AARSs when challenged to express a protein with only three nsAAs, but became evident when challenged to express a protein with 30 nsAAs or when expressed from a chromosomal copy. Importantly, several of the selected AARS variants are unique in that when expressed from multi-copy plasmids, they support high levels of protein expression in the absence of an nsAA and death in the presence of the negative selection marker. This confirms that the evolved variants would not survive the negative selection from conventional approaches that employ plasmid-based OTS libraries and consequently could not have been isolated from such libraries. Despite this property, high fidelity of nsAA incorporation was observed, indicating that enhancement of AARS efficiency may be achieved if AARS levels are lowered during negative selection such as by reduction of arabinose concentration, reduced strength promoters, or low-copy number plasmids, or if selection stringencies are lowered as has been previously suggested (Cooley, et al., Biochemistry (2014)).

Site-specific multi-site nsAA incorporation with high yields and high purity (i.e., ~50 mg/L for biopolymers containing 30 instances of an nsAA at >95% correct nsAA incorporation) was accomplished using the GRO and newly evolved AARS variants. Incorporation accuracy is independent of TAG codon positioning with respect to the protein N-terminus, and thus that misincorporation is not biased and should not affect bulk polymer properties. Previous attempts to incorporate more than one instance of an nsAA per protein in strains with no or attenuated RF1 activity showed at best 33% yield of WT protein when incorporating three instances of an NSAA into superfolder GFP (<20.5 mg/L) (Wu, et al., Chembiochem, 14:968-78 (2013)) and 3% yield of WT when incorporating 10 instances of an NSAA into GFP (0.4 mg/L) produced in RF1 deficient, non-recoded E. coli (Johnson, et al., Nat Chem Biol, 7:779-86 (2011)). While ELPs are a well expressed family of proteins (Meyer, et al., Biomacromolecules, 5:846-851 (2004)), it is believed that the improvement in nsAA incorporation achieved by expression in GROs with the evolved AARSs will improve multi-site nsAA incorporation in a diverse set of natural and recombinant proteins and protein polymers.

New OTSs for nsAAs carrying a variety of chemical groups can be used to increase the chemical diversity of proteins and biomaterials. In this regard, similar OTS libraries can be constructed for the Methanosarcina mazei PylRS31 and the O-phosphoseryl-tRNA20 synthetase or for co-evolution of multiple OTS components (e.g., AARS, tRNA, EF-Tu) to enable incorporation of chemically diverse, bulky, and highly charged amino acids (O'Donoghue, et al., Nat Chem Biol, 9:594-8 (2013); Park, et al., Science, 333:1151-4 (2011)). In addition, to further enhance the activity of evolved OTSs toward that of natural translation systems, increasing the targeted residue pool (>12 sites), integrated with computational protein design (Tinberg, et al., Nature, 501:212-6 (2013)), will enable strategic targeting and partial randomization of specified residues to increase library coverage.

This work enabled efficient incorporation of up to 30 nsAAs into protein polymers, which has been previously shown to affect and direct polymer properties (Strzegowski, et al., Journal of the American Chemical Society, 116:813-814 (1994); Nishi, et al., Biochemistry, 44:6034-42 (2005); Tang, et al., Angew Chem Int Ed Engl, 40:1494-1496 (2001)). Since ELPs undergo a sharp soluble-to-insoluble phase transition at their transition temperature (Tt), which depends on the ELP composition (Meyer, et al., Biomacromolecules, 5:846-851 (2004)), the ELP templates used for nsAA incorporation in this study can be utilized as a scaffold for the design of smart biomaterials in which nsAA functionality can be translated to stimuli-responsiveness to light, electro-magnetic field, and various analytes. Multi-site nsAA incorporation into these and other protein-based biomaterials at high purity can modify and expand their chemical or physical properties to generate new materials. Indeed, limited to only one or a few instances of site-specific nsAA incorporation, most previous work have centered on tag and modify approaches or simple protein decorations.

The above Examples show that the disclosed compositions and methods enable site-specific nsAA incorporation where multiple identical nsAAs provide the dominant physical and biophysical properties to biopolymers. Multi-site nsAA incorporation will also enable design and production of post-translationally modified proteins (e.g., kinases (Park, et al., Science, 333:1151-4 (2011)) for the study and treatment of disease or of new biologics (e.g., antibodies (Sun, et al., Chembiochem (2014)) with multiple instances of new chemical functionalities. As GROs with more free codon channels are constructed (Lajoie, et al., Science, 342: 357-60 (2013); Lajoie, et al., Science, 342:361-3 (2013)), the selection of AARS variants with tunable or exclusive nsAA specificities enabled by the disclosed evolution platform, could be used for orthogonal coding channels for multi-site incorporation of 2+ nsAAs within a single protein. Multi-site nsAA incorporation allows for the design and production of existing and new proteins and biomaterials at an increased level of complexity and scale.

We claim:

1. A composition comprising
    a plurality of a translated peptide or polypeptide comprising at least one instance of a non-standard amino acid,
    mRNA encoding the peptide or polypeptide, and
    a non-auxotrophic translation system comprising a heterologous, multiplex automated genome evolution (MAGE) evolved aminoacyl tRNA synthetase (AARS) and a cognate tRNA that can be charged with the non-standard amino acid by the AARS and express an elastin-like (ELP) green fluorescent protein (GFP) fusion protein of SEQ ID NO:33 comprising thirty instances of the non-standard amino acid at an average yield of more than 18% of the corresponding ELP-GFP of SEQ ID NO:34 with no non-standard amino acids, wherein the translated peptide or polypeptide is prepared by translation of the mRNA encoding the peptide or polypeptide in genomically recoded organism (GRO) E. coli cells expressing the translation system.

2. The composition of claim 1, wherein the MAGE comprises
    carrying out one or more rounds of mutagenesis on host organism cells comprising an orthogonal translation system comprising a precursor heterologous AARS integrated into the host's genome and a cognate tRNA to form a library of variants of the precursor heterologous AARS,
    carrying out one or more rounds of selection on the library of variants to identify host cells comprising variant AARS with improved or altered specificity and/or activity for the non-standard amino and/or the cognate tRNA, and selecting the heterologous AARS from the library of variant AARS.

3. The composition of claim 2, wherein the mutagenesis is targeted to the AARS alone or in combination with one or more of tRNA, EF-Tu, RNA components of the ribosome, and protein components of the ribosome.

4. The composition of claim 2, wherein the site(s) for introducing an amino acid sequence variation in the AARS are predetermined, but the mutation(s) per se are random, semi-random, degenerate, or specific and introduce mismatch(es), deletion(s), and/or insertion(s).

5. The composition of claim 4, wherein the mutagenesis comprises one or more rounds of transforming or transfecting host cells using transformation medium or transfection medium including at least one nucleic acid oligomer containing one or more mutations, replacing the transformation medium or transfection medium with growth medium, incubating the cells in the growth medium, and optionally repeating the steps if necessary or desired until the sequence(s) of the one or more nucleic acid oligomer is introduced into the host cells' genome or vector within the host cells.

6. The composition of claim 5 wherein, the one or more nucleic acid oligomers is a pool of oligomers having a diversity of different random or non-random mutations at the location(s) of desired mutagenesis.

7. The composition of claim 2 wherein selection comprises negative selection comprising removal of host cells comprising undesirable AARS variants from the library of AARS variants.

8. The composition of claim 7 wherein negative selection comprises TolC-based selection wherein mutated AARS variants capable of mischarging the cognate tRNA with natural amino acids permit read-through of a tolC construct in the host genome, rendering the organism sensitive to colicin E1.

9. The composition of claim 2 wherein selection comprises positive selection comprising choosing desirable AARS variants from the library of AARS variants.

10. The composition of claim 2 wherein positive selection comprises selecting host cells that have improved yield of a protein of interest encoded by an mRNA comprising at least one codon recognized by the orthogonal translation system tRNA anticodon and expressed in the host cell.

11. The composition of claim 2 wherein the selection comprises Rec negative selection in the presence of one or more of the undesirable non-standard amino acids to establish orthogonality toward the undesirable non-standard amino acid(s) in addition to the twenty canonical amino acids, followed by positive selection for increased activity for one or more desired non-standard amino acids.

12. The composition of claim 1, wherein the AARS comprises at least 90% sequence identity, but not 100% sequence identity, to the non-standard amino acid (amino acid ligand) binding pocket of any of SEQ ID NOS:2-15, the tRNA anticodon recognition interface of any of SEQ ID NO:2-15, or a combination thereof, or SEQ ID NO:1.

13. The composition of claim 12, wherein the AARS comprises amino acids 65, 107, 108, 109, 158, 159, 162, 167, 257, and 261 of any of SEQ ID NOS:2-15.

14. The composition of claim 1, wherein the AARS comprises the non-standard amino acid (amino acid ligand) binding pocket of any of SEQ ID NOS:2-15, the tRNA anticodon recognition interface of any of SEQ ID NO:2-15, or a combination thereof.

15. The composition of claim 14, wherein the AARS comprises the amino acid sequence of any of SEQ ID NOS:2-15.

16. The composition of claim 1, wherein the AARS and its cognate tRNA are operably linked to expression control sequences and transformed, transfected, or integrated into the GRO, wherein the heterologous mRNA comprises a nucleic acid sequence comprising at least one instance of a codon absent from the GRO, and wherein the tRNA comprises an anticodon that can bind to the codon absent from the GRO and introduce the non-standard amino acid into the nascent peptide or polypeptide during translation of the heterologous mRNA.

17. The composition of claim 16 wherein the GRO wherein the codon absent from the GRO is a non-sense codon recoded as a sense codon, and wherein expression of the corresponding non-sense codon release factor is reduced or absent.

18. The composition of claim 17 wherein the non-sense codon is TAG.

19. The composition of claim 1 wherein the non-standard amino acid is selected is pAcF, pAzF, StyA, 4IF, 4BrF, 4ClF, 4MeF, 4Cf3F, MeY, 4NO$_2$F, 4BuF, BuY, 2NaA, PhF, or 3,4-dihydroxyphenylalanine.

20. The composition of claim 1 comprising at least 20 instances of the non-standard amino acid.

21. The composition of claim 1 wherein the *E. coli* is C321.Δ A.

22. The composition of claim 1 comprising one or more instances of pAzF.

23. The composition of claim 22, wherein the side chain of pAzF is conjugated to another molecule.

24. The composition of claim 23, wherein the molecule is a drug or an imaging molecule.

25. The composition of claim 1, wherein the translation system can express the ELP-GFP fusion protein of SEQ ID NO:33 comprising thirty instances of the non-standard amino acid at an average yield of more than 66.5% of the corresponding ELP-GFP of SEQ ID NO:34 with no non-standard amino acids.

26. The composition of claim 1, wherein the plurality of the peptide or polypeptide has at least 95% correct non-standard amino acid incorporated at the desired residue(s) relative to an undesired amino acid at the same residue.

27. The composition of claim 1, wherein the peptide or polypeptide comprises the sequence (VPGXG)$_n$ (SEQ ID NO:19), wherein "X" is the non-standard amino acid and wherein "n" is an integer from 1 to 500.

28. The composition of claim 1, wherein the peptide or polypeptide is an Elastin-like Protein (ELP).

29. The composition of claim 28, wherein the ELP comprises the amino acid sequence of any of SEQ ID NOS:20-27.

30. The composition of claim 29 wherein "X" in SEQ ID NO:20-27 is pAcF, pAzF, StyA, 4IF, 4BrF, 4ClF, 4MeF, 4Cf3F, MeY, 4NO$_2$F, 4BuF, BuY, 2NaA, PhF, or 3,4-dihydroxyphenylalanine.

31. The composition of claim 28, wherein the ELP comprises the amino acid sequence of any of SEQ ID NOS:19-27, wherein "X" is 3,4-dihydroxyphenylalanine.

32. The composition of claim 28, wherein the ELP comprises the amino acid sequence of SEQ ID NOS:19-27 wherein "X" is pAzF and the side chain of pAzF is conjugated to a molecule.

33. The composition of claim 32, wherein molecule is a fatty acid.

34. The composition of claim 33, wherein the fatty acid is palmitic acid.

35. The composition of claim 1, wherein the peptide or polypeptide is a protein polymer.

36. The composition of claim 18, wherein the release factor is release factor 1 (RF1).

37. A composition comprising
 a plurality of a translated peptide or polypeptide comprising at least four instances of a non-standard amino acid,
 mRNA encoding the peptide or polypeptide, and
 a translation system comprising a heterologous aminoacyl tRNA synthetase (AARS) and a cognate tRNA that can be charged with the non-standard amino acid by the AARS express a superfolder green fluorescent protein (GFP) comprising three instances of the non-standard amino acid at more than 33% yield of the corresponding wildtype superfolder green fluorescent protein (GFP) with no non-standard amino acids,
 wherein the translated peptide or polypeptide is prepared by translation of the mRNA encoding the peptide or polypeptide in genomically recoded organism (GRO) *E. coli* cells expressing the translation system, and
 wherein the plurality of the peptide has at least 95% correct non-standard amino acid incorporated at the desired residue(s) relative to an undesired amino acid at the same residue.

38. The composition of claim 37 wherein the *E. coli* is C321.Δ A.

* * * * *

UNITED STATES PATENT AND TRADEMARK OFFICE
CERTIFICATE OF CORRECTION

PATENT NO. : 10,501,734 B2
APPLICATION NO. : 15/117406
DATED : December 10, 2019
INVENTOR(S) : Farren Isaacs et al.

It is certified that error appears in the above-identified patent and that said Letters Patent is hereby corrected as shown below:

In the Specification

Column 1, Lines 22-25, replace the following paragraph:
"This invention was made with government support under Grant N66001-12-C-4211 awarded by the National Institutes of Health. The government has certain rights in the invention."

With the following paragraph:
--This invention was made with Government support under Agreement No. N66001-12-C-4211 awarded by DARPA. The Government has certain rights in the invention.--

Signed and Sealed this
Eighteenth Day of April, 2023

Katherine Kelly Vidal
*Director of the United States Patent and Trademark Office*

SEQUENCE LISTING

<160> NUMBER OF SEQ ID NOS: 114

<210> SEQ ID NO 1
<211> LENGTH: 306
<212> TYPE: PRT
<213> ORGANISM: Methanocaldococcus jannaschii

<400> SEQUENCE: 1

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Leu
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Gly Cys His
145                 150                 155                 160

Tyr Arg Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Arg Leu Lys
        275                 280                 285

Asn Ala Val Ala Glu Glu Leu Ile Lys Ile Leu Glu Pro Ile Arg Lys
    290                 295                 300

Arg Leu
305

<210> SEQ ID NO 2
<211> LENGTH: 306
<212> TYPE: PRT
<213> ORGANISM: Artificial Sequence
<220> FEATURE:
<223> OTHER INFORMATION: synthetic polypeptide

<400> SEQUENCE: 2

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Leu
            20                  25                  30

```
Ile Gly Phe Glu Pro Ser Gly Lys Ile His Leu Gly His Tyr Leu Gln
            35                  40                  45

Ile Lys Lys Met Ile Asp Leu Gln Asn Ala Gly Phe Asp Ile Ile Ile
 50                  55                  60

Leu Leu Ala Asp Leu His Ala Tyr Leu Asn Gln Lys Gly Glu Leu Asp
 65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Phe Gln Leu Asp Lys
            100                 105                 110

Asp Tyr Thr Leu Asn Val Tyr Arg Leu Ala Leu Lys Thr Thr Leu Lys
            115                 120                 125

Arg Ala Arg Arg Ser Met Glu Leu Ile Ala Arg Glu Asp Glu Asn Pro
130                 135                 140

Lys Val Ala Glu Val Ile Tyr Pro Ile Met Gln Val Asn Gly Cys His
145                 150                 155                 160

Tyr Arg Gly Val Asp Val Asp Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
            195                 200                 205

Lys Gly Asn Phe Ile Ala Val Asp Asp Ser Pro Glu Glu Ile Arg Ala
            210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Arg Leu Lys
            275                 280                 285

Asn Ala Val Ala Glu Glu Leu Ile Lys Ile Leu Glu Pro Ile Arg Lys
            290                 295                 300

Arg Leu
305

<210> SEQ ID NO 3
<211> LENGTH: 306
<212> TYPE: PRT
<213> ORGANISM: Artificial Sequence
<220> FEATURE:
<223> OTHER INFORMATION: synthetic polypeptide

<400> SEQUENCE: 3

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Leu
            20                  25                  30

Ile Gly Phe Glu Pro Ser Gly Lys Ile His Leu Gly His Tyr Leu Gln
            35                  40                  45

Ile Lys Lys Met Ile Asp Leu Gln Asn Ala Gly Phe Asp Ile Ile Ile
 50                  55                  60

Leu Leu Ala Asp Leu His Ala Tyr Leu Asn Gln Lys Gly Glu Leu Asp
 65                  70                  75                  80
```

```
Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Gly Cys His
145                 150                 155                 160

Tyr Arg Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Gly Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Arg Leu Lys
        275                 280                 285

Asn Ala Val Ala Glu Glu Leu Ile Lys Ile Leu Glu Pro Ile Arg Lys
    290                 295                 300

Arg Leu
305

<210> SEQ ID NO 4
<211> LENGTH: 306
<212> TYPE: PRT
<213> ORGANISM: Artificial Sequence
<220> FEATURE:
<223> OTHER INFORMATION: synthetic polypeptide

<400> SEQUENCE: 4

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Leu
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Phe Gln Leu Asp Lys
            100                 105                 110

Asp Tyr Thr Leu Asn Val Tyr Arg Leu Ala Leu Lys Thr Thr Leu Lys
        115                 120                 125
```

```
Arg Ala Arg Arg Ser Met Glu Leu Ile Ala Arg Glu Asp Glu Asn Pro
        130                 135                 140

Lys Val Ala Glu Val Ile Tyr Pro Ile Met Gln Val Asn Gly Cys His
145                 150                 155                 160

Tyr Arg Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
                195                 200                 205

Lys Gly Asn Phe Ile Ala Val Asp Asp Ser Pro Glu Glu Ile Arg Ala
210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Cys Pro Glu Lys Glu Gly Gly Asp Leu Thr Val Asn Ser Tyr Glu Glu
                260                 265                 270

Leu Glu Ser Leu Phe Lys Asn Lys Glu Leu His Pro Met Arg Leu Lys
            275                 280                 285

Asn Ala Val Ala Glu Glu Leu Ile Lys Ile Leu Glu Pro Ile Arg Lys
        290                 295                 300

Arg Leu
305

<210> SEQ ID NO 5
<211> LENGTH: 306
<212> TYPE: PRT
<213> ORGANISM: Artificial Sequence
<220> FEATURE:
<223> OTHER INFORMATION: synthetic polypeptide

<400> SEQUENCE: 5

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Leu
                20                  25                  30

Ile Gly Phe Glu Pro Ser Gly Lys Ile His Leu Gly His Tyr Leu Gln
            35                  40                  45

Ile Lys Lys Met Ile Asp Leu Gln Asn Ala Gly Phe Asp Ile Ile Ile
        50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
        130                 135                 140

Lys Val Ala Glu Val Ile Tyr Pro Ile Met Gln Val Asn Gly Cys His
145                 150                 155                 160

Tyr Arg Gly Val Asp Val Ala Val Gly Gly Met Glu Gln Arg Lys Ile
                165                 170                 175
```

```
His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Gly Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Arg Leu Lys
        275                 280                 285

Asn Ala Val Ala Glu Glu Leu Ile Lys Ile Leu Glu Pro Ile Arg Lys
    290                 295                 300

Arg Leu
305

<210> SEQ ID NO 6
<211> LENGTH: 306
<212> TYPE: PRT
<213> ORGANISM: Artificial Sequence
<220> FEATURE:
<223> OTHER INFORMATION: synthetic polypeptide

<400> SEQUENCE: 6

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Leu
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
130                 135                 140

Lys Val Ala Glu Val Ile Tyr Pro Ile Met Gln Val Asn Gly Cys His
145                 150                 155                 160

Tyr Arg Gly Val Asp Val Asp Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220
```

```
Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
            245                 250                 255

Cys Pro Glu Lys Glu Gly Gly Asp Leu Thr Val Asn Ser Tyr Glu Glu
        260                 265                 270

Leu Glu Ser Leu Phe Lys Asn Lys Glu Leu His Pro Met Arg Leu Lys
    275                 280                 285

Asn Ala Val Ala Glu Glu Leu Ile Lys Ile Leu Glu Pro Ile Arg Lys
290                 295                 300

Arg Leu
305

<210> SEQ ID NO 7
<211> LENGTH: 306
<212> TYPE: PRT
<213> ORGANISM: Artificial Sequence
<220> FEATURE:
<223> OTHER INFORMATION: synthetic polypeptide

<400> SEQUENCE: 7

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Leu
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Val Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
130                 135                 140

Lys Val Ala Glu Val Ile Tyr Pro Ile Met Gln Val Asn Gly Cys His
145                 150                 155                 160

Tyr Arg Gly Val Asp Val Asp Val Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270
```

```
Leu Glu Ser Leu Phe Lys Asn Lys Glu Leu His Pro Met Arg Leu Lys
            275                 280                 285

Asn Ala Val Ala Glu Glu Leu Ile Lys Ile Leu Glu Pro Ile Arg Lys
        290                 295                 300

Arg Leu
305

<210> SEQ ID NO 8
<211> LENGTH: 306
<212> TYPE: PRT
<213> ORGANISM: Artificial Sequence
<220> FEATURE:
<223> OTHER INFORMATION: synthetic polypeptide

<400> SEQUENCE: 8

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Leu
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
50                  55                  60

Val Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
130                 135                 140

Lys Val Ala Glu Val Ile Tyr Pro Ile Met Gln Val Asn Gly Cys His
145                 150                 155                 160

Tyr Arg Gly Val Asp Val Asp Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Gly Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Arg Leu Lys
        275                 280                 285

Asn Ala Val Ala Glu Glu Leu Ile Lys Ile Leu Glu Pro Ile Arg Lys
290                 295                 300

Arg Leu
305
```

<210> SEQ ID NO 9
<211> LENGTH: 306
<212> TYPE: PRT
<213> ORGANISM: Artificial Sequence
<220> FEATURE:
<223> OTHER INFORMATION: synthetic polypeptide

<400> SEQUENCE: 9

```
Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Leu
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile
    50                  55                  60

Val Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Gly Cys His
145                 150                 155                 160

Tyr Arg Gly Val Asp Val Asp Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Cys Pro Glu Lys Glu Gly Gly Asp Leu Thr Val Asn Ser Tyr Glu Glu
            260                 265                 270

Leu Glu Ser Leu Phe Lys Asn Lys Glu Leu His Pro Met Arg Leu Lys
        275                 280                 285

Asn Ala Val Ala Glu Glu Leu Ile Lys Ile Leu Glu Pro Ile Arg Lys
    290                 295                 300

Arg Leu
305
```

<210> SEQ ID NO 10
<211> LENGTH: 306
<212> TYPE: PRT
<213> ORGANISM: Artificial Sequence
<220> FEATURE:
<223> OTHER INFORMATION: synthetic polypeptide

<400> SEQUENCE: 10

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Leu
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Val Phe Glu Ala Met
                85                  90                  95

Gly Leu Lys Ala Lys Tyr Val Tyr Gly Ser Glu Phe Gln Leu Asp Lys
            100                 105                 110

Asp Tyr Thr Leu Asn Val Tyr Arg Leu Ala Leu Lys Thr Thr Leu Lys
            115                 120                 125

Arg Ala Arg Arg Ser Met Glu Leu Ile Ala Arg Glu Asp Glu Asn Pro
130                 135                 140

Lys Val Ala Glu Val Ile Tyr Pro Ile Met Gln Val Asn Val Met His
145                 150                 155                 160

Tyr Asp Gly Val Asp Val Tyr Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
            195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Arg Leu Lys
            275                 280                 285

Asn Ala Val Ala Glu Glu Leu Ile Lys Ile Leu Glu Pro Ile Arg Lys
            290                 295                 300

Arg Leu
305

<210> SEQ ID NO 11
<211> LENGTH: 307
<212> TYPE: PRT
<213> ORGANISM: Artificial Sequence
<220> FEATURE:
<223> OTHER INFORMATION: synthetic polypeptide

<400> SEQUENCE: 11

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Leu
            20                  25                  30

Ile Gly Phe Glu Pro Ser Gly Lys Ile His Leu Gly His Tyr Leu Gln
        35                  40                  45

```
Ile Lys Lys Met Ile Asp Leu Gln Asn Ala Gly Phe Asp Ile Ile Ile
 50                  55                  60

Leu Leu Ala Asp Leu His Ala Tyr Leu Asn Gln Lys Gly Glu Leu Asp
 65                  70                  75                  80

Glu Ile Arg Lys Ile Gly Asp Tyr Asn Lys Lys Val Phe Glu Ala Met
                 85                  90                  95

Gly Leu Lys Ala Lys Tyr Val Tyr Gly Ser Glu Phe Gln Leu Asp Lys
                100                 105                 110

Asp Tyr Thr Leu Asn Val Tyr Arg Leu Ala Leu Lys Thr Thr Leu Lys
            115                 120                 125

Arg Ala Arg Arg Ser Met Glu Leu Ile Ala Arg Glu Asp Glu Asn Pro
130                 135                 140

Lys Val Ala Glu Val Ile Tyr Pro Ile Met Gln Val Asn Val Met His
145                 150                 155                 160

Tyr Asp Gly Val Asp Val Tyr Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
            195                 200                 205

Lys Gly Asn Phe Ile Ala Val Asp Asp Ser Pro Glu Glu Ile Arg Ala
            210                 215                 220

Lys Ile Lys Lys Ala Tyr Cys Pro Ala Gly Val Val Glu Gly Asn Pro
225                 230                 235                 240

Ile Met Met Glu Ile Ala Lys Tyr Phe Leu Glu Tyr Pro Leu Thr Ile
                245                 250                 255

Lys Gly Pro Glu Lys Phe Gly Gly Asp Leu Thr Val Asn Ser Tyr Glu
                260                 265                 270

Glu Leu Glu Ser Leu Phe Lys Asn Lys Glu Leu His Pro Met Arg Leu
            275                 280                 285

Lys Asn Ala Val Ala Glu Glu Leu Ile Lys Ile Leu Glu Pro Ile Arg
            290                 295                 300

Lys Arg Leu
305

<210> SEQ ID NO 12
<211> LENGTH: 307
<212> TYPE: PRT
<213> ORGANISM: Artificial Sequence
<220> FEATURE:
<223> OTHER INFORMATION: synthetic polypeptide

<400> SEQUENCE: 12

Met Asp Glu Phe Glu Met Ile Lys Arg Asn Thr Ser Glu Ile Ile Ser
 1               5                  10                  15

Glu Glu Glu Leu Arg Glu Val Leu Lys Lys Asp Glu Lys Ser Ala Leu
                20                  25                  30

Ile Gly Phe Glu Pro Ser Gly Lys Ile His Leu Gly His Tyr Leu Gln
            35                  40                  45

Ile Lys Lys Met Ile Asp Leu Gln Asn Ala Gly Phe Asp Ile Ile Ile
 50                  55                  60

Leu Leu Ala Asp Leu His Ala Tyr Leu Asn Gln Lys Gly Glu Leu Asp
 65                  70                  75                  80

Glu Ile Arg Lys Ile Gly Asp Tyr Asn Lys Lys Val Phe Glu Ala Met
                 85                  90                  95
```

Gly Leu Lys Ala Lys Tyr Val Tyr Gly Ser Glu Phe Gln Leu Asp Lys
            100                 105                 110

Asp Tyr Thr Leu Asn Val Tyr Arg Leu Ala Leu Lys Thr Thr Leu Lys
            115                 120                 125

Arg Ala Arg Arg Ser Met Glu Leu Ile Ala Arg Glu Asp Glu Asn Pro
        130                 135                 140

Lys Val Ala Glu Val Ile Tyr Pro Ile Met Gln Val Asn Val Met His
145                 150                 155                 160

Tyr Asp Gly Val Asp Val Tyr Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Met Glu Ile Ala Lys Tyr Phe Leu Glu Tyr Pro Leu Thr Ile
                245                 250                 255

Lys Cys Pro Glu Lys Glu Gly Gly Asp Leu Thr Val Asn Ser Tyr Glu
            260                 265                 270

Glu Leu Glu Ser Leu Phe Lys Asn Lys Glu Leu His Pro Met Arg Leu
        275                 280                 285

Lys Asn Ala Val Ala Glu Leu Ile Lys Ile Leu Glu Pro Ile Arg
    290                 295                 300

Lys Arg Leu
305

<210> SEQ ID NO 13
<211> LENGTH: 306
<212> TYPE: PRT
<213> ORGANISM: Artificial Sequence
<220> FEATURE:
<223> OTHER INFORMATION: synthetic polypeptide

<400> SEQUENCE: 13

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Leu
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Thr Tyr Met Leu Asp Lys
            100                 105                 110

Asp Tyr Thr Leu Asn Val Tyr Arg Leu Ala Leu Lys Thr Thr Leu Lys
            115                 120                 125

Arg Ala Arg Arg Ser Met Glu Leu Ile Ala Arg Glu Asp Glu Asn Pro
        130                 135                 140

```
Lys Val Ala Glu Val Ile Tyr Pro Ile Met Gln Val Asn Gly Cys His
145                 150                 155                 160

Tyr Arg Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
                260                 265                 270

Leu Glu Ser Leu Phe Lys Asn Lys Glu Leu His Pro Met Arg Leu Lys
                275                 280                 285

Asn Ala Val Ala Glu Leu Ile Lys Ile Leu Glu Pro Ile Arg Lys
        290                 295                 300

Arg Leu
305

<210> SEQ ID NO 14
<211> LENGTH: 306
<212> TYPE: PRT
<213> ORGANISM: Artificial Sequence
<220> FEATURE:
<223> OTHER INFORMATION: synthetic polypeptide

<400> SEQUENCE: 14

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Leu
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Thr Tyr Met Leu Asp Lys
                100                 105                 110

Asp Tyr Thr Leu Asn Val Tyr Arg Leu Ala Leu Lys Thr Thr Leu Lys
            115                 120                 125

Arg Ala Arg Arg Ser Met Glu Leu Ile Ala Arg Glu Asp Glu Asn Pro
130                 135                 140

Lys Val Ala Glu Val Ile Tyr Pro Ile Met Gln Val Asn Gly Cys His
145                 150                 155                 160

Tyr Arg Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190
```

```
Asn Pro Val Leu Thr Gly Leu Asp Gly Glu Gly Lys Met Ser Ser Ser
            195                 200                 205

Lys Gly Asn Phe Ile Ala Val Asp Asp Ser Pro Glu Glu Ile Arg Ala
        210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
            245                 250                 255

Gly Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Arg Leu Lys
            275                 280                 285

Asn Ala Val Ala Glu Glu Leu Ile Lys Ile Leu Glu Pro Ile Arg Lys
        290                 295                 300

Arg Leu
305

<210> SEQ ID NO 15
<211> LENGTH: 306
<212> TYPE: PRT
<213> ORGANISM: Artificial Sequence
<220> FEATURE:
<223> OTHER INFORMATION: synthetic polypeptide

<400> SEQUENCE: 15

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Leu
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Thr Tyr Met Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
130                 135                 140

Lys Val Ala Glu Val Ile Tyr Pro Ile Met Gln Val Asn Gly Cys His
145                 150                 155                 160

Tyr Arg Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240
```

Ile Met Glu Ile Ala Lys Tyr Phe Leu Glu Tyr Pro Leu Thr Ile Lys
              245                 250                 255

Cys Pro Glu Lys Glu Gly Gly Asp Leu Thr Val Asn Ser Tyr Glu Glu
          260                 265                 270

Leu Glu Ser Leu Phe Lys Asn Lys Glu Leu His Pro Met Arg Leu Lys
      275                 280                 285

Asn Ala Val Ala Glu Glu Leu Ile Lys Ile Leu Glu Pro Ile Arg Lys
  290                 295                 300

Arg Leu
305

<210> SEQ ID NO 16
<211> LENGTH: 924
<212> TYPE: DNA
<213> ORGANISM: Methanocaldococcus jannaschii

<400> SEQUENCE: 16
atggacgaat ttgaaatgat aaagagaaac acatctgaaa ttatcagcga ggaagagtta    60
agagaggttt taaaaaaaga tgaaaaatct gctctgatag gttttgaacc aagtggtaaa   120
atacatttag ggcattatct ccaaataaaa agatgattg atttacaaaa tgctggattt    180
gatataatta tattgttggc tgatttacac gcctatttaa accagaaagg agagttggat   240
gagattagaa aaataggaga ttataacaaa aaagttttg aagcaatggg gttaaaggca    300
aaatatgttt atggaagtga attccagctt gataaggatt atacactgaa tgtctataga   360
ttggctttaa aaactacctt aaaaagagca agaaggagta tggaacttat agcaagagag   420
gatgaaaatc caaggttgc tgaagttatc tatccaataa tgcaggttaa tggttgtcat    480 tatagggggcg ttgatgttgc tgttggaggg atggagcaga aaaaatac catgttagca    540 agggagcttt taccaaaaaa ggttgtttgt attcacaacc ctgtcttaac gggtttggat   600
ggagaaggaa agatgagttc ttcaaaaggg aatttttatag ctgttgatga ctctccagaa   660
gagattaggg ctaagataaa gaaagcatac tgcccagctg gagttgttga aggaaatcca   720
ataatggaga tagctaaata cttccttgaa tatcctttaa ccataaaaag gccagaaaaa   780
tttggtggag atttgacagt aatagctat gaggagttag agagtttatt taaaaataag   840
gaattgcatc caatgcgctt aaaaaatgct gtagctgaag aacttataaa gattttagag   900
ccaattagaa agagattata ataa                                         924

<210> SEQ ID NO 17
<211> LENGTH: 3816
<212> TYPE: DNA
<213> ORGANISM: Artificial Sequence
<220> FEATURE:
<223> OTHER INFORMATION: Synthetic DNA Sequence

<400> SEQUENCE: 17
tttgcgtagg gatttccttc ccgcgcatca ataaaaatgg cgctgaaaaa acttttcata    60
ctcccgccat tcagagaaga aaccaattgt ccatattgca tcagacattg ccgtcactgc   120
gtcttttact ggctcttctc gctaaccaaa ccggtaaccc cgcttattaa aagcattctg   180
taacaaagcg ggaccaaagc catgacaaaa acgcgtaaca aaagtgtcta atcacggc    240 agaaaagtcc acattgatta tttgcacggc gtcacacttt gctatgccat agcatttta    300 tccataagat tagcggatcc tacctgacgc ttttatcgc aactctctac tgtttctcca   360
tacccgtttt tttgggctaa caggaggaat tagatctatg gacgaatttg aaatgataaa   420

```
gagaaacaca tctgaaatta tcagcgagga agagttaaga gaggttttaa aaaaagatga    480
aaaatctgct ctgataggtt ttgaaccaag tggtaaaata catttagggc attatctcca    540
aataaaaaag atgattgatt tacaaaatgc tggatttgat ataattatat tgttggctga    600
tttacacgcc tatttaaacc agaaaggaga gttggatgag attagaaaaa taggagatta    660
taacaaaaaa gttttttgaag caatggggtt aaaggcaaaa tatgtttatg gaagtgaatt    720
ccagcttgat aaggattata cactgaatgt ctatagattg gctttaaaaa ctaccttaaa    780
aagagcaaga aggagtatgg aacttatagc aagagaggat gaaaatccaa aggttgctga    840
agttatctat ccaataatgc aggttaatgg ttgtcattat aggggcgttg atgttgctgt    900
tggagggatg gagcagagaa aaatacacat gttagcaagg gagcttttac caaaaaaggt    960
tgtttgtatt cacaaccctg tcttaacggg tttggatgga gaaggaaaga tgagttcttc   1020
aaaagggaat tttatagctg ttgatgactc tccagaagag attagggcta agataaagaa   1080
agcatactgc ccagctggag ttgttgaagg aaatccaata atggagatag ctaaatactt   1140
ccttgaatat cctttaacca taaaaaggcc agaaaaattt ggtggagatt tgacagttaa   1200
tagctatgag gagttagaga gtttatttaa aaataaggaa ttgcatccaa tgcgcttaaa   1260
aaatgctgta gctgaagaac ttataaagat tttagagcca attagaaaga gattataata   1320
agtcgaccat catcatcatc atcattgagt ttaaacggtc tccagcttgg ctgttttggc   1380
ggatgagaga agattttcag cctgatacag attaaatcag aacgcagaag cggtctgata   1440
aaacagaatt tgcctggcgg cagtagcgcg gtggtcccac ctgaccccat gccgaactca   1500
gaagtgaaac gccgtagcgc cgatggtagt gtggggtctc cccatgcgag agtagggaac   1560
tgccaggcat caaataaaac gaaaggctca gtcgaaagac tgggccttgt ttgtgagctc   1620
ccggtcatca atcataattc cgcttcgcaa catgtgagca ccggtttatt gactaccgga   1680
agcagtgtga ccgtgtgctt ctcaaatgcc tgaggccagt ttgctcaggc tctcccgtg    1740 gaggtaataa ttgacgatat gatcagtgca cggctaacta agcggcctgc tgactttctc   1800
gccgatcaaa aggcattttg ctattaaggg attgacgagg gcgtatctgc gcagtaagat   1860
gcgccccgca ttccggcggt agttcagcag ggcagaacgg cggactctaa atccgcatgg   1920
caggggttca atcccctcc gccggaccaa attcgaaaag cctgctcaac gagcaggctt    1980
ttttgcatgc tcgagcagct cagggtcgaa tttgctttcg ttgaggcaca ttaacgccct   2040
atggcacgta acgccaacct tttgcggtag cggcttctgc tagaatccgc aataatttta   2100
cagtttgatc gcgctaaata ctgcttcacc acaaggaatg caaatgaaga aattgctccc   2160
cattcttatc ggcctgagcc tttctggggtt cagttcgttg agccaggccg agaacctgat   2220
gcaagtttat cagcaagcac gccttagtaa cccggaattg cgtaagtctg ccgccgatcg   2280
tgatgctgcc tttgaaaaaa ttaatgaagc gcgcagtcca ttactgccac agctaggttt   2340
aggtgcagat tacacctata gcaacggcta ccgcgacgcg aacggcatca actctaacgc   2400
gaccagtgcg tccttgcagt taactcaatc cattttttgat atgtcgaaat ggcgtgcgtt   2460
aacgctgcag gaaaaagcag cagggattca ggacgtcacg tatcagaccg atcagcaaac   2520
cttgatcctc aacaccgcga ccgcttattt caacgtgttg aatgctattg acgttctttc   2580
ctatacacag gcacaaaaag aagcgatcta ccgtcaatta gatcaaacca cccaacgttt   2640
taacgtgggc ctggtagcga tcaccgacgt gcagaacgcc cgcgcacagt acgataccgt   2700
gctggcgaac gaagtgaccg cacgtaataa ccttgataac gcggtagagc agctgcgcca   2760
```

```
gatcaccggt aactactatc cggaactggc tgcgctgaat gtcgaaaact ttaaaaccga   2820
caaaccacag ccggttaacg cgctgctgaa agaagccgaa aaacgcaacc tgtcgctgtt   2880
acaggcacgc ttgagccagg acctggcgcg cgagcaaatt cgccaggcgc aggatggtca   2940
cttaccgact ctggatttaa cggcttctac cgggatttct gacacctctt atagcggttc   3000
gaaaacccgt ggtgccgctg gtacccagta tgacgatagc aatatgggcc agaacaaagt   3060
tggcctgagc ttctcgctgc cgatttatca gggcggaatg gttaactcgc aggtgaaaca   3120
ggcacagtac aactttgtcg gtgccagcga gcaactggaa agtgcccatc gtagcgtcgt   3180
gcagaccgtg cgttcctcct tcaacaacat taatgcatct atcagtagca ttaacgccta   3240
caaacaagcc gtagtttccg ctcaaagctc attagacgcg atggaagcgg gctactcggt   3300
cggtacgcgt accattgttg atgtgttgga tgcgaccacc acgttgtaca acgccaagca   3360
agagctggcg aatgcgcgtt ataactacct gattaatcag ctgaatatta agtcagctct   3420
gggtacgttg aacgagcagg atctgctggc actgaacaat gcgctgagca aaccggtttc   3480
cactaatccg gaaaacgttg caccgcaaac gccggaacag aatgctattg ctgatggtta   3540
tgcgcctgat agcccggcac cagtcgttca gcaaacatcc gcacgcacta ccaccagtaa   3600
cggtcataac cctttccgta actgatgacg acgacgggga agcttaatta gctgatctag   3660
aggcatcaaa taaaacgaaa ggctcagtcg aaagactggg cctttcgttt tatctgttgt   3720
ttgtcggtga acgctctcct gagtaggaca aatccgccgc cctagaatat tcaacgccat   3780
cgacttttta tgcctttgcg gcatcgggca atgcgt                             3816
```

<210> SEQ ID NO 18
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa = Any standard or non-standard amino acid

<400> SEQUENCE: 18

Val Pro Gly Xaa Gly
1               5

<210> SEQ ID NO 19
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: REPEAT
<222> LOCATION: (1)..(5)
<223> OTHER INFORMATION: The sequence of the peptide can be repeated up
      to more than 500 times.
<220> FEATURE:
<221> NAME/KEY: MISC_FEATURE
<222> LOCATION: (4)..(4)
<223> OTHER INFORMATION: Xaa = Any standard or non-standard amino acid

<400> SEQUENCE: 19

Val Pro Gly Xaa Gly
1               5

<210> SEQ ID NO 20
<211> LENGTH: 156
<212> TYPE: PRT

```
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (20)..(20)
<223> OTHER INFORMATION: Xaa = Non-standard amino acid, prefarably a
      non-standard amino acid disclosed in the specification.
<220> FEATURE:
<221> NAME/KEY: MISC_FEATURE
<222> LOCATION: (35)..(35)
<223> OTHER INFORMATION: Xaa = Non-standard amino acid, prefarably a
      non-standard amino acid disclosed in the specification.
<220> FEATURE:
<221> NAME/KEY: MISC_FEATURE
<222> LOCATION: (50)..(50)
<223> OTHER INFORMATION: Xaa = Non-standard amino acid, prefarably a
      non-standard amino acid disclosed in the specification.
<220> FEATURE:
<221> NAME/KEY: MISC_FEATURE
<222> LOCATION: (65)..(65)
<223> OTHER INFORMATION: Xaa = Non-standard amino acid, prefarably a
      non-standard amino acid disclosed in the specification.
<220> FEATURE:
<221> NAME/KEY: MISC_FEATURE
<222> LOCATION: (80)..(80)
<223> OTHER INFORMATION: Xaa = Non-standard amino acid, prefarably a
      non-standard amino acid disclosed in the specification.
<220> FEATURE:
<221> NAME/KEY: MISC_FEATURE
<222> LOCATION: (95)..(95)
<223> OTHER INFORMATION: Xaa = Non-standard amino acid, prefarably a
      non-standard amino acid disclosed in the specification.
<220> FEATURE:
<221> NAME/KEY: MISC_FEATURE
<222> LOCATION: (110)..(110)
<223> OTHER INFORMATION: Xaa = Non-standard amino acid, prefarably a
      non-standard amino acid disclosed in the specification.
<220> FEATURE:
<221> NAME/KEY: MISC_FEATURE
<222> LOCATION: (125)..(125)
<223> OTHER INFORMATION: Xaa = Non-standard amino acid, prefarably a
      non-standard amino acid disclosed in the specification.
<220> FEATURE:
<221> NAME/KEY: MISC_FEATURE
<222> LOCATION: (140)..(140)
<223> OTHER INFORMATION: Xaa = Non-standard amino acid, prefarably a
      non-standard amino acid disclosed in the specification.
<220> FEATURE:
<221> NAME/KEY: MISC_FEATURE
<222> LOCATION: (155)..(155)
<223> OTHER INFORMATION: Xaa = Non-standard amino acid, prefarably a
      non-standard amino acid disclosed in the specification.

<400> SEQUENCE: 20

Met Ser Lys Gly Pro Gly Val Pro Gly Gly Val Pro Gly Ala Gly
1               5                   10                  15

Val Pro Gly Xaa Gly Val Pro Gly Gly Val Pro Gly Ala Gly Val
                20                  25                  30

Pro Gly Xaa Gly Val Pro Gly Gly Gly Val Pro Gly Ala Gly Val Pro
            35                  40                  45

Gly Xaa Gly Val Pro Gly Gly Gly Val Pro Gly Ala Gly Val Pro Gly
    50                  55                  60

Xaa Gly Val Pro Gly Gly Gly Val Pro Gly Ala Gly Val Pro Gly Xaa
65                  70                  75                  80

Gly Val Pro Gly Gly Gly Val Pro Gly Ala Gly Val Pro Gly Xaa Gly
                85                  90                  95

Val Pro Gly Gly Gly Val Pro Gly Ala Gly Val Pro Gly Xaa Gly Val
                100                 105                 110

Pro Gly Gly Gly Val Pro Gly Ala Gly Val Pro Gly Xaa Gly Val Pro
            115                 120                 125
```

Gly Gly Gly Val Pro Gly Ala Gly Val Pro Gly Xaa Gly Val Pro Gly
        130                 135                 140

Gly Gly Val Pro Gly Ala Gly Val Pro Gly Xaa Gly
145                 150                 155

<210> SEQ ID NO 21
<211> LENGTH: 400
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (20)..(20)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (35)..(35)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (50)..(50)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (65)..(65)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (80)..(80)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (95)..(95)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (110)..(110)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (125)..(125)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (140)..(140)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (155)..(155)
<223> OTHER INFORMATION: Xaa = Non-standard amino acid, preferably a
      non-standard amino acid disclosed in the application.

<400> SEQUENCE: 21

Met Ser Lys Gly Pro Gly Val Pro Gly Gly Val Pro Gly Ala Gly
1               5                   10                  15

Val Pro Gly Xaa Gly Val Pro Gly Gly Gly Val Pro Gly Ala Gly Val
                20                  25                  30

Pro Gly Xaa Gly Val Pro Gly Gly Gly Val Pro Gly Ala Gly Val Pro
            35                  40                  45

Gly Xaa Gly Val Pro Gly Gly Gly Val Pro Gly Ala Gly Val Pro Gly
        50                  55                  60

Xaa Gly Val Pro Gly Gly Val Pro Gly Ala Gly Val Pro Gly Xaa
65                  70                  75                  80

Gly Val Pro Gly Gly Val Pro Gly Ala Gly Val Pro Gly Xaa Gly
                85                  90                  95

Val Pro Gly Gly Val Pro Gly Ala Gly Val Pro Gly Xaa Gly Val
            100                 105                 110

Pro Gly Gly Val Pro Gly Ala Gly Val Pro Gly Xaa Gly Val Pro
        115                 120                 125

Gly Gly Val Pro Gly Ala Gly Val Pro Gly Xaa Gly Val Pro Gly
    130                 135                 140

Gly Gly Val Pro Gly Ala Gly Val Pro Gly Xaa Gly Pro Gly Gly
145                 150                 155                 160

Gly Ser Lys Gly Glu Glu Leu Phe Thr Gly Val Val Pro Ile Leu Val
                165                 170                 175

Glu Leu Asp Gly Asp Val Asn Gly His Lys Phe Ser Val Arg Gly Glu
            180                 185                 190

Gly Glu Gly Asp Ala Thr Asn Gly Lys Leu Thr Leu Lys Phe Ile Cys
    195                 200                 205

Thr Thr Gly Lys Leu Pro Val Pro Trp Pro Thr Leu Val Thr Thr Leu
210                 215                 220

Thr Tyr Gly Val Gln Cys Phe Ser Arg Tyr Pro Asp His Met Lys Arg
225                 230                 235                 240

His Asp Phe Phe Lys Ser Ala Met Pro Glu Gly Tyr Val Gln Glu Arg
                245                 250                 255

Thr Ile Ser Phe Lys Asp Asp Gly Thr Tyr Lys Thr Arg Ala Glu Val
            260                 265                 270

Lys Phe Glu Gly Asp Thr Leu Val Asn Arg Ile Glu Leu Lys Gly Ile
        275                 280                 285

Asp Phe Lys Glu Asp Gly Asn Ile Leu Gly His Lys Leu Glu Tyr Asn
    290                 295                 300

Phe Asn Ser His Asn Val Tyr Ile Thr Ala Asp Lys Gln Lys Asn Gly
305                 310                 315                 320

Ile Lys Ala Asn Phe Lys Ile Arg His Asn Val Glu Asp Gly Ser Val
                325                 330                 335

Gln Leu Ala Asp His Tyr Gln Gln Asn Thr Pro Ile Gly Asp Gly Pro
            340                 345                 350

Val Leu Leu Pro Asp Asn His Tyr Leu Ser Thr Gln Ser Val Leu Ser
        355                 360                 365

Lys Asp Pro Asn Glu Lys Arg Asp His Met Val Leu Leu Glu Phe Val
    370                 375                 380

Thr Ala Ala Gly Ile Thr His Gly Met Asp Glu Leu Tyr Lys Gly Ser
385                 390                 395                 400

<210> SEQ ID NO 22
<211> LENGTH: 456
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (20)..(20)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (35)..(35)
<223> OTHER INFORMATION: Xaa = Non-standard amino acid, preferably a

```
       non-standard amino acid disclosed in the application.
<220>  FEATURE:
<221>  NAME/KEY: MISC_FEATURE
<222>  LOCATION: (50)..(50)
<223>  OTHER INFORMATION: Xaa = Non-standard amino acid, preferably a
       non-standard amino acid disclosed in the application.
<220>  FEATURE:
<221>  NAME/KEY: MISC_FEATURE
<222>  LOCATION: (65)..(65)
<223>  OTHER INFORMATION: Xaa = Non-standard amino acid, preferably a
       non-standard amino acid disclosed in the application.
<220>  FEATURE:
<221>  NAME/KEY: MISC_FEATURE
<222>  LOCATION: (80)..(80)
<223>  OTHER INFORMATION: Xaa = Non-standard amino acid, preferably a
       non-standard amino acid disclosed in the application.
<220>  FEATURE:
<221>  NAME/KEY: MISC_FEATURE
<222>  LOCATION: (95)..(95)
<223>  OTHER INFORMATION: Xaa = Non-standard amino acid, preferably a
       non-standard amino acid disclosed in the application.
<220>  FEATURE:
<221>  NAME/KEY: MISC_FEATURE
<222>  LOCATION: (110)..(110)
<223>  OTHER INFORMATION: Xaa = Non-standard amino acid, preferably a
       non-standard amino acid disclosed in the application.
<220>  FEATURE:
<221>  NAME/KEY: MISC_FEATURE
<222>  LOCATION: (125)..(125)
<223>  OTHER INFORMATION: Xaa = Non-standard amino acid, preferably a
       non-standard amino acid disclosed in the application.
<220>  FEATURE:
<221>  NAME/KEY: MISC_FEATURE
<222>  LOCATION: (140)..(140)
<223>  OTHER INFORMATION: Xaa = Non-standard amino acid, preferably a
       non-standard amino acid disclosed in the application.
<220>  FEATURE:
<221>  NAME/KEY: MISC_FEATURE
<222>  LOCATION: (155)..(155)
<223>  OTHER INFORMATION: Xaa = Non-standard amino acid, preferably a
       non-standard amino acid disclosed in the application.
<220>  FEATURE:
<221>  NAME/KEY: MISC_FEATURE
<222>  LOCATION: (170)..(170)
<223>  OTHER INFORMATION: Xaa = Non-standard amino acid, preferably a
       non-standard amino acid disclosed in the application.
<220>  FEATURE:
<221>  NAME/KEY: MISC_FEATURE
<222>  LOCATION: (185)..(185)
<223>  OTHER INFORMATION: Xaa = Non-standard amino acid, preferably a
       non-standard amino acid disclosed in the application.
<220>  FEATURE:
<221>  NAME/KEY: MISC_FEATURE
<222>  LOCATION: (200)..(200)
<223>  OTHER INFORMATION: Xaa = Non-standard amino acid, preferably a
       non-standard amino acid disclosed in the application.
<220>  FEATURE:
<221>  NAME/KEY: MISC_FEATURE
<222>  LOCATION: (215)..(215)
<223>  OTHER INFORMATION: Xaa = Non-standard amino acid, preferably a
       non-standard amino acid disclosed in the application.
<220>  FEATURE:
<221>  NAME/KEY: MISC_FEATURE
<222>  LOCATION: (230)..(230)
<223>  OTHER INFORMATION: Xaa = Non-standard amino acid, preferably a
       non-standard amino acid disclosed in the application.
<220>  FEATURE:
<221>  NAME/KEY: MISC_FEATURE
<222>  LOCATION: (245)..(245)
<223>  OTHER INFORMATION: Xaa = Non-standard amino acid, preferably a
       non-standard amino acid disclosed in the application.
<220>  FEATURE:
<221>  NAME/KEY: MISC_FEATURE
<222>  LOCATION: (260)..(260)
<223>  OTHER INFORMATION: Xaa = Non-standard amino acid, preferably a
       non-standard amino acid disclosed in the application.
<220>  FEATURE:
<221>  NAME/KEY: MISC_FEATURE
<222>  LOCATION: (275)..(275)
```

```
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (290)..(290)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (305)..(305)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (320)..(320)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (335)..(335)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (350)..(350)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (365)..(365)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (380)..(380)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (395)..(395)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (410)..(410)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (425)..(425)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (440)..(440)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (455)..(455)
<223> OTHER INFORMATION: Xaa = Non-standard amino acid, preferably a
      non-standard amino acid disclosed in the application.

<400> SEQUENCE: 22

Met Ser Lys Gly Pro Gly Val Pro Gly Gly Val Pro Gly Ala Gly
1               5                   10                  15

Val Pro Gly Xaa Gly Val Pro Gly Gly Gly Val Pro Gly Ala Gly Val
            20                  25                  30

Pro Gly Xaa Gly Val Pro Gly Gly Gly Val Pro Gly Ala Gly Val Pro
        35                  40                  45

Gly Xaa Gly Val Pro Gly Gly Gly Val Pro Gly Ala Gly Val Pro Gly
    50                  55                  60

Xaa Gly Val Pro Gly Gly Gly Val Pro Gly Ala Gly Val Pro Gly Xaa
65                  70                  75                  80
```

Gly Val Pro Gly Gly Val Pro Gly Ala Gly Val Pro Gly Xaa Gly
                85                  90                  95

Val Pro Gly Gly Gly Val Pro Gly Ala Gly Val Pro Gly Xaa Gly Val
            100                 105                 110

Pro Gly Gly Gly Val Pro Gly Ala Gly Val Pro Gly Xaa Gly Val Pro
        115                 120                 125

Gly Gly Gly Val Pro Gly Ala Gly Val Pro Gly Xaa Gly Val Pro Gly
    130                 135                 140

Gly Gly Val Pro Gly Ala Gly Val Pro Gly Xaa Gly Val Pro Gly Gly
145                 150                 155                 160

Gly Val Pro Gly Ala Gly Val Pro Gly Xaa Gly Val Pro Gly Gly Gly
                165                 170                 175

Val Pro Gly Ala Gly Val Pro Gly Xaa Gly Val Pro Gly Gly Gly Val
            180                 185                 190

Pro Gly Ala Gly Val Pro Gly Xaa Gly Val Pro Gly Gly Gly Val Pro
        195                 200                 205

Gly Ala Gly Val Pro Gly Xaa Gly Val Pro Gly Gly Gly Val Pro Gly
    210                 215                 220

Ala Gly Val Pro Gly Xaa Gly Val Pro Gly Gly Gly Val Pro Gly Ala
225                 230                 235                 240

Gly Val Pro Gly Xaa Gly Val Pro Gly Gly Gly Val Pro Gly Ala Gly
                245                 250                 255

Val Pro Gly Xaa Gly Val Pro Gly Gly Gly Val Pro Gly Ala Gly Val
            260                 265                 270

Pro Gly Xaa Gly Val Pro Gly Gly Gly Val Pro Gly Ala Gly Val Pro
        275                 280                 285

Gly Xaa Gly Val Pro Gly Gly Gly Val Pro Gly Ala Gly Val Pro Gly
    290                 295                 300

Xaa Gly Val Pro Gly Gly Gly Val Pro Gly Ala Gly Val Pro Gly Xaa
305                 310                 315                 320

Gly Val Pro Gly Gly Gly Val Pro Gly Ala Gly Val Pro Gly Xaa Gly
                325                 330                 335

Val Pro Gly Gly Gly Val Pro Gly Ala Gly Val Pro Gly Xaa Gly Val
            340                 345                 350

Pro Gly Gly Gly Val Pro Gly Ala Gly Val Pro Gly Xaa Gly Val Pro
        355                 360                 365

Gly Gly Gly Val Pro Gly Ala Gly Val Pro Gly Xaa Gly Val Pro Gly
    370                 375                 380

Gly Gly Val Pro Gly Ala Gly Val Pro Gly Xaa Gly Val Pro Gly Gly
385                 390                 395                 400

Gly Val Pro Gly Ala Gly Val Pro Gly Xaa Gly Val Pro Gly Gly Gly
                405                 410                 415

Val Pro Gly Ala Gly Val Pro Gly Xaa Gly Val Pro Gly Gly Gly Val
            420                 425                 430

Pro Gly Ala Gly Val Pro Gly Xaa Gly Val Pro Gly Gly Gly Val Pro
        435                 440                 445

Gly Ala Gly Val Pro Gly Xaa Gly
    450                 455

<210> SEQ ID NO 23
<211> LENGTH: 700
<212> TYPE: PRT
<213> ORGANISM: Artificial Sequence
<220> FEATURE:

```
<223> OTHER INFORMATION: Synthetic Polypeptide
<220> FEATURE:
<221> NAME/KEY: MISC_FEATURE
<222> LOCATION: (20)..(20)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (35)..(35)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (50)..(50)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (65)..(65)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (80)..(80)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (95)..(95)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (110)..(110)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (125)..(125)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (140)..(140)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (155)..(155)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (170)..(170)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (185)..(185)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (200)..(200)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (215)..(215)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (230)..(230)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (245)..(245)
```

```
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (260)..(260)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (275)..(275)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (290)..(290)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (305)..(305)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (320)..(320)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (335)..(335)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (350)..(350)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (365)..(365)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (380)..(380)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (395)..(395)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (410)..(410)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (425)..(425)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (440)..(440)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (455)..(455)
<223> OTHER INFORMATION: Xaa = Non-standard amino acid, preferably a
      non-standard amino acid disclosed in the application.

<400> SEQUENCE: 23

Met Ser Lys Gly Pro Gly Val Pro Gly Gly Val Pro Gly Ala Gly
1               5                   10                  15

Val Pro Gly Xaa Gly Val Pro Gly Gly Gly Val Pro Gly Ala Gly Val
```

-continued

```
                20                  25                  30
Pro Gly Xaa Gly Val Pro Gly Gly Val Pro Gly Ala Gly Val Pro
            35                  40                  45
Gly Xaa Gly Val Pro Gly Gly Val Pro Gly Ala Gly Val Pro Gly
        50                  55                  60
Xaa Gly Val Pro Gly Gly Val Pro Gly Ala Gly Val Pro Gly Xaa
65                  70                  75                  80
Gly Val Pro Gly Gly Val Pro Gly Ala Gly Val Pro Gly Xaa Gly
                85                  90                  95
Val Pro Gly Gly Val Pro Gly Ala Gly Val Pro Gly Xaa Gly Val
            100                 105                 110
Pro Gly Gly Val Pro Gly Ala Gly Val Pro Gly Xaa Gly Val Pro
        115                 120                 125
Gly Gly Val Pro Gly Ala Gly Val Pro Gly Xaa Gly Val Pro Gly
    130                 135                 140
Gly Gly Val Pro Gly Ala Gly Val Pro Gly Xaa Gly Val Pro Gly Gly
145                 150                 155                 160
Gly Val Pro Gly Ala Gly Val Pro Gly Xaa Gly Val Pro Gly Gly
                165                 170                 175
Val Pro Gly Ala Gly Val Pro Gly Xaa Gly Val Pro Gly Gly Val
            180                 185                 190
Pro Gly Ala Gly Val Pro Gly Xaa Gly Val Pro Gly Gly Gly Val Pro
        195                 200                 205
Gly Ala Gly Val Pro Gly Xaa Gly Val Pro Gly Gly Gly Val Pro Gly
    210                 215                 220
Ala Gly Val Pro Gly Xaa Gly Val Pro Gly Gly Gly Val Pro Gly Ala
225                 230                 235                 240
Gly Val Pro Gly Xaa Gly Val Pro Gly Gly Gly Val Pro Gly Ala Gly
                245                 250                 255
Val Pro Gly Xaa Gly Val Pro Gly Gly Gly Val Pro Gly Ala Gly Val
            260                 265                 270
Pro Gly Xaa Gly Val Pro Gly Gly Gly Val Pro Gly Ala Gly Val Pro
        275                 280                 285
Gly Xaa Gly Val Pro Gly Gly Gly Val Pro Gly Ala Gly Val Pro Gly
    290                 295                 300
Xaa Gly Val Pro Gly Gly Gly Val Pro Gly Ala Gly Val Pro Gly Xaa
305                 310                 315                 320
Gly Val Pro Gly Gly Gly Val Pro Gly Ala Gly Val Pro Gly Xaa Gly
                325                 330                 335
Val Pro Gly Gly Gly Val Pro Gly Ala Gly Val Pro Gly Xaa Gly Val
            340                 345                 350
Pro Gly Gly Gly Val Pro Gly Ala Gly Val Pro Gly Xaa Gly Val Pro
        355                 360                 365
Gly Gly Gly Val Pro Gly Ala Gly Val Pro Gly Xaa Gly Val Pro Gly
    370                 375                 380
Gly Gly Val Pro Gly Ala Gly Val Pro Gly Xaa Gly Val Pro Gly Gly
385                 390                 395                 400
Gly Val Pro Gly Ala Gly Val Pro Gly Xaa Gly Val Pro Gly Gly Gly
                405                 410                 415
Val Pro Gly Ala Gly Val Pro Gly Xaa Gly Val Pro Gly Gly Gly Val
            420                 425                 430
Pro Gly Ala Gly Val Pro Gly Xaa Gly Val Pro Gly Gly Gly Val Pro
        435                 440                 445
```

```
Gly Ala Gly Val Pro Gly Xaa Gly Pro Gly Gly Gly Ser Lys Gly
        450                 455                 460

Glu Glu Leu Phe Thr Gly Val Val Pro Ile Leu Val Glu Leu Asp Gly
465                 470                 475                 480

Asp Val Asn Gly His Lys Phe Ser Val Arg Gly Glu Gly Glu Gly Asp
                485                 490                 495

Ala Thr Asn Gly Lys Leu Thr Leu Lys Phe Ile Cys Thr Thr Gly Lys
            500                 505                 510

Leu Pro Val Pro Trp Pro Thr Leu Val Thr Thr Leu Thr Tyr Gly Val
        515                 520                 525

Gln Cys Phe Ser Arg Tyr Pro Asp His Met Lys Arg His Asp Phe Phe
    530                 535                 540

Lys Ser Ala Met Pro Glu Gly Tyr Val Gln Glu Arg Thr Ile Ser Phe
545                 550                 555                 560

Lys Asp Asp Gly Thr Tyr Lys Thr Arg Ala Glu Val Lys Phe Glu Gly
                565                 570                 575

Asp Thr Leu Val Asn Arg Ile Glu Leu Lys Gly Ile Asp Phe Lys Glu
            580                 585                 590

Asp Gly Asn Ile Leu Gly His Lys Leu Glu Tyr Asn Phe Asn Ser His
        595                 600                 605

Asn Val Tyr Ile Thr Ala Asp Lys Gln Lys Asn Gly Ile Lys Ala Asn
    610                 615                 620

Phe Lys Ile Arg His Asn Val Glu Asp Gly Ser Val Gln Leu Ala Asp
625                 630                 635                 640

His Tyr Gln Gln Asn Thr Pro Ile Gly Asp Gly Pro Val Leu Leu Pro
                645                 650                 655

Asp Asn His Tyr Leu Ser Thr Gln Ser Val Leu Ser Lys Asp Pro Asn
            660                 665                 670

Glu Lys Arg Asp His Met Val Leu Leu Glu Phe Val Thr Ala Ala Gly
        675                 680                 685

Ile Thr His Gly Met Asp Glu Leu Tyr Lys Gly Ser
        690                 695                 700

<210> SEQ ID NO 24
<211> LENGTH: 161
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (16)..(16)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (32)..(32)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (48)..(48)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (64)..(64)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (80)..(80)
```

<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (96)..(96)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (112)..(112)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (128)..(128)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (144)..(144)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (160)..(160)
<223> OTHER INFORMATION: Xaa = Non-standard amino acid, preferably a
      non-standard amino acid disclosed in the application.

<400> SEQUENCE: 24

Met Ser Lys Gly Pro Gly Lys Val Pro Gly Ala Gly Val Pro Gly Xaa
1               5                   10                  15

Gly Val Pro Gly Val Gly Lys Val Pro Gly Ala Gly Val Pro Gly Xaa
            20                  25                  30

Gly Val Pro Gly Val Gly Lys Val Pro Gly Ala Gly Val Pro Gly Xaa
        35                  40                  45

Gly Val Pro Gly Val Gly Lys Val Pro Gly Ala Gly Val Pro Gly Xaa
    50                  55                  60

Gly Val Pro Gly Val Gly Lys Val Pro Gly Ala Gly Val Pro Gly Xaa
65                  70                  75                  80

Gly Val Pro Gly Val Gly Lys Val Pro Gly Ala Gly Val Pro Gly Xaa
                85                  90                  95

Gly Val Pro Gly Val Gly Lys Val Pro Gly Ala Gly Val Pro Gly Xaa
            100                 105                 110

Gly Val Pro Gly Val Gly Lys Val Pro Gly Ala Gly Val Pro Gly Xaa
        115                 120                 125

Gly Val Pro Gly Val Gly Lys Val Pro Gly Ala Gly Val Pro Gly Xaa
    130                 135                 140

Gly Val Pro Gly Val Gly Lys Val Pro Gly Ala Gly Val Pro Gly Xaa
145                 150                 155                 160

Gly

<210> SEQ ID NO 25
<211> LENGTH: 410
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (16)..(16)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (32)..(32)
<223> OTHER INFORMATION: Xaa = Non-standard amino acid, preferably a
      non-standard amino acid disclosed in the application.

```
<220> FEATURE:
<221> NAME/KEY: MISC_FEATURE
<222> LOCATION: (48)..(48)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (64)..(64)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (80)..(80)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (96)..(96)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (112)..(112)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (128)..(128)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (144)..(144)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (160)..(160)
<223> OTHER INFORMATION: Xaa = Non-standard amino acid, preferably a
      non-standard amino acid disclosed in the application.

<400> SEQUENCE: 25

Met Ser Lys Gly Pro Gly Lys Val Pro Gly Ala Gly Val Pro Gly Xaa
1               5                   10                  15

Gly Val Pro Gly Val Gly Lys Val Pro Gly Ala Gly Val Pro Gly Xaa
            20                  25                  30

Gly Val Pro Gly Val Gly Lys Val Pro Gly Ala Gly Val Pro Gly Xaa
        35                  40                  45

Gly Val Pro Gly Val Gly Lys Val Pro Gly Ala Gly Val Pro Gly Xaa
    50                  55                  60

Gly Val Pro Gly Val Gly Lys Val Pro Gly Ala Gly Val Pro Gly Xaa
65                  70                  75                  80

Gly Val Pro Gly Val Gly Lys Val Pro Gly Ala Gly Val Pro Gly Xaa
                85                  90                  95

Gly Val Pro Gly Val Gly Lys Val Pro Gly Ala Gly Val Pro Gly Xaa
            100                 105                 110

Gly Val Pro Gly Val Gly Lys Val Pro Gly Ala Gly Val Pro Gly Xaa
        115                 120                 125

Gly Val Pro Gly Val Gly Lys Val Pro Gly Ala Gly Val Pro Gly Xaa
    130                 135                 140

Gly Val Pro Gly Val Gly Lys Val Pro Gly Ala Gly Val Pro Gly Xaa
145                 150                 155                 160

Gly Val Pro Gly Val Gly Pro Gly Gly Gly Ser Lys Gly Glu Glu
                165                 170                 175

Leu Phe Thr Gly Val Val Pro Ile Leu Val Glu Leu Asp Gly Asp Val
            180                 185                 190
```

```
Asn Gly His Lys Phe Ser Val Arg Gly Glu Gly Gly Asp Ala Thr
            195                 200                 205

Asn Gly Lys Leu Thr Leu Lys Phe Ile Cys Thr Thr Gly Lys Leu Pro
210                 215                 220

Val Pro Trp Pro Thr Leu Val Thr Thr Leu Thr Tyr Gly Val Gln Cys
225                 230                 235                 240

Phe Ser Arg Tyr Pro Asp His Met Lys Arg His Asp Phe Phe Lys Ser
                245                 250                 255

Ala Met Pro Glu Gly Tyr Val Gln Glu Arg Thr Ile Ser Phe Lys Asp
            260                 265                 270

Asp Gly Thr Tyr Lys Thr Arg Ala Glu Val Lys Phe Glu Gly Asp Thr
        275                 280                 285

Leu Val Asn Arg Ile Glu Leu Lys Gly Ile Asp Phe Lys Glu Asp Gly
    290                 295                 300

Asn Ile Leu Gly His Lys Leu Glu Tyr Asn Phe Asn Ser His Asn Val
305                 310                 315                 320

Tyr Ile Thr Ala Asp Lys Gln Lys Asn Gly Ile Lys Ala Asn Phe Lys
                325                 330                 335

Ile Arg His Asn Val Glu Asp Gly Ser Val Gln Leu Ala Asp His Tyr
            340                 345                 350

Gln Gln Asn Thr Pro Ile Gly Asp Gly Pro Val Leu Leu Pro Asp Asn
        355                 360                 365

His Tyr Leu Ser Thr Gln Ser Val Leu Ser Lys Asp Pro Asn Glu Lys
    370                 375                 380

Arg Asp His Met Val Leu Leu Glu Phe Val Thr Ala Ala Gly Ile Thr
385                 390                 395                 400

His Gly Met Asp Glu Leu Tyr Lys Gly Ser
                405                 410

<210> SEQ ID NO 26
<211> LENGTH: 481
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (16)..(16)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (32)..(32)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (48)..(48)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (64)..(64)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (80)..(80)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (96)..(96)
<223> OTHER INFORMATION: Xaa = Non-standard amino acid, preferably a
      non-standard amino acid disclosed in the application.
```

```
<220> FEATURE:
<221> NAME/KEY: MISC_FEATURE
<222> LOCATION: (112)..(112)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (128)..(128)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (144)..(144)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (160)..(160)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (176)..(176)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (192)..(192)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (208)..(208)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (224)..(224)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (240)..(240)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (256)..(256)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (272)..(272)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (288)..(288)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (304)..(304)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (320)..(320)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (336)..(336)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (352)..(352)
<223> OTHER INFORMATION: Xaa = Non-standard amino acid, preferably a
``` non-standard amino acid disclosed in the application.
<220> FEATURE:
<221> NAME/KEY: MISC_FEATURE
<222> LOCATION: (368)..(368)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (384)..(384)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (400)..(400)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (416)..(416)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (432)..(432)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (448)..(448)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (464)..(464)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (480)..(480)
<223> OTHER INFORMATION: Xaa = Non-standard amino acid, preferably a
      non-standard amino acid disclosed in the application.

<400> SEQUENCE: 26

Met Ser Lys Gly Pro Gly Lys Val Pro Gly Ala Gly Val Pro Gly Xaa
1               5                   10                  15

Gly Val Pro Gly Val Gly Lys Val Pro Gly Ala Gly Val Pro Gly Xaa
                20                  25                  30

Gly Val Pro Gly Val Gly Lys Val Pro Gly Ala Gly Val Pro Gly Xaa
            35                  40                  45

Gly Val Pro Gly Val Gly Lys Val Pro Gly Ala Gly Val Pro Gly Xaa
        50                  55                  60

Gly Val Pro Gly Val Gly Lys Val Pro Gly Ala Gly Val Pro Gly Xaa
65                  70                  75                  80

Gly Val Pro Gly Val Gly Lys Val Pro Gly Ala Gly Val Pro Gly Xaa
                85                  90                  95

Gly Val Pro Gly Val Gly Lys Val Pro Gly Ala Gly Val Pro Gly Xaa
            100                 105                 110

Gly Val Pro Gly Val Gly Lys Val Pro Gly Ala Gly Val Pro Gly Xaa
        115                 120                 125

Gly Val Pro Gly Val Gly Lys Val Pro Gly Ala Gly Val Pro Gly Xaa
    130                 135                 140

Gly Val Pro Gly Val Gly Lys Val Pro Gly Ala Gly Val Pro Gly Xaa
145                 150                 155                 160

Gly Val Pro Gly Val Gly Lys Val Pro Gly Ala Gly Val Pro Gly Xaa
                165                 170                 175

Gly Val Pro Gly Val Gly Lys Val Pro Gly Ala Gly Val Pro Gly Xaa
            180                 185                 190

Gly Val Pro Gly Val Gly Lys Val Pro Gly Ala Gly Val Pro Gly Xaa
            195                 200                 205

Gly Val Pro Gly Val Gly Lys Val Pro Gly Ala Gly Val Pro Gly Xaa
        210                 215                 220

Gly Val Pro Gly Val Gly Lys Val Pro Gly Ala Gly Val Pro Gly Xaa
225                 230                 235                 240

Gly Val Pro Gly Val Gly Lys Val Pro Gly Ala Gly Val Pro Gly Xaa
            245                 250                 255

Gly Val Pro Gly Val Gly Lys Val Pro Gly Ala Gly Val Pro Gly Xaa
        260                 265                 270

Gly Val Pro Gly Val Gly Lys Val Pro Gly Ala Gly Val Pro Gly Xaa
    275                 280                 285

Gly Val Pro Gly Val Gly Lys Val Pro Gly Ala Gly Val Pro Gly Xaa
            290                 295                 300

Gly Val Pro Gly Val Gly Lys Val Pro Gly Ala Gly Val Pro Gly Xaa
305                 310                 315                 320

Gly Val Pro Gly Val Gly Lys Val Pro Gly Ala Gly Val Pro Gly Xaa
            325                 330                 335

Gly Val Pro Gly Val Gly Lys Val Pro Gly Ala Gly Val Pro Gly Xaa
        340                 345                 350

Gly Val Pro Gly Val Gly Lys Val Pro Gly Ala Gly Val Pro Gly Xaa
    355                 360                 365

Gly Val Pro Gly Val Gly Lys Val Pro Gly Ala Gly Val Pro Gly Xaa
            370                 375                 380

Gly Val Pro Gly Val Gly Lys Val Pro Gly Ala Gly Val Pro Gly Xaa
385                 390                 395                 400

Gly Val Pro Gly Val Gly Lys Val Pro Gly Ala Gly Val Pro Gly Xaa
            405                 410                 415

Gly Val Pro Gly Val Gly Lys Val Pro Gly Ala Gly Val Pro Gly Xaa
        420                 425                 430

Gly Val Pro Gly Val Gly Lys Val Pro Gly Ala Gly Val Pro Gly Xaa
    435                 440                 445

Gly Val Pro Gly Val Gly Lys Val Pro Gly Ala Gly Val Pro Gly Xaa
        450                 455                 460

Gly Val Pro Gly Val Gly Lys Val Pro Gly Ala Gly Val Pro Gly Xaa
465                 470                 475                 480

Gly

<210> SEQ ID NO 27
<211> LENGTH: 730
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (16)..(16)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (32)..(32)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (48)..(48)
<223> OTHER INFORMATION: Xaa = Non-standard amino acid, preferably a
      non-standard amino acid disclosed in the application.

-continued

```
<220> FEATURE:
<221> NAME/KEY: MISC_FEATURE
<222> LOCATION: (64)..(64)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (80)..(80)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (96)..(96)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (112)..(112)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (128)..(128)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (144)..(144)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (160)..(160)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (176)..(176)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (192)..(192)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (208)..(208)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (224)..(224)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (240)..(240)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (256)..(256)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (272)..(272)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (288)..(288)
<223> OTHER INFORMATION: Xaa = Non-standard amino acid, preferably a
      non-standard amino acid disclosed in the application.
<220> FEATURE:
<221> NAME/KEY: MISC_FEATURE
<222> LOCATION: (304)..(304)
<223> OTHER INFORMATION: Xaa = Non-standard amino acid, preferably a
```

```
          non-standard amino acid disclosed in the application.
<220> FEATURE:
<221> NAME/KEY: MISC_FEATURE
<222> LOCATION: (320)..(320)
<223> OTHER INFORMATION: Xaa = Non-standard amino acid, preferably a
          non-standard amino acid disclosed in the application.
<220> FEATURE:
<221> NAME/KEY: MISC_FEATURE
<222> LOCATION: (336)..(336)
<223> OTHER INFORMATION: Xaa = Non-standard amino acid, preferably a
          non-standard amino acid disclosed in the application.
<220> FEATURE:
<221> NAME/KEY: MISC_FEATURE
<222> LOCATION: (352)..(352)
<223> OTHER INFORMATION: Xaa = Non-standard amino acid, preferably a
          non-standard amino acid disclosed in the application.
<220> FEATURE:
<221> NAME/KEY: MISC_FEATURE
<222> LOCATION: (368)..(368)
<223> OTHER INFORMATION: Xaa = Non-standard amino acid, preferably a
          non-standard amino acid disclosed in the application.
<220> FEATURE:
<221> NAME/KEY: MISC_FEATURE
<222> LOCATION: (384)..(384)
<223> OTHER INFORMATION: Xaa = Non-standard amino acid, preferably a
          non-standard amino acid disclosed in the application.
<220> FEATURE:
<221> NAME/KEY: MISC_FEATURE
<222> LOCATION: (400)..(400)
<223> OTHER INFORMATION: Xaa = Non-standard amino acid, preferably a
          non-standard amino acid disclosed in the application.
<220> FEATURE:
<221> NAME/KEY: MISC_FEATURE
<222> LOCATION: (416)..(416)
<223> OTHER INFORMATION: Xaa = Non-standard amino acid, preferably a
          non-standard amino acid disclosed in the application.
<220> FEATURE:
<221> NAME/KEY: MISC_FEATURE
<222> LOCATION: (432)..(432)
<223> OTHER INFORMATION: Xaa = Non-standard amino acid, preferably a
          non-standard amino acid disclosed in the application.
<220> FEATURE:
<221> NAME/KEY: MISC_FEATURE
<222> LOCATION: (448)..(448)
<223> OTHER INFORMATION: Xaa = Non-standard amino acid, preferably a
          non-standard amino acid disclosed in the application.
<220> FEATURE:
<221> NAME/KEY: MISC_FEATURE
<222> LOCATION: (464)..(464)
<223> OTHER INFORMATION: Xaa = Non-standard amino acid, preferably a
          non-standard amino acid disclosed in the application.
<220> FEATURE:
<221> NAME/KEY: MISC_FEATURE
<222> LOCATION: (480)..(480)
<223> OTHER INFORMATION: Xaa = Non-standard amino acid, preferably a
          non-standard amino acid disclosed in the application.

<400> SEQUENCE: 27

Met Ser Lys Gly Pro Gly Lys Val Pro Gly Ala Gly Val Pro Gly Xaa
1               5                   10                  15

Gly Val Pro Gly Val Gly Lys Val Pro Gly Ala Gly Val Pro Gly Xaa
            20                  25                  30

Gly Val Pro Gly Val Gly Lys Val Pro Gly Ala Gly Val Pro Gly Xaa
        35                  40                  45

Gly Val Pro Gly Val Gly Lys Val Pro Gly Ala Gly Val Pro Gly Xaa
    50                  55                  60

Gly Val Pro Gly Val Gly Lys Val Pro Gly Ala Gly Val Pro Gly Xaa
65                  70                  75                  80

Gly Val Pro Gly Val Gly Lys Val Pro Gly Ala Gly Val Pro Gly Xaa
                85                  90                  95

Gly Val Pro Gly Val Gly Lys Val Pro Gly Ala Gly Val Pro Gly Xaa
            100                 105                 110
```

-continued

Gly Val Pro Gly Val Gly Lys Val Pro Gly Ala Gly Val Pro Gly Xaa
            115                 120                 125

Gly Val Pro Gly Val Gly Lys Val Pro Gly Ala Gly Val Pro Gly Xaa
        130                 135                 140

Gly Val Pro Gly Val Gly Lys Val Pro Gly Ala Gly Val Pro Gly Xaa
145                 150                 155                 160

Gly Val Pro Gly Val Gly Lys Val Pro Gly Ala Gly Val Pro Gly Xaa
            165                 170                 175

Gly Val Pro Gly Val Gly Lys Val Pro Gly Ala Gly Val Pro Gly Xaa
        180                 185                 190

Gly Val Pro Gly Val Gly Lys Val Pro Gly Ala Gly Val Pro Gly Xaa
    195                 200                 205

Gly Val Pro Gly Val Gly Lys Val Pro Gly Ala Gly Val Pro Gly Xaa
210                 215                 220

Gly Val Pro Gly Val Gly Lys Val Pro Gly Ala Gly Val Pro Gly Xaa
225                 230                 235                 240

Gly Val Pro Gly Val Gly Lys Val Pro Gly Ala Gly Val Pro Gly Xaa
            245                 250                 255

Gly Val Pro Gly Val Gly Lys Val Pro Gly Ala Gly Val Pro Gly Xaa
        260                 265                 270

Gly Val Pro Gly Val Gly Lys Val Pro Gly Ala Gly Val Pro Gly Xaa
    275                 280                 285

Gly Val Pro Gly Val Gly Lys Val Pro Gly Ala Gly Val Pro Gly Xaa
        290                 295                 300

Gly Val Pro Gly Val Gly Lys Val Pro Gly Ala Gly Val Pro Gly Xaa
305                 310                 315                 320

Gly Val Pro Gly Val Gly Lys Val Pro Gly Ala Gly Val Pro Gly Xaa
            325                 330                 335

Gly Val Pro Gly Val Gly Lys Val Pro Gly Ala Gly Val Pro Gly Xaa
        340                 345                 350

Gly Val Pro Gly Val Gly Lys Val Pro Gly Ala Gly Val Pro Gly Xaa
    355                 360                 365

Gly Val Pro Gly Val Gly Lys Val Pro Gly Ala Gly Val Pro Gly Xaa
370                 375                 380

Gly Val Pro Gly Val Gly Lys Val Pro Gly Ala Gly Val Pro Gly Xaa
385                 390                 395                 400

Gly Val Pro Gly Val Gly Lys Val Pro Gly Ala Gly Val Pro Gly Xaa
            405                 410                 415

Gly Val Pro Gly Val Gly Lys Val Pro Gly Ala Gly Val Pro Gly Xaa
        420                 425                 430

Gly Val Pro Gly Val Gly Lys Val Pro Gly Ala Gly Val Pro Gly Xaa
    435                 440                 445

Gly Val Pro Gly Val Gly Lys Val Pro Gly Ala Gly Val Pro Gly Xaa
450                 455                 460

Gly Val Pro Gly Val Gly Lys Val Pro Gly Ala Gly Val Pro Gly Xaa
465                 470                 475                 480

Gly Val Pro Gly Val Gly Pro Gly Gly Gly Ser Lys Gly Glu Glu
            485                 490                 495

Leu Phe Thr Gly Val Val Pro Ile Leu Val Glu Leu Asp Gly Asp Val
            500                 505                 510

Asn Gly His Lys Phe Ser Val Arg Gly Glu Gly Glu Gly Asp Ala Thr
            515                 520                 525

```
Asn Gly Lys Leu Thr Leu Lys Phe Ile Cys Thr Thr Gly Lys Leu Pro
    530                 535                 540

Val Pro Trp Pro Thr Leu Val Thr Thr Leu Thr Tyr Gly Val Gln Cys
545                 550                 555                 560

Phe Ser Arg Tyr Pro Asp His Met Lys Arg His Asp Phe Phe Lys Ser
                565                 570                 575

Ala Met Pro Glu Gly Tyr Val Gln Glu Arg Thr Ile Ser Phe Lys Asp
                580                 585                 590

Asp Gly Thr Tyr Lys Thr Arg Ala Glu Val Lys Phe Glu Gly Asp Thr
            595                 600                 605

Leu Val Asn Arg Ile Glu Leu Lys Gly Ile Asp Phe Lys Glu Asp Gly
610                 615                 620

Asn Ile Leu Gly His Lys Leu Glu Tyr Asn Phe Asn Ser His Asn Val
625                 630                 635                 640

Tyr Ile Thr Ala Asp Lys Gln Lys Asn Gly Ile Lys Ala Asn Phe Lys
                645                 650                 655

Ile Arg His Asn Val Glu Asp Gly Ser Val Gln Leu Ala Asp His Tyr
                660                 665                 670

Gln Gln Asn Thr Pro Ile Gly Asp Gly Pro Val Leu Leu Pro Asp Asn
            675                 680                 685

His Tyr Leu Ser Thr Gln Ser Val Leu Ser Lys Asp Pro Asn Glu Lys
690                 695                 700

Arg Asp His Met Val Leu Leu Glu Phe Val Thr Ala Ala Gly Ile Thr
705                 710                 715                 720

His Gly Met Asp Glu Leu Tyr Lys Gly Ser
                725                 730

<210> SEQ ID NO 28
<211> LENGTH: 77
<212> TYPE: DNA
<213> ORGANISM: Artificial Sequence
<220> FEATURE:
<223> OTHER INFORMATION: tRNA Sequence

<400> SEQUENCE: 28
ccggcggtag ttcagcaggg cagaacggcg gactctaaat ccgcatggca ggggttcaaa     60 tccccctccgc cggacca                                                  77

<210> SEQ ID NO 29
<211> LENGTH: 239
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (38)..(38)
<223> OTHER INFORMATION: Xaa = Non-standard amino acid
<220> FEATURE:
<221> NAME/KEY: MISC_FEATURE
<222> LOCATION: (150)..(150)
<223> OTHER INFORMATION: Xaa = Non-standard amino acid
<220> FEATURE:
<221> NAME/KEY: MISC_FEATURE
<222> LOCATION: (181)..(181)
<223> OTHER INFORMATION: Xaa = Non-standard amino acid

<400> SEQUENCE: 29

Ser Lys Gly Glu Glu Leu Phe Thr Gly Val Val Pro Ile Leu Val Glu
1               5                   10                  15

Leu Asp Gly Asp Val Asn Gly His Lys Phe Ser Val Arg Gly Glu Gly
```

```
            20                  25                  30
Glu Gly Asp Ala Thr Xaa Gly Lys Leu Thr Leu Lys Phe Ile Cys Thr
         35                  40                  45
Thr Gly Lys Leu Pro Val Pro Trp Pro Thr Leu Val Thr Thr Leu Thr
     50                  55                  60
Tyr Gly Val Gln Cys Phe Ser Arg Tyr Pro Asp His Met Lys Arg His
 65                  70                  75                  80
Asp Phe Phe Lys Ser Ala Met Pro Glu Gly Tyr Val Gln Glu Arg Thr
                 85                  90                  95
Ile Ser Phe Lys Asp Asp Gly Thr Tyr Lys Thr Arg Ala Glu Val Lys
             100                 105                 110
Phe Glu Gly Asp Thr Leu Val Asn Arg Ile Glu Leu Lys Gly Ile Asp
         115                 120                 125
Phe Lys Glu Asp Gly Asn Ile Leu Gly His Lys Leu Glu Tyr Asn Phe
     130                 135                 140
Asn Ser His Asn Val Xaa Ile Thr Ala Asp Lys Gln Lys Asn Gly Ile
145                 150                 155                 160
Lys Ala Asn Phe Lys Ile Arg His Asn Val Glu Asp Gly Ser Val Gln
                165                 170                 175
Leu Ala Asp His Xaa Gln Gln Asn Thr Pro Ile Gly Asp Gly Pro Val
             180                 185                 190
Leu Leu Pro Asp Asn His Tyr Leu Ser Thr Gln Ser Val Leu Ser Lys
         195                 200                 205
Asp Pro Asn Glu Lys Arg Asp His Met Val Leu Leu Glu Phe Val Thr
     210                 215                 220
Ala Ala Gly Ile Thr His Gly Met Asp Glu Leu Tyr Lys Gly Ser
225                 230                 235

<210> SEQ ID NO 30
<211> LENGTH: 239
<212> TYPE: PRT
<213> ORGANISM: Artificial Sequence
<220> FEATURE:
<223> OTHER INFORMATION: Synthetic Polypeptide

<400> SEQUENCE: 30

Ser Lys Gly Glu Glu Leu Phe Thr Gly Val Val Pro Ile Leu Val Glu
 1               5                  10                  15
Leu Asp Gly Asp Val Asn Gly His Lys Phe Ser Val Arg Gly Glu Gly
             20                  25                  30
Glu Gly Asp Ala Thr Asn Gly Lys Leu Thr Leu Lys Phe Ile Cys Thr
         35                  40                  45
Thr Gly Lys Leu Pro Val Pro Trp Pro Thr Leu Val Thr Thr Leu Thr
     50                  55                  60
Tyr Gly Val Gln Cys Phe Ser Arg Tyr Pro Asp His Met Lys Arg His
 65                  70                  75                  80
Asp Phe Phe Lys Ser Ala Met Pro Glu Gly Tyr Val Gln Glu Arg Thr
                 85                  90                  95
Ile Ser Phe Lys Asp Asp Gly Thr Tyr Lys Thr Arg Ala Glu Val Lys
             100                 105                 110
Phe Glu Gly Asp Thr Leu Val Asn Arg Ile Glu Leu Lys Gly Ile Asp
         115                 120                 125
Phe Lys Glu Asp Gly Asn Ile Leu Gly His Lys Leu Glu Tyr Asn Phe
     130                 135                 140
Asn Ser His Asn Val Tyr Ile Thr Ala Asp Lys Gln Lys Asn Gly Ile
```

```
                145                 150                 155                 160
Lys Ala Asn Phe Lys Ile Arg His Asn Val Glu Asp Gly Ser Val Gln
                165                 170                 175

Leu Ala Asp His Tyr Gln Gln Asn Thr Pro Ile Gly Asp Gly Pro Val
            180                 185                 190

Leu Leu Pro Asp Asn His Tyr Leu Ser Thr Gln Ser Val Leu Ser Lys
        195                 200                 205

Asp Pro Asn Glu Lys Arg Asp His Met Val Leu Leu Glu Phe Val Thr
    210                 215                 220

Ala Ala Gly Ile Thr His Gly Met Asp Glu Leu Tyr Lys Gly Ser
225                 230                 235

<210> SEQ ID NO 31
<211> LENGTH: 160
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (18)..(18)
<223> OTHER INFORMATION: Xaa = Non-standard amino acid
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: MISC_FEATURE
<222> LOCATION: (34)..(34)
<223> OTHER INFORMATION: Xaa = Non-standard amino acid
<220> FEATURE:
<221> NAME/KEY: MISC_FEATURE
<222> LOCATION: (49)..(49)
<223> OTHER INFORMATION: Xaa = Non-standard amino acid
<220> FEATURE:
<221> NAME/KEY: MISC_FEATURE
<222> LOCATION: (64)..(64)
<223> OTHER INFORMATION: Xaa = Non-standard amino acid
<220> FEATURE:
<221> NAME/KEY: MISC_FEATURE
<222> LOCATION: (79)..(79)
<223> OTHER INFORMATION: Xaa = Non-standard amino acid
<220> FEATURE:
<221> NAME/KEY: MISC_FEATURE
<222> LOCATION: (94)..(94)
<223> OTHER INFORMATION: Xaa = Non-standard amino acid
<220> FEATURE:
<221> NAME/KEY: MISC_FEATURE
<222> LOCATION: (109)..(109)
<223> OTHER INFORMATION: Xaa = Non-standard amino acid
<220> FEATURE:
<221> NAME/KEY: MISC_FEATURE
<222> LOCATION: (124)..(124)
<223> OTHER INFORMATION: Xaa = Non-standard amino acid
<220> FEATURE:
<221> NAME/KEY: MISC_FEATURE
<222> LOCATION: (139)..(139)
<223> OTHER INFORMATION: Xaa = Non-standard amino acid
<220> FEATURE:
<221> NAME/KEY: MISC_FEATURE
<222> LOCATION: (154)..(154)
<223> OTHER INFORMATION: Xaa = Non-standard amino acid
<220> FEATURE:
<221> NAME/KEY: MISC_FEATURE
<222> LOCATION: (160)..(160)
<223> OTHER INFORMATION: C-Terminal GFP tag

<400> SEQUENCE: 31

Ser Lys Gly Pro Gly Val Pro Gly Gly Val Pro Gly Ala Gly Val
1               5                   10                  15

Pro Gly Xaa Gly Val Pro Gly Gly Gly Val Pro Gly Ala Gly Val Pro
```

```
              20                  25                  30

Gly Xaa Gly Val Pro Gly Gly Val Pro Gly Ala Gly Val Pro Gly
         35                  40                  45

Xaa Gly Val Pro Gly Gly Val Pro Gly Ala Gly Val Pro Gly Xaa
 50                  55                  60

Gly Val Pro Gly Gly Val Pro Gly Ala Gly Val Pro Gly Xaa Gly
 65                  70                  75                  80

Val Pro Gly Gly Val Pro Gly Ala Gly Val Pro Gly Xaa Gly Val
             85                  90                  95

Pro Gly Gly Gly Val Pro Gly Ala Gly Val Pro Gly Xaa Gly Val Pro
             100                 105                 110

Gly Gly Val Pro Gly Ala Gly Val Pro Gly Xaa Gly Val Pro Gly
         115                 120                 125

Gly Gly Val Pro Gly Ala Gly Val Pro Gly Xaa Gly Val Pro Gly
             130                 135                 140

Gly Val Pro Gly Ala Gly Val Pro Gly Xaa Gly Pro Gly Gly Gly
 145                 150                 155                 160

<210> SEQ ID NO 32
<211> LENGTH: 160
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (160)..(160)
<223> OTHER INFORMATION: C-Terminal GFP tag

<400> SEQUENCE: 32

Ser Lys Gly Pro Gly Val Pro Gly Gly Val Pro Gly Ala Gly Val
 1               5                  10                  15

Pro Gly Tyr Gly Val Pro Gly Gly Val Pro Gly Ala Gly Val Pro
             20                  25                  30

Gly Tyr Gly Val Pro Gly Gly Val Pro Gly Ala Gly Val Pro Gly
         35                  40                  45

Tyr Gly Val Pro Gly Gly Val Pro Gly Ala Gly Val Pro Gly Tyr
 50                  55                  60

Gly Val Pro Gly Gly Val Pro Gly Ala Gly Val Pro Gly Tyr Gly
 65                  70                  75                  80

Val Pro Gly Gly Val Pro Gly Ala Gly Val Pro Gly Tyr Gly Val
             85                  90                  95

Pro Gly Gly Gly Val Pro Gly Ala Gly Val Pro Gly Tyr Gly Val Pro
             100                 105                 110

Gly Gly Val Pro Gly Ala Gly Val Pro Gly Tyr Gly Val Pro Gly
         115                 120                 125

Gly Gly Val Pro Gly Ala Gly Val Pro Gly Tyr Gly Val Pro Gly Gly
             130                 135                 140

Gly Val Pro Gly Ala Gly Val Pro Gly Tyr Gly Pro Gly Gly Gly Gly
 145                 150                 155                 160

<210> SEQ ID NO 33
<211> LENGTH: 460
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
```

```
<222> LOCATION: (19)..(19)
<223> OTHER INFORMATION: Xaa = Non-standard amino acid
<220> FEATURE:
<221> NAME/KEY: MISC_FEATURE
<222> LOCATION: (34)..(34)
<223> OTHER INFORMATION: Xaa = Non-standard amino acid
<220> FEATURE:
<221> NAME/KEY: MISC_FEATURE
<222> LOCATION: (49)..(49)
<223> OTHER INFORMATION: Xaa = Non-standard amino acid
<220> FEATURE:
<221> NAME/KEY: MISC_FEATURE
<222> LOCATION: (64)..(64)
<223> OTHER INFORMATION: Xaa = Non-standard amino acid
<220> FEATURE:
<221> NAME/KEY: MISC_FEATURE
<222> LOCATION: (79)..(79)
<223> OTHER INFORMATION: Xaa = Non-standard amino acid
<220> FEATURE:
<221> NAME/KEY: MISC_FEATURE
<222> LOCATION: (94)..(94)
<223> OTHER INFORMATION: Xaa = Non-standard amino acid
<220> FEATURE:
<221> NAME/KEY: MISC_FEATURE
<222> LOCATION: (109)..(109)
<223> OTHER INFORMATION: Xaa = Non-standard amino acid
<220> FEATURE:
<221> NAME/KEY: MISC_FEATURE
<222> LOCATION: (124)..(124)
<223> OTHER INFORMATION: Xaa = Non-standard amino acid
<220> FEATURE:
<221> NAME/KEY: MISC_FEATURE
<222> LOCATION: (139)..(139)
<223> OTHER INFORMATION: Xaa = Non-standard amino acid
<220> FEATURE:
<221> NAME/KEY: MISC_FEATURE
<222> LOCATION: (154)..(154)
<223> OTHER INFORMATION: Xaa = Non-standard amino acid
<220> FEATURE:
<221> NAME/KEY: MISC_FEATURE
<222> LOCATION: (169)..(169)
<223> OTHER INFORMATION: Xaa = Non-standard amino acid
<220> FEATURE:
<221> NAME/KEY: MISC_FEATURE
<222> LOCATION: (184)..(184)
<223> OTHER INFORMATION: Xaa = Non-standard amino acid
<220> FEATURE:
<221> NAME/KEY: MISC_FEATURE
<222> LOCATION: (199)..(199)
<223> OTHER INFORMATION: Xaa = Non-standard amino acid
<220> FEATURE:
<221> NAME/KEY: MISC_FEATURE
<222> LOCATION: (214)..(214)
<223> OTHER INFORMATION: Xaa = Non-standard amino acid
<220> FEATURE:
<221> NAME/KEY: MISC_FEATURE
<222> LOCATION: (229)..(229)
<223> OTHER INFORMATION: Xaa = Non-standard amino acid
<220> FEATURE:
<221> NAME/KEY: MISC_FEATURE
<222> LOCATION: (244)..(244)
<223> OTHER INFORMATION: Xaa = Non-standard amino acid
<220> FEATURE:
<221> NAME/KEY: MISC_FEATURE
<222> LOCATION: (259)..(259)
<223> OTHER INFORMATION: Xaa = Non-standard amino acid
<220> FEATURE:
<221> NAME/KEY: MISC_FEATURE
<222> LOCATION: (274)..(274)
<223> OTHER INFORMATION: Xaa = Non-standard amino acid
<220> FEATURE:
<221> NAME/KEY: MISC_FEATURE
<222> LOCATION: (289)..(289)
<223> OTHER INFORMATION: Xaa = Non-standard amino acid
<220> FEATURE:
<221> NAME/KEY: MISC_FEATURE
<222> LOCATION: (304)..(304)
<223> OTHER INFORMATION: Xaa = Non-standard amino acid
<220> FEATURE:
```

```
<221> NAME/KEY: MISC_FEATURE
<222> LOCATION: (319)..(319)
<223> OTHER INFORMATION: Xaa = Non-standard amino acid
<220> FEATURE:
<221> NAME/KEY: MISC_FEATURE
<222> LOCATION: (334)..(334)
<223> OTHER INFORMATION: Xaa = Non-standard amino acid
<220> FEATURE:
<221> NAME/KEY: MISC_FEATURE
<222> LOCATION: (349)..(349)
<223> OTHER INFORMATION: Xaa = Non-standard amino acid
<220> FEATURE:
<221> NAME/KEY: MISC_FEATURE
<222> LOCATION: (364)..(364)
<223> OTHER INFORMATION: Xaa = Non-standard amino acid
<220> FEATURE:
<221> NAME/KEY: MISC_FEATURE
<222> LOCATION: (379)..(379)
<223> OTHER INFORMATION: Xaa = Non-standard amino acid
<220> FEATURE:
<221> NAME/KEY: MISC_FEATURE
<222> LOCATION: (394)..(394)
<223> OTHER INFORMATION: Xaa = Non-standard amino acid
<220> FEATURE:
<221> NAME/KEY: MISC_FEATURE
<222> LOCATION: (409)..(409)
<223> OTHER INFORMATION: Xaa = Non-standard amino acid
<220> FEATURE:
<221> NAME/KEY: MISC_FEATURE
<222> LOCATION: (424)..(424)
<223> OTHER INFORMATION: Xaa = Non-standard amino acid
<220> FEATURE:
<221> NAME/KEY: MISC_FEATURE
<222> LOCATION: (439)..(439)
<223> OTHER INFORMATION: Xaa = Non-standard amino acid
<220> FEATURE:
<221> NAME/KEY: MISC_FEATURE
<222> LOCATION: (454)..(454)
<223> OTHER INFORMATION: Xaa = Non-standard amino acid
<220> FEATURE:
<221> NAME/KEY: MISC_FEATURE
<222> LOCATION: (460)..(460)
<223> OTHER INFORMATION: C-Terminal GFP tag

<400> SEQUENCE: 33

Ser Lys Gly Pro Gly Val Pro Gly Gly Gly Val Pro Gly Ala Gly Val
1               5                   10                  15

Pro Gly Xaa Gly Val Pro Gly Gly Gly Val Pro Gly Ala Gly Val Pro
            20                  25                  30

Gly Xaa Gly Val Pro Gly Gly Gly Val Pro Gly Ala Gly Val Pro Gly
        35                  40                  45

Xaa Gly Val Pro Gly Gly Gly Val Pro Gly Ala Gly Val Pro Gly Xaa
    50                  55                  60

Gly Val Pro Gly Gly Gly Val Pro Gly Ala Gly Val Pro Gly Xaa Gly
65                  70                  75                  80

Val Pro Gly Gly Gly Val Pro Gly Ala Gly Val Pro Gly Xaa Gly Val
                85                  90                  95

Pro Gly Gly Gly Val Pro Gly Ala Gly Val Pro Gly Xaa Gly Val Pro
            100                 105                 110

Gly Gly Gly Val Pro Gly Ala Gly Val Pro Gly Xaa Gly Val Pro Gly
        115                 120                 125

Gly Gly Val Pro Gly Ala Gly Val Pro Gly Xaa Gly Val Pro Gly Gly
    130                 135                 140

Gly Val Pro Gly Ala Gly Val Pro Gly Xaa Gly Val Pro Gly Gly Gly
145                 150                 155                 160

Val Pro Gly Ala Gly Val Pro Gly Xaa Gly Val Pro Gly Gly Gly Val
                165                 170                 175
```

```
Pro Gly Ala Gly Val Pro Gly Xaa Gly Val Pro Gly Gly Gly Val Pro
            180                 185                 190

Gly Ala Gly Val Pro Gly Xaa Gly Val Pro Gly Gly Gly Val Pro Gly
        195                 200                 205

Ala Gly Val Pro Gly Xaa Gly Val Pro Gly Gly Gly Val Pro Gly Ala
    210                 215                 220

Gly Val Pro Gly Xaa Gly Val Pro Gly Gly Gly Val Pro Gly Ala Gly
225                 230                 235                 240

Val Pro Gly Xaa Gly Val Pro Gly Gly Gly Val Pro Gly Ala Gly Val
            245                 250                 255

Pro Gly Xaa Gly Val Pro Gly Gly Gly Val Pro Gly Ala Gly Val Pro
        260                 265                 270

Gly Xaa Gly Val Pro Gly Gly Gly Val Pro Gly Ala Gly Val Pro Gly
    275                 280                 285

Xaa Gly Val Pro Gly Gly Gly Val Pro Gly Ala Gly Val Pro Gly Xaa
290                 295                 300

Gly Val Pro Gly Gly Gly Val Pro Gly Ala Gly Val Pro Gly Xaa Gly
305                 310                 315                 320

Val Pro Gly Gly Gly Val Pro Gly Ala Gly Val Pro Gly Xaa Gly Val
            325                 330                 335

Pro Gly Gly Gly Val Pro Gly Ala Gly Val Pro Gly Xaa Gly Val Pro
        340                 345                 350

Gly Gly Gly Val Pro Gly Ala Gly Val Pro Gly Xaa Gly Val Pro Gly
    355                 360                 365

Gly Gly Val Pro Gly Ala Gly Val Pro Gly Xaa Gly Val Pro Gly Gly
370                 375                 380

Gly Val Pro Gly Ala Gly Val Pro Gly Xaa Gly Val Pro Gly Gly Gly
385                 390                 395                 400

Val Pro Gly Ala Gly Val Pro Gly Xaa Gly Val Pro Gly Gly Gly Val
            405                 410                 415

Pro Gly Ala Gly Val Pro Gly Xaa Gly Val Pro Gly Gly Gly Val Pro
        420                 425                 430

Gly Ala Gly Val Pro Gly Xaa Gly Val Pro Gly Gly Gly Val Pro Gly
    435                 440                 445

Ala Gly Val Pro Gly Xaa Gly Pro Gly Gly Gly Gly
    450                 455                 460

<210> SEQ ID NO 34
<211> LENGTH: 460
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (460)..(460)
<223> OTHER INFORMATION: C-Terminal GFP tag

<400> SEQUENCE: 34

Ser Lys Gly Pro Gly Val Pro Gly Gly Gly Val Pro Gly Ala Gly Val
1               5                   10                  15

Pro Gly Tyr Gly Val Pro Gly Gly Gly Val Pro Gly Ala Gly Val Pro
            20                  25                  30

Gly Tyr Gly Val Pro Gly Gly Gly Val Pro Gly Ala Gly Val Pro Gly
        35                  40                  45

Tyr Gly Val Pro Gly Gly Gly Val Pro Gly Ala Gly Val Pro Gly Tyr
    50                  55                  60
```

Gly Val Pro Gly Gly Gly Val Pro Gly Ala Gly Val Pro Gly Tyr Gly
65                  70                  75                  80

Val Pro Gly Gly Gly Val Pro Gly Ala Gly Val Pro Gly Tyr Gly Val
                85                  90                  95

Pro Gly Gly Gly Val Pro Gly Ala Gly Val Pro Gly Tyr Gly Val Pro
            100                 105                 110

Gly Gly Gly Val Pro Gly Ala Gly Val Pro Gly Tyr Gly Val Pro Gly
        115                 120                 125

Gly Gly Val Pro Gly Ala Gly Val Pro Gly Tyr Gly Val Pro Gly Gly
    130                 135                 140

Gly Val Pro Gly Ala Gly Val Pro Gly Tyr Gly Val Pro Gly Gly Gly
145                 150                 155                 160

Val Pro Gly Ala Gly Val Pro Gly Tyr Gly Val Pro Gly Gly Gly Val
                165                 170                 175

Pro Gly Ala Gly Val Pro Gly Tyr Gly Val Pro Gly Gly Gly Val Pro
            180                 185                 190

Gly Ala Gly Val Pro Gly Tyr Gly Val Pro Gly Gly Gly Val Pro Gly
        195                 200                 205

Ala Gly Val Pro Gly Tyr Gly Val Pro Gly Gly Gly Val Pro Gly Ala
    210                 215                 220

Gly Val Pro Gly Tyr Gly Val Pro Gly Gly Gly Val Pro Gly Ala Gly
225                 230                 235                 240

Val Pro Gly Tyr Gly Val Pro Gly Gly Gly Val Pro Gly Ala Gly Val
                245                 250                 255

Pro Gly Tyr Gly Val Pro Gly Gly Gly Val Pro Gly Ala Gly Val Pro
            260                 265                 270

Gly Tyr Gly Val Pro Gly Gly Gly Val Pro Gly Ala Gly Val Pro Gly
        275                 280                 285

Tyr Gly Val Pro Gly Gly Gly Val Pro Gly Ala Gly Val Pro Gly Tyr
    290                 295                 300

Gly Val Pro Gly Gly Gly Val Pro Gly Ala Gly Val Pro Gly Tyr Gly
305                 310                 315                 320

Val Pro Gly Gly Gly Val Pro Gly Ala Gly Val Pro Gly Tyr Gly Val
                325                 330                 335

Pro Gly Gly Gly Val Pro Gly Ala Gly Val Pro Gly Tyr Gly Val Pro
            340                 345                 350

Gly Gly Gly Val Pro Gly Ala Gly Val Pro Gly Tyr Gly Val Pro Gly
        355                 360                 365

Gly Gly Val Pro Gly Ala Gly Val Pro Gly Tyr Gly Val Pro Gly Gly
    370                 375                 380

Gly Val Pro Gly Ala Gly Val Pro Gly Tyr Gly Val Pro Gly Gly Gly
385                 390                 395                 400

Val Pro Gly Ala Gly Val Pro Gly Tyr Gly Val Pro Gly Gly Gly Val
                405                 410                 415

Pro Gly Ala Gly Val Pro Gly Tyr Gly Val Pro Gly Gly Gly Val Pro
            420                 425                 430

Gly Ala Gly Val Pro Gly Tyr Gly Val Pro Gly Gly Gly Val Pro Gly
        435                 440                 445

Ala Gly Val Pro Gly Tyr Gly Pro Gly Gly Gly
    450                 455                 460

<210> SEQ ID NO 35
<211> LENGTH: 170

```
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (15)..(15)
<223> OTHER INFORMATION: Xaa = Non-Standard amino acid
<220> FEATURE:
<221> NAME/KEY: MISC_FEATURE
<222> LOCATION: (31)..(31)
<223> OTHER INFORMATION: Xaa = Non-Standard amino acid
<220> FEATURE:
<221> NAME/KEY: MISC_FEATURE
<222> LOCATION: (47)..(47)
<223> OTHER INFORMATION: Xaa = Non-Standard amino acid
<220> FEATURE:
<221> NAME/KEY: MISC_FEATURE
<222> LOCATION: (63)..(63)
<223> OTHER INFORMATION: Xaa = Non-Standard amino acid
<220> FEATURE:
<221> NAME/KEY: MISC_FEATURE
<222> LOCATION: (79)..(79)
<223> OTHER INFORMATION: Xaa = Non-Standard amino acid
<220> FEATURE:
<221> NAME/KEY: MISC_FEATURE
<222> LOCATION: (95)..(95)
<223> OTHER INFORMATION: Xaa = Non-Standard amino acid
<220> FEATURE:
<221> NAME/KEY: MISC_FEATURE
<222> LOCATION: (111)..(111)
<223> OTHER INFORMATION: Xaa = Non-Standard amino acid
<220> FEATURE:
<221> NAME/KEY: MISC_FEATURE
<222> LOCATION: (127)..(127)
<223> OTHER INFORMATION: Xaa = Non-Standard amino acid
<220> FEATURE:
<221> NAME/KEY: MISC_FEATURE
<222> LOCATION: (143)..(143)
<223> OTHER INFORMATION: Xaa = Non-Standard amino acid
<220> FEATURE:
<221> NAME/KEY: MISC_FEATURE
<222> LOCATION: (159)..(159)
<223> OTHER INFORMATION: Xaa = Non-Standard amino acid
<220> FEATURE:
<221> NAME/KEY: MISC_FEATURE
<222> LOCATION: (170)..(170)
<223> OTHER INFORMATION: C-Terminal GFP tag

<400> SEQUENCE: 35

Ser Lys Gly Pro Gly Lys Val Pro Gly Ala Gly Val Pro Gly Xaa Gly
1               5                   10                  15

Val Pro Gly Val Gly Lys Val Pro Gly Ala Gly Val Pro Gly Xaa Gly
            20                  25                  30

Val Pro Gly Val Gly Lys Val Pro Gly Ala Gly Val Pro Gly Xaa Gly
        35                  40                  45

Val Pro Gly Val Gly Lys Val Pro Gly Ala Gly Val Pro Gly Xaa Gly
    50                  55                  60

Val Pro Gly Val Gly Lys Val Pro Gly Ala Gly Val Pro Gly Xaa Gly
65                  70                  75                  80

Val Pro Gly Val Gly Lys Val Pro Gly Ala Gly Val Pro Gly Xaa Gly
                85                  90                  95

Val Pro Gly Val Gly Lys Val Pro Gly Ala Gly Val Pro Gly Xaa Gly
            100                 105                 110

Val Pro Gly Val Gly Lys Val Pro Gly Ala Gly Val Pro Gly Xaa Gly
        115                 120                 125

Val Pro Gly Val Gly Lys Val Pro Gly Ala Gly Val Pro Gly Xaa Gly
    130                 135                 140

Val Pro Gly Val Gly Lys Val Pro Gly Ala Gly Val Pro Gly Xaa Gly
```

Val Pro Gly Val Gly Pro Gly Gly Gly Gly
                165                    170

```
<210> SEQ ID NO 36
<211> LENGTH: 90
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(2)
<223> OTHER INFORMATION: Phosphothioate bond between nucleotide 1 and 2
<220> FEATURE:
<221> NAME/KEY: misc_feature
<222> LOCATION: (2)..(3)
<223> OTHER INFORMATION: Phosphothioate bond between nucleotide 2 and 3
<220> FEATURE:
<221> NAME/KEY: misc_feature
<222> LOCATION: (42)..(43)
<223> OTHER INFORMATION: N = any nucleotide
<220> FEATURE:
<221> NAME/KEY: misc_feature
<222> LOCATION: (44)..(44)
<223> OTHER INFORMATION: K = Guanine or Thymine
<220> FEATURE:
<221> NAME/KEY: misc_feature
<222> LOCATION: (48)..(49)
<223> OTHER INFORMATION: N = any nucleotide
<220> FEATURE:
<221> NAME/KEY: misc_feature
<222> LOCATION: (50)..(50)
<223> OTHER INFORMATION: K = Guanine or Thymine

<400> SEQUENCE: 36
aagagttaag agaggtttta aaaaaagatg aaaaatctgc tnnkatannk tttgaaccaa    60
gtggtaaaat acatttaggg cattatctcc                                    90

<210> SEQ ID NO 37
<211> LENGTH: 90
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(2)
<223> OTHER INFORMATION: Phosphothioate bond between nucleotide 1 and 2
<220> FEATURE:
<221> NAME/KEY: misc_feature
<222> LOCATION: (2)..(3)
<223> OTHER INFORMATION: Phosphothioate bond between nucleotide 2 and 3
<220> FEATURE:
<221> NAME/KEY: misc_feature
<222> LOCATION: (42)..(43)
<223> OTHER INFORMATION: N = Any Nucleotide
<220> FEATURE:
<221> NAME/KEY: misc_feature
<222> LOCATION: (44)..(44)
<223> OTHER INFORMATION: K = Guanine or Thymine
<220> FEATURE:
<221> NAME/KEY: misc_feature
<222> LOCATION: (48)..(49)
<223> OTHER INFORMATION: N = Any Nucleotide
<220> FEATURE:
<221> NAME/KEY: misc_feature
<222> LOCATION: (50)..(50)
<223> OTHER INFORMATION: K = Guanine or Thymine

<400> SEQUENCE: 37
agatgattga tttacaaaat gctggatttg atataattat annkttgnnk gatttacacg    60
```

```
cctatttaaa ccagaaagga gagttggatg                                     90
```

<210> SEQ ID NO 38
<211> LENGTH: 90
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(2)
<223> OTHER INFORMATION: Phosphothioate bond between nucleotide 1 and 2
<220> FEATURE:
<221> NAME/KEY: misc_feature
<222> LOCATION: (2)..(3)
<223> OTHER INFORMATION: Phosphothioate bond between nucleotide 2 and 3
<220> FEATURE:
<221> NAME/KEY: misc_feature
<222> LOCATION: (45)..(46)
<223> OTHER INFORMATION: N = Any Nucleotide
<220> FEATURE:
<221> NAME/KEY: misc_feature
<222> LOCATION: (47)..(47)
<223> OTHER INFORMATION: K = Guanine or Thymine
<220> FEATURE:
<221> NAME/KEY: misc_feature
<222> LOCATION: (48)..(49)
<223> OTHER INFORMATION: N = Any Nucleotide
<220> FEATURE:
<221> NAME/KEY: misc_feature
<222> LOCATION: (50)..(50)
<223> OTHER INFORMATION: K = Guanine or Thymine
<220> FEATURE:
<221> NAME/KEY: misc_feature
<222> LOCATION: (51)..(52)
<223> OTHER INFORMATION: N = Any Nucleotide
<220> FEATURE:
<221> NAME/KEY: misc_feature
<222> LOCATION: (53)..(53)
<223> OTHER INFORMATION: K = Guanine or Thymine

<400> SEQUENCE: 38

```
tttttgaagc aatggggtta aaggcaaaat atgtttatgg aagtnnknnk nnkcttgata    60
aggattatac actgaatgtc tatagattgg                                     90
```

<210> SEQ ID NO 39
<211> LENGTH: 90
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(2)
<223> OTHER INFORMATION: Phosphothioate bond between nucleotide 1 and 2
<220> FEATURE:
<221> NAME/KEY: misc_feature
<222> LOCATION: (2)..(3)
<223> OTHER INFORMATION: Phosphothioate bond between nucleotide 2 and 3
<220> FEATURE:
<221> NAME/KEY: misc_feature
<222> LOCATION: (70)..(71)
<223> OTHER INFORMATION: N = Any Nucleotide
<220> FEATURE:
<221> NAME/KEY: misc_feature
<222> LOCATION: (72)..(72)
<223> OTHER INFORMATION: K = Guanine or Thymine

<400> SEQUENCE: 39

```
aaaagagcaa gaaggagtat ggaacttata gcaagagagg atgaaaatcc aaaggttgct    60
gaagttatcn nkccaataat gcaggttaat                                     90
```

```
<210> SEQ ID NO 40
<211> LENGTH: 90
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(2)
<223> OTHER INFORMATION: Phosphothioate bond between nucleotide 1 and 2
<220> FEATURE:
<221> NAME/KEY: misc_feature
<222> LOCATION: (2)..(3)
<223> OTHER INFORMATION: Phosphothioate bond between nucleotide 2 and 3
<220> FEATURE:
<221> NAME/KEY: misc_feature
<222> LOCATION: (19)..(20)
<223> OTHER INFORMATION: N = Any Nucleotide
<220> FEATURE:
<221> NAME/KEY: misc_feature
<222> LOCATION: (21)..(21)
<223> OTHER INFORMATION: K = Guanine or Thymine
<220> FEATURE:
<221> NAME/KEY: misc_feature
<222> LOCATION: (22)..(23)
<223> OTHER INFORMATION: N = Any Nucleotide
<220> FEATURE:
<221> NAME/KEY: misc_feature
<222> LOCATION: (24)..(24)
<223> OTHER INFORMATION: K = Guanine or Thymine
<220> FEATURE:
<221> NAME/KEY: misc_feature
<222> LOCATION: (31)..(32)
<223> OTHER INFORMATION: N = Any Nucleotide
<220> FEATURE:
<221> NAME/KEY: misc_feature
<222> LOCATION: (33)..(33)
<223> OTHER INFORMATION: K = Guanine or Thymine
<220> FEATURE:
<221> NAME/KEY: misc_feature
<222> LOCATION: (46)..(47)
<223> OTHER INFORMATION: N = Any Nucleotide
<220> FEATURE:
<221> NAME/KEY: misc_feature
<222> LOCATION: (48)..(48)
<223> OTHER INFORMATION: K = Guanine or Thymine

<400> SEQUENCE: 40
ccaataatgc aggttaatnn knnkcattat nnkggcgttg atgttnnkgt tggagggatg    60
gagcagagaa aaatacacat gttagcaagg                                     90

<210> SEQ ID NO 41
<211> LENGTH: 90
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(2)
<223> OTHER INFORMATION: Phosphothioate bond between nucleotide 1 and 2
<220> FEATURE:
<221> NAME/KEY: misc_feature
<222> LOCATION: (2)..(3)
<223> OTHER INFORMATION: Phosphothioate bond between nucleotide 2 and 3
<220> FEATURE:
<221> NAME/KEY: misc_feature
<222> LOCATION: (38)..(39)
<223> OTHER INFORMATION: N = Any Nucleotide
<220> FEATURE:
<221> NAME/KEY: misc_feature
<222> LOCATION: (40)..(40)
<223> OTHER INFORMATION: K = Guanine or Thymine
<220> FEATURE:
<221> NAME/KEY: misc_feature
<222> LOCATION: (50)..(51)
```

```
<223> OTHER INFORMATION: N = Any Nucleotide
<220> FEATURE:
<221> NAME/KEY: misc_feature
<222> LOCATION: (52)..(52)
<223> OTHER INFORMATION: K = Guanine or Thymine

<400> SEQUENCE: 41
agctaaatac ttccttgaat atcctttaac cataaaannk ccagaaaaan nkggtggaga        60
tttgacagtt aatagctatg aggagttaga                                        90

<210> SEQ ID NO 42
<211> LENGTH: 90
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(2)
<223> OTHER INFORMATION: Phosphothioate bond between nucleotide 1 and 2
<220> FEATURE:
<221> NAME/KEY: misc_feature
<222> LOCATION: (2)..(3)
<223> OTHER INFORMATION: Phosphothioate bond between nucleotide 2 and 3
<220> FEATURE:
<221> NAME/KEY: misc_feature
<222> LOCATION: (40)..(41)
<223> OTHER INFORMATION: N = Any Nucleotide
<220> FEATURE:
<221> NAME/KEY: misc_feature
<222> LOCATION: (42)..(42)
<223> OTHER INFORMATION: K = Guanine or Thymine
<220> FEATURE:
<221> NAME/KEY: misc_feature
<222> LOCATION: (46)..(47)
<223> OTHER INFORMATION: n is a, c, g, or t
<220> FEATURE:
<221> NAME/KEY: misc_feature
<222> LOCATION: (48)..(48)
<223> OTHER INFORMATION: K = Guanine or Thymine
<220> FEATURE:
<221> NAME/KEY: misc_feature
<222> LOCATION: (49)..(50)
<223> OTHER INFORMATION: N = Any Nucleotide
<220> FEATURE:
<221> NAME/KEY: misc_feature
<222> LOCATION: (51)..(51)
<223> OTHER INFORMATION: K = Guanine or Thymine

<400> SEQUENCE: 42
tatgaggagt tagagagttt atttaaaaat aaggaattgn nkccannknn kttaaaaaat        60
gctgtagctg aagaacttat aaagatttta                                        90

<210> SEQ ID NO 43
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 43

Val Pro Gly Ala Gly Val Pro Gly Glu Gly Val Pro Gly Val Gly Lys
1               5                   10                  15

<210> SEQ ID NO 44
<211> LENGTH: 16
<212> TYPE: PRT
<213> ORGANISM: Artificial Sequence
<220> FEATURE:
<223> OTHER INFORMATION: Synthetic Peptide
```

```
<400> SEQUENCE: 44

Val Pro Gly Ala Gly Val Pro Gly Phe Gly Val Pro Gly Val Gly Lys
1               5                   10                  15

<210> SEQ ID NO 45
<211> LENGTH: 32
<212> TYPE: PRT
<213> ORGANISM: Artificial Sequence
<220> FEATURE:
<223> OTHER INFORMATION: Synthetic Peptide

<400> SEQUENCE: 45

Val Pro Gly Ala Gly Val Pro Gly Phe Gly Val Pro Gly Val Gly Lys
1               5                   10                  15

Val Pro Gly Ala Gly Val Pro Gly Phe Gly Val Pro Gly Val Gly Lys
            20                  25                  30

<210> SEQ ID NO 46
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 46

Val Pro Gly Ala Gly Val Pro Gly Gly Gly Val Pro Gly Val Gly Lys
1               5                   10                  15

<210> SEQ ID NO 47
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa = Lysine or Arginine

<400> SEQUENCE: 47

Xaa Gly Val Pro Gly Val Gly Lys
1               5

<210> SEQ ID NO 48
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 48

Val Pro Gly Ala Gly Val Pro Gly Leu Gly Val Pro Gly Val Gly Lys
1               5                   10                  15

<210> SEQ ID NO 49
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 49

Val Pro Gly Ala Gly Val Pro Gly Pro Gly Val Pro Gly Val Gly Lys
1               5                   10                  15

<210> SEQ ID NO 50
```

<211> LENGTH: 16
<212> TYPE: PRT
<213> ORGANISM: Artificial Sequence
<220> FEATURE:
<223> OTHER INFORMATION: Synthetic Peptide

<400> SEQUENCE: 50

Val Pro Gly Ala Gly Val Pro Gly Gln Gly Val Pro Gly Val Gly Lys
1               5                   10                  15

<210> SEQ ID NO 51
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 51

Val Pro Gly Ala Gly Val Pro Gly Ser Gly Val Pro Gly Val Gly Lys
1               5                   10                  15

<210> SEQ ID NO 52
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 52

Val Pro Gly Ala Gly Val Pro Gly Trp Gly Val Pro Gly Val Gly Lys
1               5                   10                  15

<210> SEQ ID NO 53
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 53

Gly Pro Gly Lys Val Pro Gly Ala Gly Val Pro Gly Tyr Gly Val Pro
1               5                   10                  15

Gly Val Gly Lys
            20

<210> SEQ ID NO 54
<211> LENGTH: 22
<212> TYPE: PRT
<213> ORGANISM: Artificial Sequence
<220> FEATURE:
<223> OTHER INFORMATION: Synthetic Peptide

<400> SEQUENCE: 54

Ser Lys Gly Pro Gly Lys Val Pro Gly Ala Gly Val Pro Gly Tyr Gly
1               5                   10                  15

Val Pro Gly Val Gly Lys
            20

<210> SEQ ID NO 55
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 55

```
Val Pro Gly Ala Gly Val Pro Gly Tyr Gly Val Pro Gly Val Gly Lys
1               5                  10                  15
```

<210> SEQ ID NO 56
<211> LENGTH: 32
<212> TYPE: PRT
<213> ORGANISM: Artificial Sequence
<220> FEATURE:
<223> OTHER INFORMATION: Synthetic Peptide

<400> SEQUENCE: 56

```
Val Pro Gly Ala Gly Val Pro Gly Tyr Gly Val Pro Gly Val Gly Lys
1               5                  10                  15

Val Pro Gly Ala Gly Val Pro Gly Tyr Gly Val Pro Gly Val Gly Lys
            20                  25                  30
```

<210> SEQ ID NO 57
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 57

```
Val Pro Gly Ala Gly Val Pro Gly Phe Gly Val Pro Gly Val Gly Lys
1               5                  10                  15
```

<210> SEQ ID NO 58
<211> LENGTH: 16
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (9)..(9)
<223> OTHER INFORMATION: Oxidation modification

<400> SEQUENCE: 58

```
Val Pro Gly Ala Gly Val Pro Gly Met Gly Val Pro Gly Val Gly Lys
1               5                  10                  15
```

<210> SEQ ID NO 59
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 59

```
Val Pro Gly Ala Gly Val Pro Gly Pro Gly Val Pro Gly Val Gly Lys
1               5                  10                  15
```

<210> SEQ ID NO 60
<211> LENGTH: 16
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (9)..(9)
<223> OTHER INFORMATION: Xaa = the Non-Standard amino acid pAcF

<400> SEQUENCE: 60

```
Val Pro Gly Ala Gly Val Pro Gly Xaa Gly Val Pro Gly Val Gly Lys
1               5                  10                  15
```

<210> SEQ ID NO 61
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 61

Val Pro Gly Ala Gly Val Pro Gly Gln Gly Val Pro Gly Val Gly Lys
1               5                   10                  15

<210> SEQ ID NO 62
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 62

Val Pro Gly Ala Gly Val Pro Gly Tyr Gly Val Pro Gly Val Gly Lys
1               5                   10                  15

<210> SEQ ID NO 63
<211> LENGTH: 16
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (9)..(9)
<223> OTHER INFORMATION: pAcF, delta H2C2 modification, + 26.101565 Da
<220> FEATURE:
<221> NAME/KEY: MISC_FEATURE
<222> LOCATION: (16)..(16)
<223> OTHER INFORMATION: Labeled with an isotopically light probe

<400> SEQUENCE: 63

Val Pro Gly Ala Gly Val Pro Gly Tyr Gly Val Pro Gly Val Gly Lys
1               5                   10                  15

<210> SEQ ID NO 64
<211> LENGTH: 16
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (9)..(9)
<223> OTHER INFORMATION: pAzF, delta N3H(-1) modification, + 41.00140 Da
      and pAzF_am
<220> FEATURE:
<221> NAME/KEY: MISC_FEATURE
<222> LOCATION: (16)..(16)
<223> OTHER INFORMATION: Labeled with an isotopically light probe

<400> SEQUENCE: 64

Val Pro Gly Ala Gly Val Pro Gly Phe Gly Val Pro Gly Val Gly Lys
1               5                   10                  15

<210> SEQ ID NO 65
<211> LENGTH: 16
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (16)..(16)

```
<223> OTHER INFORMATION: Labeled with an isotopically light probe

<400> SEQUENCE: 65

Val Pro Gly Ala Gly Val Pro Gly Trp Gly Val Pro Gly Val Gly Lys
1               5                   10                  15

<210> SEQ ID NO 66
<211> LENGTH: 16
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (16)..(16)
<223> OTHER INFORMATION: Labeled with an isotopically heavy probe

<400> SEQUENCE: 66

Val Pro Gly Ala Gly Val Pro Gly Tyr Gly Val Pro Gly Val Gly Lys
1               5                   10                  15

<210> SEQ ID NO 67
<211> LENGTH: 16
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (16)..(16)
<223> OTHER INFORMATION: Labeled with an isotopically light probe

<400> SEQUENCE: 67

Val Pro Gly Ala Gly Val Pro Gly Tyr Gly Val Pro Gly Val Gly Lys
1               5                   10                  15

<210> SEQ ID NO 68
<211> LENGTH: 16
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (9)..(9)
<223> OTHER INFORMATION: Delta HN modification, +15.01090 Da.
<220> FEATURE:
<221> NAME/KEY: MISC_FEATURE
<222> LOCATION: (16)..(16)
<223> OTHER INFORMATION: Labeled with an isotopically light probe

<400> SEQUENCE: 68

Val Pro Gly Ala Gly Val Pro Gly Phe Gly Val Pro Gly Val Gly Lys
1               5                   10                  15

<210> SEQ ID NO 69
<211> LENGTH: 16
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (16)..(16)
<223> OTHER INFORMATION: Labeled with an isotopically heavy probe

<400> SEQUENCE: 69

Val Pro Gly Ala Gly Val Pro Gly Phe Gly Val Pro Gly Val Gly Lys
1               5                   10                  15
```

```
<210> SEQ ID NO 70
<211> LENGTH: 16
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (16)..(16)
<223> OTHER INFORMATION: Labeled with an isotopically light probe

<400> SEQUENCE: 70

Val Pro Gly Ala Gly Val Pro Gly Phe Gly Val Pro Gly Val Gly Lys
1               5                   10                  15

<210> SEQ ID NO 71
<211> LENGTH: 16
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (16)..(16)
<223> OTHER INFORMATION: Labeled with an isotopically light probe

<400> SEQUENCE: 71

Val Pro Gly Ala Gly Val Pro Gly His Gly Val Pro Gly Val Gly Lys
1               5                   10                  15

<210> SEQ ID NO 72
<211> LENGTH: 16
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (9)..(9)
<223> OTHER INFORMATION: Deamination modification, +1.0 Da
<220> FEATURE:
<221> NAME/KEY: MISC_FEATURE
<222> LOCATION: (16)..(16)
<223> OTHER INFORMATION: Labeled with an isotopically light probe

<400> SEQUENCE: 72

Val Pro Gly Ala Gly Val Pro Gly Gln Gly Val Pro Gly Val Gly Lys
1               5                   10                  15

<210> SEQ ID NO 73
<211> LENGTH: 16
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (16)..(16)
<223> OTHER INFORMATION: Labeled with an isotopically light probe

<400> SEQUENCE: 73

Val Pro Gly Ala Gly Val Pro Gly Lys Gly Val Pro Gly Val Gly Lys
1               5                   10                  15

<210> SEQ ID NO 74
<211> LENGTH: 16
<212> TYPE: PRT
<213> ORGANISM: Artificial Sequence
<220> FEATURE:
<223> OTHER INFORMATION: Synthetic Peptide
```

```
<220> FEATURE:
<221> NAME/KEY: MISC_FEATURE
<222> LOCATION: (16)..(16)
<223> OTHER INFORMATION: Labeled with an isotopically light probe

<400> SEQUENCE: 74

Val Pro Gly Ala Gly Val Pro Gly Gln Gly Val Pro Gly Val Gly Lys
1               5                   10                  15

<210> SEQ ID NO 75
<211> LENGTH: 16
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (16)..(16)
<223> OTHER INFORMATION: Labeled with an isotopically light probe

<400> SEQUENCE: 75

Val Pro Gly Ala Gly Val Pro Gly Ile Gly Val Pro Gly Val Gly Lys
1               5                   10                  15

<210> SEQ ID NO 76
<211> LENGTH: 16
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (16)..(16)
<223> OTHER INFORMATION: Labeled with an isotopically light probe

<400> SEQUENCE: 76

Val Pro Gly Ala Gly Val Pro Gly Leu Gly Val Pro Gly Val Gly Lys
1               5                   10                  15

<210> SEQ ID NO 77
<211> LENGTH: 16
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (16)..(16)
<223> OTHER INFORMATION: Labeled with an isotopically light probe

<400> SEQUENCE: 77

Val Pro Gly Ala Gly Val Pro Gly Pro Gly Val Pro Gly Val Gly Lys
1               5                   10                  15

<210> SEQ ID NO 78
<211> LENGTH: 16
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (16)..(16)
<223> OTHER INFORMATION: Labeled with an isotopically light probe

<400> SEQUENCE: 78

Val Pro Gly Ala Gly Val Pro Gly Ser Gly Val Pro Gly Val Gly Lys
1               5                   10                  15
```

```
<210> SEQ ID NO 79
<211> LENGTH: 16
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (16)..(16)
<223> OTHER INFORMATION: Labeled with an isotopically light probe

<400> SEQUENCE: 79

Val Pro Gly Ala Gly Val Pro Gly Gly Val Pro Gly Val Gly Lys
1               5                   10                  15

<210> SEQ ID NO 80
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (11)..(11)
<223> OTHER INFORMATION: Labeled with an isotopically heavy probe

<400> SEQUENCE: 80

Ser Ala Met Pro Glu Gly Tyr Val Gln Glu Arg
1               5                   10

<210> SEQ ID NO 81
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (11)..(11)
<223> OTHER INFORMATION: Labeled with an isotopically light probe

<400> SEQUENCE: 81

Ser Ala Met Pro Glu Gly Tyr Val Gln Glu Arg
1               5                   10

<210> SEQ ID NO 82
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (9)..(9)
<223> OTHER INFORMATION: Labeled with an isotopically heavy probe

<400> SEQUENCE: 82

Phe Glu Gly Asp Thr Leu Val Asn Arg
1               5

<210> SEQ ID NO 83
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (9)..(9)
<223> OTHER INFORMATION: Labeled with an isotopically light probe
```

```
<400> SEQUENCE: 83

Phe Glu Gly Asp Thr Leu Val Asn Arg
1               5

<210> SEQ ID NO 84
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (9)..(9)
<223> OTHER INFORMATION: Labeled with an isotopically light probe

<400> SEQUENCE: 84

Val Pro Gly Ala Gly Val Pro Gly Arg
1               5

<210> SEQ ID NO 85
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (9)..(9)
<223> OTHER INFORMATION: Labeled with an isotopically light probe

<400> SEQUENCE: 85

Val Pro Gly Ala Gly Val Pro Gly Lys
1               5

<210> SEQ ID NO 86
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (7)..(7)
<223> OTHER INFORMATION: Labeled with an isotopically light probe

<400> SEQUENCE: 86

Gly Val Pro Gly Val Gly Lys
1               5

<210> SEQ ID NO 87
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (7)..(7)
<223> OTHER INFORMATION: Labeled with an isotopically light probe

<400> SEQUENCE: 87

Gly Val Pro Gly Val Gly Lys
1               5

<210> SEQ ID NO 88
<211> LENGTH: 9
<212> TYPE: PRT
<213> ORGANISM: Artificial Sequence
<220> FEATURE:
```

```
<223> OTHER INFORMATION: Synthetic Peptide
<220> FEATURE:
<221> NAME/KEY: MISC_FEATURE
<222> LOCATION: (9)..(9)
<223> OTHER INFORMATION: Labeled with an isotopically light probe

<400> SEQUENCE: 88

Val Pro Gly Ala Gly Val Pro Gly Lys
1               5

<210> SEQ ID NO 89
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (9)..(9)
<223> OTHER INFORMATION: Labeled with an isotopically light probe

<400> SEQUENCE: 89

Val Pro Gly Ala Gly Val Pro Gly Arg
1               5

<210> SEQ ID NO 90
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (11)..(11)
<223> OTHER INFORMATION: Labeled with an isotopically heavy probe

<400> SEQUENCE: 90

Ser Ala Met Pro Glu Gly Tyr Val Gln Glu Arg
1               5                   10

<210> SEQ ID NO 91
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (11)..(11)
<223> OTHER INFORMATION: Labeled with an isotopically light probe

<400> SEQUENCE: 91

Ser Ala Met Pro Glu Gly Tyr Val Gln Glu Arg
1               5                   10

<210> SEQ ID NO 92
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (9)..(9)
<223> OTHER INFORMATION: Labeled with an isotopically light probe

<400> SEQUENCE: 92

Phe Glu Gly Asp Thr Leu Val Asn Arg
1               5
```

<210> SEQ ID NO 93
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (9)..(9)
<223> OTHER INFORMATION: Labeled with an isotopically heavy probe

<400> SEQUENCE: 93

Phe Glu Gly Asp Thr Leu Val Asn Arg
1               5

<210> SEQ ID NO 94
<211> LENGTH: 16
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (9)..(9)
<223> OTHER INFORMATION: Delta HN modification, +15.01090 Da.
<220> FEATURE:
<221> NAME/KEY: MISC_FEATURE
<222> LOCATION: (16)..(16)
<223> OTHER INFORMATION: Labeled with an isotopically light probe

<400> SEQUENCE: 94

Val Pro Gly Ala Gly Val Pro Gly Phe Gly Val Pro Gly Val Gly Lys
1               5                   10                  15

<210> SEQ ID NO 95
<211> LENGTH: 16
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (16)..(16)
<223> OTHER INFORMATION: Labeled with an isotopically light probe

<400> SEQUENCE: 95

Val Pro Gly Ala Gly Val Pro Gly Gln Gly Val Pro Gly Val Gly Lys
1               5                   10                  15

<210> SEQ ID NO 96
<211> LENGTH: 16
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (16)..(16)
<223> OTHER INFORMATION: Labeled with an isotopically light probe

<400> SEQUENCE: 96

Val Pro Gly Ala Gly Val Pro Gly Lys Gly Val Pro Gly Val Gly Lys
1               5                   10                  15

<210> SEQ ID NO 97
<211> LENGTH: 16
<212> TYPE: PRT
<213> ORGANISM: Artificial Sequence
<220> FEATURE:
<223> OTHER INFORMATION: Synthetic Peptide

```
<220> FEATURE:
<221> NAME/KEY: MISC_FEATURE
<222> LOCATION: (9)..(9)
<223> OTHER INFORMATION: Deamination modification, +1.0 Da
<220> FEATURE:
<221> NAME/KEY: MISC_FEATURE
<222> LOCATION: (16)..(16)
<223> OTHER INFORMATION: Labeled with an isotopically light probe

<400> SEQUENCE: 97

Val Pro Gly Ala Gly Val Pro Gly Gln Gly Val Pro Gly Val Gly Lys
1               5                   10                  15

<210> SEQ ID NO 98
<211> LENGTH: 16
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (16)..(16)
<223> OTHER INFORMATION: Labeled with an isotopically light probe

<400> SEQUENCE: 98

Val Pro Gly Ala Gly Val Pro Gly Pro Gly Val Pro Gly Val Gly Lys
1               5                   10                  15

<210> SEQ ID NO 99
<211> LENGTH: 16
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (16)..(16)
<223> OTHER INFORMATION: Labeled with an isotopically light probe

<400> SEQUENCE: 99

Val Pro Gly Ala Gly Val Pro Gly Ser Gly Val Pro Gly Val Gly Lys
1               5                   10                  15

<210> SEQ ID NO 100
<211> LENGTH: 16
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (16)..(16)
<223> OTHER INFORMATION: Labeled with an isotopically light probe

<400> SEQUENCE: 100

Val Pro Gly Ala Gly Val Pro Gly Gly Gly Val Pro Gly Val Gly Lys
1               5                   10                  15

<210> SEQ ID NO 101
<211> LENGTH: 16
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (16)..(16)
<223> OTHER INFORMATION: Labeled with an isotopically light probe

<400> SEQUENCE: 101
```

```
Val Pro Gly Ala Gly Val Pro Gly Tyr Gly Val Pro Gly Val Gly Lys
1               5                   10                  15
```

<210> SEQ ID NO 102
<211> LENGTH: 16
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (16)..(16)
<223> OTHER INFORMATION: Labeled with an isotopically heavy probe

<400> SEQUENCE: 102

```
Val Pro Gly Ala Gly Val Pro Gly Tyr Gly Val Pro Gly Val Gly Lys
1               5                   10                  15
```

<210> SEQ ID NO 103
<211> LENGTH: 16
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (16)..(16)
<223> OTHER INFORMATION: Labeled with an isotopically light probe

<400> SEQUENCE: 103

```
Val Pro Gly Ala Gly Val Pro Gly Trp Gly Val Pro Gly Val Gly Lys
1               5                   10                  15
```

<210> SEQ ID NO 104
<211> LENGTH: 16
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (16)..(16)
<223> OTHER INFORMATION: Labeled with an isotopically light probe

<400> SEQUENCE: 104

```
Val Pro Gly Ala Gly Val Pro Gly His Gly Val Pro Gly Val Gly Lys
1               5                   10                  15
```

<210> SEQ ID NO 105
<211> LENGTH: 16
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (16)..(16)
<223> OTHER INFORMATION: Labeled with an isotopically light probe

<400> SEQUENCE: 105

```
Val Pro Gly Ala Gly Val Pro Gly Leu Gly Val Pro Gly Val Gly Lys
1               5                   10                  15
```

<210> SEQ ID NO 106
<211> LENGTH: 16
<212> TYPE: PRT
<213> ORGANISM: Artificial Sequence
<220> FEATURE:
<223> OTHER INFORMATION: Synthetic Peptide
<220> FEATURE:

```
<221> NAME/KEY: MISC_FEATURE
<222> LOCATION: (16)..(16)
<223> OTHER INFORMATION: Labeled with an isotopically light probe

<400> SEQUENCE: 106

Val Pro Gly Ala Gly Val Pro Gly Ile Gly Val Pro Gly Val Gly Lys
1               5                   10                  15

<210> SEQ ID NO 107
<211> LENGTH: 16
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (9)..(9)
<223> OTHER INFORMATION: pAcF, delta H2C2 modification, + 26.101565 Da
<220> FEATURE:
<221> NAME/KEY: MISC_FEATURE
<222> LOCATION: (16)..(16)
<223> OTHER INFORMATION: Labeled with an isotopically light probe

<400> SEQUENCE: 107

Val Pro Gly Ala Gly Val Pro Gly Tyr Gly Val Pro Gly Val Gly Lys
1               5                   10                  15

<210> SEQ ID NO 108
<211> LENGTH: 16
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (16)..(16)
<223> OTHER INFORMATION: Labeled with an isotopically light probe

<400> SEQUENCE: 108

Val Pro Gly Ala Gly Val Pro Gly Phe Gly Val Pro Gly Val Gly Lys
1               5                   10                  15

<210> SEQ ID NO 109
<211> LENGTH: 16
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (16)..(16)
<223> OTHER INFORMATION: Labeled with an isotopically heavy probe

<400> SEQUENCE: 109

Val Pro Gly Ala Gly Val Pro Gly Phe Gly Val Pro Gly Val Gly Lys
1               5                   10                  15

<210> SEQ ID NO 110
<211> LENGTH: 16
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (9)..(9)
<223> OTHER INFORMATION: pAzF, delta N3H(-1) modification, + 41.00140 Da
      and pAzF_am
<220> FEATURE:
<221> NAME/KEY: MISC_FEATURE
<222> LOCATION: (16)..(16)
```

<223> OTHER INFORMATION: Labeled with an isotopically light probe

<400> SEQUENCE: 110

Val Pro Gly Ala Gly Val Pro Gly Phe Gly Val Pro Gly Val Gly Lys
1               5                   10                  15

<210> SEQ ID NO 111
<211> LENGTH: 1482
<212> TYPE: DNA
<213> ORGANISM: Artificial Sequence
<220> FEATURE:
<223> OTHER INFORMATION: Synthetic DNA Sequence

<400> SEQUENCE: 111

```
atgaagaaat tgctccccat tcttatcggc ctgagccttt ctgggttcag ttcgttgagc      60
caggccgaga acctgatgca agtttatcag caagcacgcc ttagtaaccc ggaattgcgt     120
aagtctgccg ccgatcgtga tgctgccttt gaaaaaatta atgaagcgcg cagtccatta     180
ctgccacagc taggtttagg tgcagattac acctatagca acggctaccg cgacgcgaac     240
ggcatcaact ctaacgcgac cagtgcgtcc ttgcagttaa ctcaatccat ttttgatatg     300
tcgaaatggc gtgcgttaac gctgcaggaa aaagcagcag ggattcagga cgtcacgtat     360
cagaccgatc agcaaacctt gatcctcaac accgcgaccg cttatttcaa cgtgttgaat     420
gctattgacg ttctttccta tacacaggca caaaaagaag cgatctaccg tcaattagat     480
caaaccaccc aacgttttaa cgtgggcctg gtagcgatca ccgacgtgca gaacgcccgc     540
gcacagtacg ataccgtgct ggcgaacgaa gtgaccgcac gtaataacct tgataacgcg     600
gtagagcagc tgcgccagat caccggtaac tactatccgg aactggctgc gctgaatgtc     660
tagaaccttta aaacctagaa accacagccg gttaacgcgc tgctgaaaga agccgaaaaa     720
cgcaacctgt cgctgttaca ggcacgcttg agccaggacc tggcgcgcga gcaaattcgc     780
caggcgcagg atggtcactt accgactctg gatttaacgg cttctaccgg gatttctgac     840
acctcttata gcggttcgaa aacccgtggt tagtagggta cccagtatga cgatagcaat     900
atgggccaga caaagttgg cctgagcttc tcgctgccga tttatcaggg cggaatggtt     960
aactcgcagg tgaaacaggc acagtacaac tttgtcggtg ccagcgagca actggaaagt    1020
gcccatcgta gcgtcgtgca gaccgtgcgt tcctccttca acaacattaa tgcatctatc    1080
agtagcatta cgcctacaa acaagccgta gtttccgctc aaagctcatt agacgcgatg    1140
gaagcgggct actcggtcgg tacgcgtacc attgttgatg tgttggatgc gaccaccacg    1200
ttgtacaacg ccaagcaaga gctggcgaat gcgcgttata actacctgat taatcagctg    1260
aatattaagt cagctctggg tacgttgaac gagcaggatc tgctggcact gaacaatgcg    1320
ctgagcaaac cggtttccac taatccggaa aacgttgcac cgcaaacgcc ggaacagaat    1380
gctattgctg atggttatgc gcctgatagc ccggcaccag tcgttcagca acatccgca    1440
cgcactacca ccagtaacgg tcataaccct ttccgtaact ga                       1482
```

<210> SEQ ID NO 112
<211> LENGTH: 720
<212> TYPE: DNA
<213> ORGANISM: Artificial Sequence
<220> FEATURE:
<223> OTHER INFORMATION: Synthetic DNA Sequence

<400> SEQUENCE: 112

```
atgagcaagg gcgaagaact gtttacgggc gtggtgccga ttctggtgga actggatggt      60
```

```
gatgtcaatg gtcacaaatt cagcgtgcgc ggcgaaggtg aaggcgatgc aacctagggt    120
aaactgacgc tgaagtttat ttgcaccacg ggtaaactgc cggttccgtg gccgaccctg    180
gtcaccacgc tgacgtatgg tgttcagtgt ttcagtcgtt acccggatca catgaaacgc    240
cacgactttt tcaagtccgc gatgccggaa ggttatgtcc aagaacgtac catctcattt    300
aaagatgacg gcacctacaa aacgcgcgcc gaagtgaaat tcgaaggtga tacgctggtt    360
aaccgtattg aactgaaagg catcgatttt aaggaagacg gtaatattct gggccataaa    420
ctggaatata acttcaattc gcacaacgtg tagatcaccg cagataagca gaagaacggt    480
atcaaggcta acttcaagat ccgccataat gtggaagatg gcagcgttca actggccgac    540
cactagcagc aaaacacccc gattggtgat ggcccggtcc tgctgccgga caatcattac    600
ctgagcacgc agtctgtgct gagtaaagat ccgaacgaaa agcgtgacca catggtcctg    660
ctggaattcg tgaccgcggc cggcatcacg cacggtatgg acgaactgta taaaggctca    720
```

```
<210> SEQ ID NO 113
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(5)
<223> OTHER INFORMATION: The sequence of the peptide can be repeated up
      to more than 500 times.
<220> FEATURE:
<221> NAME/KEY: MISC_FEATURE
<222> LOCATION: (4)..(4)
<223> OTHER INFORMATION: Xaa = the Non-Standard amino acid pAzF

<400> SEQUENCE: 113

Val Pro Gly Xaa Gly
1               5

<210> SEQ ID NO 114
<211> LENGTH: 16
<212> TYPE: PRT
<213> ORGANISM: Artificial Sequence
<220> FEATURE:
<223> OTHER INFORMATION: Synthetic Peptide.
<220> FEATURE:
<221> NAME/KEY: MISC_FEATURE
<222> LOCATION: (9)..(9)
<223> OTHER INFORMATION: Xaa = stop codon

<400> SEQUENCE: 114

Val Pro Gly Ala Gly Val Pro Gly Xaa Gly Val Pro Gly Val Gly Lys
1               5                   10                  15
```